US007887805B2

(12) United States Patent
Pedersen et al.

(10) Patent No.: US 7,887,805 B2
(45) Date of Patent: Feb. 15, 2011

(54) RECOMBINANT ANTI-EPIDERMAL GROWTH FACTOR RECEPTOR ANTIBODY COMPOSITIONS

(75) Inventors: Mikkel Wandahl Pedersen, Alleroed (DK); Lucilla Steinaa, Hoersholm (DK); Allan Jensen, Fredensborg (DK); Klaus Koefoed, Copenhagen S (DK); Per-Johan Meijer, Copenhangen N (DK); Robert Carlsson, Malmoe (SE); Charles Pyke, Hilleroed (DK); Lars S. Nielsen, Nivaa (DK)

(73) Assignee: Symphogen A/S, Lyngby (DK)

( * ) Notice: Subject to any disclaimer, the term of this patent is extended or adjusted under 35 U.S.C. 154(b) by 78 days.

(21) Appl. No.: 12/074,056

(22) Filed: Feb. 29, 2008

(65) Prior Publication Data

US 2009/0004192 A1    Jan. 1, 2009

Related U.S. Application Data

(60) Provisional application No. 60/904,773, filed on Mar. 5, 2007, provisional application No. 60/929,727, filed on Jul. 11, 2007.

(30) Foreign Application Priority Data

Mar. 1, 2007 (DK) .......... PA 2007 00317
Jul. 10, 2007 (DK) .......... PA 2007 01016

(51) Int. Cl.
*A61K 39/395* (2006.01)
*C07K 14/71* (2006.01)
*C12N 15/13* (2006.01)

(52) U.S. Cl. .......... 424/143.1; 424/135.1; 424/136.1; 424/138.1; 424/141.1; 424/155.1; 435/69.1; 536/23.1

(58) Field of Classification Search .......... None
See application file for complete search history.

(56) References Cited

U.S. PATENT DOCUMENTS 4,943,533 A    7/1990    Mendelsohn et al.

(Continued)

FOREIGN PATENT DOCUMENTS

WO    WO 94/00136 A1    1/1994

(Continued)

OTHER PUBLICATIONS

Bui et al., Liposarcoma: Patterns of tumor differentiation following induction of chemotherapy, Oncology, 41(3):170, abstract only, 1984.*

(Continued)

*Primary Examiner*—Gary B. Nickol
*Assistant Examiner*—Claire Kaufman
(74) *Attorney, Agent, or Firm*—Sterne, Kessler, Goldstein & Fox P.L.L.C.

(57) ABSTRACT

The invention relates to the field of recombinant antibodies for use in human cancer therapy. More specifically the invention provides compositions or mixtures of antibodies capable of binding human EGFR. Antibody compositions with 3 or more antibodies showed synergy in reduction of proliferation of representative cancer cell lines. Advantageous results have also been obtained with a composition comprising two different chimeric anti-hEGFR antibodies which show a new mechanism of action based on rapid and efficient receptor internalisation, induction of terminal differentiation and subsequent tumour eradication in an animal model. The antibodies of the invention can be manufactured in one bioreactor as a polyclonal antibody.

53 Claims, 47 Drawing Sheets

U.S. PATENT DOCUMENTS

| | | | |
|---|---|---|---|
| 5,459,061 | A | 10/1995 | Sato et al. |
| 6,217,866 | B1 | 4/2001 | Schlessinger et al. |
| 6,235,883 | B1 | 5/2001 | Jakobovits et al. |
| 6,849,259 | B2 | 2/2005 | Haurum et al. |
| 2006/0073140 | A1 | 4/2006 | Greene et al. |
| 2006/0275766 | A1 | 12/2006 | Haurum et al. |
| 2007/0009972 | A1 | 1/2007 | Chao et al. |
| 2007/0141048 | A1 | 6/2007 | Oleksiewicz et al. |
| 2008/0069822 | A1 | 3/2008 | Jensen et al. |
| 2008/0131882 | A1 | 6/2008 | Rasmussen et al. |
| 2008/0227660 | A1 | 9/2008 | Kastrup et al. |
| 2009/0137784 | A1 | 5/2009 | Chao et al. |

FOREIGN PATENT DOCUMENTS

| | | | |
|---|---|---|---|
| WO | WO 02/092771 | A2 | 11/2002 |
| WO | WO 02/100348 | A2 | 12/2002 |
| WO | WO 03/074705 | A1 | 9/2003 |
| WO | WO 03/097086 | A2 | 11/2003 |
| WO | WO 03/099205 | A2 | 12/2003 |
| WO | WO 2004/008099 | A2 | 1/2004 |
| WO | WO 2004/009618 | A2 | 1/2004 |
| WO | WO 2004/032960 | A1 | 4/2004 |
| WO | WO 2004/032961 | A1 | 4/2004 |
| WO | WO 2004/056847 | A2 | 7/2004 |
| WO | WO 2004/061104 | A2 | 7/2004 |
| WO | WO 2004/085474 | A2 | 10/2004 |
| WO | WO 2004/106379 | A1 | 12/2004 |
| WO | WO 2005/042774 | A2 | 5/2005 |
| WO | WO 2005/071075 | A1 | 8/2005 |
| WO | WO 2006/007850 | A1 | 1/2006 |
| WO | WO 2006/007853 | A2 | 1/2006 |
| WO | WO 2006/009694 | A2 | 1/2006 |
| WO | WO 2006/078307 | A1 | 7/2006 |
| WO | WO 2006/091693 | A2 | 8/2006 |
| WO | WO 2006/091899 | A2 | 8/2006 |
| WO | WO 2006/102504 | A2 | 9/2006 |
| WO | WO 2006/108627 | A1 | 10/2006 |
| WO | WO 2006/110478 | A2 | 10/2006 |
| WO | WO 2006/116001 | A2 | 11/2006 |
| WO | WO 2007/065433 | A2 | 6/2007 |
| WO | WO 2007/101441 | A1 | 9/2007 |
| WO | WO 2008/104184 | A2 | 9/2008 |

OTHER PUBLICATIONS

Pendersen et al., Sym004: A novel synergistic anti-epidermal growth factor receptor antibody mix with superior anticancer efficacy, Cancer Res. 70(2):588-597, 2010.*

Arteaga, C.L., The epidermal growth factor receptor: from mutant oncogene in nonhuman cancers to therapeutic target in human neoplasia, J. Clin. Oncol. 19: 32s-40s, Sep. 2001.*

Patel et al., Activity and binding mechanism of cetuximab (Erbitux R) to the type III EGF delettion-mutant receptor [abstract]. In: Proceedings of the 97th Annual Meeting of the American Association for Cancer Research (AACR); Apr. 1-5, 2006; Washington, DC. USA, vol. 47, p. 293, Abstract 1238, Apr. 2006.*

Rudikoff et al., Single amino acid substitution altering antigen-binding specificity, Proc. Natl. Acad. Sci. USA, 79:1979-1983, 1982.*

MacCallum et al., Antibody-antigen interactions: Contact analysis and binding site topograpyt, J. Mol. Biol. 262:732-745, 1996.*

Giudicell et al., IMGT/LIGM-DB, the IMGT comprehensive database of immunoglobulin and T cell receptor nucleotide sequences, Nucleic Acid Res. 34: D781-D784, 2006.*

M. LeFranc, IMGT-Ontology and IMGT databases, tools and web resources for immunogenetics and immunoinformatics, Mol. Immunol. 40(10):647-659, Jan. 2004.*

Database UniProt Accession No. Q68GS6, "Cloning of the CDNA for the extracellular domain of EGF receptor from human placenta" (Oct. 11, 2004).

International Search Report for International Application No. PCT/DK2008/050047, mailed on Sep. 26, 2008, European Patent Office, Rijswijk, Netherlands.

Baselga, J. and Mendelsohn, J., "Receptor Blockade with Monoclonal Antibodies as Anti-Cancer Therapy," *Pharmac. Ther.* 64:127-154, Pergamon Press (1994).

Bregenholt, S., et al., "Recombinant Human Polyclonal Antibodies: A New Class of Therapeutic Antibodies Against Viral Infections," *Curr. Pharm. Des.* 12:2007-2015, Bentham Science Publishers (Jan. 2006).

Cochran, J.R., et al., "Domain-level antibody epitope mapping through yeast surface display of epidermal growth factor receptor fragments," *J. Immunol. Meth.* 287:147-158, Elsevier Science (2004).

Drug information sheet for Erbitux® (Cetuximab), 6 pages, ImClone Systems Incorporated and Bristol-Myers Squibb Company (Mar. 2006).

Drug information sheet for Vectibix™ (panitumumab), 14 pages, Amgen Inc. (Sep. 2006).

Ferguson, K.M., et al., "EGF Activates its Receptor by Removing Interactions that Autoinhibit Ectodomain Dimerization," *Mol. Cell* 11:507-517, Cell Press (2003).

Friedman, L.M., et al., "Synergistic down-regulation of receptor tyrosine kinases by combinations of mAbs: Implications for cancer immunotherapy," *Proc. Natl. Acad. Sci.* 102:1915-1920, The National Academy of Sciences (2005).

Garrett, T.P., et al., "Crystal Structure of a Truncated Epidermal Growth Factor Receptor Extracellular Domain Bound to Transforming Growth Factor α," *Cell* 110:763-773, Cell Press (2002).

Harwerth, I.-M., et al., "Monoclonal antibodies directed to the erbB-2 receptor inhibit in vivo tumour cell growth," *Br. J. Cancer* 68:1140-1145, Macmillan Press (1993).

Haurum, J.S., "Recombinant polyclonal antibodies: the next generation of antibody therapeutics?," *Drug Discov. Today* 11:655-660, Elsevier Science (Jul. 2006).

Ivascu, A. and Kubbies, M., "Rapid Generation of Single-Tumor Spheroid for High-Throughput Cell Function and Toxicity Analysis," *J. Biomol.* 11:1-11, Society for Biomolecular Sciences (Sep. 2006).

Karnes, W.E., Jr., et al., "Inhibition of Epidermal Growth Factor Receptor Kinase Induces Protease-Dependent Apoptosis in Human Colon Cancer Cells," *Gastroenterology* 114:930-939, W.B. Saunders (1998).

Kawamata, H., et al., "Differentiation-Inducing Therapy for Solid Tumors," *Curr. Pharm. Des.* 12:379-385, Bentham Science Publishers (Jan. 2006).

Larbouret, C., et al., "In vivo Therapeutic Synergism of Anti-Epidermal Growth Factor Receptor and Anti-HER2 Monoclonal Antibodies against Pancreatic Carcinomas," *Clin. Cancer Res.* 13:3356-3362, American Association for Cancer Research (Jun. 2007).

Li, D., et al., "Therapeutic anti-EGFR antibody 806 generates responses in murine de novo EGFR mutant—dependent lung carcinomas," *J. Clin. Invest.* 117:346-352, American Society for Clinical Investigation (Feb. 2007).

Logtenberg, T., "Antibody cocktails: next-generation bipharmaceuticals with improved potency," *Trends Biotechnol.* 25:390-394, Elsevier Science (2007).

Masui, H., et al., "Mechanism of Antitumor Activity in Mice for Anti-Epidermal Growth Factor Receptor Monoclonal Antibodies with Different Isotypes," *Cancer Res.* 46:5592-5598, American Association for Cancer Research (1986).

Meijer, P.-R., et al., "Isolation of Human Antibody Repertoires with Preservation of the Natural Heavy and Light Chain Pairing," J. Mol. Biol. 358:764-772, Elsevier Science (May 2006).

Modjtahedi, H., et al., "Antitumor Activity of Combinations of Antibodies Directed Against Different Epitopes on the Extracellular Domain of the Human EGF Receptor," *Cell Biophys.* 22:129-146, Humana Press (1993).

Modjtahedi, H., et al., "Immunotherapy of human tumour xenografts overexpressing the EGF receptor with rat antibodies that block growth factor-receptor interaction," *Br. J. Cancer* 67:254-261, Macmillan Press (1993).

Modjtahedi, H., et al., "Differentiation or Immune Destruction: Two Pathways for Therapy of Squamous Cell Carcinomas with Antibodies to the Epidermal Growth Factor Receptor," Cancer Research 54:1695-1701, American Association for Cancer Research (1994).

Modjtahedi, H. and Dean, C., "The receptor for EGF and its ligands: Expression, prognostic value and target for therapy in cancer (Review)," *Int. J. Oncol.* 4:277-296, Spandidos Publications Ltd. (1994).

Nahta, R., et al., "The HER-2-Targeting Antibodies Trastuzumab and Pertuzumab Synergistically Inhibit the Survival of Breast Cancer Cells," *Cancer Res.* 64:2343-2346, American Association for Cancer Research (2004).

Normanno, N., et al., "Cooperative inhibitory effect of ZD1839 (Iressa) in combination with trastuzumab (Herceptin) on human breast cancer cell growth," *Ann. Oncol.* 13:65-72, Oxford University Press (2002).

Ogiso, H., et al., "Crystal Structure of the Complex of Human Epidermal Growth Factor and Receptor Extracellular Domains," *Cell* 110:775-787, Cell Press (2002).

Perera, R.M., et al., "Treatment of Human Tumor Xenografts with Monoclonal Antibody 806 in Combination with a Prototypical Epidermal Growth Factor Receptor-Specific Antibody Generates Enhanced Antitumor Activity," *Clin. Cancer Res.* 11:6390-6399, American Association for Cancer Research (2005).

Poulsen, T.R., et al., "Kinetic, Affinity, and Diversity Limits of Human Polyclonal Antibody Responses against Tetanus Toxoid," *J. Immunol.* 179:3841-3850, The American Association of Immunologists (Sep. 2007).

Price, J.T., et al., "Epidermal Growth Factor (EGF) Increases the in Vitro Invasion, Motility and Adhesion Interactions of the Primary Renal Carcinoma Cell Line, A704," *Eur. J. Canc.* 32:1977-1982, Elsevier Science (1996).

Salomon, D.S., et al., "Epidermal growth factor-related peptides and their receptors in human malignancies," *Crit. Rev. Oncol. Hematol.* 19:183-232, Elsevier Science (1995).

Sharon, J., et al., "Recombinant Polyclonal Antibodies for Cancer Therapy," *J. Cell. Biochem.* 96:305-313, Wiley-Liss (2005).

Spiridon, C.I., et al., "A Comparison of the in Vitro and in Vivo Activities of IgG and F(ab')$_2$ Fragments of a Mixture of Three Monoclonal Anti-Her-2 Antibodies," *Clin. Cancer Res.* 10:3542-3551, American Association for Cancer Research (2004).

Spiridon, C.I., et al., "Targeting Multiple Her-2 Epitopes with Monoclonal Antibodies Results in Improved Antigrowth Activity of a Human Breast Cancer Cell Line in Vitro and in Vivo," *Clin. Cancer Res.* 8:1720-1730, American Association for Cancer Research (2002).

Tolstrup, A.B., et al., "Development of recombinant human polyclonal antibodies for the treatment of complex human diseases," *Expert Opin. Biol. Ther.* 6:905-912, Ashley Publications (Sep. 2006).

Ullrich, A., et al., "Human epidermal growth factor receptor cDNA sequence and aberrant expression of the amplified gene in A431 epidermoid carcinoma cells," *Nature* 309:418-425, Nature Publishing Group (1984).

NCBI Entrez, Genbank Report, Accession No. X00588 (1995).

Verheul, H.M., et al., "Sequence-dependent antitumor effects of differentiation agents in combination with cell cycle-dependent cytotoxic drugs," *Cancer Chemother. Pharmacol.* 60:329-339, Springer Verlag (Oct. 2006).

Welsh, J.B., et al., "A Negative Feedback Loop Attenuates EGF-induced Morphological Changes," *J. Cell. Biol.* 114:533-543, Rockefeller University Press (1991).

Wiberg, F.C., et al., "Production of Target-Specific Recombinant Human Polyclonal Antibodies in Mammalian Cells," *Biotechnol. Bioeng.* 94:396-405, Wiley (Jun. 2006).

Whitson, K.B., et al., "Functional Effects of Glycosylation at Asn-579 of the Epidermal Growth Factor Receptor," *Biochemistry* 44:14920-14931, American Chemical Society (2005).

Woodburn, J.R., "The Epidermal Growth Factor Receptor and Its Inhibition in Cancer Therapy," *Pharmacol. Ther.* 82:241-250, Elsevier Science (1999).

Wu, X., et al., "Apoptosis Induced by an Anti-Epidermal Growth Factor Receptor Monoclonal Antibody in a Human Colorectal Carcinoma Cell Line and Its Delay by Insulin," *J. Clin. Invest.* 95:1897-1905, American Society for Clinical Investigation (1995).

Zhen, Y., et al., "Characterization of Glycosylation Sites of the Epidermal Growth Factor Receptor," *Biochemistry* 42:5478-5492, American Chemical Association (2003).

Chao, G., et al., "Engineering anti-Epidermal Growth Factor Receptor (EGFR) Antibodies to Block Receptor Dimerization," Department of Chemical Engineering and Division of Biological Engineering, Massachusetts Institute of Technology, Cambridge, MA 02139, Poster 108 and Poster Abstract presented Feb. 18, 2005, at Keystone Symposium entitled "Antibody-Based Therapeutics for Cancer" held Feb. 17-22, 2005, in Santa Fe, New Mexico.

Chao, G., et al., "Engineering Antibodies against the Epidermal Growth Factor Receptor to Block Dimerization,"Massachusetts Institute of Technology, 77 Massachusetts Ave. 56-478, Cambridge, MA 02139, Abstract 457c presented Nov. 3, 2005, at The AICheE 2005 Annual Meeting, held Oct. 30 to Nov. 4, 2005, in Cincinnati, Ohio.

* cited by examiner

Fig. 6A

| Clone | I | | II | III | | | |
|---|---|---|---|---|---|---|---|
| | ICR10 | Ab-11 | Ab-3 | Ab-5 | Ab-10 | Ab-1 | Ab-2 |
| 992 | -20 | -2 | -21 | -3 | -14 | 78 | 77 |
| 1024 | 11 | 16 | 11 | 12 | 27 | 3 | 75 |
| 1030 | 12 | -20 | -35 | 82 | 82 | 81 | -1 |
| 1042 | 7 | 7 | -26 | -7 | 18 | 24 | 85 |
| 1208 | -21 | 3 | -10 | 84 | 86 | 82 | 20 |
| 1229 | | | | | | | |
| 1257 | 78 | 82 | 77 | 25 | 33 | 6 | 37 |
| 1260 | 86 | 82 | 12 | 17 | 24 | 12 | 6 |
| 1261 | 87 | 88 | 30 | 6 | 15 | 3 | 6 |
| 1277 | 32 | 28 | 5 | 77 | 86 | 81 | 20 |
| 1284 | 88 | 82 | 9 | 31 | 30 | 12 | 28 |
| 1308 | 71 | 81 | 16 | 6 | 12 | 4 | 11 |
| 1326 | 2 | 8 | 0 | 6 | 7 | 9 | 9 |
| 1344 | 86 | 82 | 40 | 28 | 36 | 19 | 12 |
| 1428 | 81 | 84 | 34 | 11 | 17 | 18 | 14 |
| Erbitux | -17 | 4 | -4 | 21 | -70 | 78 | 85 |
| Erbitux | -22 | 7 | -5 | 22 | -41 | 76 | 85 |
| Vectibix | -30 | -12 | -24 | 6 | 83 | 80 | 42 |
| Vectibix | -13 | -1 | -5 | 18 | 84 | 86 | 45 |

Fig. 6B

| Clone | I | | II | III | | | | Epitope specificity |
|---|---|---|---|---|---|---|---|---|
| | ICR10 | Ab-11 | Ab-3 | Ab-5 | Ab-10 | Ab-1 | Ab-2 | |
| 992 | | | | | | +++ | +++ | Domain III |
| 1024 | | | | | | | +++ | Domain III |
| 1030 | | | | +++ | +++ | +++ | | Domain III |
| 1042 | | | | | | | +++ | Domain III |
| 1208 | | | | +++ | +++ | +++ | | Domain III |
| 1229 | | | | | | | | Unknown |
| 1257 | +++ | +++ | +++ | + | + | | + | Domain I / II |
| 1260 | +++ | +++ | | | | | | Domain I |
| 1261 | ++ | +++ | + | | | | | Domain I |
| 1277 | + | + | | +++ | +++ | ++ | | Domain III |
| 1284 | +++ | ++ | | + | + | | + | Domain I |
| 1308 | ++ | +++ | | | | | | Domain I |
| 1326 | | | | | | | | Unknown |
| 1344 | ++ | ++ | + | + | + | | | Domain I |
| 1428 | +++ | +++ | + | | | | | Domain I |
| Erbitux | | | | | | +++ | ++ | Domain III |
| Erbitux | | | | | | +++ | ++ | Domain III |
| Vectibix | | | | | ++ | ++ | + | Domain III |
| Vectibix | | | | | ++ | ++ | + | Domain III |

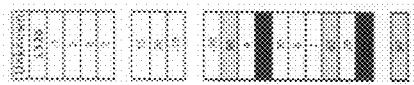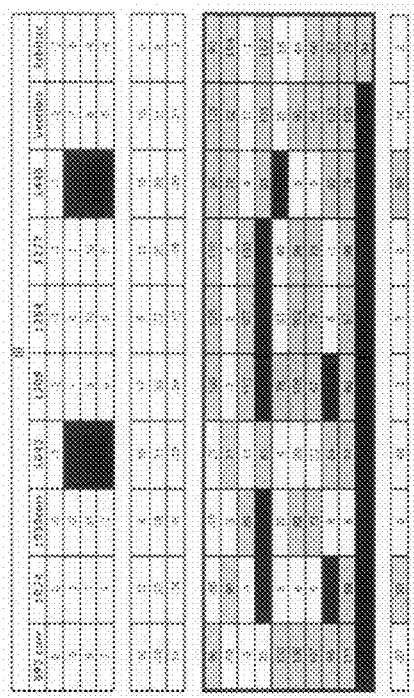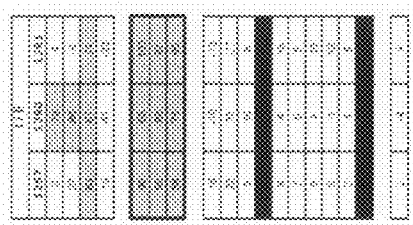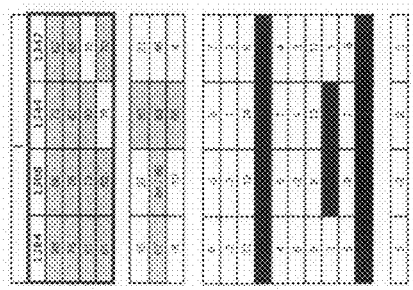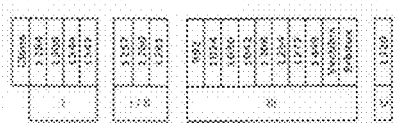
Fig. 9A
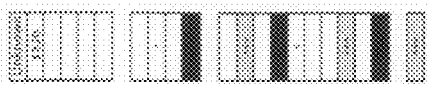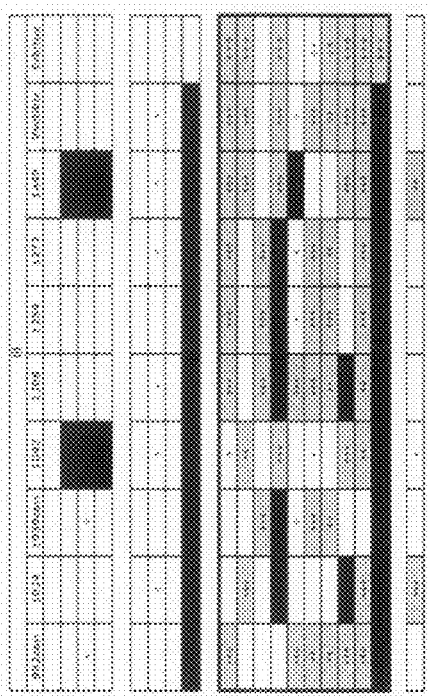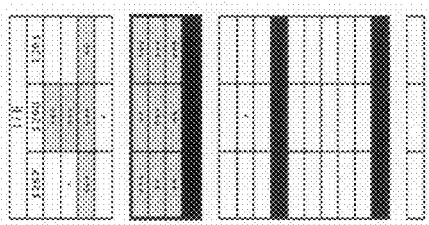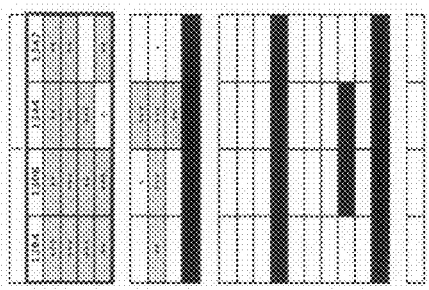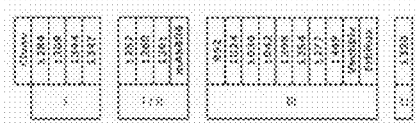
Fig. 9B

Fig. 11A

| Sample mAb | Inhibition Sample mAb | Rumax Reference cycle | Rumax Competition cycle |
|---|---|---|---|
| Domain III 992 | 1030 Vs. 992 | 81 | 85^^ |
| Domain III 1024 | 992 + 1030 Vs. 1024 | 100 | 128^^ |
| Domain I/II 1261 | 992 + 1030 + 1024 Vs. 1261 | 157 | 177^^ |
| Domain I 1347 | 992 + 1030 + 1024 Vs. 1347 | 75 | 79^^ |
| Unknown Domain 1361 | 992+1030+1024 Vs. 1361 | 162 | 181^^ |

Fig. 11B

| Sample mAb | Antibody mix (N=6) 1261+1347+992+1024+1030+1361 Inhibition Sample mAb | Rumax Reference Cycle | Rumax Competition Cycle | Antibody mix (N=6-1) Without tested sample mAb Inhibition Sample mAb | Rumax Reference Cycle | Rumax Competition Cycle |
|---|---|---|---|---|---|---|
| Domain I/II 1261 | 1261+1347+992+1024+1030+1361 Vs. 1261 | 135 | 7 | 1347+992+1024+1030+1361 Vs. 1261 | 139 | 199^^ |
| Domain I 1347 | 1261+1347+992+1024+1030+1361 Vs. 1347 | 91 | 19 | 1261+992+1024+1030+1361 Vs. 1347 | 107 | 92 |
| Domain III 992 | 1261+1347+992+1024+1030+1361 Vs. 992 | 85 | -14* | 1261+1347+1024+1030+1361 Vs. 992 | 71 | 111^^ |
| Domain III 1024 | 1261+1347+992+1024+1030+1361 Vs. 1024 | 110 | -14* | 1261+1347+992+1030+1361 Vs. 1024 | 122 | 152^^ |
| Domain III 1030 | 1261+1347+992+1024+1030+1361 Vs. 1030 | 87 | 12 | 1261+1347+992+1024+1361 Vs. 1030 | 74 | 82^^ |
| Unknown Domain 1361 | 1261+1347+992+1024+1030+1361 Vs. 1361 | 178 | -3* | 1261+1347+992+1024+1030 Vs. 1361 | 139 | 152 |

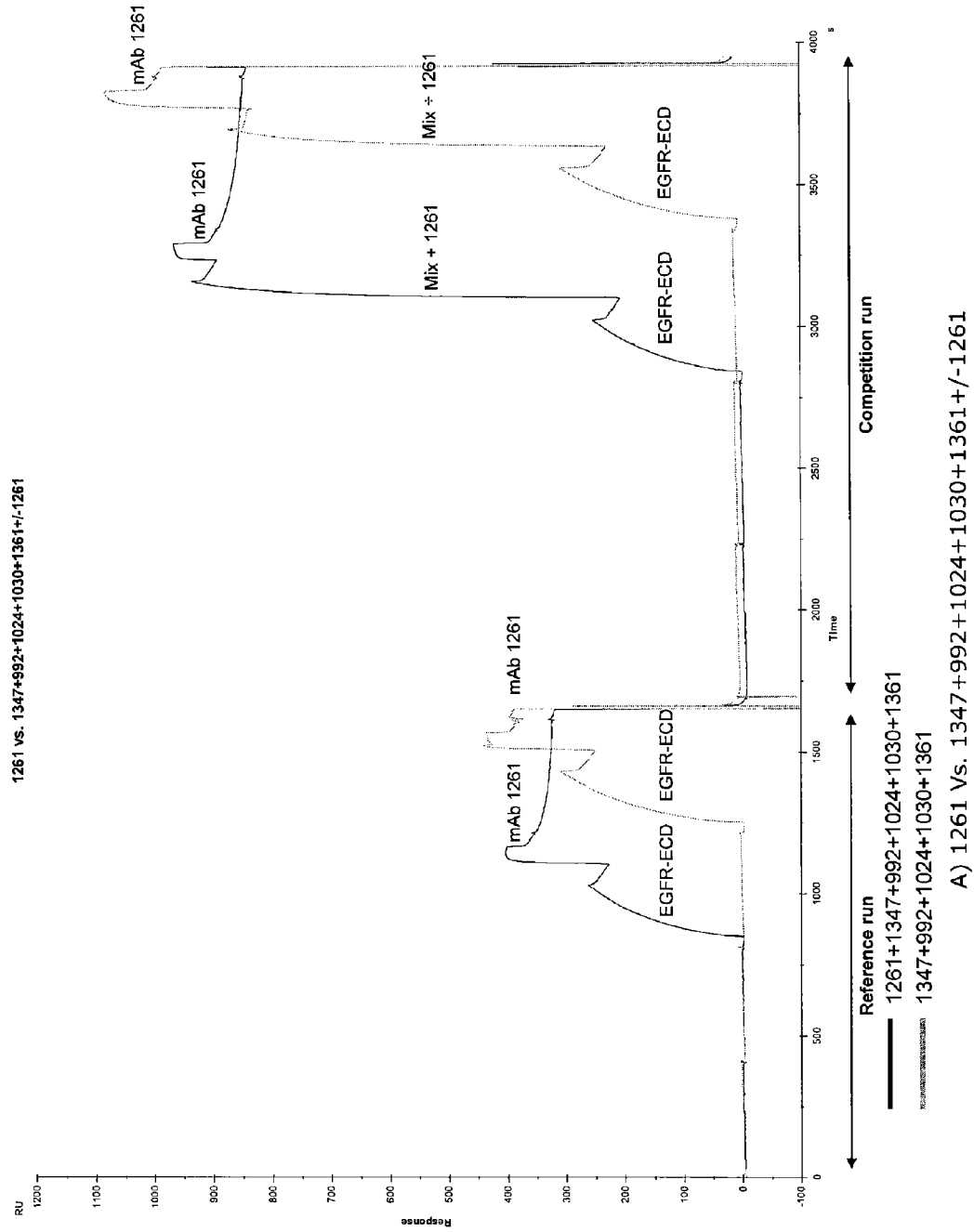

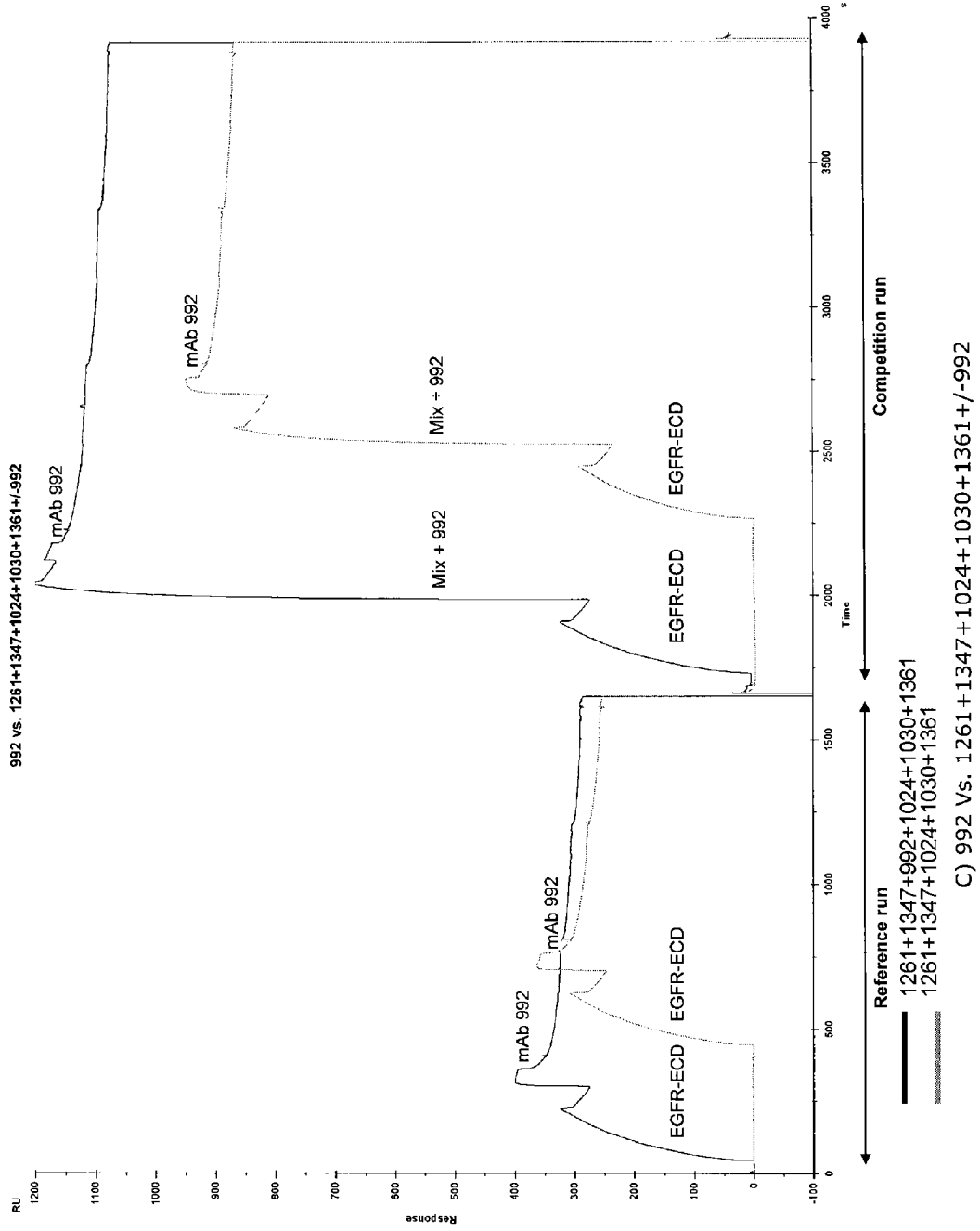

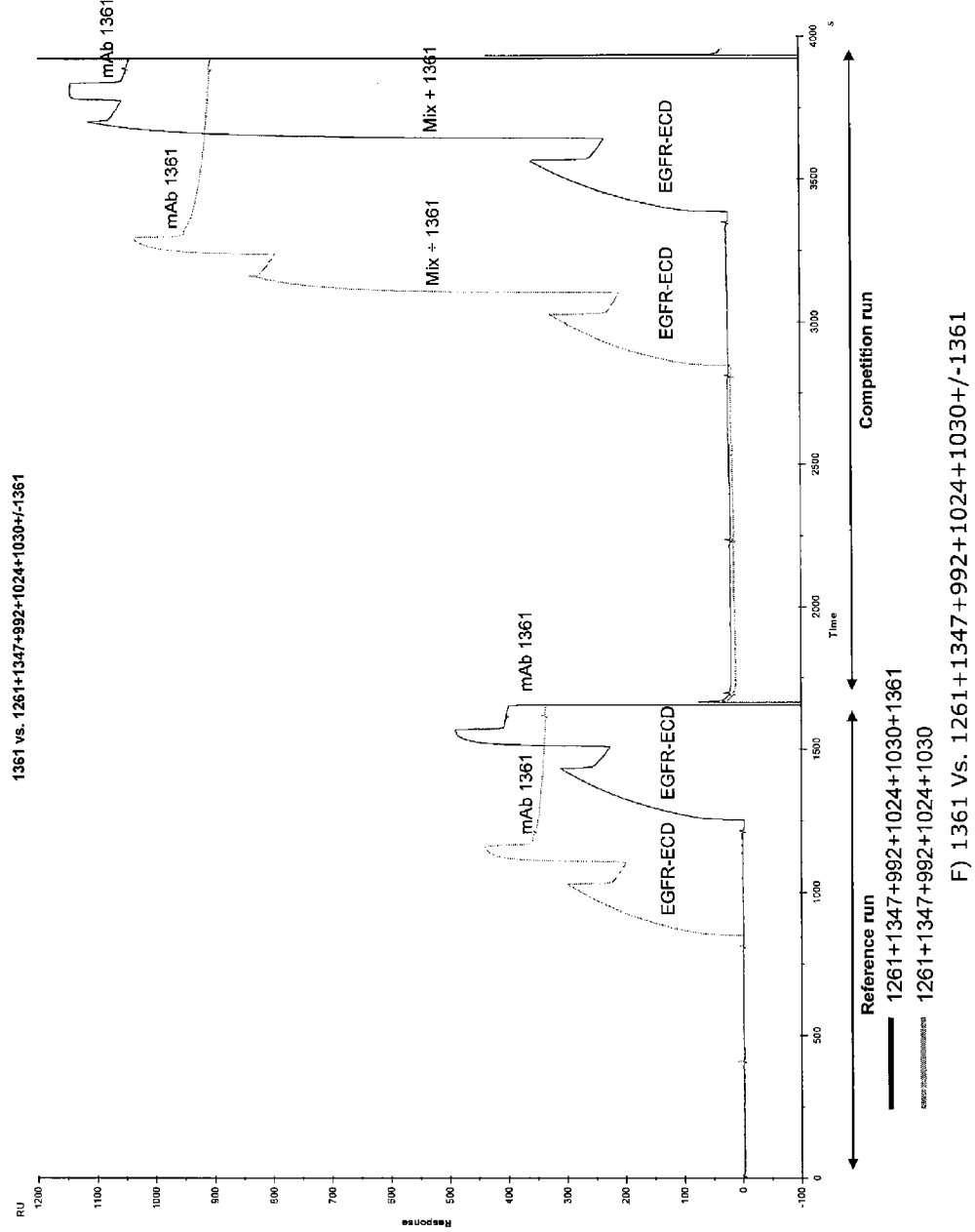

Fig. 11D
| Domain I | 1261+1347+992+1024+1030+1361 Vs. 1284 | | |
|---|---|---|---|
| 1284 | 78 | 68 | 17 |
| Domain I/II | 1261+1347+992+1024+1030+1361 Vs. 1257 | | |
| 1257 | 106 | 107 | -7* |
| Unknown Domain | 1261+1347+992+1024+1030+1361 Vs. 1183 | | |
| 1183 | 112 | 58 | -7* |
| Unknown Domain | 1261+1347+992+1024+1030+1361 Vs. 1255 | | |
| 1255 | 107 | 79 | -5* |
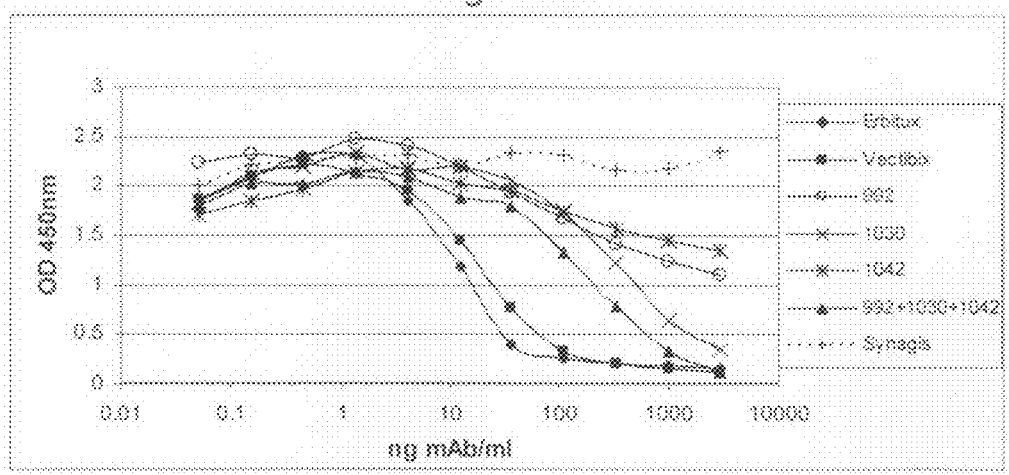
Fig. 12A
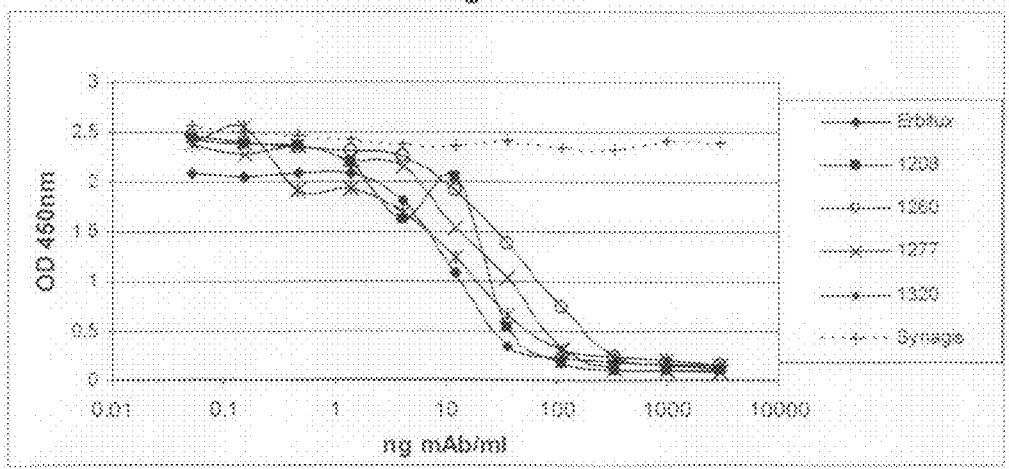
Fig. 12B

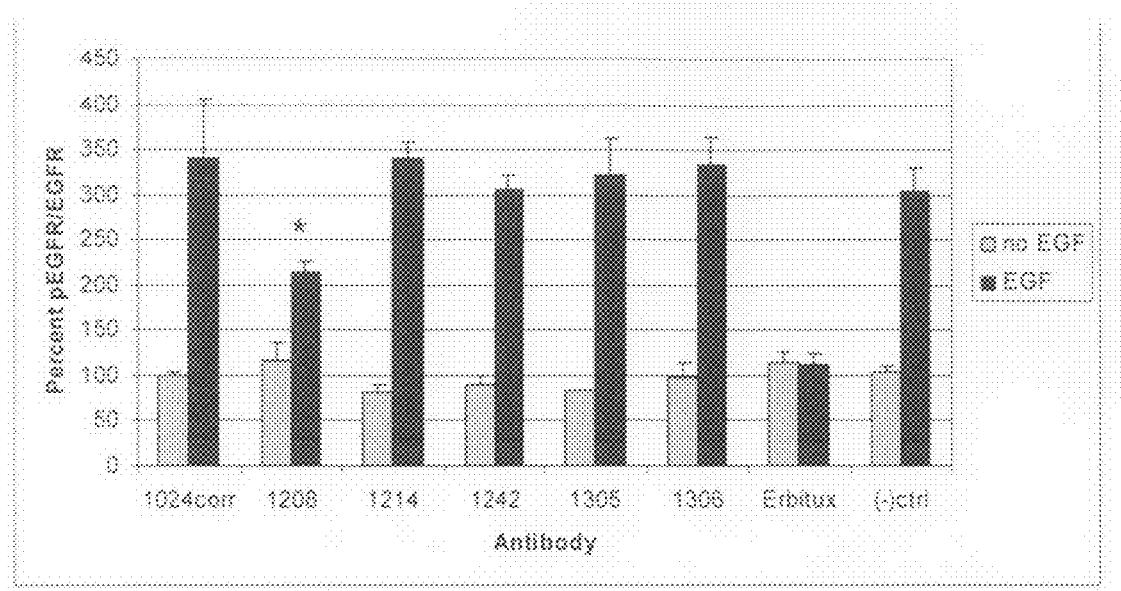
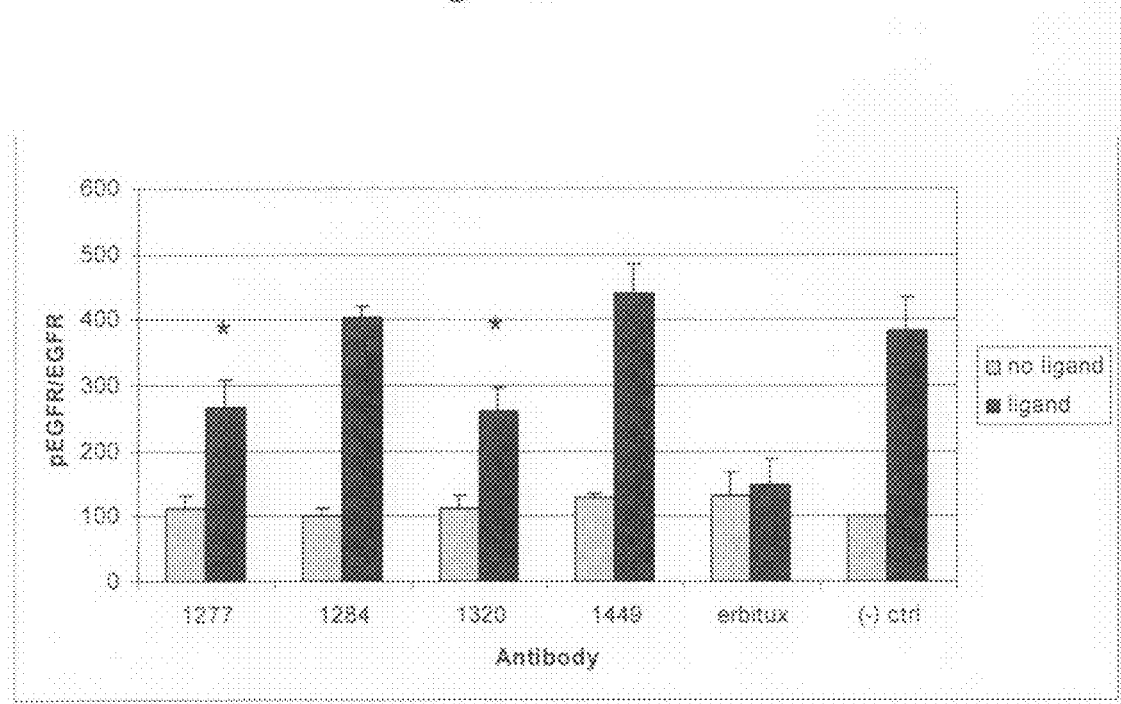

Fig. 23A

```
ctggaggaaaagaaagtttgccaaggcacgagtaacaaactcacgcagttgggcacttttgaagatcatt
ttctcagcctccagaggatgttcaataactgtgaggtggtccttgggaatttggaaattacctacgtgca
gaggaattatgatctttccttcttaaagaccatccaggaggtggctggttatgtcctcatcgccctcaac
acagtggagcggattcctttggaaaacctgcagatcatcagaggaaacatgtactatgaaaattcctatg
ccttagcagtcttatctaactatgatgcaaataaaaccggactgaaggagctgcccatgagaaacttaca
ggaaatcctgcatggcgccgtgcggttcagcaacaaccctgccctgtgcaacgtggagagcatccagtgg
cgggacatagtcagcagcgagtttctcagcaacatgtcgatggacttccagaaccacctgggcagctgcc
aaaagtgtgatccaagctgtcccaatggagctgctggggtgcaggagaggagaactgccagaaactgac
caaaatcatctgtgcccagcagtgctccgggcgctgccgcggcaagtccccagtgactgctgccacaac
cagtgtgccgcgggctgcacgggcccccggagagcgactgcctggtctgccgcaaattccgagacgaag
ccacgtgcaaggacacctgccccccactcatgctctacaaccccaccacataccagatggatgtgaaccc
cgagggcaaatacagctttggtgccacctgcgtgaagaagtgtccccgtaattatgtggtgacagatcac
ggctcgtgcgtccgagcctgcggggccgacagctatgagatggaggaagacggcgtccgcaagtgtaaga
agtgcgaagggccttgccgcaaagtgtgtaatggaataggtattggtgaatttaaagacacactctccat
aaatgctacaaatattaaacacttcaaaaactgcacctccatcagtggcgatctccacatcctgccggtg
gcatttaggggtgactccttcacacacactccgcctctggatccacaggaactggatattctgaaaaccg
taaaggaaatcacagggttttttgctgattcaggcttggcctgaaaacaggacggacctccatgcttttga
gaacctagaaatcatacgtggcaggaccaagcaacacggtcagttttctcttgcggtcgtcagcctgaac
ataacatccttgggattacgctccctcaaggagataagcgatggagatgtgataatttcaggaaacaaaa
atttgtgctatgcaaatacaataaactggaaaaaactgtttgggacctccagtcagaaaaccaaaattat
aagcaacagaggtgaaaacagctgcaaggccacgggccaggtctgccatgccttgtgctccccgagggc
tgctggggcccggagcccagggactgcgtctcctgccagaatgtcagccgaggcagagaatgcgtggaca
agtgcaacatcctggagggcgagccaagggagtttgtggagaactctgagtgcatacagtgccacccaga
atgcctgccccaggtcatgaacatcacctgcacaggacggggaccagacaactgtatccagtgtgcccac
tacattgacggccccactgcgtcaagacctgcccagcaggagtcatgggagaaaacaacaccctggtct
ggaagtacgcagacgccggccacgtgtgccacctgtgccatccaaactgcacctacggatgcactgggcc
aggtcttgaaggctgtgcaaggaacgggcctaagatcccatcc
```

Fig. 23B

```
LEEKKVCQGTSNKLTQLGTFEDHFLSLQRMFNNCEVVLGNLEITYVQRNYDLSFLKTIQEVAGYVLIALN
TVERIPLENLQIIRGNMYYENSYALAVLSNYDANKTGLKELPMRNLQEILHGAVRFSNNPALCNVESIQW
RDIVSSEFLSNMSMDFQNHLGSCQKCDPSCPNGSCWGAGEENCQKLTKIICAQQCSGRCRGKSPSDCCHN
QCAAGCTGPRESDCLVCRKFRDEATCKDTCPPLMLYNPTTYQMDVNPEGKYSFGATCVKKCPRNYVVTDH
GSCVRACGADSYEMEEDGVRKCKKCEGPCRKVCNGIGIGEFKDTLSINATNIKHFKNCTSISGDLHILPV
AFRGDSFTHTPPLDPQELDILKTVKEITGFLLIQAWPENRTDLHAFENLEIIRGRTKQHGQFSLAVVSLN
ITSLGLRSLKEISDGDVIISGNKNLCYANTINWKKLFGTSSQKTKIISNRGENSCKATGQVCHALCSPEG
CWGPEPRDCVSCQNVSRGRECVDKCNILEGEPREFVENSECIQCHPECLPQVMNITCTGRGPDNCIQCAH
YIDGPHCVKTCPAGVMGENNTLVWKYADAGHVCHLCHPNCTYGCTGPGLEGCARNGPKIPS
```

Fig.24

```
                           (1) 1         10        20         30            47
Cynomolgus EGFR ECD        (1) LEEKKVCQGTSNKLTQLGTFEDHFLSLQRMFNNCEVVLGNLEITYVQ
     Human EGFR ECD        (1) LEEKKVCQGTSNKLTQLGTFEDHFLSLQRMFNNCEVVLGNLEITYVQ
           Consensus       (1) LEEKKVCQGTSNKLTQLGTFEDHFLSLQRMFNNCEVVLGNLEITYVQ
                                                                            Section 2
                          (48) 48         60        70         80           94
Cynomolgus EGFR ECD       (48) RNYDLSFLKTIQEVAGYVLIALNTVERIPLENLQIIRGNMYYENSYA
     Human EGFR ECD       (48) RNYDLSFLKTIQEVAGYVLIALNTVERIPLENLQIIRGNMYYENSYA
           Consensus      (48) RNYDLSFLKTIQEVAGYVLIALNTVERIPLENLQIIRGNMYYENSYA
                                                                            Section 3
                          (95) 95       100        110        120       130     141
Cynomolgus EGFR ECD       (95) LAVLSNYDANKTGLKELPMRNLQEILHGAVRFSNNPALCNVESIQWR
     Human EGFR ECD       (95) LAVLSNYDANKTGLKELPMRNLQEILHGAVRFSNNPALCNVESIQWR
           Consensus      (95) LAVLSNYDANKTGLKELPMRNLQEILHGAVRFSNNPALCNVESIQWR
                                                                            Section 4
                         (142) 142       150        160        170          188
Cynomolgus EGFR ECD      (142) DIVSSEFLSNMSMDFQNHLGSCQKCDPSCPNGSCWGAGEENCQKLTK
     Human EGFR ECD      (142) DIVSSDFLSNMSMDFQNHLGSCQKCDPSCPNGSCWGAGEENCQKLTK
           Consensus     (142) DIVSSDFLSNMSMDFQNHLGSCQKCDPSCPNGSCWGAGEENCQKLTK
                                                                            Section 5
                         (189) 189        200        210        220          235
Cynomolgus EGFR ECD      (189) IICAQQCSGRCRGKSPSDCCHNQCAAGCTGPRESDCLVCRKFRDEAT
     Human EGFR ECD      (189) IICAQQCSGRCRGKSPSDCCHNQCAAGCTGPRESDCLVCRKFRDEAT
           Consensus     (189) IICAQQCSGRCRGKSPSDCCHNQCAAGCTGPRESDCLVCRKFRDEAT
                                                                            Section 6
                         (236) 236        250        260        270         282
Cynomolgus EGFR ECD      (236) CKDTCPPLMLYNPTTYQMDVNPEGKYSFGATCVKKCPRNYVVTDHGS
     Human EGFR ECD      (236) CKDTCPPLMLYNPTTYQMDVNPEGKYSFGATCVKKCPRNYVVTDHGS
           Consensus     (236) CKDTCPPLMLYNPTTYQMDVNPEGKYSFGATCVKKCPRNYVVTDHGS
                                                                            Section 7
                         (283) 283        290        300        310         329
Cynomolgus EGFR ECD      (283) CVRACGADSYEMEEDGVRKCKKCEGPCRKVCNGIGIGEFKDTLSINA
     Human EGFR ECD      (283) CVRACGADSYEMEEDGVRKCKKCEGPCRKVCNGIGIGEFKDSLSINA
           Consensus     (283) CVRACGADSYEMEEDGVRKCKKCEGPCRKVCNGIGIGEFKDSLSINA
                                                                            Section 8
                         (330) 330        340        350        360         376
Cynomolgus EGFR ECD      (330) TNIKHFKNCTSISGDLHILPVAFRGDSFTHTPPLDPQELDILKTVKE
     Human EGFR ECD      (330) TNIKHFKNCTSISGDLHILPVAFRGDSFTHTPPLDPQELDILKTVKE
           Consensus     (330) TNIKHFKNCTSISGDLHILPVAFRGDSFTHTPPLDPQELDILKTVKE
                                                                            Section 9
                         (377) 377        390        400        410         423
Cynomolgus EGFR ECD      (377) ITGFLLIQAWPENRTDLHAFENLEIIRGRTKQHGQFSLAVVSLNITS
     Human EGFR ECD      (377) ITGFLLIQAWPENRTDLHAFENLEIIRGRTKQHGQFSLAVVSLNITS
           Consensus     (377) ITGFLLIQAWPENRTDLHAFENLEIIRGRTKQHGQFSLAVVSLNITS
```

Fig.24 (cont.)

```
                         (424) 424      430         440        450         460       470
Cynomolgus EGFR ECD (424) LGLRSLKEISDGDVIISGNKNLCYANTINWKKLFGTSSQKTKIISNR
     Human EGFR ECD (424) LGLRSLKEISDGDVIISGNKNLCYANTINWKKLFGTSGQKTKIISNR
           Consensus (424) LGLRSLKEISDGDVIISGNKNLCYANTINWKKLFGTS QKTKIISNR
                                                                              Section 11
                         (471) 471      480         490        500                   517
Cynomolgus EGFR ECD (471) GENSCKATGQVCHALCSPEGCWGPEPRDCVSCQNVSRGRECVDKCNI
     Human EGFR ECD (471) GENSCKATGQVCHALCSPEGCWGPEPKDCVSCRNVSRGRECVDKCNL
           Consensus (471) GENSCKATGQVCHALCSPEGCWGPEPKDCVSC NVSRGRECVDKCNI
                                                                              Section 12
                         (518) 518          530        540        550                564
Cynomolgus EGFR ECD (518) LEGEPREFVENSECIQCHPECLPQVMNITCTGRGPDNCIQCAHYIDG
     Human EGFR ECD (518) LEGEPREFVENSECIQCHPECLPQAMNITCTGRGPDNCIQCAHYIDG
           Consensus (518) LEGEPREFVENSECIQCHPECLPQ MNITCTGRGPDNCIQCAHYIDG
                                                                              Section 13
                         (565) 565   570       580        590         600            611
Cynomolgus EGFR ECD (565) PHCVKTCPAGVMGENNTLVWKYADAGHVCHLCHPNCTYGCTGPGLEG
     Human EGFR ECD (565) PHCVKTCPAGVMGENNTLVWKYADAGHVCHLCHPNCTYGCTGPGLEG
           Consensus (565) PHCVKTCPAGVMGENNTLVWKYADAGHVCHLCHPNCTYGCTGPGLEG
                                                                              Section 14
                         (612) 612        622
Cynomolgus EGFR ECD (612) CARNGPKIPS-
     Human EGFR ECD (612) CPTNGPKIPS-
           Consensus (612) C  NGPKIPS
```

Fig. 27
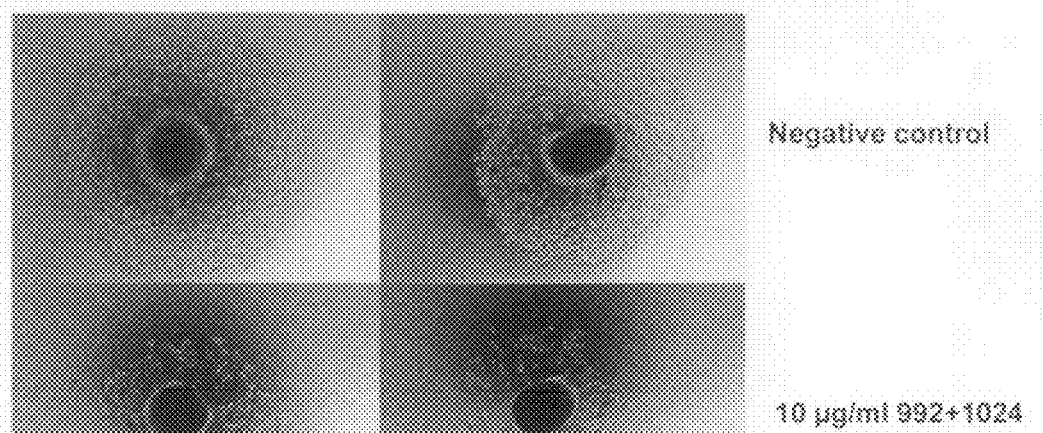
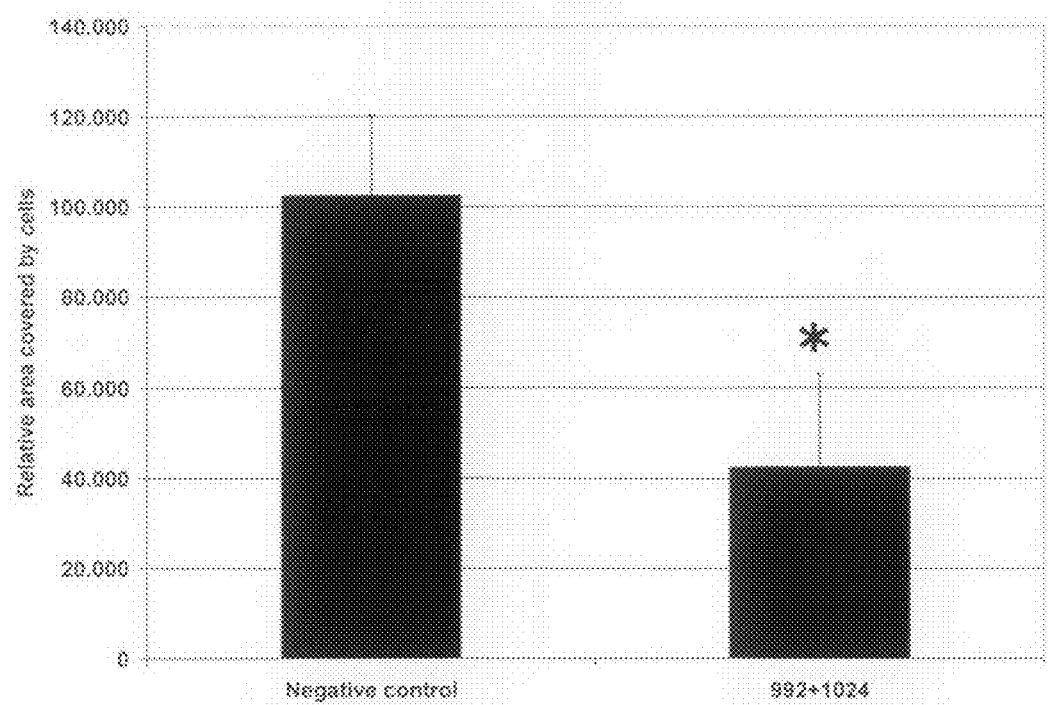

Fig. 29
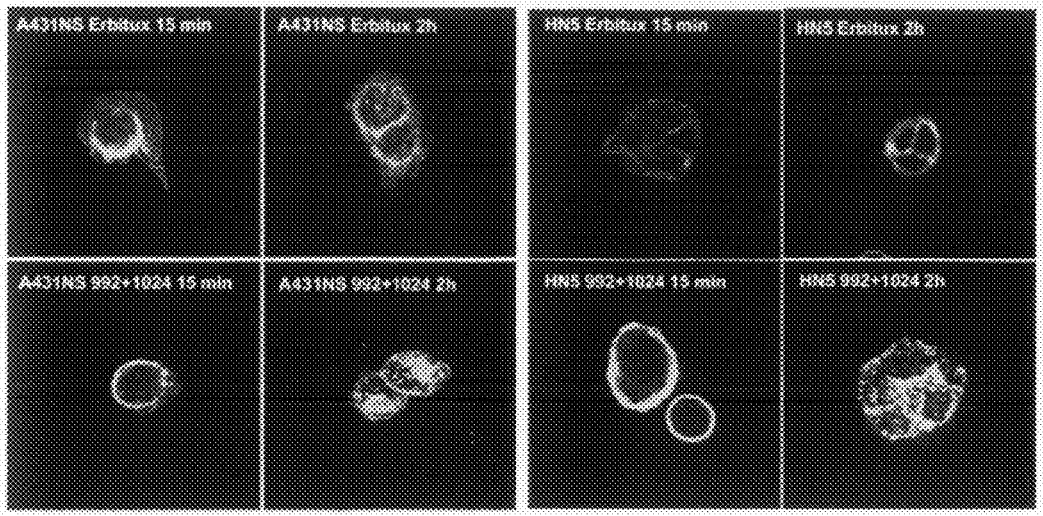
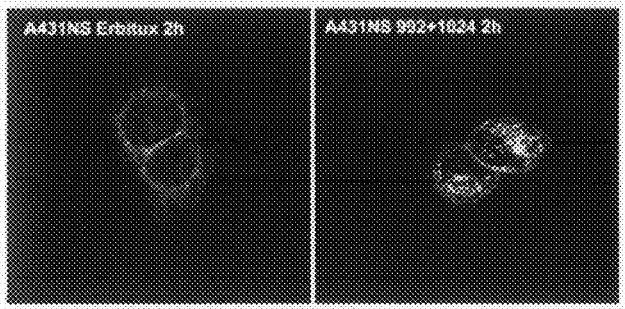
Fig. 30
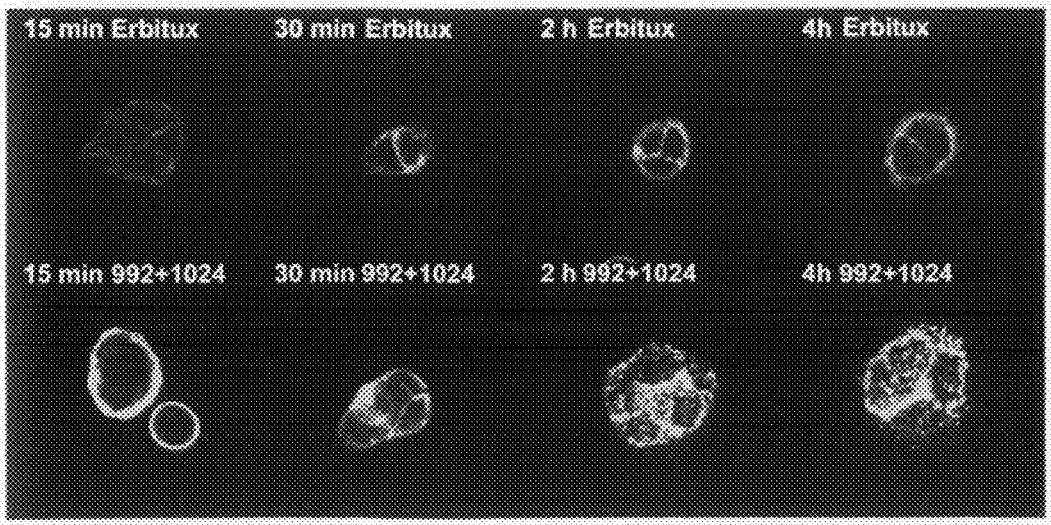

Fig. 34A

```
atgcgaccctccgggacggccggggccgcgctcctggcgctgctggctgcgctttgcccgcgagtcgggctctggagga
aaagaaagtttgccaaggcacgagtaacaaactcacgcagttgggcacttttgaagatcatttctcagcctccagagga
tgttcaataactgtgaggtggtccttgggaatttggaaattacctacgtgcagaggaattatgatctttccttcttaaag
accatccaggaggtggctggttatgtcctcatcgccctcaacacagtggagcggattcctttggaaaacctgcagatcat
cagaggaaacatgtactatgaaaattcctatgccttagcagtcttatctaactatgatgcaaataaaaccggactgaagg
agctgcccatgagaaacttacaggaaatcctgcatggcgccgtgcggttcagcaacaaccctgccctgtgcaacgtggag
agcatccagtggcgggacatagtcagcagcgagtttctcagcaacatgtcgatggacttccagaaccacctgggcagctg
ccaaaagtgtgatccaagctgtcccaatgggagctgctggggtgcaggagaggagaactgccagaaactgaccaaaatca
tctgtgcccagcagtgctccgggcgctgccgcggcaagtccccagtgactgctgccacaaccagtgtgccgcgggctgc
acgggcccccgggagagcgactgcctggtctgccgcaaattccgagacgaagccacgtgcaaggacacctgcccccccact
catgctctacaaccccaccacataccagatggatgtgaaccccgagggcaaatacagctttggtgccacctgcgtgaaga
agtgtccccgtaattatgtggtgacagatcacggctcgtgcgtccgagcctgcggggccgacagctatgagatggaggaa
gacggcgtccgcaagtgtaagaagtgcgaagggccttgccgcaaagtgtgtaatggaataggtattggtgaatttaaaga
cacactctccataaatgctacaaatattaaacacttcaaaaactgcacctccatcagtggcgatctccacatcctgccgg
tggcatttagggtgactccttcacacacactccgcctctggatccacaggaactggatattctgaaaaccgtaaggaa
atcacagggttttgctgattcaggcttggcctgaaaacaggacggacctccatgcttttgagaacctagaaatcatacg
tggcaggaccaagcaacacggtcagttttctcttgcggtcgtcagcctgaacataacatccttgggattacgctccctca
aggagataagcgatggagatgtgataatttcaggaaacaaaaatttgtgctatgcaaatacaataaactggaaaaaactg
tttgggacctccagtcagaaaaccaaaattataagcaacagaggtgaaaacagctgcaaggccacgggccaggtctgcca
tgccttgtgctccccgagggctgctggggcccggagcccagggactgcgtctcctgtcagaatgtcagccgaggcagag
aatgcgtggacaagtgcaacatcctggagggcgagccaagggagtttgtggagaactctgagtgcatacagtgtcaccca
gaatgcctgccccaggtcatgaacatcacctgcacaggacggggaccagacaactgtatccagtgtgcccactacattga
cggcccccactgcgtcaagacctgcccagcaggagtcatgggagaaaacaacaccctggtctggaagtacgcagacgccg
gccacgtgtgccacctgtgccatccaaactgcacctacggatgcactgggccaggtcttgaaggctgtgcaaggaacggg
cctaagatcccatccatcgccactgggatggtgggggccctcctcttgctgctggtggtggccctggggatcggcctctt
catgcgaaggcgccacatcgttcggaagcgcacactgcggaggctgctgcaggagagggagcttgtggagcctcttacgc
ccagtggagaagctcccaaccaagctctcttgaggatcttgaaggaaactgaattcaagaagatcaaagtgctgggctcc
ggtgcgttcggaactgtgtataagggactctggatcccagaaggtgagaaagttaaaattcccgtcgctatcaaggaatt
aagagaagcaacatctccgaaagccaacaaggaaatcctcgatgaagcctacgtgatggccagcgtggacaaccccccatg
tgtgccgcctgctgggcatctgcctcacctccaccgtgcagctcattacgcagctcatgcccttcggctgcctcctggac
tacgtccgggaacacaaggacaatatcggctcccagtacctgctcaactggtgtgtgcagattgcaaagggcatgaacta
cttggaggaccggcgcttggtgcaccgcgacctggcagccaggaacgtactggtgaaaacgccacagcatgtcaagatca
cagattttgggctggccaaactgctgggtgcagaagagaaagaataccatgcagaaggaggcaaagtgcctatcaagtgg
atggcgttggaatcaatttacaccgaatttatacccaccagagtgatgtctggagctacggggtgaccgtttgggagtt
gatgacctttggatccaagccatatgacggaatccctgccagcgagatctcctccatcctggagaaaggagaacgcctcc
cccagccacccatatgtaccatcgatgtctacatgatcatggtcaagtgctggatgatagacgcagatagtcgcccaaag
ttccgtgagttgatcattgaattctccaaaatggcccgagaccccagcgctaccttgttattcaggggatgaaagaat
gcatttgccaagccctacagactccaacttctaccgtgccctgatggatgaagaagacatggacgacgtggtggatgccg
acgagtacctcatcccacagcaaggcttcttcagcagcccctccacgtcacggactcccctcctgagctctctgagtgca
actagcaacaattccactgtggcttgcattgata
```

Fig. 34A (cont.)

```
gaaatgggctgcaaagctgttccatcaaggaagacagcttcttacagcgatacagctcagaccccacaggcgccttgact
gaggacagcatagacgacaccttcctcccagtgcctgaatacataaaccagtctgttcccaaaaggcccgctggctctgt
gcagaatcctgtctatcacaatcagcctctgaaccctgcgcccagcagagacccacactaccaggaccccacagcaccg
cagtgggcaaccccgagtatctcaacactgtccagcccacctgtgtcaacagcacattcgacagccctgctcattgggcc
cagaaaggcagccaccaaattagcctggacaaccctgactaccagcaggacttctttcccaaggaagccaagccaaatgg
catctttaagggctccacagctgaaaatgcagaatacctaagggtcgcaccacaaagcagtgaatttattggagcatga
```

Fig. 34B

```
MRPSGTAGAALLALLAALCPASRALEEKKVCQGTSNKLTQLGTFEDHFLSLQRMFNNCEV
VLGNLEITYVQRNYDLSFLKTIQEVAGYVLIALNTVERIPLENLQIIRGNMYYENSYALA
VLSNYDANKTGLKELPMRNLQEILHGAVRFSNNPALCNVESIQWRDIVSSEFLSNMSMDF
QNHLGSCQKCDPSCPNGSCWGAGEENCQKLTKIICAQQCSGRCRGKSPSDCCHNQCAAGC
TGPRESDCLVCRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDTLSINATNIKHFK
NCTSISGDLHILPVAFRGDSFTHTPPLDPQELDILKTVKEITGFLLIQAWPENRTDLHAF
ENLEIIRGRTKQHGQFSLAVVSLNITSLGLRSLKEISDGDVIISGNKNLCYANTINWKKL
FGTSSQKTKIISNRGENSCKATGQVCHALCSPEGCWGPEPRDCVSCQNVSRGRECVDKCN
ILEGEPREFVENSECIQCHPECLPQVMNITCTGRGPDNCIQCAHYIDGPHCVKTCPAGVM
GENNTLVWKYADAGHVCHLCHPNCTYGCTGPGLEGCARNGPKIPSIATGMVGALLLLLVV
ALGIGLFMRRRHIVRKRTLRRLLQERELVEPLTPSGEAPNQALLRILKETEFKKIKVLGS
GAFGTVYKGLWIPEGEKVKIPVAIKELREATSPKANKEILDEAYVMASVDNPHVCRLLGI
CLTSTVQLITQLMPFGCLLDYVREHKDNIGSQYLLNWCVQIAKGMNYLEDRRLVHRDLAA
RNVLVKTPQHVKITDFGLAKLLGAEEKEYHAEGGKVPIKWMALESILHRIYTHQSDVWSY
GVTVWELMTFGSKPYDGIPASEISSILEKGERLPQPPICTIDVYMIMVKCWMIDADSRPK
FRELIIEFSKMARDPQRYLVIQGDERMHLPSPTDSNFYRALMDEEDMDDVVDADEYLIPQ
QGFFSSPSTSRTPLLSSLSATSNNSTVACIDRNGLQSCSIKEDSFLQRYSSDPTGALTED
SIDDTFLPVPEYINQSVPKRPAGSVQNPVYHNQPLNPAPSRDPHYQDPHSTAVGNPEYLN
TVQPTCVNSTFDSPAHWAQKGSHQISLDNPDYQQDFFPKEAKPNGIFKGSTAENAEYLRV
APQSSEFIGA
```

Fig. 41A

```
hu992VH    QVQLVQSGA-EVKKPGASVKVSCKASGYTFTSYW----MHWVRQAPGQGLEWMGIIYPGS  60
chi992VH   EVQLQQPGS-ELVRPGASVKLSCKASGYTFTSYW----MHWVKQRPGQGLEWIGNIYPGS  60
            :*** *.*; *; :****:********      **:* *******:* ***** hu992VH    RST--SYAQKFQ-GRVTMTRDTSTSTVYMELSSLRSEDTAVYYCTRNGDYYVSSGDAMDY  117
chi992VH   RST--NYDEKFK-SKATLTVDTSSSTAYMQLSSLTSEDSAVYYCTRNGDYYVSSGDAMDY  117
            ***  .* :**: . ;.*:* *:.:  *:****************** hu992VH    WGQGTLVTVS  127
chi992VH   WGQGTSVTVS  127
            *** ** hu992VL    DIQMTQSPSSLSASVGDRVTITCRASQDIGNY------LAWYQQKPGKVPKLLIYYTS--  60
chi992VL   DIQMTQTTSSLSASLGDRVTISCRTSQDIGNY------LNWYQQKPDGTVKLLIYYTS--  60
            ** ***:.****** ******:**:*******        * ******.  . *******

Hu992VL    -----TLQSGVP-SRFSGSG—SGTDFTLTISSLQPEDVATYYCQHYNT----VPPTFGGGTKV  124
chi992VL   -----RLHSGVP-SRFSGSG—SGTDFSLTINNVEQEDVATYFCQHYNT----VPPTFGGGTKL  124
                *:**** *******  *****:***..::  ******:*****       ******:

hu992VL    EIK  127
chi992VL   EIK  127
           ***
```

Fig. 41B

```
hu1024VH   QVQLVQSGA-EVKKPGASVKVSCKASGYTFTSHW----MHWVRQAPGQGLEWMGWINPSS  60
chi1024VH  QVQLQQPGA-ELVEPGGSVKLSCKASGYTFTSHW----MHWVKQRPGQGLEWIGEINPSS  60
            **** *.*;  :. *;********     **:* *******;* ***** hu1024VH   GRN--NYAQKFQ-GRVTMTRDTSISTAYMELSRLTSDDTAVYYCARYYGYDE-AMDYWGQG  121
chi1024VH  GRN--NYNEKFK-SKATLTVDKSSSTAYMQFSSLTSEDSAVYYCVRYYGYDE-AMDYWGQG  121
            *    :**: . ;.*:* *.* ******:*:****:*.***  ***** hu1024VH   TSVTVS  127
chi1024VH  TLVTVS  127
           * **** chi1024VL  DIVMTQAAFSNPVTLGTSASISCRSSKSLLHSNGITY-LYWYLQKPGQSPQLLIYQMS--  65
hu1024VL   DIVMTQSPLSLPVTPGEPASISCRSSKSLLHSNGITY-LDWYLQKPGQSPQLLIYQMS--  65
            ******:..:* *** *  .******************  * ******************** chi1024VL  -----NLASGVP-DRFSSSG--SGTDFTLRISRVEAEDVGVYYCAQNLE----LPYTFGGGTKL  124
hu1024VL   -----NRASGVP-DRFSGSG--SGTDFTLKISRVEAEDVGVYYCAQNLE----LPYTFGGGTKV  124
                * ***** **.** ********:***************         **********:

chi1024VL  EIK  127
hu1024VL   EIK  127
           ***
```

RECOMBINANT ANTI-EPIDERMAL GROWTH FACTOR RECEPTOR ANTIBODY COMPOSITIONS

This applications claims the benefit of the filing date of U.S. Provisional Appl. No. 60/904,773, filed Mar. 5, 2007, U.S. Provisional Appl. No. 60/929,727, filed Jul. 11, 2007, Danish Appl. No. PA 2007 00317, filed Mar. 1, 2007, and Danish Appl. No. PA 2007 01016, filed Jul. 10, 2007, all of which are incorporated by reference in their entirety.

SEQUENCE LISTING INFORMATION

The Sequence Listing written in the file named "Sequence_listing.ascii.txt", 149,504 bytes, created on Feb. 28, 2008, on two (2) duplicate copies (Copy 1 and Copy 2) of U.S. application Ser. No. 12/074,056, Pedersen, M., et al., Recombinant Anti-Epidermal Growth Factor Receptor Antibody Compositions, is herein incorporated by reference.

FIELD OF THE INVENTION

The invention relates to the field of recombinant antibodies for use in human cancer therapy.

BACKGROUND OF THE INVENTION

Epidermal Growth Factor Receptor (EGFR) plays an important role in cellular proliferation as well as apoptosis, angiogenesis and metastatic spread, processes that are crucial to tumour progression (Salomon et al, Crit. Rev. Oncology/Haematology, 19:183-232 (1995); Wu et al, J. Clin. Invest., 95:1897-1905 (1995); Karnes et al, Gastroenterology, 114: 930-939 (1998); Woodburn et al, Pharmacol. Therap. 82: 241-250 (1999); Price et al, Eur. J. Cancer, 32A:1977-1982 (1996)). Indeed, studies have shown that EGFR-mediated cell growth is increased in a variety of solid tumours including non-small cell lung cancer, prostate cancer, breast cancer, gastric cancer, and tumours of the head and neck (Salomon D S et al, Critical Reviews in Oncology/Haematology, 19:183-232 (1995)). Furthermore, excessive activation of EGFR on the cancer cell surface is now known to be associated with advanced disease, the development of a metastatic phenotype and a poor prognosis in cancer patients (Salomon D S et al., Critical Reviews in Oncology/Haematology 19:183-232 (1995)).

Furthermore, EGFR expression is frequently accompanied by the production of EGFR-ligands, TGF-alpha and EGF among others, by EGFR-expressing tumour cells which suggests that an autocrine loop participates in the progression of these cells (Baselga, et al. (1994) Pharmac. Therapeut. 64: 127-154; Modjtahedi, et al. (1994) Int. J. Oncology. 4: 277-296). Blocking the interaction between such EGFR ligands and EGFR therefore can inhibit tumor growth and survival (Baselga, et al. (1994) Pharmac. Therapeut. 64: 127-154).

The EGFR is a membrane bound glycoprotein with a molecular weight of approximately 170 kDa. EGFR consists of a glycosylated external ligand-binding domain (621 residues) and a cytoplasmic domain (542 residues) connected by a short 23 amino acid transmembrane linker. The extracellular part of EGFR contains 25 disulfide bonds and 12 N-linked glycosylation sites, and is generally considered to consist of four sub-domains. X-ray crystal structures of the EGFR suggest that the receptor adopts both an autoinhibited tethered-conformation that cannot bind EGF (Ferguson et al, Mol Cell, 2003, vol 11: 507-517) and an active conformation that may mediate EGF ligand binding and receptor dimerisation (Garret et al, Cell 2002, vol 110:763-773; Ogiso et al, Cell, 2002, vol 110:775-787). In particular, domain I and domain III have been suggested to provide additive contributions for formation of a high-affinity ligand binding site. Domains II and IV are cysteine-rich laminin-like regions that stabilise protein folding and contain a possible EGFR dimerisation interface.

EGFR is known to exist in a number of different conformations on the cell surface, where the tethered or locked confirmation is the most frequent. The tethered conformation cannot dimerise and hence is inactive. The therapeutic antibody Erbitux is known to stabilise the tethered conformation by binding to domain III and sterically hampering the receptor in reaching the untethered state. However, some receptors may still be able to adopt the untethered conformation, bind ligand and dimerise. A monoclonal antibody (mAb) will typically only be effective in binding against one of the conformations and therefore cannot effectively target cancer cells exhibiting other conformations or cancer cells exhibiting a variety of conformations.

Monoclonal antibodies (mAbs) directed to the ligand-binding domain of EGFR can block the interaction with EGFR ligands and, concomitantly, the resultant intracellular signaling pathway.

Erbitux™ (Cetuximab) is a recombinant, human/mouse chimeric monoclonal antibody that binds specifically to the extracellular domain of the human (EGFR). Erbitux is composed of the Fv regions of a murine anti-EGFR antibody with human IgG1 heavy and kappa light chain constant regions and has an approximate molecular weight of 152 kDa. Erbitux is produced in mammalian cell culture (murine myeloma). Erbitux is approved for the treatment of patients with metastatic colorectal cancer and whose tumor expresses EGFR. In addition, Erbitux is used in combination with radiation therapy to treat patients with squamous cell cancer of the head and neck that cannot be removed by surgery or as second line treatment of squamous cell cancer of the head and neck that have failed standard platinum-based therapy.

Vectibix™ (panitumumab) is a recombinant, human IgG2 kappa monoclonal antibody that binds specifically to the human EGFR. Vectibix has an approximate molecular weight of 147 kDa. Panitumumab is produced in genetically engineered mammalian cells (Chinese Hamster Ovary). Vectibix is approved for the treatment of patients with metastatic colorectal cancer and whose tumor expresses EGFR with disease progression on or following fluoropyrimidine-, oxaliplatin-, and irinotecan-containing chemotherapy regimens.

A number of mutant EGF receptors have been identified on human tumour cells. These may render the receptor activity independently of ligand binding (EGFRvIII) leading to enhanced tumorigenicity. Monoclonal antibodies against a mutant EGFR may be generated, but such a monoclonal antibody will not necessarily be effective against non-mutated EGFR.

Mutations of EGFR have been identified in human cancer patients that affect their response to chemotherapy directed toward EGFR. WO 2006/110478 (Novartis) disclosed 43 mutations as well as 18 SNPs in the EGFR open reading frame. Some missense mutations are identified in two or more types of tumour types. WO 2006/091899 (Amgen) disclosed eight further mutations identified in various cancer cells. One or more of these mutations may be located in the epitope or affect the structure of the epitope bound by one of the currently approved monoclonal antibodies. Patients carrying such mutation(s) will not be treatable by a monoclonal antibody.

Furthermore, there are reports in literature showing heterogeneity in glycosylation of at least one of the glycosylation sites (Whitson et al., 2005 Biochemistry 44:14920-31; Zhen et al. 2003 Biochemistry 42; 5478-92). Such heterogeneity may directly or indirectly result in differential exposure of epitopes that vary among tumour cells.

Antibody dependent cellular cytotoxicity (ADCC) is an alternative mechanism by which antibodies mediate killing of tumour cells. The level of ADCC is dependent on several factors including IgG subtype (IgM>IgG1>IgG2), antibody density on target cells, antibody glycosylation pattern as well as the properties of the target itself.

Friedmann et al (PNAS 2005, 102:1915-20) have shown that two murine monoclonal antibodies selected for their ability to inhibit EGF binding to EGFR by binding distinct EGFR epitopes are able to synergistically down-regulate receptor expression in KB cells and CHO cells transiently expressing EGFR. Cross competitive EGF inhibiting antibodies did not exhibit any synergy.

Modjtahedi et al (Cell Biophysics vol 22, 1993, 129-146) has tested combinations of several rat anti-EGFR antibodies with non-overlapping epitopes. The antibodies were of different isotypes. In all cases the effect of using two antibodies was intermediate between the effects of using similar amounts of the two monoclonal antibodies alone. This was confirmed both in vivo and in vitro.

WO 2004/032960 (Merck patent) discloses that the combined use of two monoclonal antibodies, Mab425 and Mab225 (Cetuximab), results in an increased amount of antibodies bound to the surface of EGFR expressing cancer cells compared to a similar amount of each of the monoclonal antibodies alone. The publication also discloses increased down-regulation of EGFR when using the combination of antibodies compared to the two monoclonal antibodies.

Perera et al (Clin Cancer Res 2005; 11 (17):6390-99) disclosed a synergistic effect of treating mice bearing U87MG.de2-7 xenografts with a combination of two murine monoclonal antibodies. One of the antibodies (mAb 528) binds all of the EGFR subtypes with similar specificity to cetuximab. The other one (mAB 806) only binds the de2-7 EGFR. The U87MG.de2-7 cell line is a de2-7EGFR transfected cell line. The U87MG.DK cell line expresses a kinase inactive variant of the de2-7 EGFR. No synergy was observed when the two antibodies were used against mice bearing U87MG.DK xenografts. In a xenograft model with the A431 cell line expressing wildtype EGFR, the authors provided no evidence of synergy. The de2-7 EGFR is only present in a limited number of cancer types, such as glioma, to some extent breast cancer and lung cancers.

While these studies have indicated that in some cases synergy may exist between two murine monoclonal antibodies, they also show that in many cases, no synergy is seen. The studies also do not provide an anti-EGFR antibody composition that is effective against a wide range of clinically relevant cancer cell lines.

Accordingly, the need exists for improved therapeutic antibodies against EGFR which are effective at treating and/or preventing diseases related to overexpression of EGFR when administered at low dosages. There is also a need for broadly applicable therapeutic cancer-antibodies which can be used without possessing intimate knowledge about the structure of EGFR expressed by the cancer cells in question.

SUMMARY OF THE INVENTION

In one aspect, the invention relates to a recombinant antibody composition comprising at least 3 distinct anti-EGFR antibody molecules, wherein the antibodies bind distinct first, second and third epitopes of EGFR.

In a further aspect the invention relates to a recombinant antibody composition comprising at least two distinct EGFR antibody molecules, wherein one distinct anti-EGFR antibody molecule is selected from the group consisting of antibodies: 992, 1024, 1030, 1042, 1208, 1229, 1254, 1257, 1260, 1261, 1277, 1284, 1308, 1320, 1344, and 1347 or antibodies having the CDRs of these antibodies.

Preferably at least one distinct anti-EGFR antibody molecule is selected from the group consisting of antibodies 992, 1030, 1024, 1347, 1277, 1254, 1320, 1260, 1261, and 1284 or antibodies having the CDRs of these antibodies. In a particularly preferred embodiment of the invention, the antibody composition comprises antibodies 992 and 1024 or two antibodies based on their CDR3 sequences, or on their VL and VH sequences, or comprises two antibodies with essentially the same binding specificity.

Representative antibody compositions of the invention have proven effective in inhibition of proliferation of representative cancer cell lines, which is indicative of an in vivo use in the treatment of cancer. These results have been confirmed in an assay with cancer cell spheroids, which may be more representative of the situation in vivo, where cancer cells form tumours. Furthermore, an antibody composition of the invention appears to reduce the cell motility from cancer spheroids and thus reduce the propensity to form metastases. In vivo efficacy in a xenograft model has also been demonstrated with a representative antibody composition. These results have been confirmed with a particularly preferred antibody composition consisting of antibodies 992 and 1024.

In a xenograft model of human cancer in mice, a representative antibody composition of the invention has resulted in significantly higher degree of terminal differentiation of the tumour cells as compared to commercially available monoclonal antibodies, Vectibix and Erbitux. It appears that the preferred antibody composition of the invention works through a different mechanism of action compared to monoclonal antibodies as no tumour regrowth was observed after termination of the treatment with the antibody composition of the invention. Tumour regrowth is observed after termination of treatment with monoclonal antibodies.

In binding studies, the inventors have demonstrated that some of the antibodies provided with the present application appear to facilitate the binding of further antibodies, thereby increasing the total amount of antibody bound to the receptor. It has also been demonstrated that binding three Domain III antibodies facilitates the subsequent binding of further antibodies. These observations clearly support the concept of using a composition with at least 3 distinct anti-EGFR antibody molecules, wherein the antibodies bind distinct first, second and third epitopes of EGFR. The effect may also be obtained by using specific combinations of two antibodies of the invention by selecting antibodies providing this specific effect. Such antibodies are preferred candidates for mixing with other antibodies.

The compositions of the invention may provide several further advantages. Cancer cells express a variety of EGFR. Variation is seen in conformation, in glycosylation and in primary structure (mutations and SNPs). A single monoclonal antibody may target some but not all of these EGFR variations. EGFR mutants may be escape mutants for monoclonal antibodies. An antibody comprising two antibodies of the invention or three or more distinct antibodies binding distinct EGFR epitopes is less susceptible to mutants, SNPs, deletion mutants and variations in glycosylation. This is evidenced by the broad efficacy of the antibody mixes of the present invention against a panel of human cancer cell lines, representing diverse EGFR conformations and variations.

Administration of one monoclonal antibody may also not shut down kinase activity of EGFR completely. A more efficient inhibition of signalling may be achieved by a combination of antibodies.

It may therefore be beneficial to include antibodies which bind to different EGFR conformations (e.g. untethered conformation and receptor dimer) in an antibody mixture. Such a mixture of antibodies may be more potent at inhibiting EGFR activity than a monoclonal antibody binding only one of the conformations.

Furthermore by using an approach with three or more anti-EGFR antibodies in the composition it may be possible to raise the density of antibodies on the tumour cell surface thereby increasing the killing through ADCC as compared to the monoclonal antibodies.

In a further aspect, the invention relates to a method for manufacturing an antibody composition comprising:

transfecting a first population of eukaryotic cells with a first expression construct coding for a first antibody comprising a first cognate pair of $V_H$ and $V_L$ chains capable of binding a first distinct EGFR epitope;

transfecting a second population of eukaryotic cells with a second expression construct coding for a second antibody comprising a second cognate pair of $V_H$ and $V_L$ chains capable of binding a second distinct EGFR epitope;

optionally repeating step b) for third or further populations, expression constructs, cognate pairs, and EGFR epitopes;

selecting transfected first, second and optionally further cell populations;

combining the transfected populations in one pot to obtain a cell bank;

culturing cells from the cell bank under conditions allowing expression of the antibodies; and recovering and purifying the antibody composition from the supernatant.

For ease of manufacture, down stream processing and characterisation all antibodies comprise the same heavy chain constant region.

In a further aspect, the invention relates to a cell bank comprising at least two sub-populations of eukaryotic cells; each sub-population transfected or transduced with one expression construct coding for an antibody comprising a cognate pair of $V_H$ and $V_L$ chains capable of binding a distinct EGFR epitope. Preferably, the cells are transfected using site-specific integration.

Furthermore, the invention relates to a method of reducing EGFR signalling comprising administering to a composition of cells expressing EGFR, an antibody composition of the invention and reducing the EGFR signalling.

The invention also relates to a method of killing cells expressing EGFR comprising administering to a composition of cells expressing EGFR, an antibody composition of any the invention and killing the EGFR expressing cells.

There is also provided a method of inducing apoptosis in cells expressing EGFR, comprising administering to a composition of cells expressing EGFR, an antibody composition of the invention, thereby inducing apoptosis.

A further aspect relates to a method of inhibiting proliferation of cells expressing EGFR comprising administering to a composition of cells expressing EGFR, an antibody composition of the invention thereby inhibiting proliferation.

The invention relates to a method of inducing differentiation of tumour cells in vivo, comprising administering to an individual inflicted with cancer, an antibody composition of the invention, thereby inducing differentiation of the tumour cells. This aspect is based on the observed effects on in vivo terminal differentiation of cancer cells when exposed to an antibody composition of the invention.

In a further aspect, the invention relates to pharmaceutical articles comprising an antibody composition of the invention and at least one compound capable inducing differentiation of cancer cells as a combination for the simultaneous, separate or successive administration in cancer therapy. By combining the antibody compositions of the invention with agents known to induce terminal differentiation of cancer cells, the effect can be improved further.

In a still further aspect, the invention relates to pharmaceutical articles comprising an antibody composition of the invention and at least one chemotherapeutic or antineoplastic compound as a combination for the simultaneous, separate or successive administration in cancer therapy. It is likely that the antibody composition of the invention can be used for a second line treatment, i.e. after or simultaneously with treatment using conventional chemotherapeutic or antineoplastic agents, or after or simultaneously with radiation therapy and/or surgery.

In a separate aspect there is provided a polynucleotide selected from the group consisting of a nucleic acid having the nucleic acid sequence shown in FIG. 23A (SEQ ID NO 100); a nucleic acid coding for a polypeptide having the amino acid sequence shown in FIG. 23B (SEQ ID NO 101); a nucleic acid having the nucleic acid sequence shown in FIG. 34A (SEQ ID NO 102); and a nucleic acid coding for a polypeptide having the amino acid sequence shown in FIG. 34B (SEQ ID NO 103). Furthermore there is provided a polypeptide comprising the amino acid sequence shown in FIG. 23B (SEQ ID NO 101) and a polypeptide comprising the amino acid sequence shown in FIG. 34B (SEQ ID NO 103), expression vectors comprising said nucleic acid as defined above operably linked to a promoter sequence capable of directing the expression of said nucleic acid, and a cell transfected or transduced with said expression vector.

These sequences constitute the polynucleotide and polypeptide sequences of Cynomolgus EGFR, i.e. from *Macaca fascicularis*. This species of monkey is a widely used animal for toxicology studies. For an animal species to be of any value in a toxicology study involving antibodies against human self-antigens, it is essential that the antibodies also bind the target protein in the tox-animal, preferably with approximately the same affinity. Testing antibodies for binding to cynomolgus EGFR has now been made possible with the contribution of the present inventors. Cynomolgus and human EGFR are highly homologous proteins but surprisingly a number of antibodies with very different affinity to human and Cynomolgus EGFR have been found. This stresses the importance of using the exact Cynomolgus EGFR protein for screening, which has been provided by the present inventors.

Furthermore there is provided a method for screening antibodies for binding to cynomolgus EGFR, comprising the steps of providing at least one test antibody;

performing an assay to determine antibody binding to the extracellular domain of cynomolgus EGFR (FIG. 23B, SEQ ID NO 101)) or full length cynomolgus EGFR (FIG. 34B, SEQ ID NO 103)); or the surface of cells expressing the extracellular domain of cynomolgus EGFR or expressing full length cynomolgus EGFR;

and selecting at least one antibody that binds cynomolgus EGFR extracellular domain.

The method may further comprise screening for binding to human EGFR extracellular domain or binding to cells expressing human EGFR.

In a further aspect the invention relates to a method for identifying anti-EGFR antibodies capable of enhancing the simultaneous binding of another anti-EGFR antibody to EGFR, said method comprising a. In a first assay, determining the maximum binding capacity of a first antibody with respect to a fixed amount of EGFR antigen, b. In a second assay, saturating a fixed amount of EGFR antigen with a second anti-EGFR antibody, c. Contacting the EGFR-antibody complex with said first antibody and determining the maximum binding capacity, and d. Comparing the binding capacities to determine whether the maximum binding capacity of step c. exceeds the maximum binding capacity of step a.

This assay may be used to identify further combinations of antibodies having properties similar to those of antibodies 992 and 1024.

DEFINITIONS

The term "antibody" describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of two or more different antibody molecules reacting with the same or different epitopes on the same antigen or even on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulins. The terms antibody or antibodies as used herein are also intended to include chimeric and single chain antibodies, as well as binding fragments of antibodies, such as Fab, Fv fragments or scFv fragments, as well as multimeric forms such as dimeric IgA molecules or pentavalent IgM. An antibody may be human, murine, chimeric, humanised, or reshaped.

The term "cognate $V_H$ and $V_L$ coding pair" describes an original pair of $V_H$ and $V_L$ coding sequences contained within or derived from the same antibody producing cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or similar containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

The term "CDR"—complementarity determining region is as defined in Lefranc et al (2003) IMGT unique numbering for immunoglobulin and T cell receptor variable domains and Ig superfamily V-like domains. Dev. Comp Immunol 27, 55-77.

The terms "a distinct member of a recombinant polyclonal protein" denotes one protein molecule of a protein composition comprising different, but homologous protein molecules, where each protein molecule is homologous to the other molecules of the composition, but also contains one or more stretches of variable polypeptide sequence, which is/are characterized by differences in the amino acid sequence between the individual members of the polyclonal protein.

The term "head-to-head promoters" refers to a promoter pair being placed in close proximity so that transcription of two gene fragments driven by the promoters occurs in opposite directions. A head-to-head promoter can also be constructed with a stuffer composed of irrelevant nucleic acids between the two promoters. Such a stuffer fragment can easily contain more than 500 nucleotides. Head-to-head promoters can also be termed bi-directional promoters.

The term "immunoglobulin" commonly is used as a collective designation of the mixture of antibodies found in blood or serum, but may also be used to designate a mixture of antibodies derived from other sources.

The term "immunoglobulin molecule" denotes an individual antibody molecule, e.g., as being a part of immunoglobulin, or part of any polyclonal or monoclonal antibody composition.

The term "a library of variant nucleic acid molecules of interest" is used to describe the collection of nucleic acid molecules, which collectively encode a "recombinant polyclonal protein of interest". When used for transfection, the library of variant nucleic acid molecules of interest is contained in a library of expression vectors. Such a library typically have at least 2, 3, 5, 10, 20, 50, 1000, $10^4$, $10^5$ or $10^6$ distinct members.

The term "mass transfer" is used to describe the transfer of nucleic acid sequences of interest from one population of vectors to another population of vectors and doing so for each DNA simultaneously without resorting to isolation of the individual DNA's of interest. Such populations of vectors can be libraries containing for example variable regions, promoters, leaders or enhancing elements of interest. These sequences can then be moved without prior isolation from for example a phage vector to a mammalian expression vector. Especially for antibody sequences this technique ensures that the linkage between $V_H$ and $V_L$ diversity is not lost while moving libraries from, for example, a selection vector (e.g., a phage display vector) to a mammalian expression vector. Hereby the original pairing of $V_H$ and $V_L$ is retained.

As used herein, the term "operably linked" refers to a segment being linked to another segment when placed into a functional relationship with the other segment. For example, DNA encoding a signal sequence is operably linked to DNA encoding a polypeptide if it is expressed as a leader that participates in the transfer of the polypeptide to the endoplasmic reticulum. Also, a promoter or enhancer is operably linked to a coding sequence if it stimulates the transcription of the sequence.

The term "polyclonal antibody" describes a composition of different antibody molecules which is capable of binding to or reacting with several different specific antigenic determinants on the same or on different antigens. Usually, the variability of a polyclonal antibody is thought to be located in the so-called variable regions of the polyclonal antibody. However, in the context of the present invention, polyclonality can also be understood to describe differences between the individual antibody molecules residing in so-called constant regions, e.g., as in the case of mixtures of antibodies containing two or more antibody isotypes such as the human isotypes IgG1, IgG2, IgG3, IgG4, IgA1, and IgA2, or the murine isotypes IgG1, IgG2a, IgG2b, IgG3, and IgA. For purposes of the present invention such a polyclonal antibody may also be termed "an antibody composition".

The term "epitope" is commonly used to describe a proportion of a larger molecule or a part of a larger molecule (e.g. antigen or antigenic site) having antigenic or immunogenic activity in an animal, preferably a mammal, and most preferably in a human. An epitope having immunogenic activity is a portion of a larger molecule that elicits an antibody response in an animal. An epitope having antigenic activity is a portion of a larger molecule to which an antibody immunospecifically binds as determined by any method well known in the art, for example, by the immunoassays described herein. Antigenic epitopes need not necessarily be immunogenic. An antigen is a substance to which an antibody or antibody fragment immunospecifically binds, e.g. toxin, virus, bacteria, proteins or DNA. An antigen or antigenic site often has more than one epitope, unless they are very small, and is often capable of stimulating an immune response. Epitopes may be linear or conformational. A linear epitope consists of about 6 to 10 adjacent amino acids on a protein molecule that is recognized by an antibody. In contrast, conformational epitope consists of amino acids that are not arranged sequentially. Here the antibody recognizes only the 3-dimensional structure. When a protein molecule folds into a three dimensional structure the amino acids forming the epitope are juxtaposed enabling the antibody to recognize the sequence. In a denatured protein only the linear epitope may be recognized. A conformational epitope, by definition, must be on the outside of the folded protein. An antibody that recognizes the conformational epitope may only bind under mild, non-denaturing procedures. Antibodies binding to different epitopes on the same antigen can have varying effects on the activity of the antigen they bind depending on the location of the epitope. An antibody binding to an epitope in an active site of the antigen may block the function of the antigen completely, whereas another antibody binding at a different epitope may have no or little effect on the activity of the antigen alone. Such antibodies may however still activate complement and thereby result in the elimination of the antigen, and may result in synergistic effects when combined with one or more antibodies binding at different epitopes on the same antigen. In the present invention, the epitope is preferably a proportion of the extracellular domain of EGFR. Antigens of the present invention are preferably extracellular domain EGFR proteins, polypeptides or fragments thereof to which an antibody or antibody fragment immunospecifically binds. An EGFR associated antigen may also be an analog or derivative of the extracellular domain of EGFR polypeptide or fragment thereof to which an antibody or antibody fragment immunospecifically binds.

Antibodies capable of competing with each other for binding to the same antigen may bind the same or overlapping epitopes or may have a binding site in the close vicinity of one another, so that competition is mainly caused by steric hindrance. Methods for determining competition between antibodies are described in the examples.

As used herein, the term "polyclonal protein" or "polyclonality" refers to a protein composition comprising different, but homologous protein molecules, preferably selected from the immunoglobulin superfamily. Thus, each protein molecule is homologous to the other molecules of the composition, but also contains one or more stretches of variable polypeptide sequence, which is/are characterized by differences in the amino acid sequence between the individual members of the polyclonal protein. Known examples of such polyclonal proteins include antibody or immunoglobulin molecules, T cell receptors and B cell receptors. A polyclonal protein may consist of a defined subset of protein molecules, which has been defined by a common feature such as the shared binding activity towards a desired target, e.g., in the case of a polyclonal antibody against the desired target antigen.

By "protein" or "polypeptide" is meant any chain of amino acids, regardless of length or post-translational modification. Proteins can exist as monomers or multimers, comprising two or more assembled polypeptide chains, fragments of proteins, polypeptides, oligopeptides, or peptides.

The term "RFLP" refers to "restriction fragment length polymorphism", a method whereby the migratory gel pattern of nucleic acid molecule fragments are analyzed after cleavage with restriction enzymes.

The term "scrambling" describes situations where two or more distinct members of a polyclonal protein comprised of two different polypeptide chains, e.g. from the immunoglobulin superfamily, are expressed from an individual cell. This situation may arise when the individual cell has integrated, into the genome, more than one pair of gene segments, where each pair of gene segments encode a distinct member of the polyclonal protein. In such situations unintended combinations of the polypeptide chains expressed from the gene segments can be made. These unintended combinations of polypeptide chains might not have any therapeutic effect.

The term "$V_H$-$V_L$ chain scrambling" is an example of the scrambling defined above. In this example the $V_H$ and $V_L$ encoding gene segments constitute a pair of gene segments. The scrambling occurs when unintended combinations of $V_H$ and $V_L$ polypeptides are produced from a cell where two different $V_H$ and $V_L$ encoding gene segment pairs are integrated into the same cell. Such a scrambled antibody molecule is not likely to retain the original specificity, and thus might not have any therapeutic effect.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

The terms "variable polypeptide sequence" and "variable region" are used interchangeably.

The term "distinct epitopes" means that when two different antibodies bind distinct epitopes, there is less than 100% competition for antigen binding, preferably less than 50% competition for antigen binding, more preferably essentially no competition for antigen binding. An analysis for "distinct epitopes" of antibody pairs is typically determined by binding experiments under saturating antibody conditions with either FACS analysis on cells expressing EGFR and individually fluorescent labelled antibodies, or Surface Plasmon Resonance using EGFR antigen captured or conjugated to a flow cell surface as described in the examples.

The term being capable of "inhibiting EGF binding" when applied to one antibody molecule means that the antibody molecule exhibits an IC 50 value with respect to EGF binding to EGFR of less than 10 nM, preferably less than 8 nM, more preferably less than 7 nM, more preferably less than 5 nM, more preferably less than 4 nM, more preferably less than 3 nM, more preferably less than 2 nM, more preferably less than 2 nM, more preferably less than 1 nM.

The terms "epidermal growth factor receptor" "EGFR" and "EGFR antigen" are used interchangeably herein, and include variants, isoforms and species homologs of human EGFR. In a preferred embodiment, binding of an antibody of the invention to the EGFR-antigen inhibits the growth of cells expressing EGFR (e.g., a tumor cell) by inhibiting or blocking binding of EGFR ligand to EGFR. The term "EGFR ligand" encompasses all (e.g., physiological) ligands for EGFR, including but nor limited to EGF, TGF-alpha, heparin binding EGF (HB-EGF), amphiregulin (AR), heregulin, betacellulin, and epiregulin (EPI). In another preferred embodiment, binding of an antibody of the invention to the EGFR-antigen mediates effector cell phagocytosis and/or killing of cells expressing EGFR.

EGFR domain structure: The extracellular part of the mature EGFR (SwissProt acc.#P00533) consists of 621 amino acids and four receptor domains: Domain I encompasses residues 1-165, domain II residues 166-312, domain III residues 313-481 and domain IV 482-621 (Cochran et al. 2004 J immunol. Methods 287, 147-158). Domains I and III have been suggested to contribute to the formation of high affinity binding sites for ligands. Domains II and IV are cysteine rich, laminin-like regions that stabilize protein folding and contain a possible EGFR dimerization interface.

As used herein, the term "inhibits growth" (e.g., referring to cells) is intended to include any measurable decrease in the proliferation (increase in number of cells) or metabolism of a cell when contacted with an anti-EGFR antibody as compared to the growth of the same cells not in contact with an anti-EGFR antibody, e.g, the inhibition of growth of a cell culture by at least about 10%, 20%, 30%, 40%, 50%, 60%, 70%, 80%, 90%, 99%, or 100%.

As used herein, the terms "inhibits binding" and "blocks binding" (e.g., referring to inhibition/blocking of binding of EGFR ligand to EGFR) are used interchangeably and encompass both partial and complete inhibition/blocking. The inhibition/blocking of EGFR ligand to EGFR preferably reduces or alters the normal level or type of cell signaling that occurs when EGFR ligand binds to EGFR without inhibition or blocking. Inhibition and blocking are also intended to include any measurable decrease in the binding affinity of EGFR ligand to EGFR when in contact with an anti-EGFR antibody as compared to the ligand not in contact with an anti-EGFR antibody, e.g., the blocking of EGFR ligands to EGFR by at least about 10%, 20%, 30%, 40%, 50%, 60%, 70%, 80%, 90%, 99%, or 100%.

The term "recombinant antibody" is used to describe an antibody molecule or several molecules that is/are expressed from a cell or cell line transfected with an expression vector comprising the coding sequence of the antibody which is not naturally associated with the cell.

DESCRIPTION OF THE DRAWINGS

FIGS. 6A and 6B. Degree of inhibition of Anti-EGFR antibodies with listed reference antibodies directed against specific EGFR domains as determined in a competition ELISA. FIG. 6A) Calculation of inhibition. FIG. 6B) Scoring of inhibition as follows: 25-49%: Moderate competition (+); 50-74%: Strong competition (++); 75-100%: Very strong competition (+++). Boxes displaying significant inhibition (50-100%) are shaded in gray. Erbitux and Vectibix are shown in duplicates (four independent experiments) to illustrate the reproducibility of the assay. Ab2 (225) is the murine precursor that lead to Erbitux.

FIGS. 8A and 8B: Degree of inhibition of Anti-EGFR antibodies with listed reference antibodies directed against specific EGFR domains as determined by competition analysis with SPR technology. FIG. 8A) Calculation of inhibition. FIG. 8B) Scoring of inhibition as follows: 25-49%: Moderate competition (+); 50-74%: Strong competition (++); 75-100%: Very strong competition (+++). Cells displaying significant inhibition (50-100%) are shaded in gray. Clone 1229 marked * did not bind in the Biacore assay.

FIGS. 9A and 9B: Determination of epitope clusters within the Anti-EGFR antibody repertoire by SPR competition analysis of Anti-EGFR antibody pairs. Antibodies are grouped according to presumed EGFR domain recognition. Cells in which antibody combinations were found to bind overlapping epitopes resulting in more than 50% inhibition are shaded in grey. Cells in which determinations were not done are colored in black. FIG. 9A) Calculation of inhibition. FIG. 9B) Scoring of inhibition as follows: 25-49%: Moderate competition (+); 50-74%: Strong competition (++); 75-100%: Very strong competition (+++).

FIG. 10A) Epitope map of antibodies directed against domain I or domain I/II of EGFR Extra-Cellular Domain (ECD). FIG. 10B) Epitope map of antibodies directed against domain III of EGFR ECD.

FIGS. 11A-11D: Investigation of the simultaneous binding of an oligoclonal mix of antibodies directed against non overlapping epitopes on EGFR. FIG. 11A) Sequential addition of antibodies against domain III, domain I or unknown specificity. Inhibition values of single sample mAbs tested against different mAb mixtures or single mAb are shown in shaded boxes. The Ru max values used to calculate inhibition are also shown. FIG. 11B) Competition analysis of six distinct sample mAbs directed against non-overlapping epitopes on EGFR and an antibody mixture containing the six tested antibodies. Antibody mixes where the tested sample antibody was not included served as a positive control. Inhibition values of single sample mAbs tested against different mAb mixtures are shown in shaded boxes. The Ru max values used to calculate inhibition are also shown. FIG. 11C) Corresponding sensograms from the analysis in B illustrating antibody blockage and in some cases antibody enhancement of binding. FIG. 11D) Test of additional antibodies directed against domain I, I/II and unknown specificity against the six mAb antibody mixture.

FIGS. 12A and 12B: Determination of antibody mediated EGF ligand blockage by antibody titration on full length EGFR and detection of biotinylated EGF ligand binding with a streptavidin HRP reagent. Erbitux, Vectibix and Synagis IgG (palivizumab) were used as positive and negative controls respectively. After blockage of recognized antibody epitope with tested antibodies, the degree of EGF ligand competition was visualized by addition of 0.1 μg/ml biotinylated EGF ligand and a secondary Streptavidin-HRP conjugate for detection.

FIGS. 13A and 13B. Effect of pretreatment with the indicated antibodies on EGF (50 ng/ml) induced EGFR phosphorylation in HN5 cells. The antibodies (10 μg/ml) as named in the graph were incubated with the cells for 30 min prior to addition of the EGF for 7.5 min. Data sets marked * were significantly different from the control ((-)ctrl) data set ($p<0.05$). FIG. 13A. 1208 had a significant protective effect on EGFR phosphorylation. FIG. 13B. 1277 and 1320 significantly protects against EGF induced phosphorylation. Error bars represent standard deviations of three independent experiments.

FIGS. 23A and 23B: DNA (SEQ ID No. 100) and protein sequence (SEQ ID NO. 101) of extra-cellular domain of Cynomolgus EGFR cloned from cDNA derived from Cynomolgus monkey skin epidermis.

FIG. 24: Alignment of obtained protein sequence of Cynomolgus EGFR ECD (SEQ ID NO. 101) with human EGFR ECD (SEQ ID NO 108) obtained from GENBANK accession number X00588. Also shown is a consensus sequence (SEQ ID NO 109).

FIGS. 27A and 27B: FIG. 27A) Images taken at 40× magnification of HN5 spheroids 24 hours after addition of 10 μg/ml of the control antibody. (Rituximab, anti CD-20) or the anti EGFR antibody mix of 992 and 1024. FIG. 27B) Quantifiaction of the area covered by cells using the software Image J (*$p<0.01$).

FIGS. 29A and 29B. FIG. 29A) Images taken at 60× magnifications of HN5 and A431NS cells incubated with 10 μg/ml Alexa-488 labeled Erbitux or 992+1024 for 2 hours. FIG. 29B) Images taken at 60× magnifications with a small pin-hole of A431NS cells incubated with 10 μg/ml Alexa-488 labeled Erbitux or 992+1024 for 2 hours.

FIG. 30A) Images taken at 60× magnifications of HN5 cells incubated with 10 μg/ml Alexa-488 labeled Erbitux or 992+1024 for the indicated periods of time.

FIG. 31A) Fab antibodies tested against purified full length EGFR from A431 cells. FIG. 31B) Fab antibodies tested against EGFR expressed on the surface of A431-NS cells.

FIG. 32A) Functional binding of IgG antibodies to A431-NS cells. FIG. 32B) Functional binding of Fab antibodies to A431-NS cells.

FIG. 33A) Binding characteristics of IgG 992 to A431-NS cells with or without prior receptor saturation with indicated Fab fragments. FIG. 33B) Binding characteristics of IgG 1024 to A431-NS cells with or without prior receptor saturation with indicated Fab fragments. FIG. 33C) Binding characteristics of IgG 1030 to A431-NS cells with or without prior receptor saturation with indicated Fab fragments.

FIGS. 34A and 34B: Cynomolgus full length EGFR cDNA (FIG. 34A; SEQ ID NO 102) and encoded protein (FIG. 34B; SEQ ID NO 103).

FIGS. 41A and 41B: Clustalw2 alignment of the amino acids sequences of the variable regions of the murine (chi) and humanized (hu) candidate variable regions of both heavy and light chains of 992 (A) and 1024 (B). The CDR regions as defined by IMGT are underlined; gaps presented by (-), identical amino acids by (*), conservative mutations as (:), semi-conservative (.). The bold amino acid indicates amino acid positions where back-mutations to the original identified murine residue will be performed if the fully human frame work variants display decreased binding affinity. Sequence ID numbers as follows: Humanized 992 VH (SEQ ID NO 104). Humanized 992 VL (SEQ ID NO 105). Humanized 1024 VH (SEQ ID NO 106). Humanized 1024 VL (SEQ ID NO 107). Chimeric 992 VH (aa 3-124 of SEQ ID NO 40). Chimeric 992 VL (aa 3-109 of SEQ ID No 72). Chimeric 1024 VH (aa 3-120 of SEQ ID NO 41). Chimeric 1024 VL (aa 3-114 of SEQ ID NO 73).

DETAILED DESCRIPTION OF THE INVENTION

Antibody mixtures

Figure 37:
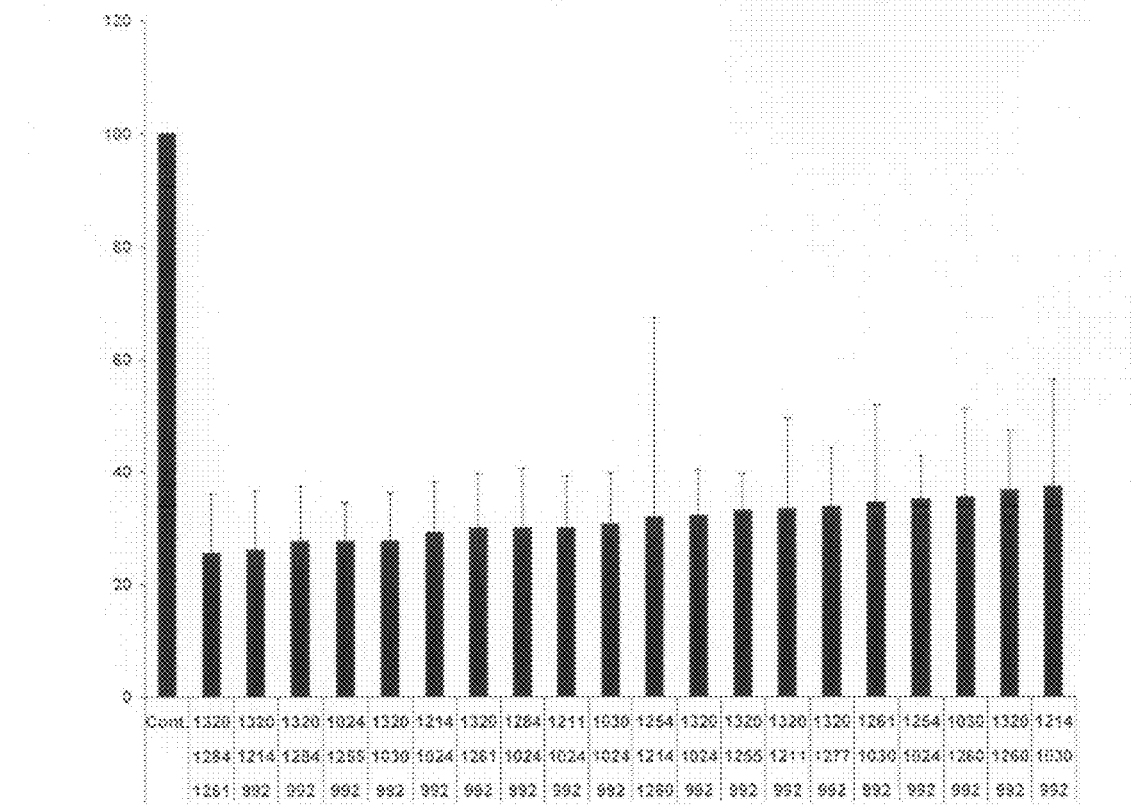
FIG. 37: Inhibition of proliferation of A431NS. The X axis shows different representative combinations of 3 antibodies of the invention. The Y axis shows Metabolic activity as percent of untreated control (control). Errorbars represent +/−SEM. For additional details see Example 6.

In one embodiment, the invention relates to an antibody composition comprising antibody molecules capable of binding at least three distinct EGFR epitopes, preferably three non-overlapping EGFR epitopes. The non-overlapping nature of the antibodies is preferably determined using differently labelled antibodies in a FACS analysis with EGFR expressing cells or by using Surface Plasmon Resonance using EGFR antigen captured or conjugated to a flow cell surface. ELISA based methods as described in the examples may also be used. A composition binding three non-overlapping EGFR epitopes can be used against a wider range of EGFR dependent cancer types as it may be less vulnerable to differences in EGFR conformation and less vulnerable to mutations compared to composition of monoclonal antibodies targeting one or two epitopes. Furthermore, the antibody composition binding three non-overlapping EGFR epitopes may provide superior efficacy compared to composition targeting fewer epitopes. In particular, the antibody composition may provide superior efficacy with respect to terminal differentiation of cancer cells in vivo. FIG. 37 numerous examples of potent antibody compositions binding three distinct hEGFR epitopes illustrating the general applicability of the concept.

For a monoclonal anti-EGFR antibody therapy a certain proportion of patients will not respond effectively to the antibody treatment. For some of the patients, this may be due to rapid clearing of the antibody or because the antibody generates an immune response in the patient against the antibody. For some patients, the lack of response may be because their particular EGFR dependent cancer expresses EGFR in a conformation where the monoclonal antibody cannot bind its epitope. This could be because of differences in glycosylation, because of domain deletion, or because of mutations and/or SNP(s).

Also for some cancers the autocrine EGFR-stimulation caused by the cancer cells' production of ligand is of importance, while in other cases the EGFR expressed by the cancer cells does not need ligand stimulation. For the latter cancer types, an antibody capable of inhibiting ligand binding may not be effective.

An antibody composition wherein the antibodies are capable of binding at least three distinct epitopes on EGFR will be more broadly applicable, since the likelihood that all three epitopes are changed compared to the epitope(s) recognised by the antibodies is diminished. Furthermore, the likelihood that all antibodies are either cleared by the patient is much smaller. Finally, the examples show that in functional assays, a mixture comprising three antibodies binding distinct epitopes is superior to a monoclonal antibody and to a mixture comprising two antibodies. Superiority has been shown most clearly in terms of induction of terminal differentiation of the cancer cells using three Domain III antibodies with non-overlapping epitopes. Such efficient antibody-induced terminal differentiation of cancer cells has not been reported before and represents a significant step forward in designing efficient antibody-based cancer therapies. Later results have shown that similar or even superior results can be obtained with a particular combination of two antibodies.

For improved clinical efficacy and broader utility against a wider range of EGFR dependent cancer types, the number of antibodies in the composition can be increased. Thus, the composition may comprise antibodies capable of binding four non-overlapping epitopes. The composition may comprise antibodies capable of binding five non-overlapping epitopes. The composition may comprise antibodies capable of binding six non-overlapping epitopes. The examples of the present application show that at least six distinct antibodies can bind to EGFR at one time (Example 3). This does not exclude that it is possible or even advantageous to design a composition comprising antibodies capable of binding more than six, such as seven or eight non-overlapping epitopes by carefully selecting antibodies.

In another embodiment, the composition comprises more than one antibody molecule binding one epitope, such as two antibodies binding different but overlapping epitopes. There may be advantages of including antibodies with overlapping epitopes as this increases the likelihood that the epitope is bound. One rationale behind this is that the epitope in some patients and/or in some cancer cells may be changed due to conformational changes or mutations or SNPs. While this may affect the binding of one antibody, it may not affect the binding of another antibody binding an overlapping epitope. Furthermore, there is a risk that one of the antibodies is cleared by the patients, because it is seen as an antigen. By including two antibodies binding different but overlapping epitopes the consequence of clearance of one of the two antibodies and the consequence of a mutation in an epitope is diminished.

Thus in one embodiment the composition comprises two antibodies binding different but overlapping epitopes. In another embodiment the composition comprises two distinct antibody molecules binding the same epitope. Antibodies binding the same or overlapping epitopes may be of the same or of different isotype.

An antibody composition comprising antibodies directed against three non-overlapping epitopes may thus comprise four, five or six distinct antibody molecules so that two antibodies bind two overlapping epitopes or the same first epitope, two other antibodies bind two other overlapping epitopes or the same second epitope, and two antibodies bind two further other overlapping epitopes or the same third epitope. Of course, the composition may comprise more than two, such as three or four antibody molecules capable of binding overlapping epitopes or capable of binding the same epitope. Thus the total number of antibodies included in the composition may exceed 6 by having more than one antibody for each epitope or by having several antibodies with overlapping epitopes. Keeping the total dosage of antibody constant, for each further antibody included in the composition, the concentration of each antibody decreases. Therefore it is expected that there is a limit to the number of antibodies that can be included in a composition while maintaining an acceptable efficacy. Based on observations from the Surface Plasmon Resonance binding studies and proliferation assays and taking due account of the manufacture challenges, it is expected that the limited (if any) additional advantage is obtainable by increasing the number of antibodies from 6 to 7, 8, 9, 10 or more. Of course, this does not exclude that the composition comprises more than 10 antibodies, such as 11, 12, 13, 14, 15, 16, 17, 18, 19, or 20 antibodies or more, such as 25 antibodies or more, for example 30 antibodies or more, such as 40 antibodies or more, such as 50 antibodies or more.

While it is preferred to include in an antibody composition of the invention, antibodies capable of binding at least three non-overlapping EGFR epitopes, superior results have also been obtained with specific combinations of antibodies capable of binding two non-overlapping EGFR epitopes. These preferred "two antibody" compositions are described in more detail below together with guidance relating to how to design antibody compositions of the invention. It has turned out that compared to the three antibody composition comprising antibodies 992, 1030, and 1042 similar or even improved efficacy could be obtained when using a composition with only two antibodies: 992 and 1024. As antibodies 1024 and 1042 belong to the same cluster and therefore have the same binding specificity, in effect, the results observed for the three antibody composition including the effect on terminal differentiation may be attributed to only two of the binding specificities (992 and 1024/1042) in the composition.

In one embodiment at least one antibody in the composition binds a domain III epitope, more preferably the composition comprises at least two antibodies binding domain III epitopes, and the composition may also comprise three antibodies binding domain III epitopes.

Preferably the composition comprises at least one antibody binding a domain I epitope and it may comprise at least two antibodies binding domain I epitopes.

Preferably the composition comprises at least one antibody binding a domain II epitope, and may comprise antibodies binding two domain II epitopes.

The composition may also comprise an antibody binding a domain I/II epitope as defined herein.

The composition may comprise an antibody capable of binding a domain IV epitope.

Preferably the composition comprises at least one antibody molecule capable of inhibiting EGF binding.

In another preferred embodiment, the composition may comprise an antibody capable of preventing phosphorylation of EGFR.

Furthermore the composition may comprise an antibody capable of enhancing internalisation/degradation of EGFR.

In a preferred embodiment, the composition comprises at least one domain III antibody and at least one domain I/II antibody. In another preferred embodiment, the composition comprises at least two domain III antibodies and one domain I antibody.

In a further preferred embodiment, the composition comprises at least two domain III antibodies, such as at least three domain III antibodies.

ogy studies prior to clinical experiments. Preferably, the non-human primate is cynomolgus monkey (*Macaca fascicularis*).

In order to support the above identified concept of treating EGFR dependent cancer using antibodies binding three of more distinct epitopes, the present inventors have have identified, manufactured, and characterised a series of chimeric mouse/human antibodies directed against EGFR. These chimeric antibodies have been compared individually and in mixtures to state of the art monoclonal antibodies, exemplified with Erbitux™ and Vectibix™.

Table 1 shows a summary of the individual chimeric antibodies and the features associated with these. Antibody no is a reference number used throughout the present application. Specificity is the EGFR domain to which the antibody binds as evidenced in Example 3. deltaEGFR is the ability of the antibody to bind to EGFR mutant (EGFRvIII) as described in example 1. Cynomolgus EGFR is the ability of the antibody to bind cynomolgus EGFR (example 10). EGF inhib is the ability of the antibody to inhibit EGF binding (Example 4) Proliferation is the ability of the antibody to inhibit proliferation of cancer cell lines, A431 and HN-5 (Example 6).

TABLE 1

Antibodies of the invention

| Antibody no. | Specificity | deltaEGFR | Cynomolgous EGFR | EGF inhib | Proliferation |
|---|---|---|---|---|---|
| 992 | Domain III | no/weak | yes | yes/weak | Yes |
| 1030 | Domain III | yes | yes | yes | yes |
| 1024 | Domain III | yes | yes | | yes |
| 1042 | Domain III | weak | yes | (yes) | yes |
| 1277 | Domain III | yes | Yes | yes | HN5 |
| 1254 | Domain III | yes | Yes | yes | HN5 |
| 1208 | Domain III | yes | yes | yes | yes HN5 +/− 992 |
| 1320 | Domain III | weak | No | yes | yes |
| 1257 | Domain I/II | no | yes | no | yes |
| 1261 | Domain I | no | Yes | no | yes |
| 1229 | Not domain I/II | yes | No | no | yes (A431) |
| 1284 | Domain I | no | Yes | yes | yes |
| 1344 | Domain I/II | no | yes | nd | HN5 w/992 |
| 1260 | Domain I/II | no | Yes | yes | A431 |
| 1308 | Domain I | no | yes | nd | HN5 w/992 |
| 1347 | Domain I | no | yes | nd | HN5 w/992 |
| 1428 | Domain I & II | no | Yes | yes | HN5 w/992 |

The antibodies of the composition may be chimeric antibodies with non-human variable chains and human constant chains. The non-human variable chains may be from mouse, rat, sheep, pig, chicken, non-human primate or other suitable animal. In order to obtain fully human antibodies the antibodies can be generated in a transgenic animal with human antibody genes. The antibodies may also be so-called humanised antibodies, where the non-human CDR sequences have been grafted into human framework sequences.

Preferably the human constant chain is IgG1 or IgG2 isotype. More preferably all antibodies in the composition have the same isotype for ease of manufacturing. However, it may be advantageous to include in the composition antibodies of different isotype.

Preferably the antibody compositions of the invention comprise antibodies capable of binding to EGFR selected from the group consisting of human EGFR, mutated human EGFR, and deletion variants of human EGFR. Preferably the antibodies are capable of binding both human and non-human primate EGFR, so that they can be tested in relevant toxicol- From the data generated with the chimeric antibodies tested alone and in combination in proliferation, binding, receptor degradation/inactivation, and motility assays, and in animal models, a number of conclusions can be drawn.

The results obtained with two cancer cell lines, HN-5 and A431 (Example 6) have been repeated with different cancer cell lines (MDA-MB-468 a breast cancer cell line; DU145—prostate cancer cell line). What is evident from these experiments is that combinations of antibodies provided by the present inventors display efficacy against a very wide range of cancer cell lines, supporting the efficacy of the antibody compositions against a range of EGFR conformations.

Figure 17:
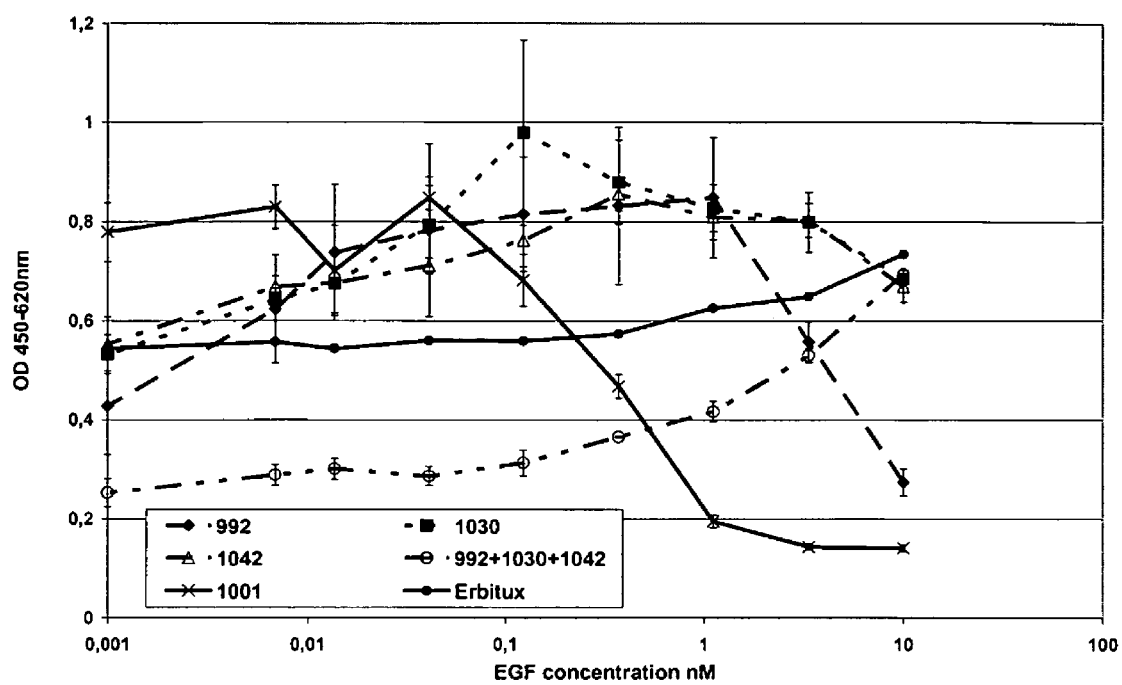
FIG. 17: Growth curves of A431-NS cells in the presence of 10 μg/ml of the antibodies 992, 1030 and 1042 and mixes hereof and varying concentrations of the EGFR ligand EGF as measured by the absorbance at 450 nm. 1001 is a non-functional antibody with similar isotype used as negative control.

It has also been shown that the superiority of antibody mixes is higher in proliferation assays where physiological concentrations of ligand (EGF) is added to the growth medium than when EGF is not added (FIG. 17). According to literature (Hayashi and Sakamoto 1998 J Pharmacobiodyn 11; 146-51) serum contains approximately 1-1.8 ng/ml or 0.2-0.3 nM EGF while gastric juice is reported to contain 0.3 ng/ml (ca. 0.05 nM) (Pessonen et al. 1987 Life Sci. 40; 2489-94). In an in vivo setting, EGF and other EGFR ligands are likely to be present and the ability of the antibody mix to be effective in the presence of EGFR ligand is therefore an important feature of the antibody mixes of the present invention.

The chimeric mouse/human antibodies of the present invention provide better results when used in combination than when used alone. This is exemplified in several experiments (see e.g. Example 6)), where antibodies when tested alone show only moderate antiproliferative effects on a cancer cell line (A431-NS), but when used in either combination, show remarkably superior results. These results have been confirmed with numerous combinations of the chimeric antibodies of the present invention. Particularly superior results have been obtained with a composition comprising antibodies 992 and 1024.

For example several of the antibodies have been tested in an antiproliferation assay with A431-NS and HN-5 together with either of Antibodies 992, 1208, 1254, and 1277.

Receptor binding studies have shown that some antibodies may actually stimulate the binding of further antibodies, such that a particular antibody binds in higher quantities to the receptor after receptor saturation with one or several antibodies. The binding of antibody 992, directed against domain III, clearly benefits from this synergistic effect obtained by prior receptor saturation with one or more antibodies binding non-overlapping epitopes. Another example of this co-operative effect is seen when antibody 1396 directed against an unknown epitope is tested against EGFR saturated with antibodies binding non-overlapping epitopes.

Receptor binding studies have also shown that it is possible to bind at least 6 antibodies to the extracellular domain of EGFR simultaneously. These 6 antibodies represent 3 Domain III antibodies, one Domain I antibody, one Domain I/II antibody, and one antibody binding an unknown epitope. Interestingly, binding of the three Domain III antibodies seems to facilitate the subsequent binding of further antibodies. This clearly supports the concept of providing antibody compositions with several antibodies binding distinct epitopes.

When designing the composition of an antibody composition against EGFR, antibodies with non-overlapping epitopes are preferably used as these provide a higher synergistic effect.

It is also preferable that at least one of the antibodies of the mixture (when tested alone) is capable of inhibiting ligand binding to EGFR, e.g. capable of inhibiting EGF binding, and/or capable of inhibiting TGFalpha binding, and/or capable of inhibiting amphiregulin binding. Preferably the antibody capable of inhibiting EGF binding is selected from the group consisting of Antibodies 992, 1030, 1024, 1042, 1208, 1254, 1277, 1284, 1320, and 1428, more preferably from the group consisting of antibodies 1208, 1260, 1277, and 1320.

It is likewise preferable that at least one antibody member in the antibody mix is capable of reducing EGFR phosphorylation. Examples of antibodies of the invention with this property includes: 992, 1030, 1042, 1208, 1277, and 1320.

Domain III of EGFR is of importance for ligand binding to the receptor. Furthermore, antibody binding to Domain III may stabilise EGFR in the tethered monomeric conformation, which does not lead to receptor signalling. For these reasons it is preferable that the antibody composition contains at least one antibody with specificity for Domain III. Preferred Domain III antibodies include antibodies 992, 1024, 1030, 1208, 1254, 1277, and 1320. More preferably the at least domain III antibody is selected from the group consisting of antibodies 992, 1254, 1277, 1208, and 1320. The antibody composition may preferably comprise more than one Domain III antibody such as at least 3 domain III antibodies, for example at least 4 domain III antibodies, such as at least 5 domain III antibodies, for example at least 6 domain III antibodies.

In another preferred embodiment, the antibody composition comprises at least one Domain I antibody. Preferably the at least one Domain I antibody is selected from the group consisting of antibodies 1284, 1308, 1344, and 1347. More preferably the at least one Domain I antibody is selected from the group consisting of antibodies 1284, and 1347.

In another preferred embodiment, the antibody composition comprises at least one Domain I/II antibody. Preferably the at least one Domain I/II antibody is selected from the group consisting of antibodies 1257, 1260, 1261, 1428, and 1434. More preferably the at least one Domain I/II antibody is selected from the group consisting of antibodies 1261 and 1260.

Efficient specific combinations of two antibodies from the present invention include:

Antibody 1280 together with 1024, 1320, 1308, 1284, 1260, or 1030, preferably with 1320, or 1284.

Antibody 1254 together with 1024, 1030, 1260, 1284, 1308, or 1320, preferably with 1320, 1284, or 1260.

Antibody 1277 together with 1024, 1030, 1260, 1284, 1308, or 1320, preferably with 1320, 1284, or 1260.

Antibody 992 together with 1030, 1260, 1284, 1308, 1320, or 1024, preferably with 1320, 1024, or 1284.

Examples of superior and preferred mixes of two antibodies include 992+1024; 992+1320; 992+1042; 1277+1320; 1208+1320. Particularly preferred is 992+1024.

Preferred mixes with three antibodies include: Antibodies 992+1030+1042; 992+1320+1024; 992+1024+1030; 1320+1284+1261; 1320+1214+1320; 992+1284+1320; 992+1255+1024; 992+1030+1320; 992+1024+1214; 992+1261+1320; 992+1024+1284; 992+1024+1211; 992+1024+1030; 1260+1214+1254; 992+1255+1320; 992+1211+1320; 992+1030+1261; 992+1260+1030; 992+1260+1320; 992+1030+1214.

Preferred mixes with four antibodies include: Antibodies 992+1320+1024+1030; 992+1024+1030+1284; 1277+1320+1260+1347; 1277+1320+1261+1347; 1277+1320+1261+1284; 1254+1320+1260+1347; 1254+1320+1261+1347; 1254+1320+1261+1284; 1254+1024+1260+1347; 1254+1024+1261+1347; 1254+1024+1261+1284; 1277+1024+1260+1347; 1277+1024+1261+1347; 1277+1024+1261+1284

Preferred mixes with 5 antibodies include: 992+1030+1024+1260+1347; 992+1030+1024+1261+1347; 992+1030+1024+1261+1284; 992+1030+1320+1260+1347; 992+1030+1320+1261+1347; 992+1030+1320+1261+1284;

One preferred mix with 8 antibodies includes: 992+1030+1024+1277+1254+1320+1260+1261+1284+1347;

Furthermore, in order to be able to perform a toxicology study in a non-human primate, it is preferable that all antibodies in the composition bind to human as well as to at least one further primate EGFR, such as EGFR from chimpanzee, Macaca mulatta, Rhesus monkey and other monkeys, or cynomolgus monkey. Cynomolgus monkey is a relatively small animal, and very well suited for toxicology studies, Therefore, the further primate EGFR is preferably cynomolgus EGFR. Preferably the antibodies bind with approximately the same affinity to human and non-human primate EGFR.

The present invention has shown superior results in one or more functional assays when combining 2, 3, 4, 5, 6, 7, and 8 antibodies in one composition. While these data provide guidance on selection of the number of antibodies in the composition, they are in now way to be interpreted in a limiting way. The composition may comprise more than 8 antibodies, even though the experimental data only show simultaneous binding of 6 antibodies. There may be other reasons for including more than 6 antibodies in the composition, such as e.g. differences in clearing rate of the antibody members.

A further preferred feature of the antibodies of the compositions is protein homogeneity, so that the antibodies can be purified easily. For the individual antibody members, an ion exchange chromatography profile with one distinct peak is preferred for ease of characterisation. A clear ion exchange chromatography profile is also preferred for ease of characterisation of the final antibody composition. It is also preferable when combining the antibodies that they can be distinguished using ion exchange chromatography, so that the composition with all the antibodies can be characterised in one run.

The antibodies may be or any origin such as human, murine, rabbit, chicken, pig, lama, sheep. The antibodies may also be chimeric as described in the examples or may be humanised, superhumanised or reshaped versions thereof using well-known methods described in the art.

A Preferred Antibody Composition

As shown in the appended examples, the anti-EGFR composition based on antibodies 992 and 1024 has unique and distinct properties. The binding of antibody 992 is enhanced by binding of other antibodies including 1024. In contrast to commercial antibodies, both 992 and 1024 bind preferentially to conformational epitopes presented on cells (Examples 14 and 15). The epitopes of 992 and 1024 both overlap with but are distinct from the Erbitux and Vectibix epitope(s). In contrast to a number of other two-antibody compositions where the individual antibodies bind to non-overlapping epitopes, the composition based on the binding specificities of antibodies 992 and 1024 triggers receptor internalization rapidly and effectively. A novel mechanism of action involving terminal differentiation accompanied with increased involucrin expression and the appearance of keratin pearls is observed in an animal model after treatment with antibody compositions based on antibodies 992 and 1024. This unique mechanism of action leads to more effective and sustained growth inhibition in vitro and in vivo. This is most clearly seen in the in vivo examples where the tumours continue to diminish after termination of treatment. In the control group receiving Erbitux, tumours start growing soon after termination of treatment. This clearly indicates a different mechanism of action.

It is believed that the novel mechanism of action is achieved by using the combination of two binding specificities displayed by antibodies 992 and 1024 in one antibody composition. This mechanism of action is also seen when a third antibody which does not compete with antibodies 992 and 1024 is used, e.g. in the triple combination of antibodies 992, 1024, and 1030.

These observations have let to the design of an antibody composition comprising at least 2 distinct anti-human EGFR antibody molecules, wherein a first distinct anti-EGFR antibody molecule is selected from the group consisting of antibody 992, an antibody comprising the VL (amino acids 3-109 of SEQ ID NO 72) and VH (amino acids 3-124 of SEQ ID NO 40) sequences of antibody 992, an antibody having the CDR3s of antibody 992 (SEQ ID NO 116 and 111), an antibody binding to the same epitope as antibody 992, and an antibody capable of inhibiting the binding of antibody 992 to human EGFR; and wherein a second distinct anti-EGFR antibody molecule is selected from the group consisting of antibody 1024, an antibody comprising the VL (amino acids 3-114 of SEQ ID NO 73) and VH (amino acids 3-120 of SEQ ID NO 41) sequences of antibody 1024, an antibody having the CDR3s of antibody 1024 (SEQ ID NO 120 and 114), an antibody binding to the same epitope as antibody 1024, and an antibody capable of inhibiting the binding of antibody 1024 to human EGFR.

Preferably, said first distinct anti-EGFR antibody molecule is selected from the group consisting of antibody 992, an antibody comprising the VL and VH sequences of antibody 992, an antibody having the CDR3s of antibody 992, and an antibody binding to the same epitope as antibody 992; and said second distinct anti-EGFR antibody molecule is selected from the group consisting of antibody 1024, an antibody comprising the VL and VH sequences of antibody 1024, an antibody having the CDR3s of antibody 1024, and an antibody binding to the same epitope as antibody 1024.

The present invention contemplates mutations in the CDR3 sequences of antibodies 992 and 1024 to provide antibodies with the same binding specificity. Therefore in one embodiment an antibody having the same binding specificity as antibody 992 comprises a CDRH3 having the following formula: $CTX_1X_2X_3X_4X_5X_6X_7X_8X_9X_{10}X_{11}X_{12}X_{13}X_{14}X_{15}W$ where $X_1$ to $X_{15}$ are selected individually from the groups of amino acids listed below $X_1$=R or K;
$X_2$=N, D, E or Q;
$X_3$=G, A, V, or S;
$X_4$=D, E, N or Q;
$X_5$=Y, F, W or H;
$X_6$=Y, F, W or H;
$X_7$=V, I, L or A;
$X_8$=S, T, G or A;
$X_9$=S, T, G or A;
$X_{10}$=G, A, V, or S;
$X_{11}$=D, E, N or Q;
$X_{12}$=A, G, V, or S;
$X_{13}$=M, L, I or V
$X_{14}$=D or E; and
$X_{15}$=Y, or F;

and a CDRL3 described by the following formula: $CX_1X_2X_3X_4X_5X_6PPTF$ where $X_1$ to $X_6$ are selected individually from the groups of amino acids listed below:
$X_1$=Q or H;
$X_2$=H, E or Q;
$X_3$=Y, F, W or H;
$X_4$=N, Q or H;
$X_5$=T, S, G or A; and
$X_6$=V, I, L or A.

In one embodiment an antibody having the same binding specificity as antibody 1024 comprises a CDRH3 having the following formula: $CVX_1X_2X_3X_4X_5X_6X_7X_8X_9X_{10}X_{11}W$ where $X_1$ to $X_{11}$ are selected individually from the groups of amino acids listed below
$X_1$=R or K;
$X_2$=Y, F, W or H;
$X_3$=Y, F, W or H;
$X_4$=G, A, V, or S;
$X_5$=Y, F, W or H;
$X_6$=D, E, N or Q;
$X_7$=E or D;
$X_8$=A, G, V, or S;

$X_9$=M, L, I or V;
$X_{10}$=D, E, N or Q; and
$X_{11}$=Y, or F;
and a CDRL3 described by the following formula: $CX_1X_2X_3X_4X_5X_6PX_7TF$ where $X_1$ to $X_7$ are selected individually from the groups of amino acids listed below:
$X_1$=A, G, or V;
$X_2$=Q or H;
$X_3$=N, Q or H;
$X_4$=L, I, M or V;
$X_5$=E, D, N or Q;
$X_6$=L, I, M or V; and
$X_7$=Y, F, W or H.

Antibodies with mutated CDR3s can be made using standard techniques and be expressed and tested for binding using methods described herein.

The antibodies according to this aspect of the invention may be chimeric, human, humanised, reshaped or superhumanised. This may be done by using methods known in the art. For example antibodies 992 and 1024 may be humanised using methods described in Example 18. Methods for "superhumanisation" are described in U.S. Pat. No. 6,881,557.

More preferably said first distinct anti-EGFR antibody molecule is selected from the group consisting of antibody 992, an antibody comprising the VL and VH sequences of antibody 992, and an antibody having the CDR3s of antibody 992; and said second distinct anti-EGFR antibody molecule is selected from the group consisting of antibody 1024, an antibody comprising the VL and VH sequences of antibody 1024, and an antibody having the CDR3s of antibody 1024.

More preferably said first distinct anti-EGFR antibody molecule is selected from the group consisting of antibody 992, and an antibody comprising the VL and VH sequences of antibody 992; and said second distinct anti-EGFR antibody molecule is selected from the group consisting of antibody 1024, and an antibody comprising the VL and VH sequences of antibody 1024.

Most preferably the composition comprises antibodies 992 and 1024.

As described, the first and second anti-EGFR antibodies preferably do not inhibit the binding to human EGFR of each other. Even more preferably, at least one of the antibodies is capable of increasing the maximum binding capacity of the other antibody with respect to human EGFR. This effect is observed for antibodies 992 and 1024 (Example 16).

The ratio between the two antibodies need not be exactly a 1:1 ration. Consequently, the proportion of the first antibody relative to the second antibody in the composition may be between 5 and 95%, such as between 10 and 90%, preferably between 20 and 80%, more preferably between 30 and 70, more preferably between 40 and 60, such as between 45 and 55, such as approximately 50%.

Preferably the first and second antibodies are of isotype IgG1, or IgG2.

Examples of antibodies binding to the same epitope as antibody 992 identified by the present inventors are antibodies from the antibody cluster comprising clones 1209, 1204, 992, 996, 1033, and 1220.

Examples of antibodies binding to the same epitope as antibody 1024 identified by the present inventors are antibodies from the antibody cluster comprising clones 1031, 1036, 1042, 984, 1024, 1210, 1217, 1221, and 1218.

The CDR3 determine the binding specificity of the antibodies. In preferred embodiments, the antibody comprising the CDR3 of antibody 992 additionally comprises the CDR1 and CDR2 of VH and VL of antibody 992. Likewise the antibody comprising the CDR3 of antibody 1024 additionally preferably comprises the CDR1 and CDR2 of VH and VL of antibody 1024. CDR sequences of the antibodies can be found in Table 12, example 17.

In other embodiments, the antibody competing with antibody 992 is selected from the group consisting of antibodies 1208, 1254, and 1277. Likewise, the antibody competing with antibody 1024 may be selected from the group consisting of antibodies 1042 and 1320.

In one embodiment, the composition does not contain further antibodies in addition to said first and second antibodies, more preferably not further anti-EGFR antibodies.

In other embodiments, the composition further comprises a third distinct anti-EGFR antibody, wherein said third distinct anti-EGFR antibody molecule is selected from the group consisting of antibody 1030, an antibody comprising the VL (amino acids 3-113 of SEQ ID NO 74) and VH (amino acids 3-120 of SEQ ID NO 42) sequences of antibody 1030, an antibody having the CDR3s of antibody 1030 (SEQ ID NOs 112 and 119), an antibody binding to the same epitope as antibody 1030, and an antibody capable of inhibiting the binding of antibody 1030 to human EGFR. Said third antibody preferably results in an enhanced binding to human EGFR of said first and/or second antibody. In one embodiment, the composition does not contain further antibodies in addition to said first, second, and third antibodies, more preferably not further anti-EGFR antibodies.

The antibody binding to the same epitope as antibody 1030 may be selected from the antibody cluster consisting of clones 1195, 1030, 1034, 1194, 980, 981, 1246, and 1223.

The antibody comprising the CDR3 of antibody 1030 may additionally comprise the CDR1 and CDR2 of VH and VL of antibody 1030.

The antibodies may be formulated in one container for administration. However, they may be manufactured, purified and characterised individually and be provided in two or three separate containers as a kit of parts, with one antibody in each container. As such they may be administered simultaneously, successively or separately.

In a further aspect the two binding specificities of antibodies 992 and 1024 are combined in one bi-specific binding molecule. Preferably the bispecific binding molecule comprises the CDRs of antibodies 992 and 1024, more preferably the VH and VL sequences of antibodies 992 and 1024. The bi-specific binding molecule may be a dual-variable-domain antibody as described in example 19. A bi-specific binding molecule may also be designed in the form of a bispecific Fab-fragment, a bispecific scFV, or a diabody as described in literature.

Antibody compositions based on the binding specificities pf antibodies 992 and 1024 preferably leads to one or more of receptor internalisation, to regression of A431NS tumours in vivo, to induction of terminal differentiation in A431NS cells in vivo, and to up-regulation of tumour involucrin expression in vivo.

The present application provides several examples of antibodies having the same or similar effects as the combination of antibodies 992 and 1024. Examples of these include antibodies obtained from the same immunisation and belonging to the same clusters and antibodies competing individually with one of the two antibodies. Antibody compositions with the same or similar effect may be designed based on the VL and VH sequences of antibodies 992 and 1024 and also based on the CDRs of these antibodies, in particular the CDR3s of the two antibodies.

Further antibody compositions with the same or similar effects may be made by carrying out immunisation and screening essentially as described in the examples. Antibodies with the same binding specificity as antibody 992 and 1024 may be identified in two separate competition assays as described herein. Finally, antibody compositions where one antibody enhances the binding of the other antibody may be identified by carrying out binding experiments essentially as described in Example 16. The antibody compositions may be screened further as described in the examples for effects on receptor internalisation, in vitro and in vivo efficacy, binding affinity etc.

Uses of the Antibody Compositions of the Invention

For use in in vivo treatment and prevention of diseases related to EGFR expression (e.g., over-expression), antibodies of the invention are administered to patients (e.g., human subjects) at therapeutically effective dosages (e.g., dosages which result in growth inhibition, phagocytosis, reduction of motility, terminal differentiation, and/or killing of tumour cells expressing EGFR) using any suitable route of administration, such as injection and other routes of administration known in the art for antibody-based clinical products.

Typical EGFR-related diseases which can be treated, ameliorated, and/or prevented using the antibodies of the invention include, but are not limited to, autoimmune diseases and cancers. For example, cancers which can be treated ameliorated, and/or prevented include cancer of the bladder, breast, uterine/cervical, colon, kidney, ovary, prostate, renal cell, pancreas, colon, rectum, stomach, squamous cell, lung (non-small cell), esophageal, head and neck, skin. Autoimmune diseases which may be treated include, for example, psoriasis.

In yet another embodiment, the invention relates to a method for the treatment, amelioration, and/or prevention of glioblastoma, including glioblastoma multiforme; astrocytoma, including childhood astrocytoma; glioma; neuroblastoma; neuroendocrine tumors of the gastrointestinal tract; bronchioalveolar carcinoma; follicular dendritic cell sarcoma; salivary gland carcinoma; ameloblastoma; malignant peripheral nerve sheet tumor; endocrine pancreatic tumors; or testicular germ cell tumors, including seminoma, embryonal carcinoma, yolk sac tumor, teratoma and choriocarcinoma.

Isolation and Selection of Variable Heavy Chain and Variable Light Chain Coding Pairs The process of generating an anti-EGFR recombinant antibody composition involves the isolation of sequences coding for variable heavy chains ($V_H$) and variable light chains ($V_L$) from a suitable source, thereby generating a repertoire of $V_H$ and $V_L$ coding pairs. Generally, a suitable source for obtaining $V_H$ and $V_L$ coding sequences are lymphocyte containing cell fractions such as blood, spleen or bone marrow samples from a non-human animal immunized/vaccinated with a human EGFR polypeptide or peptide or with EGFR proteins derived from a cell expressing human EGFR or with cells expressing human EGFR or fractions of such cells. Preferably, lymphocyte containing fractions are collected from non-human mammals or transgenic animals with human immunoglobulin genes. The collected lymphocyte containing cell fraction may be enriched further to obtain a particular lymphocyte population, e.g. cells from the B lymphocyte lineage. Preferably, the enrichment is performed using magnetic bead cell sorting (MACS) and/or fluorescence activated cell sorting (FACS), taking advantage of lineage-specific cell surface marker proteins for example for B cells, plasma blast and/or plasma cells. Preferably, the lymphocyte containing cell fraction is enriched or sorted with respect to B cells, plasma blasts and/or plasma cells. Even more preferably, cells with high expression of CD43 and CD138 are isolated from spleen or blood. These cells are sometimes termed circulating plasma cells, early plasma cells or plasma blasts. For ease, they are just termed plasma cells in the present invention, although the other terms may be used interchangeably.

The isolation of $V_H$ and $V_L$ coding sequences can either be performed in the classical way where the $V_H$ and $V_L$ coding sequences are combined randomly in a vector to generate a combinatorial library of $V_H$ and $V_L$ coding sequences pairs. However, in the present invention it is preferred to mirror the diversity, affinity and specificity of the antibodies produced in a humoral immune response upon EGFR immunisation. This involves the maintenance of the $V_H$ and $V_L$ pairing originally present in the donor, thereby generating a repertoire of sequence pairs where each pair encodes a variable heavy chain ($V_H$) and a variable light chain ($V_L$) corresponding to a $V_H$ and $V_L$ pair originally present in an antibody produced by the donor from which the sequences are isolated. This is also termed a cognate pair of $V_H$ and $V_L$ encoding sequences and the antibody is termed a cognate antibody. Preferably, the $V_H$ and $V_L$ coding pairs of the present invention, combinatorial or cognate, are obtained from mice donors, and therefore the sequences are murine.

There are several different approaches for the generation of cognate pairs of $V_H$ and $V_L$ encoding sequences, one approach involves the amplification and isolation of $V_H$ and $V_L$ encoding sequences from single cells sorted out from a lymphocyte-containing cell fraction. In order to obtain a repertoire of $V_H$ and $V_L$ encoding sequence pairs which resemble the diversity of $V_H$ and $V_L$ sequence pairs in the donor, a high-throughput method with as little scrambling (random combination) of the $V_H$ and $V_L$ pairs as possible, is preferred, e.g. as described in WO 2005/042774 (hereby incorporated by reference).

The $V_H$ and $V_L$ encoding sequences may be amplified separately and paired in a second step or they may be paired during the amplification (Coronella et al. 2000. Nucleic Acids Res. 28: E85; Babcook et al 1996. PNAS 93: 7843-7848 and WO 2005/042774). A second approach involves in-cell amplification and pairing of the $V_H$ and $V_L$ encoding sequences (Embleton et al. 1992. Nucleic Acids Res. 20: 3831-3837; Chapal et al. 1997. BioTechniques 23: 518-524). A third approach is selected lymphocyte antibody method (SLAM) which combines a hemolytic plaque assay with cloning of $V_H$ and $V_L$ cDNA (Babcook et al. 1996. PNAS 93:7843-7848). Another method that can be used with mice is standard hybridome technique, followed by screening and selection of lead candidates and subsequent cloning of the encoded antibodies.

In a preferred embodiment of the present invention a repertoire of $V_H$ and $V_L$ coding pairs, where the member pairs mirror the gene pairs responsible for the humoral immune response resulting from a EGFR immunisation, is generated according to a method comprising the steps i) providing a lymphocyte-containing cell fraction from an animal donor immunized with human EGFR; ii) optionally enriching B cells or plasma cells from said cell fraction; iii) obtaining a population of isolated single cells, comprising distributing cells from said cell fraction individually into a plurality of vessels; iv) amplifying and effecting linkage of the $V_H$ and $V_L$ coding pairs, in a multiplex overlap extension RT-PCR procedure, using a template derived from said isolated single cells and v) optionally performing a nested PCR of the linked $V_H$ and $V_L$ coding pairs. Preferably, the isolated cognate $V_H$ and $V_L$ coding pairs are subjected to a screening procedure as described below.

Once the $V_H$ and $V_L$ sequence pairs have been generated, a screening procedure to identify sequences encoding $V_H$ and $V_L$ pairs with binding reactivity towards an EGFR associated antigen is performed. Preferably, the EGFR associated antigen is comprises an extracellular part of EGFR such as domain III, II, I, and/or IV, fragments of the domains or the complete extracellular domain. Other antigens include mutants such as deletion mutants of EGFR or SNPs, or fragments thereof. If the $V_H$ and $V_L$ sequence pairs are combinatorial, a phage display procedure can be applied to enrich for $V_H$ and $V_L$ pairs coding for antibody fragments binding to EGFR prior to screening.

In order to minor the diversity, affinity and specificity of the antibodies produced in a humoral immune response upon immunization with EGFR, the present invention has developed a screening procedure for the cognate pairs, in order to obtain the broadest diversity possible. For screening purposes the repertoire of cognate $V_H$ and $V_L$ coding pairs are expressed individually either as antibody fragments (e.g. scFv or Fab) or as full-length antibodies using either a bacterial or mammalian screening vector transfected into a suitable host cell. The repertoire of Fabs/antibodies may be screened—without limitation—for reactivity to EGFR, for antiproliferative activity against a cancer cell line expressing EGFR, and for the ability to inhibit ligand (e.g. EGF) binding to EGFR, for inhibition of phosphorylation, induction of apoptosis, EGFR internalisation.

In parallel, the repertoire of Fabs/antibodies is screened against selected antigens such as human and optionally cynomolgus or chimpanzee or rhesus monkey EGFR peptides. The antigenic peptides can for example be selected from human EGFR extracellular domain, human mutant EGFR extracellular domain, and cynomolgus EGFR extracellular domain or fragments thereof. The peptides may be biotinylated to facilitate immobilization onto beads or plates during screening. Alternative immobilization means may be used as well. The antigens are selected based on the knowledge of the EGFR biology and the expected neutralizing and/or protective effect antibodies capable of binding to these antigens potentially can provide. This screening procedure can likewise be applied to a combinatorial phage display library.

The recombinant EGFR proteins used for screening may be expressed in bacteria, insect cells, mammalian cells or another suitable expression system. For correct processing (including glycosylation) the proteins are expressed in mammalian cells. The EGFR-ECD protein may either be expressed as a soluble protein (without the transmembrane and intracellular region) or they may be fused to a third protein, to increase stability. If the EGFR protein is expressed with a fusion tag, the fusion partner may be cleaved off prior to screening. In addition to the primary screening described above, a secondary screening may be performed, in order to ensure that none of the selected sequences encode false positives.

Generally, immunological assays are suitable for the screening performed in the present invention. Such assays are well know in the art and constitute for example ELISPOT, ELISA, FLISA, membrane assays (e.g. Western blots), arrays on filters, and FACS. The assays can either be performed without any prior enrichment steps, utilizing polypeptides produced from the sequences encoding the $V_H$ and $V_L$ pairs. In the event that the repertoire of $V_H$ and $V_L$ coding pairs are cognate pairs, no enrichment by e.g. phage display is needed prior to the screening. However, in the screening of combinatorial libraries, the immunoassays are preferably performed in combination with or following enrichment methods such as phage display, ribosome display, bacterial surface display, yeast display, eukaryotic virus display, RNA display or covalent display (reviewed in FitzGerald, K., 2000. Drug Discov. Today 5, 253-258).

The $V_H$ and $V_L$ pair encoding sequences selected in the screening are generally subjected to sequencing, and analyzed with respect to diversity of the variable regions. In particular the diversity in the CDR regions is of interest, but also the $V_H$ and $V_L$ family representation is of interest. Based on these analyses, sequences encoding $V_H$ and $V_L$ pairs representing the overall diversity of the EGFR binding antibodies isolated from one or more animal donors are selected. Preferably, sequences with differences in all the CDR regions (CDRH1, CDRH2, CDRH3 and CDRL1, CDRL2 and CDRL3) are selected. If there are sequences with one or more identical or very similar CDR regions which belong to different $V_H$ or $V_L$ families, these are also selected. Preferably, at least the CDR3 region of the variable heavy chain (CDRH3) differs among the selected sequence pairs. Potentially, the selection of $V_H$ and $V_L$ sequence pairs can be based solemnly on the variability of the CDRH3 region. During the priming and amplification of the sequences, mutations may occur in the framework regions of the variable region, in particular in the first framework region. Preferably, the errors occurring in the first framework region are corrected in order to ensure that the sequences correspond completely or at least 98% to those of the germline origin, e.g. such that the $V_H$ and $V_L$ sequences are fully murine.

When it is ensured that the overall diversity of the collection of selected sequences encoding $V_H$ and $V_L$ pairs is highly representative of the diversity seen at the genetic level in a humoral response to an EGFR immunisation, it is expected that the overall specificity of antibodies expressed from a collection of selected $V_H$ and $V_L$ coding pairs also are representative with respect to the specificity of the antibodies produced in the EGFR immunised animals. An indication of whether the specificity of the antibodies expressed from a collection of selected $V_H$ and $V_L$ coding pairs are representative of the specificity of the antibodies raised by donors can be obtained by comparing the antibody titers towards the selected antigens of the donor blood with the specificity of the antibodies expressed from a collection of selected $V_H$ and $V_L$ coding pairs. Additionally, the specificity of the antibodies expressed from a collection of selected $V_H$ and $V_L$ coding pairs can be analyzed further. The degree of specificity correlates with the number of different antigens towards which binding reactivity can be detected. In a further embodiment of the present invention the specificity of the individual antibodies expressed from a collection of selected $V_H$ and $V_L$ coding pairs is analyzed by epitope mapping.

Epitope mapping may be performed by a number of methodologies, which do not necessarily exclude each other. One way to map the epitope-specificity of an antibody molecule is to assess the binding to peptides of varying lengths derived from the primary structure of the target antigen. Such peptides may be both linear and conformational and may be used in a number of assay formats, including ELISA, FLISA and surface plasmon resonance (SPR, Biacore, FACS). Furthermore, the peptides may be rationally selected using available sequence and structure data to represent e.g. extracellular regions or conserved regions of the target antigen, or the may be designed as a panel of overlapping peptides representing a selected part or all of the antigen (Meloen R H, Puijk W C, Schaaper W M M. Epitope mapping by PEPSCAN. In: Immunology Methods Manual. Ed Iwan Lefkovits 1997, Academic Press, pp 982-988). Specific reactivity of an antibody clone with one or more such peptides will generally be an indication of the epitope specificity. However, peptides are in many cases poor mimics of the epitopes recognized by antibodies raised against proteinaceous antigens, both due to a lack of natural or specific conformation and due to the generally larger buried surface area of interaction between an antibody and a protein antigen as compared to an antibody and a peptide. A second method for epitope mapping, which allows for the definition of specificities directly on the protein antigen, is by selective epitope masking using existing, well defined antibodies. Reduced binding of a second, probing antibody to the antigen following blocking is generally indicative of shared or overlapping epitopes. Epitope mapping by selective masking may be performed by a number of immunoassays, including, but not restricted to, ELISA and Biacore, which are well known in the art (e.g. Ditzel et al. 1997. J. Mol. Biol. 267:684-695; Aldaz-Carroll et al. 2005. J. Virol. 79: 6260-6271). Yet another potential method for the determination of the epitope specificity of anti-EGFR antibodies is the selection of escape mutants in the presence of antibody. This can e.g. be performed using an alanine-scan. Sequencing of the gene(s) of interest from such escape mutants will generally reveal which amino acids in the antigen(s) that are important for the recognition by the antibody and thus constitute (part of) the epitope. Production of an anti-EGFR antibody composition from selected $V_H$ and $V_L$ coding pairs An antibody composition of the present invention may be produced from a polyclonal expression cell line in one or a few bioreactors or equivalents thereof. Following this approach the anti-EGFR antibodies can be purified from the reactor as a single preparation without having to separate the individual members constituting the anti-EGFR antibody composition during the process. If the antibody composition is produced in more than one bioreactor, the purified anti-EGFR antibody composition can be obtained by pooling the antibodies obtained from individually purified supernatants from each bioreactor.

One way of producing a recombinant antibody composition is described in WO 2004/061104 and WO 2006/007850 (these references are hereby incorporated by reference). The method described therein, is based on site-specific integration of the antibody coding sequence into the genome of the individual host cells, ensuring that the $V_H$ and $V_L$ protein chains are maintained in their original pairing during production. Furthermore, the site-specific integration minimises position effects and therefore the growth and expression properties of the individual cells in the polyclonal cell line are expected to be very similar. Generally, the method involves the following: i) a host cell with one or more recombinase recognition sites; ii) an expression vector with at least one recombinase recognition site compatible with that of the host cell; iii) generation of a collection of expression vectors by transferring the selected $V_H$ and $V_L$ coding pairs from the screening vector to an expression vector such that a full-length antibody or antibody fragment can be expressed from the vector (such a transfer may not be necessary if the screening vector is identical to the expression vector); iv) transfection of the host cell with the collection of expression vectors and a vector coding for a recombinase capable of combining the recombinase recognition sites in the genome of the host cell with that in the vector; v) obtaining/generating a polyclonal cell line from the transfected host cell and vi) expressing and collecting the antibody composition from the polyclonal cell line.

When a small number (2-3 or more) of antibodies are used for one composition these may be expressed and purified individually in a way similar to manufacture of monoclonal antibodies, for example as described in WO 2004/085474. The purified antibodies can be mixed after purification or be packaged in separate vials for mixing prior to administration or for separate administration.

Preferably mammalian cells such as CHO cells, COS cells, BHK cells, myeloma cells (e.g., Sp2/0 or NS0 cells), fibroblasts such as NIH 3T3, and immortalized human cells, such as HeLa cells, HEK 293 cells, or PER.C6, are used. However, non-mammalian eukaryotic or prokaryotic cells, such as plant cells, insect cells, yeast cells, fungi, E. coli etc., can also be employed. A suitable host cell comprises one or more suitable recombinase recognition sites in its genome. The host cell should also contain a mode of selection which is operably linked to the integration site, in order to be able to select for integrants, (i.e., cells having an integrated copy of an anti-EGFR Ab expression vector or expression vector fragment in the integration site). The preparation of cells having an FRT site at a pre-determined location in the genome was described in e.g. U.S. Pat. No. 5,677,177. Preferably, a host cell only has a single integration site, which is located at a site allowing for high expression of the integrant (a so-called hot-spot).

Figure 4:
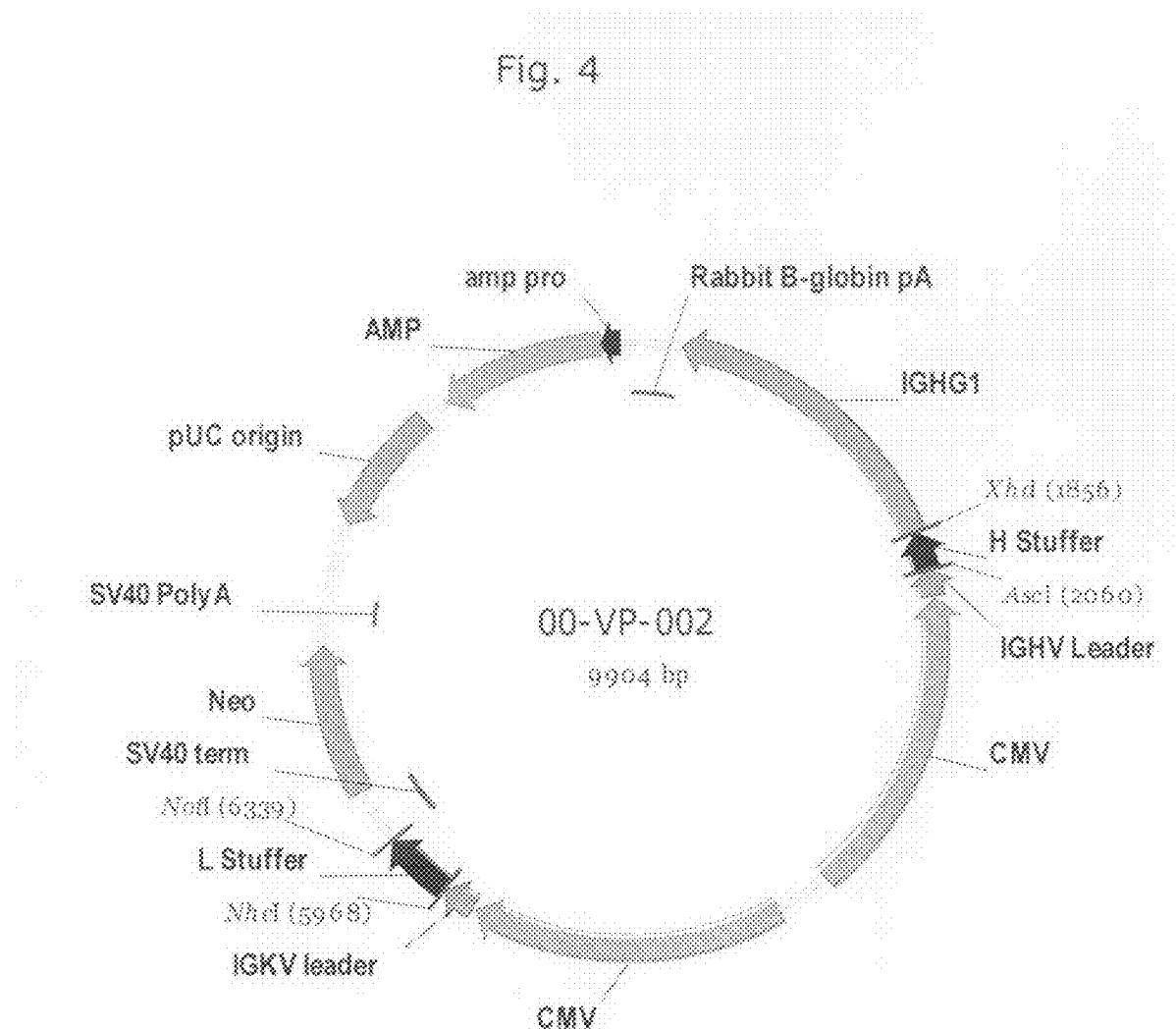
FIG. 4 A schematic representation of the mammalian full-length antibody expression vector 00-VP-002. Amp and Amp pro, ampicillin resistance gene and its promoter; pUC origin, pUC origin of replication; CMV, mammalian promoter driving the expression of the light chain and the heavy chain; IGHV Leader, genomic human heavy chain leader; H stuffer, insert that is exchanged for the heavy chain variable region encoding sequence; IGHG1, sequence coding for genomic immunoglobulin isotype G1 heavy chain constant region (sequence is shown in Appendix 2); Rabbit B-globin A, rabbit beta-globin polyA sequence; IGKV Leader, murine kappa leader; L Stuffer, insert that is exchanged for the light chain encoding sequence; SV40 term, simian virus 40 terminator sequence; FRT, Flp recognition target site; Neo, neomycin resistance gene; SV40 poly A, simian virus 40 poly A signal sequence.

A suitable expression vector comprises a recombination recognition site matching the recombinase recognition site(s) of the host cell. Preferably the recombinase recognition site is linked to a suitable selection gene different from the selection gene used for construction of the host cell. Selection genes are well known in the art, and include glutamine synthetase gene (GS), dihydrofolate reductase gene (DHFR), and neomycin, where GS or DHFR may be used for gene amplification of the inserted $V_H$ and $V_L$ sequence. The vector may also contain two different recombinase recognition sites to allow for recombinase-mediated cassette exchange (RMCE) of the antibody coding sequence instead of complete integration of the vector. RMCE is described in (Langer et al 2002; Schlake and Bode 1994). Suitable recombinase recognition sites are well known in the art, and include FRT, 10x and attP/attB sites. Preferably the integrating vector is an isotype-encoding vector, where the constant regions (preferably including introns) are present in the vector prior to transfer of the $V_H$ and $V_L$ coding pair from the screening vector (or the constant regions are already present in the screening vector if screening is performed on full-length antibodies). The constant regions present in the vector can either be the entire heavy chain constant region ($CH_1$ to $CH_3$ or to $CH_4$) or the constant region encoding the Fc part of the antibody ($CH_2$ to $CH_3$ or to $CH_4$). The light chain Kappa or Lambda constant region may also be present prior to transfer. The choice of the number of constant regions present, if any, depends on the screening and transfer system used. The heavy chain constant regions can be selected from the isotypes IgG1, IgG2, IgG3, IgG4, IgA1, IgA2, IgM, IgD and IgE. Preferred isotypes are IgG1, IgG2, and/or IgG3. Further, the expression vector for site-specific integration of the anti-EGFR antibody-encoding nucleic acid contains suitable promoters or equivalent sequences directing high levels of expression of each of the $V_H$ and $V_L$ chains. FIG. 4 illustrates one possible way to design the expression vector, although numerous other designs are possible.

The transfer of the selected $V_H$ and $V_L$ coding pairs from the screening vector can be performed by conventional restriction enzyme cleavage and ligation, such that each expression vector molecule contain one $V_H$ and $V_L$ coding pair. Preferably, the $V_H$ and $V_L$ coding pairs are transferred individually, they may, however, also be transferred in-mass if desired. When all the selected $V_H$ and $V_L$ coding pairs are transferred to the expression vector a collection or a library of expression vectors is obtained. Alternative ways of transfer may also be used if desired. If the screening vector is identical to the expression vector, the library of expression vectors is constituted of the $V_H$ and $V_L$ sequence pairs selected during screening, which are situated in the screening/expression vector.

Methods for transfecting a nucleic acid sequence into a host cell are known in the art. To ensure site-specific integration, a suitable recombinase must be provided to the host cell as well. This is preferably accomplished by co-transfection of a plasmid encoding the recombinase. Suitable recombinases are for example Flp, Cre or phage ΦC31 integrase, used together with a host cell/vector system with the corresponding recombinase recognition sites. The host cell can either be transfected in bulk, meaning that the library of expression vectors is transfected into the cell line in one single reaction thereby obtaining a polyclonal cell line. Alternatively, the collection of expression vectors can be transfected individually into the host cell, thereby generating a collection of individual cell lines (each cell line produce an antibody with a particular specificity). The cell lines generated upon transfection (individual or polyclonal) are then selected for site specific integrants, and adapted to grow in suspension and serum free media, if they did not already have these properties prior to transfection. If the transfection was performed individually, the individual cell lines are analyzed further with respect to their grow properties and antibody production. Preferably, cell lines with similar proliferation rates and antibody expression levels are selected for the generation of the polyclonal cell line. The polyclonal cell line is then generated by mixing the individual cell lines in a predefined ratio. Generally, a polyclonal master cell bank (pMCB), a polyclonal research cell bank (pRCB) and/or a polyclonal working cell bank (pWCB) are laid down from the polyclonal cell line. The polyclonal cell line is generated by mixing the individual cell lines in a predefined ratio. The polyclonal cell line is distributed into ampoules thereby generating a polyclonal research cell bank (pRCB) or master cell bank (pMCB) from which a polyclonal working cell bank (pWCB) can be generated by expanding cells from the research or master cell bank. The research cell bank is primarily for proof of concept studies, in which the polyclonal cell line may not comprise as many individual antibodies as the polyclonal cell line in the master cell bank. Normally, the pMCB is expanded further to lay down a pWCB for production purposes. Once the pWCB is exhausted a new ampoule from the pMCB can be expanded to lay down a new pWCB.

One embodiment of the present invention is a polyclonal cell line capable of expressing a recombinant anti-EGFR antibody composition of the present invention.

A further embodiment of the present invention is a polyclonal cell line wherein each individual cell is capable of expressing a single $V_H$ and $V_L$ coding pair, and the polyclonal cell line as a whole is capable of expressing a collection of $V_H$ and $V_L$ encoding pairs, where each $V_H$ and $V_L$ pair encodes an anti-EGFR antibody. Preferably the collection of $V_H$ and $V_L$ coding pairs are cognate pairs generated according to the methods of the present invention.

A recombinant antibody composition of the present invention may be manufactured by culturing one ampoule from a pWCB in an appropriate medium for a period of time allowing for sufficient expression of antibody and where the polyclonal cell line remains stable (The window is approximately between 15 days and 50 days). Culturing methods such as fed batch or perfusion may be used. The recombinant antibody composition is obtained from the culture medium and purified by conventional purification techniques. Affinity chromatography combined with subsequent purification steps such as ion-exchange chromatography, hydrophobic interactions and gel filtration has frequently been used for the purification of IgG. Following purification, the presence of all the individual members in the polyclonal antibody composition is assessed, for example by ion-exchange chromatography. The characterization of such an antibody composition is described in detail in WO 2006/007853 (hereby incorporated by reference).

An alternative method of expressing a mixture of antibodies in a recombinant host is described in WO 2004/009618. This method produces antibodies with different heavy chains associated with the same light chain from a single cell line. This approach may be applicable if the anti-EGFR antibody composition is produced from a combinatorial library.

Therapeutic Compositions

Another aspect of the invention is a pharmaceutical composition comprising as an active ingredient an anti-EGFR antibody composition or anti-EGFR recombinant Fab or another anti-EGFR recombinant antibody fragment composition, or a bi-specific binding molecule of the invention. Preferably, the active ingredient of such a composition is an anti-EGFR recombinant antibody composition as described in the present invention. Such compositions are intended for amelioration and/or prevention and/or treatment of cancer. Preferably, the pharmaceutical composition is administered to a human, a domestic animal, or a pet.

The pharmaceutical composition further comprises a pharmaceutically acceptable excipient.

Anti-EGFR antibody composition or fragments of the antibodies thereof may be administered within a pharmaceutically-acceptable diluent, carrier, or excipient, in unit dosage form. Conventional pharmaceutical practice may be employed to provide suitable formulations or compositions to administer to patients with cancer. In a preferred embodiment the administration is therapeutic, meaning that it is administered after a cancer condition has been diagnosed. Any appropriate route of administration may be employed, for example, administration may be parenteral, intravenous, intra-arterial, subcutaneous, intramuscular, intraperitoneal, intranasal, aerosol, suppository, or oral administration. For example, pharmaceutical formulations may be in the form of, liquid solutions or suspensions. For oral administration, need to be protected against degradation in the stomach. For intranasal formulations, antibodies may be administered in the form of powders, nasal drops, or aerosols.

The pharmaceutical compositions of the present invention are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (20th ed.), ed. A. R. Gennaro, 2000, Lippincott Williams & Wilkins, Philadelphia, Pa. and Encyclopedia of Pharmaceutical Technology, eds. J. Swarbrick and J. C. Boylan, 1988-1999, Marcel Dekker, New York, N.Y.).

Preferably solutions or suspensions of the active ingredient, and especially isotonic aqueous solutions or suspensions, are used to prepare pharmaceutical compositions of the present invention. In the case of lyophilized compositions that comprise the active ingredient alone or together with a carrier, for example mannitol, such solutions or suspensions may, if possible, be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

The injection compositions are prepared in customary manner under sterile conditions; the same applies also to introducing the compositions into ampoules or vials and sealing of the containers.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, tablets, pills, or capsules. The formulations can be administered to human individuals in therapeutically or prophylactically effective amounts (e.g., amounts which prevent, eliminate, or reduce a pathological condition) to provide therapy for a disease or condition. The preferred dosage of therapeutic agent to be administered is likely to depend on such variables as the severity of the cancer, the overall health status of the particular patient, the formulation of the compound excipients, and its route of administration.

Therapeutic Uses of the Compositions According to the Invention

The pharmaceutical compositions according to the present invention may be used for the treatment or amelioration of a disease in a mammal. Conditions that can be treated or prevented with the present pharmaceutical compositions include prevention, and treatment of patients cancer can preferably be subjected to therapeutic treatment with a pharmaceutical composition according to the present invention.

One embodiment of the present invention is a method of preventing, treating or ameliorating one or more symptoms associated with cancer in a mammal, comprising administering an effective amount of an anti-EGFR recombinant antibody composition of the present invention to said mammal.

A further embodiment of the present invention is the use of an anti-EGFR recombinant antibody composition of the present invention for the preparation of a composition for the treatment, amelioration or prevention of one or more symptoms associated with cancer in a mammal.

Preferably, the mammal in the embodiments above is a human, domestic animal or a pet.

Antibodies in accordance with the present invention are indicated in the treatment of certain solid tumours. Based upon a number of factors, including EGFR expression levels, among others, the following tumour types appear to present preferred indications: breast, ovarian, colon, rectum, prostate, bladder, pancreas, head and neck, and non-small cell lung cancer. In connection with each of these indications, three clinical pathways appear to offer distinct potentials for clinical success:

Adjunctive therapy: In adjunctive therapy, patients would be treated with antibodies in accordance with the present invention in combination with a chemotherapeutic or antineoplastic agent and/or radiation therapy. The primary targets listed above will be treated under protocol by the addition of antibodies of the invention to standard first and second line therapy. Protocol designs will address effectiveness as assessed by reduction in tumour mass as well as the ability to reduce usual doses of standard chemotherapy. These dosage reductions will allow additional and/or prolonged therapy by reducing dose-related toxicity of the chemotherapeutic agent. Prior art anti-EGFR antibodies have been, or are being, utilized in several adjunctive clinical trials in combination with the chemotherapeutic or antineoplastic agents adriamycin (Erbitux: advanced prostate carcinoma), cisplatin (Exbitux: advanced head and neck and lung carcinomas), taxol (Erbitux: breast cancer), and doxorubicin (Erbitux).

The invention provides pharmaceutical articles comprising an antibody composition of the invention and at least one compound capable inducing differentiation of cancer cells as a combination for the simultaneous, separate or successive administration in cancer therapy. By combining the antibody compositions of the invention with agents known to induce terminal differentiation of cancer cells, the effect can be improved further.

The at least one compound may be selected from the group consisting of retinoic acid, trans-retinoic acids, cis-retinoic acids, phenylbutyrate, nerve growth factor, dimethyl sulfoxide, active form vitamin D(3), peroxisome proliferator-activated receptorgamma, 12-O-tetradecanoylphorbol 13-acetate, hexamethylene-bis-acetamide, transforming growth factor-beta, butyric acid, cyclic AMP, and vesnarinone. Preferably the compound is selected from the group consisting of retinoic acid, phenylbutyrate, all-trans-retinoic acid, active form vitamin D.

Pharmaceutical articles comprising an antibody composition of the invention and at least one chemotherapeutic or antineoplastic compound may be used as a combination for the simultaneous, separate or successive administration in cancer therapy. The chemotherapeutic compound may be selected from the group consisting of adriamycin, cisplatin, taxol, doxorubicin, topotecan, fluoropyrimidine, oxaliplatin, and irinotecan.

Monotherapy: In connection with the use of the antibodies in accordance with the present invention in monotherapy of tumours, the antibodies may be administered to patients without a chemotherapeutic or antineoplastic agent. Preclinical results generated through use of antibodies in accordance with the present invention and discussed herein have demonstrated positive results as a stand-alone therapy.

Imaging Agent: Through binding a radionuclide (e.g., yttrium ($^{90}$Y)) to antibodies in accordance with the present invention, it is expected that radiolabeled antibodies in accordance with the present invention can be utilised as a diagnostic, imaging agent. In such a role, antibodies of the invention will localize to both solid tumours, as well as, metastatic lesions of cells expressing EGFR. In connection with the use of the antibodies of the invention as imaging agents, the antibodies can be used in assisting surgical treatment of solid tumors, as both a pre-surgical screen as well as a post operative follow to determine what tumour remain and/or returns. An ($^{111}$In)-Erbitux antibody has been used as an imaging agent in a Phase I human clinical trial in patients having unresectable squamous cell lung carcinomas. (Divgi et al. J. Natl. Cancer Inst. 83:97-104 (1991). Patients were followed with standard anterior and posterior gamma camera. Preliminary data indicated that all primary lesions and large metastatic lesions were identified, while only one-half of small metastatic lesions (under 1 cm) were detected.

Tyrosine kinase inhibitors (TKIs) are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site. Several TKIs in clinical development including Gefitinib (Iressa, ZD1839), Erlobtinib (Tarceva, OSI-774), Lapatinib, (Tykerb, GW572016), Canertinib (CI-1033), EKB-569 and PKI-166 are targeting the EGFR. Combination treatment of TKIs and anti-EGFR has shown to be beneficial both in vivo and in vitro against EGFR-dependent cancer cells. Pharmaceutical articles comprising an antibody composition of the invention and at least one TKI targeting EGFR may be used as a combination for the simultaneous, separate or successive administration in cancer therapy. Further small molecule inhibitors include: Sorafinib (raf and multiple RTKs), Sunitinib (Multiple RTKs), Temsirolimus (mTOR), RAD001 (mTOR), and AZD217 (VEGFR2).

In other embodiments, the antibody compositions of the present invention are used in combination with other antibody therapeutics. Examples of these include e.g. antibodies against HER2 (Herceptin) and VEGF (avastin). In yet other embodiments, the antibody compositions of the present invention are used in combination with an agent known to stimulate cells of the immune system, such combination treatment leading to enhanced immune-mediated enhancement of the efficacy of the antibody compositions of the invention. Examples of such immune-stimulating agents include but are not limited to recombinant interleukins (e.g. IL-21 and IL-2).

Dose and Route of Administration

While specific dosing for antibodies in accordance with the invention has not yet been determined, certain dosing considerations can be determined through comparison with the similar product (ImClone C225 (Erbitux)) that has been approved. The C225 antibody is typically being administered with doses in the range of 5 to 400 mg/m$^2$, with the lower doses used only in connection with the safety studies. Accordingly, we would expect that dosing in patients with antibodies in accordance with the invention can be in this range or lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

The prescribing information available for Erbitux (Cetuximab) includes an initial 120 minutes IV infusion of 400 mg/m$^2$, followed by weekly 60 min infusions of 250 mg/m$^2$. These dosages are recommended for stand alone treatment as well as for combination with radiation therapy. For Vectibix (panitumumab) the recommended dose is 6 mg/kg administered over 60 minutes every 14 days.

The expected clinical dosage of Genmab's HuMaxEGFr antibody (zumutumumab) is an initial dose of 8 mg/kg of HuMax-EGFr, followed by weekly infusions of a maintenance dose until disease progression. The maintenance dose will be adjusted as necessary until the patient develops a dose limiting skin rash, up to a maximum dose of 16 mg/kg of HuMax-EGFr (Dosages for pivotal Phase III study, available from Genmab's product description).

The clinical dosing of antibody compositions of the present invention are likely to be limited by the extent of skin rash as observed with monoclonal anti-EGFR antibodies (Erbitux and Vectibix) used in the clinic today. Data from a six week toxicology study in Cynomolgus monkeys showed no signs of skin rash when an antibody composition of the invention was administered at a dose equivalent to what is used for treatment with one of the monoclonal antibodies used in the clinic (example 20). Thus, antibody compositions of the invention can be administrated intravenously and with a weekly dosing of 250 mg/m$^2$ which translates into 7.5 mg/kg for a human with body surface of 1.8 m$^2$ and 60 kg body weight. Furthermore, an initial loading dose of 400 mg/m$^2$ (translates into 12 mg/kg for a human with body surface of 1.8 m$^2$ and 60 kg body weight) may be given before the subsequent weekly dosing.

Three distinct delivery approaches are expected to be useful for delivery of the antibodies in accordance with the invention. Conventional intravenous delivery will presumably be the standard delivery technique for the majority of tumours. However, in connection with tumours in the peritoneal cavity, such as tumours of the ovaries, biliary duct, other ducts, and the like, intraperitoneal administration may prove favourable for obtaining high dose of antibody at the tumour and to minimize antibody clearance. In a similar manner certain solid tumours possess vasculature that is appropriate for regional perfusion. Regional perfusion will allow the obtention of a high dose of the antibody at the site of a tumour and will minimise short term clearance of the antibody.

As with any protein or antibody infusion based therapeutic, safety concerns are related primarily to (i) cytokine release syndrome, i.e., hypotension, fever, shaking, chills, (ii) the development of an immunogenic response to the material (i.e., development of human antibodies by the patient to the antibody therapeutic, or HAHA or HACA response), and (iii) toxicity to normal cells that express the EGF receptor, e.g., hepatocytes which express EGFR. Standard tests and follow up will be utilised to monitor each of these safety concerns. In particular, liver function will be monitored frequently during clinical trails in order to assess damage to the liver, if any.

Diagnostic Use

Another embodiment of the invention is directed to diagnostic kits. Kits according to the present invention comprise an anti-EGFR antibody composition prepared according to the invention which protein may be labeled with a detectable label or non-labeled for non-label detection. The kit may be used to identify individuals inflicted with cancer associated with overexpression of EGFR.

EXAMPLES

Example 1

Cloning of Anti-EGFR Antibodies

Immunizations

Female BALB/c, strain A, or C57B16 mice (8-10 weeks old) were used for immunizations by injections with different purified proteins in addition to EGFR overexpressing cells.

Commercially available EGFR proteins (R&D systems cat#1095-ER or Sigma #E3641) were used for some of the immunizations. For other of the immunizations recombinant human EGFR and EGFRvIII produced as fusion proteins were used consisting of the ECD of EGFR or EGFRvIII and human growth hormone (hGH), also including a Tobacco Etch Virus (TEV)-cleavage site in addition to a His-tag described in Example 10b. In some cases the ECD of EGFR was isolated by TEV-protease cleavage and subsequent purification on a Nickel column.

The human head-and-neck cancer cell line, HN5 (Easty D M, Easty G C, Carter R L, Monaghan P, Butler L J. Br J. Cancer. 1981 June; 43(6):772-85. Ten human carcinoma cell lines derived from squamous carcinomas of the head and neck.) expressing approximately 10$^7$ receptors/cell were used for cell based immunizations. Cells were cultured in DMEM medium supplemented with 10% FBS (Fetal Bovine Serum), 3 mM Glycerol, 5 mM Sodium Pyruvate and 1% Penicillin Streptomycin. Before each immunization the cells were washed in PBS, trypsinized with TrypLE and resuspended in growth medium. Subsequently the cell suspensions was washed twice in PBS by centrifugation at 250×g for 5 min, dislodging and resuspension in 15 ml sterile PBS.

Cells or antigen were diluted in PBS and then mixed 1:1 with Freund's Adjuvant. Adjuvant is used to enhance and modulate the immune response. For the first immunizations Complete Freund's Adjuvant (CFA) was used whereas Incomplete Freund's Adjuvant (IFA) was used for the subsequent immunizations. IFA is an oil-in-water emulsion composed of mineral oils and CFA is IFA to which heat-killed, dried *Mycobacterium* species are added. Both adjuvants have a depot effect. CFA gives rise to long-term persistence of the immune response and is used for the first immunizations to boost the immune response and IFA is used for subsequent immunizations. The emulsions were tested by adding a drop on the surface of a glass with water. If the drop remains as one drop, the emulsion is stable and the injections can be performed. Only stable emulsions were administered to mice.

Depending on the schedule (see Table 2), 25-100 µg antigen or $10^7$ cells were used for each injection. In total, mice received 4 injections. All mice were injected with either 300 µl or 200 µl emulsion. Depending on the schedule, injections were performed subcutaneously (s.c.), intraperitoneally (i.p.) or intravenous (i.v.).

At termination, the mice were sacrificed by cervical dislocation, and the spleens were removed and transferred to a 74 µm cell strainer (Corning#136350-3479). The cells were macerated through the filter, resuspended in cold RPMI 1640 with 10% FBS and centrifuged at 300×g for 5 minutes. The cell pellet was resuspended in RPMI 1640 with 1% FBS, filtered through a 50 µm syringe filter (BD# 340603) and collected by centrifugation. The cell pellet was cryopreserved after resuspension in FCS with 10% DMSO and frozen cells stored at −80° C. until FACS sorting.

FACS Sorting of Murine Plasma Cells

Figure 1:
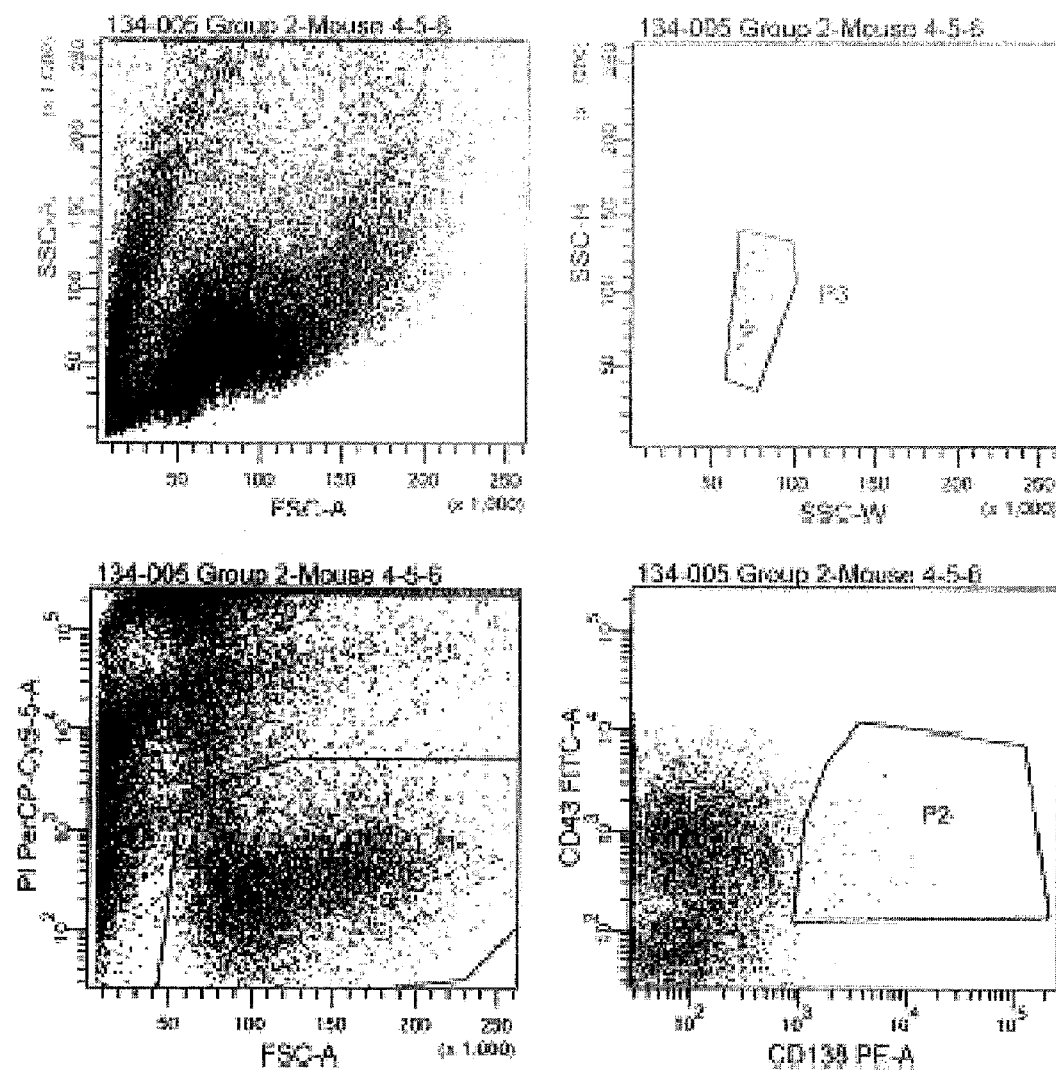
FIG. 1 Sorting of splenocytes (for details see Example 1). The following gates are made (depicted):
Gate 1: Live cells (FSC/Propidium Iodide plot). (Lower left panel)
Gate 2: Plasma cells are gated as CD43 pos/CD138 pos. (lower right panel)
Gate 3: doublet discrimination (upper right panel)

Vials with frozen splenocytes were thawed at 37° C. and transferred to 15 ml tube with ice still present. 10 ml Ice-cold RPMI, 10% FBS (foetal bovine serum) was drop-wise added to the tube while swirling. After one wash in 10 ml FACS PBS, 5 ml FCS PBS is added before filtering the cells through 50 µm Filcon. Cells were then pelleted and resuspended in 1 ml PBS with 2% FBS (final volume) and stained with anti-CD43-FITC and anti-CD138-PE according to the specific dilution to a final concentration of app. 5 µg/ml. Cells were incubated at 4° C. for 20 min in the dark. Subsequently, cells were washed 2 times with 2 ml FACS buffer. Up to 15 ml FACS PBS were added. Propidium Iodide (PI) was added at 1:100 (1 part PI to 100 parts FACS PBS buffer), and cells were subsequently sorted into 96 well PCR-plates, containing PCR reaction buffer (see below), and spun down for 2 min 400×g before the plates were frozen at −80° C. Plasma cells were gated as CD43-positive/CD-138 positive as shown in FIG. 1.

Linkage of Cognate $V_H$ and $V_L$ Pairs

Figure 2:
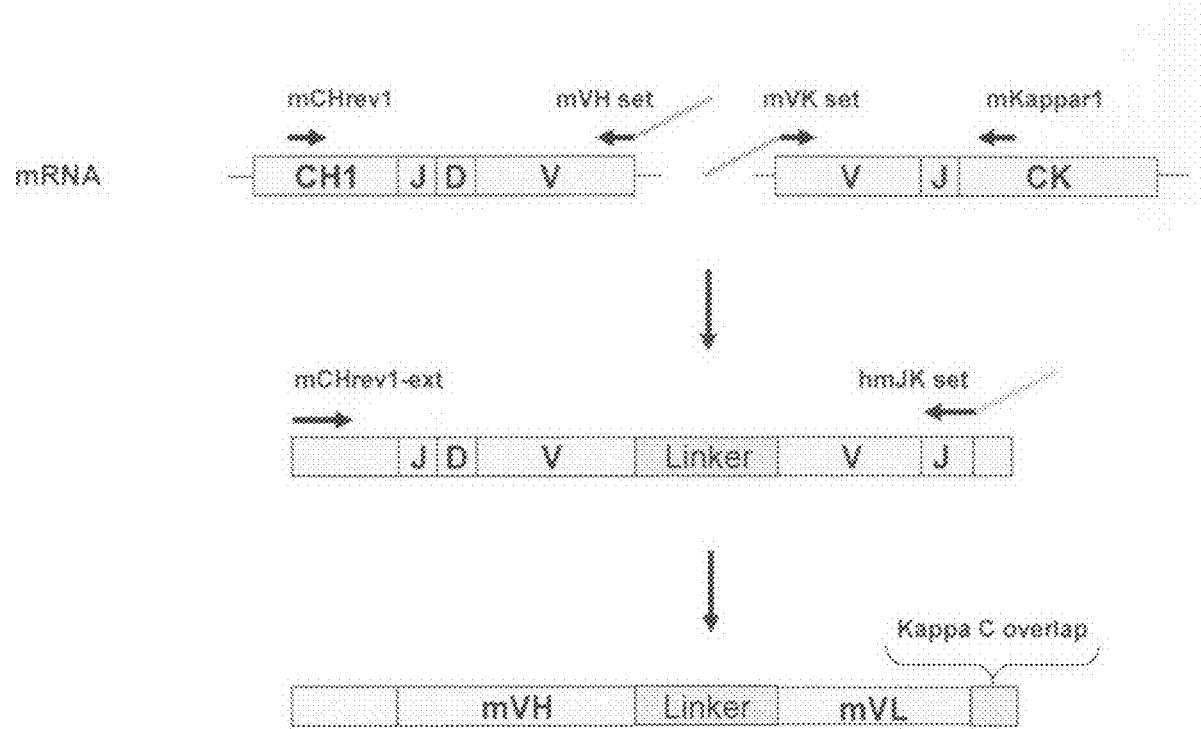
FIG. 2 Murine—mSymplex™ PCR. Multiplex overlap extension RT-PCR for the amplification and cognate linkage of heavy and light chain antibody genes from a single cell. For details refer to Example 1.

The linkage of $V_H$ and $V_L$ coding sequences was performed on the single cells gated as plasma cells, facilitating cognate pairing of the $V_H$ and $V_L$ coding sequences. The procedure utilized a two step PCR procedure based on a one-step multiplex overlap-extension RT-PCR followed by a nested PCR. The primer mixes used in the present example only amplify Kappa light chains. Primers capable of amplifying Lambda light chains could, however, be added to the multiplex primer mix and nested PCR primer mix if desired. If Lambda primers are added, the sorting procedure should be adapted such that Lambda positive cells are not excluded. The principle for linkage of cognate $V_H$ and $V_L$ sequences is illustrated in FIG. 2.

The 96-well PCR plates produced were thawed and the sorted cells served as template for the multiplex overlap-extension RT-PCR. The sorting buffer added to each well before the single-cell sorting contained reaction buffer (OneStep RT-PCR Buffer; Qiagen), primers for RT-PCR (see Table 3) and RNase inhibitor (RNasin, Promega). This was supplemented with OneStep RT-PCR Enzyme Mix (25× dilution; Qiagen) and dNTP mix (200 µM each) to obtain the given final concentration in a 20-0 reaction volume. The plates were incubated for 30 min at 55° C. to allow for reverse transcription of the RNA from each cell. Following the RT, the plates were subjected to the following PCR cycle: 10 min at 94° C., 35×(40 sec at 94° C., 40 sec at 60° C., 5 min at 72° C.), 10 min at 72° C.

The PCR reactions were performed in H20BIT Thermal cycler with a Peel Seal Basket for 24 96-well plates (ABgene) to facilitate a high-throughput. The PCR plates were stored at −20° C. after cycling.

For the nested PCR step, 96-well PCR plates were prepared with the following mixture in each well (20-µl reactions) to obtain the given final concentration: 1× FastStart buffer (Roche), dNTP mix (200 µM each), nested primer mix (see Table 4), Phusion DNA Polymerase (0.08 U; Finnzymes) and FastStart High Fidelity Enzyme Blend (0.8 U; Roche). As template for the nested PCR, 1 µl was transferred from the multiplex overlap-extension PCR reactions. The nested PCR plates were subjected to the following thermocyling: 35×(30 sec at 95° C., 30 sec at 60° C., 90 sec at 72° C.), 10 min at 72° C.

Randomly selected reactions were analyzed on a 1% agarose gel to verify the presence of an overlap-extension fragment of approximately 890 basepairs (bp).

The plates were stored at −20° C. until further processing of the PCR fragments.

Figure 3:
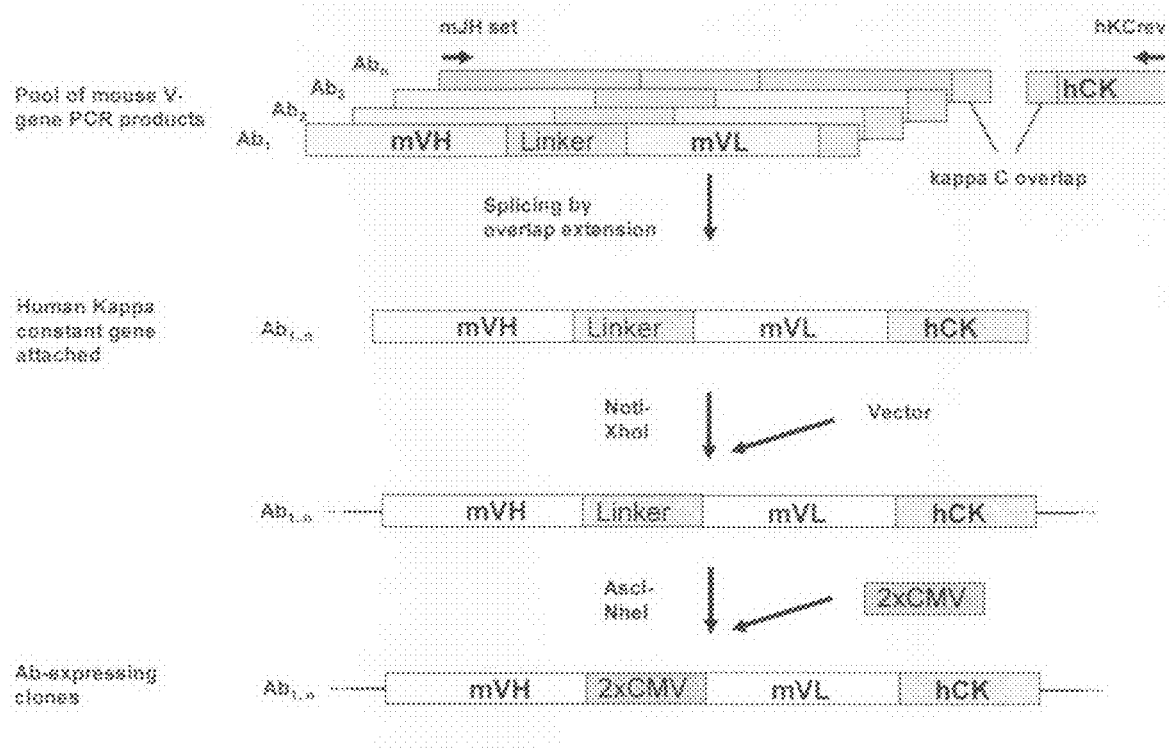
FIG. 3 Murine repertoire cloning. A pool of mSymplex™ PCR products encoding VH/VL gene pairs from single plasma cells were spliced to the gene encoding human kappa constant light chain by splicing by overlap extension. The pool of genes, encoding complete human-mouse chimeric antibodies, was inserted in an expression vector followed by an insertion of a bi-directional promoter cassette (2xCMV).

The repertoires of linked $V_H$ and $V_L$ coding pairs from the nested PCR were pooled, without mixing pairs from different donors, and were purified by preparative 1% agarose gel electrophoresis. The human kappa constant light chain encoding sequence was spliced by overlap extension to the $V_L$ coding region of the pooled PCR products of linked $V_H$ and $V_L$ coding pairs (FIG. 3). The human kappa constant light chain encoding sequence was amplified from a plasmid containing the coding sequence of a human antibody with a kappa light chain in a reaction containing: Phusion Enzyme (2 U; Finnzymes), 1× Phusion buffer, dNTP mix (200 µM each), hKCforw-v2 primer and Kappa3' primer (Table 5), and plasmid template pLL138 (10 ng/µl) in a total volume of 50 µl. The reaction was subjected to the following thermocycling: 25×(30 sec at 95° C., 30 sec at 55° C., 45 sec at 72° C.), 10 min at 72° C. The resulting PCR fragment was purified by preparative 1% agarose gel electrophoresis.

The purified pooled PCR fragments of each repertoire was spliced to the amplified and purified PCR fragment of the human kappa constant encoding region (Appendix 2) by the following splicing by overlap extension PCR (50 µl total volume) containing: human kappa constant encoding region fragment (1.4 ng/µl), purified pooled PCR fragment (1.4 ng/µl), Phusion DNA Polymerase (0.5 U; Finnzymes) and FastStart High Fidelity Enzyme Blend (0.2 U; Roche), 1× FastStart buffer (Roche), dNTP mix (200 µM each), mhKCrev primer and mJH set primers (see Table 5). The reaction was subjected to the following thermocycling: 2 min at 95° C., 25×(30 sec at 95° C., 30 sec at 55° C., 1 min at 72° C.), 10 min at 72° C. The resulting PCR fragment (approx. 1070 bp) was purified by preparative 1% agarose gel electrophoresis.

Insertion of Cognate $V_H$ and $V_L$ Coding Pairs into a Screening Vector

In order to identify antibodies with binding specificity to EGFR, the $V_H$ and $V_L$ coding sequences obtained were expressed as full-length antibodies. This involved insertion of the repertoire of $V_H$ and $V_L$ coding pairs into an expression vector and transfection into a host cell.

A two-step cloning procedure was employed for generation of a repertoire of expression vectors containing the linked $V_H$ and $V_L$ coding pairs. Statistically, if the repertoire of expression vectors contains ten times as many recombinant plasmids as the number of cognate paired $V_H$ and $V_L$ PCR products used for generation of the screening repertoire, there is 99% likelihood that all unique gene pairs are represented. Thus, if 400 overlap-extension V-gene fragments were obtained, a repertoire of at least 4000 clones was generated for screening.

Briefly, the purified PCR product of the repertoires of linked $V_H$ and $V_L$ coding pairs, spliced to the human kappa constant coding region, were cleaved with XhoI and NotI DNA endonucleases at the recognition sites introduced into the termini of PCR products. The cleaved and purified fragments were ligated into an XhoI/NotI digested mammalian IgG expression vector, OO-VP-002 (FIG. 4) by standard ligation procedures. The ligation mix was electroporated into *E. coli* and added to 2×YT plates containing the appropriate antibiotic and incubated at 37° C. over night. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional mammalian promoter-leader fragment was inserted into the AscI and NheI restriction sites by standard ligation procedures. The ligated vector was amplified in *E. coli* and the plasmid was purified using standard methods. The generated repertoire of screening vectors was transformed into *E. coli* by conventional procedures. Colonies obtained were consolidated into 384-well master plates and stored. The number of arrayed colonies exceeded the number of input PCR products by at least 3-fold, thus giving 95% percent likelihood for presence of all unique V-gene pairs obtained.

Screening for Binding to EGFR Extracellular Domain

In general, the screening was made as a two step procedure. The antibody-libraries were screened for reactivity to recombinant EGFR protein in ELISA after which FMAT (FLISA) was used as a cell based approach, with the NR6 wtEGFR cell line, for detection of EGFR-antibodies binding to cell-surface expressed EGFR. For the 101 and 108/109 libraries (Table 2) the ELISA was performed with recombinant EGFR representing the extracellular domain of the EGFR.

Briefly for the ELISA, Nunc maxisorb plates (cat no 464718) were coated with 1 µg/ml protein (in house produced), diluted in PBS at 4 C over night. Prior to blocking in 50 µl 2%-Milk-PBS-T the plates were washed once with PBS+0.05% Tween 20 (PBS-T). The plates were washed once with PBS-T, 20 µl of 2%-milk-PBS-T and 5 µl supernatants from FreeStyle CHO-S transfectants (see below) were added and incubated for 1½ hour at RT after which the plates were washed once with PBS-T 20 µl per well. Secondary antibody (HRP-Goat-anti-human IgG, Jackson, cat no 109-035-097) diluted 1:10000 in 2% milk-PBS-T was added to detect the antibodies bound to the wells and incubated for 1 hour at Room Temperature. The plates were washed once in PBS-T before addition of 25 µl substrate (Kem-en-tec Diagnostics, cat no 4390) that was incubated for 5 min. 25 µl 1M sulfuric acid was added after the incubation to stop the reaction. Specific signal was detected on an ELISA reader at 450 nm.

For the cell based FMAT detection of anti-EGFR antibodies, SKBR-3 (ATCC #HTB-30) or NR6 wtEGFR (Welsh et al, 1991, J Cell Biol, 114, 3, 533-543) cells were kept in growth medium as described. The cells were counted and diluted to 125,000 cells/ml with the Alexa-647 conjugated goat-anti-human IgG (H-L) antibody (Molecular probes No. A21445, lot no. 34686A) diluted 1:40,000. A total of 20 µl of this suspension was transferred to 384 well clear bottom Nunc plates. Subsequently 10 µl transfection supernatant was added to the cells. The FMAT signal from the reaction was measured after 6-10 hour of incubation.

The data from the screening indicates that 221 (4.8%) of the total clones were positive in the ELISA. 93 (2.0%) of those clones were also positive in FMAT. In total 220 (4.8%) of the clones were positive in the FMAT and among those 127 (220-93) uniquely positive for the cell surface antigen. The 111 library was screened in a similar fashion, but since the immunization procedure was made to generate antibodies specific for the deletion mutant EGFR receptor EGFRvIII, the ELISA screenings included assays to detect both wild-type EGFR and EGFRvIII. Seven clones were identified to be specific for the EGFRvIII in the ELISA and interestingly those clones were negative for staining of wtEGFR expressing cells in the FMAT. 13 clones were identified to be positive for the wtEGFR in FMAT and ELISA but not for the EGFRvIII, which were unique for this library compared to the 101 and 108/109 libraries. All the ELISA positive clones were selected for further analysis.

Sequence Analysis and Clone Selection

The clones identified as EGFR-specific in ELISA were retrieved from the original master plates (384-well format) and consolidated into new plates. DNA was isolated from the clones and submitted for DNA sequencing of the V-genes. The sequences were aligned and all the unique clones were selected. Multiple alignments of obtained sequences revealed the uniqueness of each particular clone and allowed for identification of unique antibodies. Following sequence analysis of 220 clones, 70 genetically distinct antibody sequence clusters were identified. Each cluster of related sequences have probably been derived through somatic hypermutations of a common precursor clone. Overall, one to two clones from each cluster was chosen for validation of sequence and specificity. Sequences of selected antibody variable sequences are shown in Appendix 1. The nucleotide sequences include restriction sites in both terminals. Consequently, the corresponding translated amino acid sequences (using the third reading frame of the DNA sequence) include in the N-terminal, two amino acids which do not form part of the VH and VL sequences according to the IMGT definition (Lefranc et al (2003) IMGT unique numbering for immunoglobulin and T cell receptor variable domains and Ig superfamily V-like domains. Dev. Comp Immunol 27, 55-77). The VL sequences shown all include the same human Kappa Constant region, which starts with amino acids—TVAAP—and ends at the C-terminal—NRGEC. For the purposes of the present invention the term VL sequence when referring to a specific antibody excludes the Kappa Constant region and the two N-terminal amino acids (LA-). The term VH sequence when referring to a specific antibody excludes the two N-terminal amino acids (RA-).

Sequence and Specificity Validation

In order to validate the antibody encoding clones, DNA plasmid was prepared and transfection of FreeStyle CHO-S cells (Invitrogen) in 2-ml scale was performed for expression. The supernatant were harvested 96 hours after transfection. Expression levels were estimated with standard anti-IgG ELISA, and the specificity was determined by EGFR- and EGFRvIII-specific ELISA. 85% of the clones were shown to have the correct specificity and sequence.

Screening for Anti-Proliferative Effects

Cellular damage will inevitably result in loss of the ability of the cell to maintain and provide energy for metabolic cell function and growth. Metabolic activity assays are based on this premise. Usually they measure mitochondrial activity. The Cell Proliferation Reagent WST-1 (Roche Cat. No. 11 644 807 001) is a ready-to-use substrate which measures the metabolic activity of viable cells. It is then assumed that the metabolic activity correlates with the number of viable cells. In this example the WST-1 assay was used to measure the number of metabolically active cells after treatment with cell culture supernatants containing different anti-EGFR antibodies.

Prior to performing the WST-1 assay different volumes of 2-ml supernatants (0, 10, 25, 50 and 150 µl) were transferred to appropriate wells in a 96 well plate.

HN5 cells were then washed with 1×PBS and detached by trypsination with 3 ml trypsin solution. 17 ml of complete media were then added and the cells spun down at 300×g (1200 rcf) for 5 min. The supernatant was removed and cells re-suspended in DMEM+0.5% FBS. Cells were counted and their concentration adjusted and 1500 cells were added to the wells with supernatants so that each well contained 200 µl media in total. The plates were incubated for 4 days in a humidified incubator at 37° C. Then 20 µl WST-1 reagent was added pr. well and the plates incubated for one hour at 37° C. Plates were then transferred to a orbital plate shaker and left another hour. The absorbance was measured at 450 and 620 nm (reference wavelength) on an ELISA reader. The difference in the levels of metabolically active cells (MAC) was calculated as percent of the control supernatants as follows:

$$\% \ MAC = \left(1 - \frac{(OD\ exp. - ODmedia)}{(ODuntreat. - ODmedia)}\right) \times 100$$

These values were then used as the basis for a supervised hierarchical cluster analysis (clustered based on reactivity in ELISA) performed using the free software Cluster and TreeView.

Figure 5:
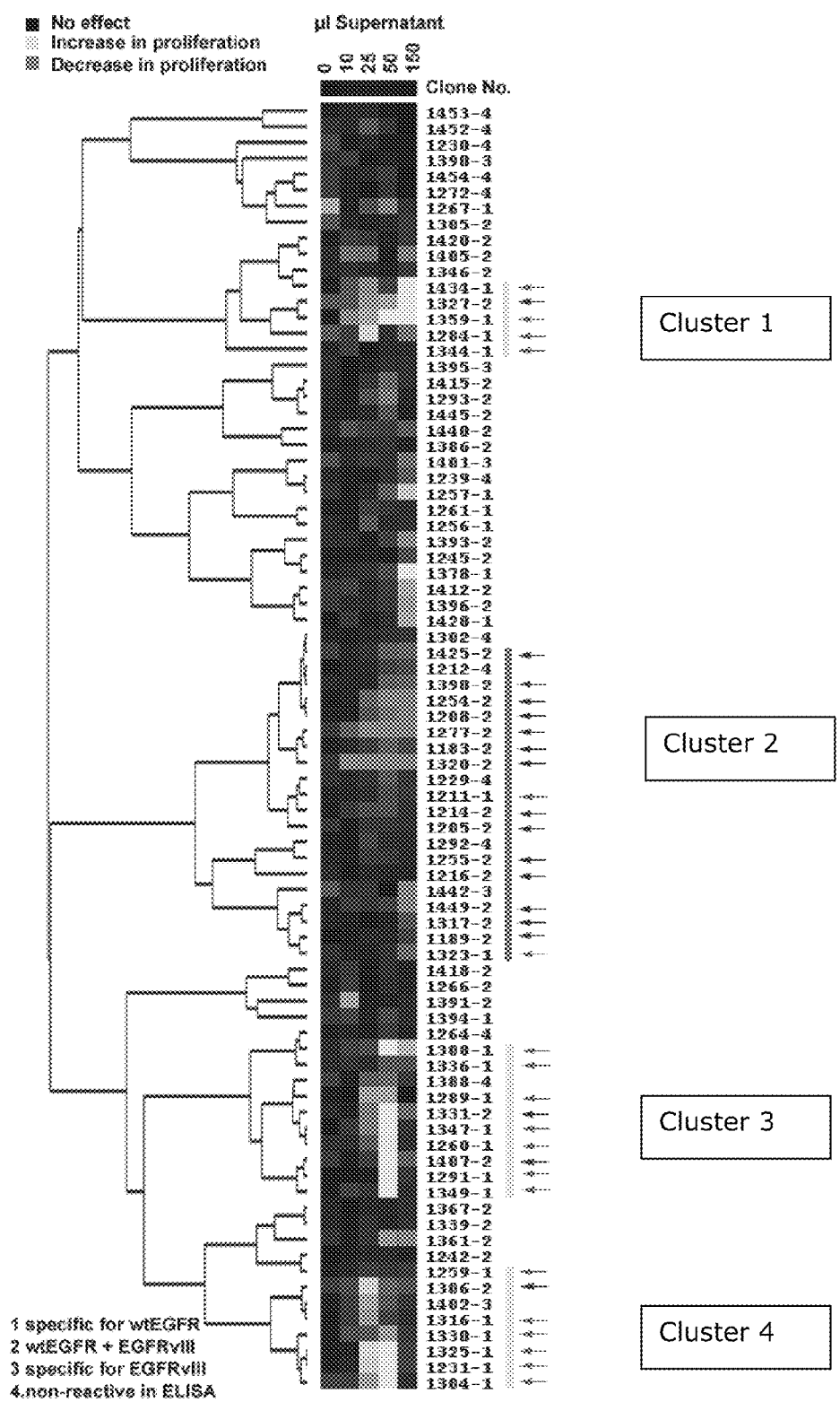
FIG. 5 Cluster analysis of the absorbance difference at 450-620 nm. Supernatants are clustered by reactivity as indicated by the number (1 to 4) following the clone no. Dark grey indicates a decrease in the number of metabolically active cells, whereas light grey indicate an increase in the number of metabolically active cells. Black indicates supernatants with no effect on the number of metabolically active cells.

It is preferable to be able to screen for functional antibodies at an early stage in the antibody selection process. The culture supernatants from 83 2-ml transfections were used to screen for growth inhibitory functions in a proliferation assay performed using HN5 cells in 0.5% FBS. Results were visualized by simple hierarchical cluster analysis. As can be seen in the cluster analysis (FIG. 5) a number of supernatants were found to decrease the number of metabolically active HN5 cells (dark grey) in a concentration dependent manner (Cluster 2). Similarly, some supernatants increased the number of metabolically active HN5 cells (light grey) in a concentration dependent manner (Clusters 1, 3 and 4). An interesting observation was that supernatants, which decreased the number of metabolically active HN5 cells, had reactivity 2 (black arrows) whereas supernatants which increased the number of metabolically active HN5 cells had reactivity 1 (grey arrows). Supernatants with reactivity 2 were positive in both wtEGFR and EGFRvIII ELISAs, while supernatants with reactivity 1 only had reactivity towards wtEGFR. Thus, such analyses may provide relationships between antibody reactivity in ELISA and functionality in cellular assays.

Clone Repair

When using a multiplex PCR approach, a certain degree of intra- and inter-V-gene family cross-priming is expected due to primer degeneracy and the high degree of homology. The cross-priming introduces amino acids that are not naturally occurring in the immunoglobulin framework with several potential consequences, e.g. structural changes and increased immunogenicity, all resulting in a decreased therapeutic activity.

In order to eliminate these drawbacks and to ensure that selected clones mirror the natural humoral immune response, such cross-priming mutations were corrected in a process called clone repair.

In the first step of the clone repair procedure, the $V_H$ sequence was PCR amplified with a primer set containing the sequence corresponding to the $V_H$-gene the clone of interest originated from, thereby correcting any mutations introduced by cross-priming. The PCR fragment was digested with XhoI and AscI and ligated back into the XhoI/AscI digested mammalian expression vector (FIG. 4) using conventional ligation procedures. The ligated vector was amplified in *E. coli* and the plasmid was purified by standard methods. The $V_H$ sequence was sequenced to verify the correction and the vector was digested with NheI/NotI to prepare it for insertion of the light chain.

In the second step the complete light chain was PCR amplified with a primer set containing the sequence corresponding to the $V_L$-gene the clone of interest originated from, thereby correcting any mutations introduced by cross-priming. The PCR fragment was digested with NheI/NotI and ligated into the $V_H$ containing vector prepared above. The ligation product was amplified in *E. coli* and the plasmid was purified by standard methods. Subsequently, the light chain was sequenced to verify the correction.

In the case where the Kappa constant region of a selected clone contains mutations, introduced during the amplification of the genes, it is replaced by an unmutated constant region. This is done in an overlap PCR where the repaired $V_L$-gene (amplified without the constant region) was fused to a constant region with correct sequence (obtained in a separate PCR). The whole sequence is amplified and cloned into the $V_H$ containing vector as described above and the repaired light chain is sequenced to verify the correction.

TABLE 2

Immunization schedules used to generate starting material for anti-EGFR cloning

| Schedule, Mouse group | Strain | Injection 1 | Injection 2 | Injection 3 | Injection 4 | Termination |
|---|---|---|---|---|---|---|
| 101 | Balb/c | Day 1 25 µg rhEGFR (R&D systems | Day 35 25 µg rhGH– EGFR | Day 56 25 µg rhEGFR* | Day 70 25 µg rhEGFR* | Day 73 |

TABLE 2-continued

Immunization schedules used to generate starting material for anti-EGFR cloning

| Schedule, Mouse group | Strain | Injection 1 | Injection 2 | Injection 3 | Injection 4 | Termination |
|---|---|---|---|---|---|---|
| 108 | Balb/c | 1095-ER) CFA s.c. Day 1 1 × 10⁷ HN5 cells CFA i.p. | (Symphogen) IFA s.c Day 28 25 µg rhEGFR* (Symphogen) IFA s.c. | (Symphogen) IFA s.c Day 42 1 × 10⁷ HN5 cells IFA i.p. | (Symphogen) IFA s.c Day 56 25 µg rhEGFR*, (Symphogen) IFA s.c. | Day 59 |
| 109 | Balb/c | Day 1 1 × 10⁷ HN5 cells CFA i.p. | Day 28 25 µg rhEGFR* (Symphogen) IFA s.c. | Day 42 1 × 10⁷ HN5 cells IFA i.p. | Day 56 25 µg rhEGFR* (Symphogen) PBS i.v. | Day 59 |
| 111 | Balb/c | Day 1 25 µg rhEGFR* (Symphogen) CFA s.c. | Day 28 25 µg rhEGFR+ rhEGFRvIII** (Symphogen) IFA s.c. | Day 42 25 µg rhEGFR+ rhEGFRvIII** (Symphogen) IFA s.c. | Day 56 25 µg rhEGFR+ rhEGFRvIII** (Symphogen) IFA s.c. | Day 59 |
| 118 | Balb/c | Day 1 1 × 10⁷ HN5 cells CFA i.p. | Day 29 100 µg rhGH-EGFR (Symphogen) IFA s.c. | Day 44 1 × 10⁷ HN5 cells IFA i.p. | Day 58 25 µg rhEGFR, (Sigma E3641) IFA s.c. | Day 61 |
| 119 | C57B | Day 1 1 × 10⁷ HN5 cells CFA i.p. | Day 29 100 µg rhGH-EGFR (Symphogen) IFA s.c. | Day 44 1 × 10⁷ HN5 cells IFA i.p. | Day 58 25 µg rhEGFR, (Sigma E3641) IFA s.c. | Day 61 |

TABLE 3

RT-PCR multiplex overlap-extension primer mix

| Primer name | Conc. (nM) | Sequence | SEQ ID |
|---|---|---|---|
| mHCrev | 0.2 | GACSGATGGGCCCTTGGTGG | 1 |
| mKappa | 0.2 | GCTGTAGGTGCTGTCTTTGC | 2 |
| mVH | | | |
| mVH A | 0.04 | TATTCCCATGGCGCGCCSAGGTCCARCTGCARCAGYCTG | 3 |
| mVH B | 0.04 | TATTCCCATGGCGCGCCGARGTGMAGCTKGTKGAGTC | 4 |
| mVH C | 0.04 | TATTCCCATGGCGCGCCSAGGTGCAGCTKMAGGAGTC | 5 |
| mVH 8 | 0.04 | TATTCCCATGGCGCGCCCAGGTTACTCTGAAAGAGTC | 6 |
| mVH 9 | 0.04 | TATTCCCATGGCGCGCCCAGATCCAGTTGGTGCAGTCTG | 7 |
| mVK | | | |
| mVK D | 0.04 | GGCGCGCCATGGGAATAGCTAGCCGAYATCCAGATGACHCARWCT | 8 |
| mVK E | 0.04 | GGCGCGCCATGGGAATAGCTAGCCRACATTGTGMTGACHCAGTC | 9 |
| mVK F | 0.04 | GGCGCGCCATGGGAATAGCTAGCCSAMATTGTKCTSACCCARTCTC | 10 |
| mVK 1- | 0.04 | GGCGCGCCATGGGAATAGCTAGCCGATRTTGTGATGACBCARRCT | 11 |

W = A/T, R = A/G, S = G/C, Y = C/T, K = G/T, M = A/C, H = ACT, B = GCT; Conc. - final concentration.

TABLE 4

Nested primer set

| Primer name | Conc. (nM) | Sequence | SEQ ID |
|---|---|---|---|
| mHCrev | 0.2 | GGACAGGGMTCCAKAGTTCCADKT | 16 |
| hmJK | | | |
| hmJK1- | 0.2 | GACAGATGGTGCAGCCACAGTTCGTTTGATTTCCAGCTTGGTG | 17 |
| hmJK2- | 0.2 | GACAGATGGTGCAGCCACAGTTCGTTTTATTTCCAGCTTGGTC | 18 |
| hmJK4- | 0.2 | GACAGATGGTGCAGCCACAGTTCGTTTTATTTCCAACTTTGTC | 19 |
| hmJK5- | 0.2 | GACAGATGGTGCAGCCACAGTTCGTTTCAGCTCCAGCTTGGTC | 20 |

K = G/T, M = A/C,DAGT; Conc. final concentration.

TABLE 5

Kappa constant splicing primer set

| Primer | Conc. (nM) | Sequence | SEQ ID |
|---|---|---|---|
| Human kappa constant amplification | | | |
| hKCforw-v2 | 0.2 | GAACTGTGGCTGCACCATCTGTC | 21 |
| Kappa3' | 0.2 | ACCGCCTCCACCGGCGGCCGCTTATTAAC ACTCTCCCCTGTTG | 22 |
| Splicing by overlap extension | | | |
| mhKCrev | 0.2 | ACCGCCTCCACCGGGGGCCGCTTATTAAC ACTCTCCCCTGTTGAAGCTCTT | 23 |
| mJH set | | | |
| mJH1 | 0.2 | GGAGGCGCTCGAGACGGTGACCGTGGTCCC | 12 |
| mJH2 | 0.2 | GGAGGCGCTCGAGACTGTGAGAGTGGTGCC | 13 |
| mJH3 | 0.2 | GGAGGGGCTCGAGACAGTGACCAGAGTCCC | 14 |
| mJH4 | 0.2 | GGAGGCGCTCGAGACGGTGACTGAGGTTCC | 15 |

Example 2

Mammalian Production of Anti-EGFR Antibodies

The FreeStyle MAX CHO expression system (Invitrogen) was used for transient expression of anti-EGFR antibodies. Antibodies were expressed in 200-2000 ml volume.

Approximately 24 hours before transfection CHO-S cells were passaged to reach a cell concentration of $0.5 \times 10^6$ cells/ml. Plasmid (1.25 μg per ml cell culture media) was diluted into OptiPro serum-free medium and mixed with a solution of FreeStyle MAX Transfection reagent as recommended by the supplier. The transfection reagents were transferred to the cell culture and supernatant were harvested 6 days later.

The expressed antibodies were purified from the culture supernatant using an affinity chromatography step employing a Protein A-Sepharose column (MabSelect Sure, GE Health Care) for purification of IgG1 molecules. The antibodies were eluted from the column using 0.1 M Glycine, 2.7. The fractions containing antibodies, determined by absorbance measurements at 280 nm, were pooled and dialyzed against 5 mM sodium acetate, 150 mM NaCl, pH 5. The purified antibody samples were tested for the presence of endototoxin by the LAL assay.

Example 3

Determination of Epitope Specificities

Competition ELISA with Reference Antibodies

By using reference antibodies binding to known domains of EGFR as published in (J. R. Cochran et. al., JIM 2004: 287; 147-158), a competition ELISA was developed that could distinguish between the binding epitopes of anti-EGFR antibodies by incubation with a secondary reagent that was specific for the human Fc region of Anti-EGFR antibodies and exhibiting no cross reactivity to mouse or rat IgG Fc. The ELISA was adapted from the descriptions published in Ditzel et al, 1995, The Journal of Immunology, Vol 154, Issue 2 893-906.

An epitope blocking ELISA was performed by diluting full length EGFR receptor antigen to 0.5 μg/ml in PBS; and coating 50 μl/ELISA well overnight at 4° C. The next morning wells were washed twice with PBS-T and blocked for one hour with PBS-T-1% BSA at room temperature followed by wash twice in PBS-T. Next 25 μl murine or Rat reference mAbs were added to independent ELISA wells in a dilution known from previous experiments to give 200 times maximal antigen binding. After 15 min, 25 μl Anti-EGFR antibodies were added in a concentration of 2 μg/ml to wells preincubated with reference antibodies or wells containing 25 μl PBS. This gave a final concentration of 1 μg/ml Anti-EGFR antibody and 100 times maximal antigen binding of reference antibodies after mixture. Antibodies were incubated for 45 min. at room temperature after which wells were washed four times with PBS-T. A secondary Goat-anti-Human IgG HRP conjugate was diluted 1:3000, and 50 μl was added to each well followed by 30 min incubation at room temperature. Finally wells were washed four times with PBS-T and plates were developed by adding 50 μl/well TMB and read at 620 nm every 5-15-30 min. The degree of inhibition was calculated from the formula: % inhibition=(1−(OD competition/OD no competition (PBS)))×100.

ELISA reagents:
Coating buffer: 1×PBS; Gibco cat:20012-019
Antigens: Wild type full length EGFR purified from A431 cells; Sigma E3641
ELISA plate: NUNC Maxisorp; cat: 442-404
Blocking/Dilution buffer: 1% BSA in PBS-T (PBS-T-1% BSA)
Washing buffer: 1×PBS/0.05% Tween 20 (PBS-T)
Positive control: Erbitux (Merck KGaA, 64271 Darmstadt, Germany, Catalogue #: 018964; Cetuximab), Vectibix (Amgen Inc, One Amgen Center Drive, Thousand Oaks Calif. 91320-1799, USA, Cat # 3241400; Panitumumab)
Reference antibodies:
ICR10 (rat), Abcam, Ab231
199.12 (murine), Lab Vision Ab-11, MS-396-PABX
EGFR.1 (murine), Lab Vision Ab-3, MS-311-PABX
H11 (murine), Lab Vision Ab-5, MS-316-PABX
B1D8 (murine), Lab Vision Ab-16, MS-666-PABX
111.6 (murine), Lab Vision Ab-10, MS-378-PABX
225 (murine), Lab Vision Ab-2, MS-269-PABX
528 (murine), Lab Vision Ab-1, MS-268-PABX
Goat-anti-Human IgG HRP conjugate; Serotec, Star 106P TMB Plus; KemEnTec, cat #4390L
1 M $H_2SO_4$ The result of the competition ELISA is shown in FIGS. 6A and 6B. ELISA competition assays were employed to rank Anti-EGFR antibody supernatants according to the domain specificity of used reference antibodies raised against the EGFR extra cellular domain. Inhibition values from 50-100% were taken as an indication of significant competition between antibody pairs binding overlapping epitopes or epitopes in close proximity on the antigen, while inhibition values below 50% indicated that the recognized epitopes by the antibody pairs were not in close proximity resulting in decreased steric hindrance. The Anti-EGFR antibodies were found to bind a variety of epitopes on EGFR ECD including domain I, II & III. For some antibodies this analysis could not distinguish whether the specific mAb was directed against domain I or domain II. Such specificities were labeled domain I/II. Further some antibodies appeared to bind unique epitopes which could not be further deduced in the employed competition ELISA (E.g. clones 1229 & 1320, FIGS. 6A and 6B). It is possible that some of these antibodies are directed against domain IV for which we did not have any reference antibody reactivities. Interestingly the domain III antibodies could further be divided in four subgroups based on the different competition patterns obtained with the tested murine reference antibodies against this domain. Group I consisted of only mAb 992 which was found to compete for binding with reference antibodies Ab1 & Ab2. Group II consisted of mAbs 1024 & 1042 which were both derived from the same Ig rearrangement and consequently showed very close sequence homology at the DNA and amino acid level. These two antibodies were found to only compete for binding with Ab2. Group III consisted of mAbs 1030, 1208 & 1277 which competed for binding with reference antibodies Ab1, Ab5 & Ab10. Finally group IV consisted of mAb 1254, which competed for binding with all the used domain III reference antibodies Ab1, Ab2, Ab5 & Ab10.

Figure 7:
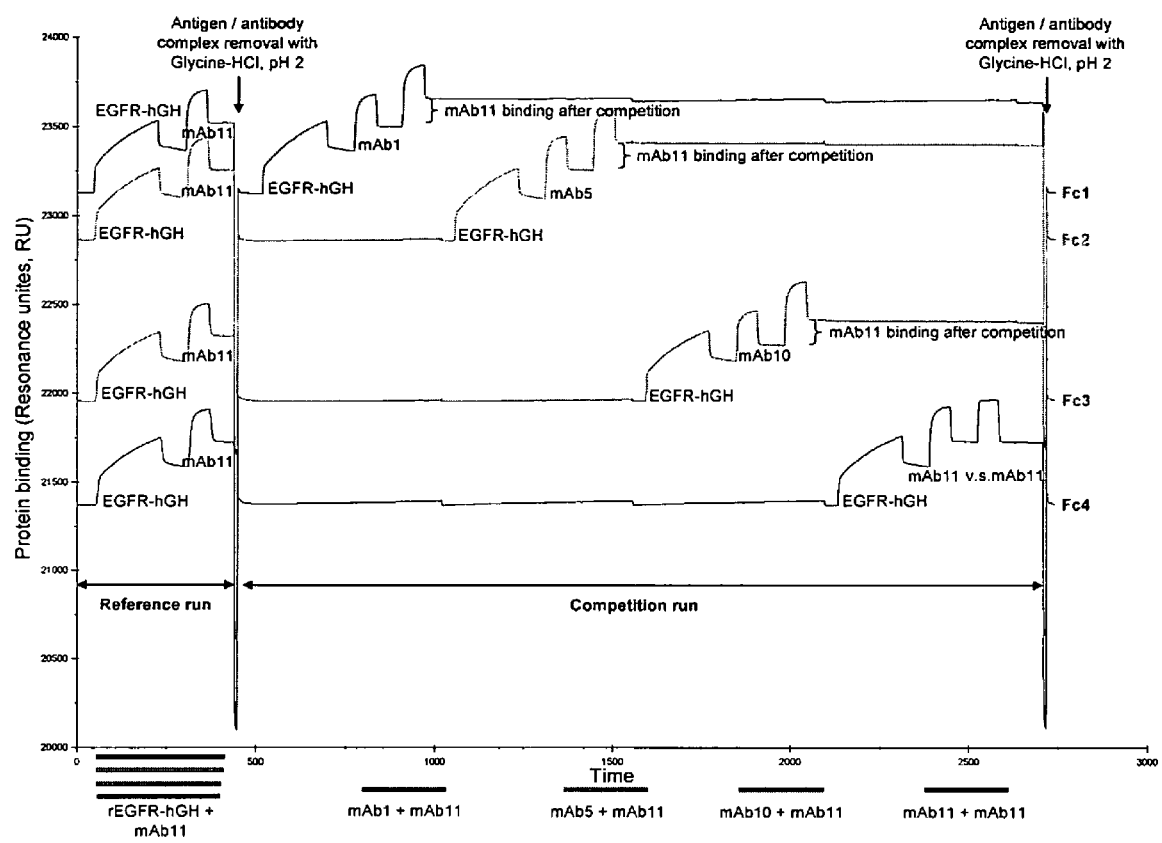
FIG. 7: Illustration of one epitope mapping cycle performed on the Biacore 3000 SPR machine, where a sample mAb is competed for binding to the extracellular domain of EGFR with four different reference antibodies.

Competition Analysis for Distinct Epitopes with Reference or Same Species Antibodies Using Surface Plasmon Resonance Technology SPR analysis was performed on a Biacore 3000 machine containing four flow cells. A CM5 Biacore chip was conjugated with 10,000 Resonance units (Ru) polyclonal anti-His antibody to flow cells 1-4 according to the manufacturer's instructions. Using a flow rate of 5 µl/min, 15 µl 6×His EGFR ECD at a concentration of 20 µg/ml was injected and captured on all four flow cells to which anti-His polyclonal antibody had been conjugated. Immediately after antigen injection the maximal binding of the Anti-EGFR mAb without competition was established in each flow cell during a reference run. Briefly 5 µl antibody at a concentration of 40 µg/ml was injected over all flow cells with captured EGFR followed by stripping of the antibody/antigen complex with a low pH acid wash (10 sec. contact time with 10 mM Glycine-HCl, pH2). After the determination of Anti-EGFR antibody maximal binding to each flow cell, a competition run was performed during the same Biacore cycle. Flow cells were first saturated with EGFR ECD antigen followed by injection of different reference antibodies or Anti-EGFR antibodies into separate flow cells using the same antigen saturating conditions as outlined above. This step was immediately followed by a second injection of Anti-EGFR antibody over the flow cell saturated with EGFR antigen and competition antibody to minimize the dissociation of either antigen or blocking antibody. Then the antibody/antigen complexes were stripped off with a low pH acid wash (10 sec. contact time with 10 mM Glycine-HCl, pH 2) and the whole cycle beginning with the reference run was repeated with a new Anti-EGFR antibody. The degree of inhibition of tested Anti-EGFR antibodies were determined by comparing the Ru max value of the individual Anti-EGFR antibody before and after competition by introduction of report points recorded two seconds before and after injection of each sample. An example of one Biacore cycle is shown in FIG. 7.

Reagents:
CM5 chip; Biacore, Cat. No. BR-1000-14
NHS; Biacore BR-1000-50
EDC; Biacore BR-1000-50
10 mM Acetate buffer pH 4.5; Biacore, Cat. No. BR-1003-50
Tetra-His antibody (BSA free); Qiagen, Cat. No. 34670
Ethanolamine, 1.0M pH 8.5; Biacore BR-1000-50
10×HBS-EP running buffer: 0.01 M HEPES pH 7.4, 0.15 M NaCl, 3 mM EDTA, 0.005% v/v Surfactant P20
Antigen: Inhouse produced recombinant human EGFR extracellular domain with 6×His.
10 mM Glycine HCl pH 2.0

Figures 8A, 8B:
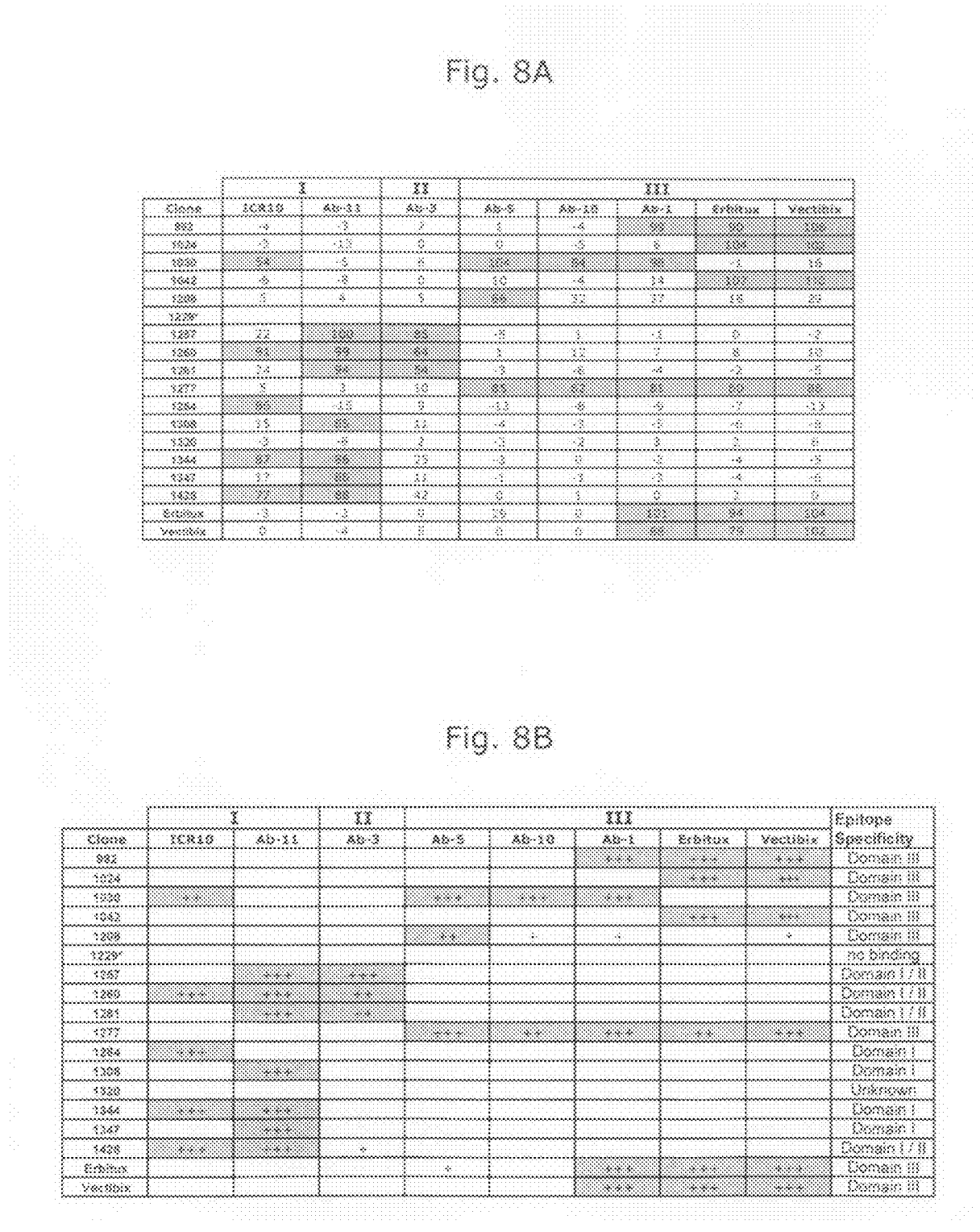

Reference Antibodies:
ICR10 (rat), Abcam, Ab231
199.12 (murine), Lab Vision Ab-11, MS-396-PABX
EGFR.1 (murine), Lab Vision Ab-3, MS-311-PABX
H11 (murine), Lab Vision Ab-5, MS-316-PABX
B1D8 (murine), Lab Vision Ab-16, MS-666-PABX
111.6 (murine), Lab Vision Ab-10, MS-378-PABX
225 (murine), Lab Vision Ab-2, MS-269-PABX
528 (murine), Lab Vision Ab-1, MS-268-PABX To confirm the epitope analysis obtained in competition ELISA and to perform further epitope analysis by competition between same species Anti-EGFR antibody pairs, a competition assay based on antibody binding measured in real time by surface plasmon resonance was established. The obtained epitope map of Anti-EGFR clones tested against the panel of reference antibodies is shown in FIGS. 8A and 8B below. Inhibition values from 50-100% were taken as an indication of significant competition between antibody pairs binding overlapping epitopes or epitopes in close proximity on the antigen, while inhibition values below 50% indicated that the recognized epitopes by the antibody pairs were not in close proximity resulting in decreased steric hindrance. Inhibition values below 25% were not included in the analysis for overlapping epitopes, because they were judged to represent nonsignificant inhibition. All tested antibodies except 1320 were found to compete with one or more of the employed reference antibodies, indicating that 1320 was directed against an unknown epitope for which we did not have any reference antibody reactivities. The fully human or humanized antibodies Vectibix and Erbitux were included in the analysis and were found to bind overlapping epitopes. The data obtained from both the competitive ELISA and competitive SPR analysis generally correlated well with respect to the established domain specificity of the Anti-EGFR antibodies. However, slight differences in the competition pattern between individual reference antibodies were sometimes observed in the two assays, perhaps due to the fact that the ELISA competition assay employed full length EGFR receptor antigen while the SPR competition assay used recombinant extra cellular domain EGFR.

Figure 10A:
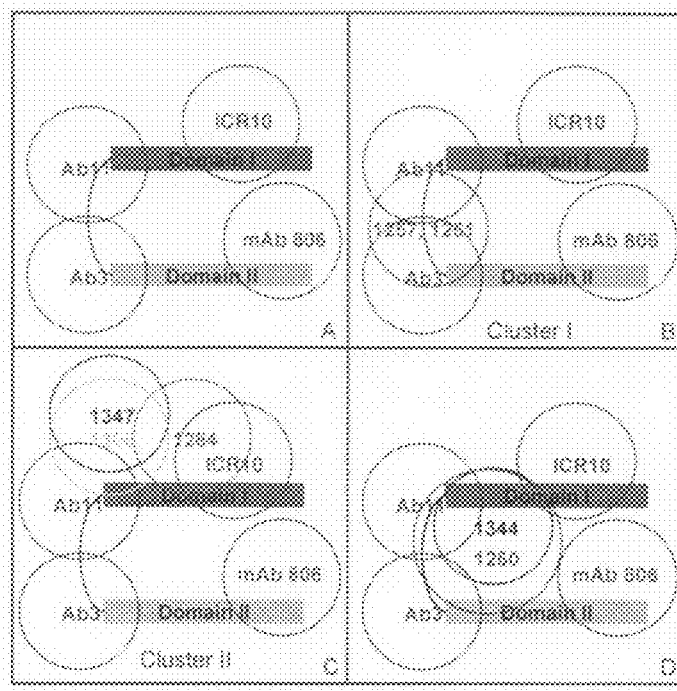
FIGS. 10A and 10B: Epitope maps of reference antibodies and Anti-EGFR antibodies directed against the extra cellular domain of EGFR as determined by Biacore analysis.
Figure 10B:
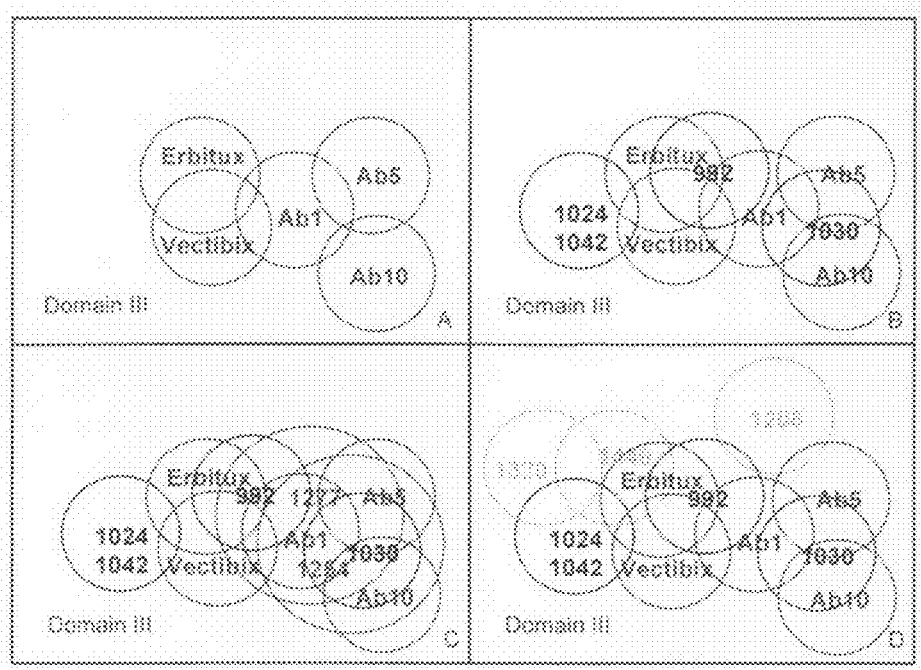

After the epitope mapping of Anti-EGFR antibodies had been confirmed in two different competition assays, competition analysis of same species combinations of Anti-EGFR antibody pairs were investigated to resolve which antibody pairs were recognizing distinct epitopes, and if antibody pairs recognizing overlapping epitopes could be further divided into epitope clusters. The result of this analysis is shown in FIGS. 9A and 9B. Again in this analysis, inhibition values from 50-100% were taken as an indication of significant competition between antibody pairs binding overlapping epitopes. This criterion seemed valid, since antibodies tested against them selves, and consequently recognizing complete overlapping epitopes resulted in values between 70%-100% inhibition as shown in FIGS. 9A and 9B. Further, this observation illustrated that dissociation of either antigen or antibody pairs within the time frame of the analysis did not appear to have an impact on the outcome of the experiment for the antibodies tested. By grouping the antibodies according to the presumed EGFR ECD domain specificity determined in the previous sections, antibodies binding exclusively to domain I or to either domain I or II (I/II) were found to mainly cluster with antibody members with same specificities, and not antibody members recognizing domain III. Likewise domain III antibodies were found to compete for binding only with antibody members recognizing domain III and not antibodies recognizing EGFR domain I or I/II. While the two domain III antibodies 1024 & 1042 derived from the same Ig rearrangement were found to recognize overlapping epitopes, pair wise combinations of either 1024 or 1042 with either 992 or 1030 were importantly not found to result in significant competition. Consequently it was concluded that antibodies 992, 1030 & 1024/1042 were recognizing three non-overlapping epitopes on the domain III of EGFR ECD. Finally mAb 1320 was found to compete for binding with mAbs 1024 and 1449, both directed against domain III, and not other domain III antibodies tested (competition of 1320 with 1042 not determined). Consequently, it was assumed that mAb 1320 was binding in the periphery of domain III on the extracellular domain of EGFR. An overview of the epitope specificities can be seen in FIGS. 10A and 10B, where epitope maps of antibodies directed against EGFR ECD domain I, I/II or III are illustrated.

Figure 11C:
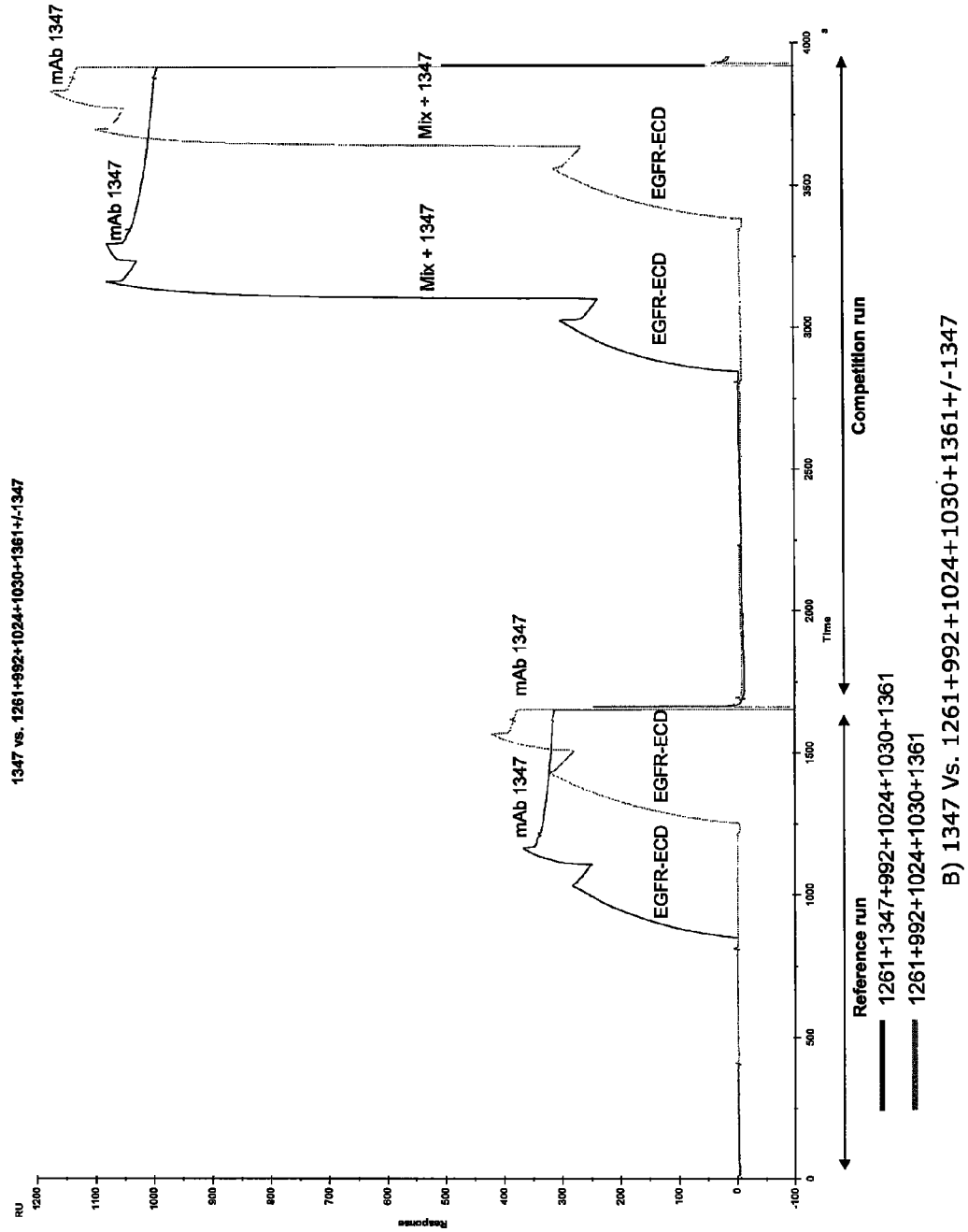
Figure 11C:
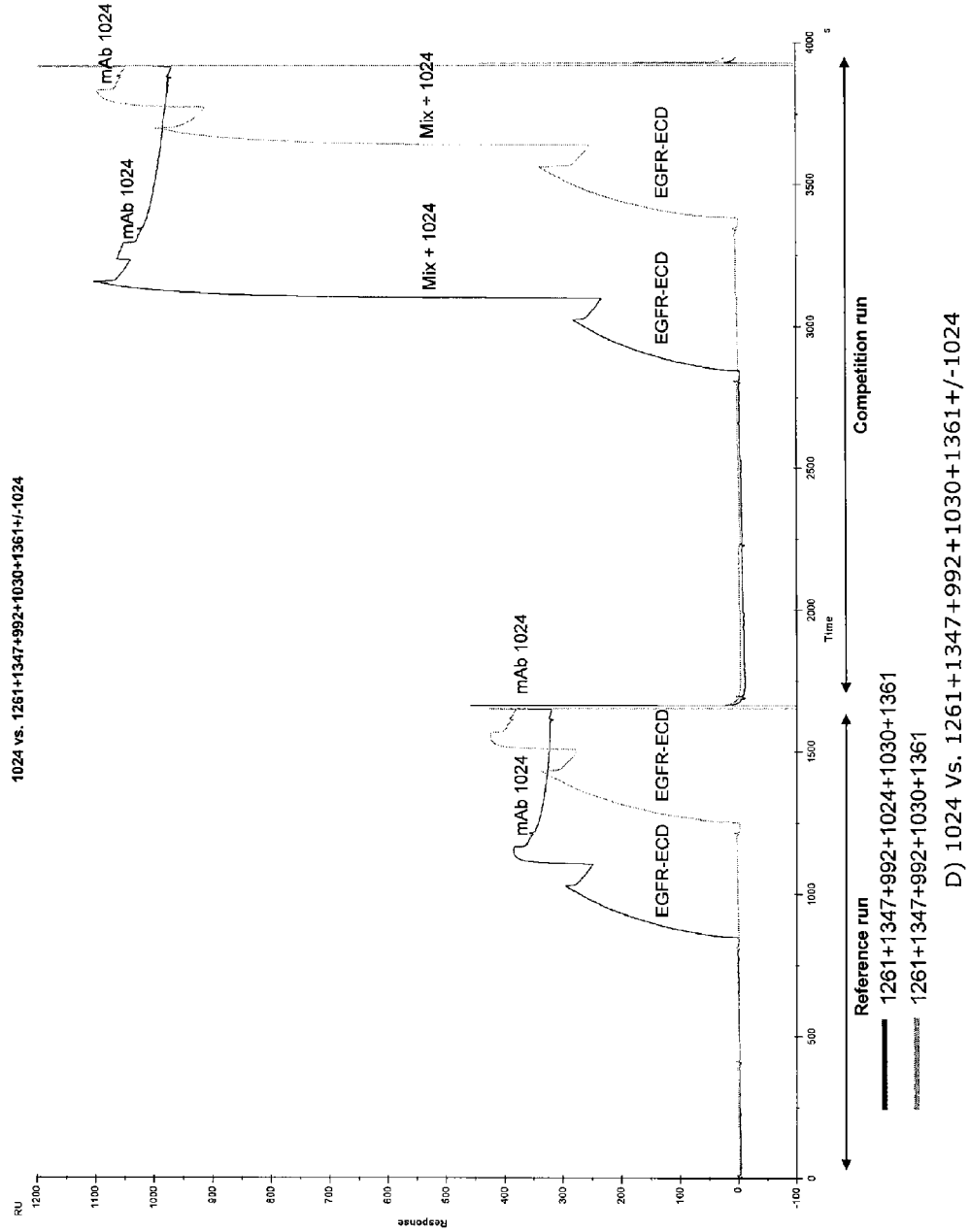
Figure 11C:
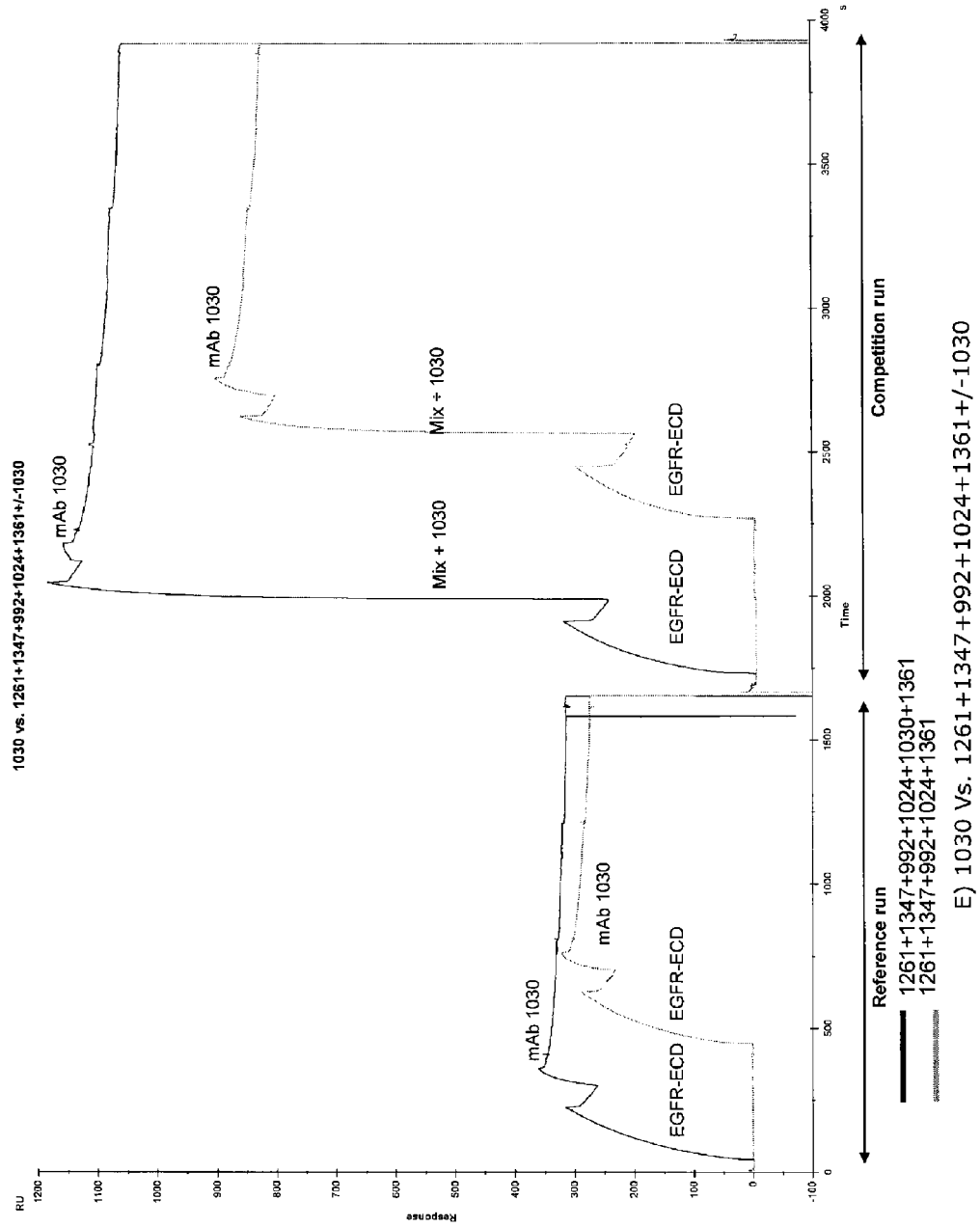

After the finding that pair wise combinations of 992, 1030 & 1024/1042 did not result in significant antibody competition as determined by SPR, new Biacore experiments were designed to examine how many antibodies that could bind to the receptor antigen simultaneously. First it was investigated what impact saturation of Domain III with the three antibodies 992, 1024 and 1030 had on the binding of antibodies directed against other EGFR specificities that were not domain III. The result from this analysis is shown in FIG. 11A. The inhibitions of single antibodies were established by testing them in combinations with either single antibody or antibody mixtures of up to three antibodies generated by sequential addition of one extra antibody during each Biacore cycle. To assure complete blockage of the recognized epitope, antibodies were tested in individual concentrations of 40 µg/ml. As shown in FIG. 11A, the three domain III antibodies 992, 1024 & 1030 were found to bind simultaneously to the receptor without any inhibition of binding. The observed negative inhibition values increasing for each antibody added further suggested a synergy in binding for the next antibody added. Importantly, once domain III was incubated with the three antibodies, other antibodies directed against non-overlapping epitopes on domain I/II (mAb 1261), domain I (1347) or an unknown specificity (1361) appeared to be binding without epitope blockage from the three mAb mixture. Further, these tested antibodies had small negative inhibition values indicating that they were binding better after receptor saturation with the three mAb mixture. Consequently this experiment suggested that the six tested antibodies could bind to the ECD of EGFR simultaneously. To further test this observed phenomenon, an antibody mix consisting of all the tested antibodies (1261, 1347, 992, 1024, 1030 & 1361) was made and tested for inhibition of each individual sample antibody in the mix. Antibody mixes where the tested sample antibody had not been included were also tested to serve as a positive control. As presented in FIG. 11B/C, all six tested antibodies were found to be inhibited from 80-116% when tested for binding to the EGF receptor incubated with the full mix of antibodies. However, when individual sample antibodies were removed from this mixture, no significant inhibition of the particular sample antibody was noted, illustrating that the antibodies in the mixture were only blocked for binding to the EGF receptor by themselves. This experiment clearly illustrated that at least six antibodies recognizing non-overlapping epitopes can bind to EGFR simultaneously. As a final experiment it was investigated if other antibodies directed against domain I (1284), I/II (1257) or unknown specificity cluster (1183, 1255) could bind to the EGFR, when this was incubated with the six antibody mixture. As presented in FIG. 11D none of the tested antibodies were able to bind significantly to the EGFR upon prior incubation with the six antibody mixture. This may be because the collection of antibodies does not include antibodies against any of the sites left unoccupied by the six bound antibodies. Alternatively, it is possible that in fact all sites on the tested domains were blocked with antibody.

TABLE 6

Commercially available antibodies with documented specificities against EGFR extracellular domains.

| Clone | Species | Domain I | Domain II | Domain III |
|---|---|---|---|---|
| ICR10 | Rat | X | | |
| 199.12/Ab11 | Mouse | X | | |
| EGFR.1/Ab3 | Mouse | | X | |
| H11/Ab5 | Mouse | | | X |
| 111.6/Ab10 | Mouse | | | X |
| 528/Ab-1 | Mouse | | | X |
| 225/Ab-2 | Mouse | | | X |

Example 4

EGFR Activation Inhibition

Determination of antibody mediated blockage of EGF ligand binding to EGFR receptor by competitive ELISA To verify that tested Anti-EGFR antibodies bound to the EGFR receptor and simultaneously blocked the binding of Biotinylated EGF ligand, ELISA wells were coated with 80 µl/well of full length EGFR at a concentration of 0.5 µg/ml in PBS overnight at 4° C. The next morning wells were washed twice with PBS-T and blocked for one hour with 150 µl PBS-T-1% BSA at room temperature, followed by wash twice in PBS-T. Next 80 µl of serially diluted Anti-EGFR antibodies and control antibodies were added to wells and incubated 30 min at room temperature. After antibody incubation 20 µL biotinylated EGF ligand at a concentration of 0.5 µg/ml was added to all wells containing Anti-EGFR antibody dilutions or to wells containing only PBS-T 1% BSA, and incubated at room temperature for 1 hour. Subsequently wells were washed five times with PBS-T, followed by incubation with 100 µl/well Streptavidin-HRP secondary reagent diluted 1:1000 in blocking buffer and incubation at room temperature for 30 min. Finally wells were washed five times with PBS-T and plates were developed by adding 100 µL/well TMB substrate and incubated for 60 min. After incubation the reaction was stopped by addition of 1 M $H_2SO_4$; 100 µl/well and plates were read at OD 450 nm.

ELISA reagents:
1) Coating buffer: 1×PBS; Gibco cat:20012-019
2) Antigen: Wild type full length EGFR purified from A431 cells; Sigma E2645
3) ELISA plate: NUNC Maxisorp; cat: 442-404
4) Blocking/Dilution buffer: 1% BSA in PBS-T (PBS-T-1% BSA)
5) Washing buffer: 1×PBS/0.05% Tween 20 (PBS-T)
6) Positive control: Erbitux, Vectibix
7) Negative control: Synagis (Medimmune Inc, Palivizumab, cat. # NDC 60574-4111-1)
8) Biotinylated EGF ligand; Invitrogen, cat E3477
9) Streptavidin-HRP, ultra sensitive: Sigma S 2438
10) TMB Plus; KemEnTec, cat #4390L
11) 1 M $H_2SO_4$ ELISA competition assays were employed to rank the ability of Anti-EGFR antibodies to inhibit the binding of biotinylated EGF ligand to full length EGFR receptor coated to ELISA wells. As presented in FIGS. 12A and 12B, both Erbitux and Vectibix appeared to very potently block EGF ligand binding while the negative control antibody Synagis, which is not directed against EGFR did not inhibit EGF ligand binding. As shown in FIG. 12A, the three antibodies 992, 1030 and 1042 directed against domain III and recognizing non overlapping epitopes were tested alone or in an equimolar mixture for their ability do inhibit EGF ligand binding. Of the three tested antibodies only mAb 1030 showed a modest EGF ligand inhibiting activity when compared to Erbitux and Vectibix. The equimolar mixture of mAbs 992, 1030 and 1042 appeared to be more efficient in inhibiting EGF ligand binding than the single antibodies tested alone. At a total IgG concentration of 1 µg/ml, the equimolar mixture was found to inhibit EGF ligand binding approximately two times more efficiently than mAb 1030 and four times more efficiently than mAbs 992 & 1042 tested alone, showing a synergistic effect of mixing three domain III antibodies recognizing non overlapping epitopes. As shown in FIG. 12B the Anti-EGFR clones 1208, 1260, 1277 & 1320 were also tested in this assay. These four clones were able to inhibit EGF ligand binding in a dose dependant manner that was more efficient than observed for clones 992, 1030 and 1042 when comparing to the Erbitux control. At concentrations above 0.33 µg/ml the Anti-EGFR clones 1208, 1260, 1277 & 1320 appeared to be just as efficient at blocking EGF ligand binding as Erbitux tested at same concentrations.

Ability to Inhibit EGF Induced EGFR Phosphorylation in HN5 Cells

Anti-EGFR antibodies were tested for reactivity on EGFR phosphorylation in an in cell western analysis. The in cell western procedure enables the detection of EGFR and phosphorylated EGFR (pEGFR) from the same sample, this in turn makes it possible to compare the ratio of EGFR to pEGFR expression for each antibody treatment and data set. HN5 cells were cultivated according to the instructions provided by ATCC in DMEM supplemented with 10% FCS and pen/strep. 43,000 HN5 cells were seeded in 96 well plates from Nunc (cat no 167008) 24 h before starvation. Cells were starved in DMEM 16 h before addition of the antibodies. Antibodies were added at a final concentration of 10 µg/ml in 200 µl DMEM and the mixture was pipetted up and down at least five times to mix. After 30 min of antibody treatment EGF was added at a concentration of 50 µg/ml to appropriate wells and left for 7.5 min. In cell westerns were performed essentially to the instructions provided by the manufacturer of the in-cell western kit (Odyssey, LI-COR biosciences).

The cells were fixed in 3.7% formaldehyde (Sigma F-8775, lot 71K500, containing ~1% methanol) for 20 min after EGF stimulation. Five PBS-Triton X-100 (0.1%) 5 min washes were used in order to permeabilize the cells membranes prior to blocking in the LI-COR blocking buffer (927-40000). Primary antibodies were added in concentrations corresponding to the instructions provided and incubated with gentle shaking at RT for 2.5 h (total EGFR mouse, 1:500 dilution biosource international, cat no AHR5062 and Phospho-EGFR Tyr1173, Rabbit 1:100 dilution, biosource, Cat no 44-794G).

Following incubation with the primary antibodies the cells were washed five times for five minutes in PBS-T (0.1% tween-20) after which the secondary antibodies were added (goat-anti-rabbit IRDye 680, 1:200 dilution, LI-COR cat no 926-32221 and goat-anti-mouse, IRDye 800CW 1:800 dilution; LI-COR cat no 926-32210) and incubated for 1 h at RT with gentle shaking of the plate covered in aluminium foil.

Prior to measurement on the Tecan fluorescence reader the plate was washed five times for five min in PBS-T. All washes were terminated by an abruptly aborted throwing motion of the plates, open side down, to dispel the washing solution, followed by knocking of the plate against paper towels. (Identical to the treatment of ELISA plates, the important thing is the notion that the cells remain on the plate during this treatment and that the wash solution can be removed by this procedure rather than by suction, that will disturb the integrity of the cell monolayer). Any residual washing solution left from the last wash was removed by gentle suction at the side of the wells with a multichannel pipette. The fluorescent signal was measured for the 680 nm channel (excitation 675 nm and emission 705 nm, both 10 nm bandwidth) and for the 800 nm channel (excitation 762 nm and emission 798 nm, both 10 nm bandwidth).

Using the in-cell Western analysis it becomes evident that the three antibodies are significantly ($p<0.05$) affecting the pEGFR status of HN5 cells; the 1208, 1277 and 1320 antibodies (FIGS. 13A and 13B).

Figure 14:
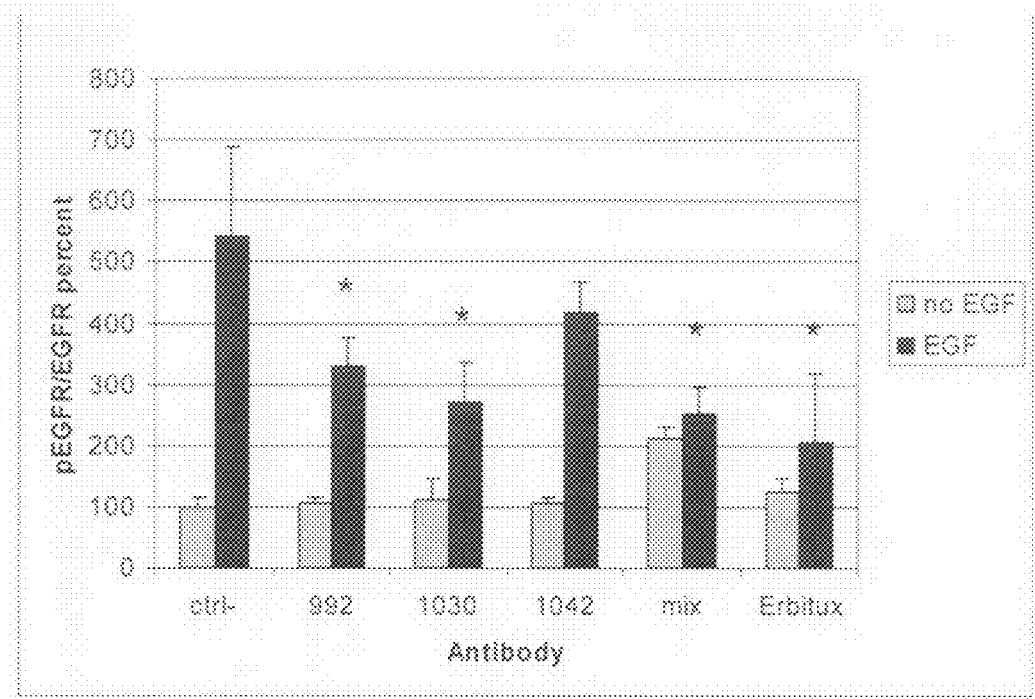
FIG. 14. In cell western analysis of phosphorylated EGFR (pEGFR) and EGFR in HN5 cells. Mix denotes the equimolar mixture of 992, 1030 and 1042 antibodies to a final concentration of 10 μg/ml, the other antibodies were used in a concentration of 10 μg/ml each. 50 μg/ml of EGF was added for 7.5 min prior to fixation to stimulate EGFR phosphorylation. Error bars represent standard deviations of 6 separate (ctlr-), or 3 separate data points (992, 1030, 1042, mix or erbitux). The 992, 1030, mix and erbitux had a significant (*=$p<0.05$) protective effect on phosphorylation.

The anti-EGFR mix (992, 1030 and 1042) of anti-EGFR antibodies and the individual antibodies therein were tested for effect in an in cell western analysis of inhibition of EGF induced EGFR phosphorylation. As seen in FIG. 14, 992 and 1030 and the anti-EGFR antibody mix significantly inhibited EGF induced EGFR phosphorylation ($p<0.05$).

Example 5

Internalisation of EGF Receptors in A431NS Cells

A431NS cells (ATCC# CRL-2592) were trypsinised from an 80-90% confluent T175 culture flask using TrypLE. Detached cells were washed in PBS and suspended in DMEM without serum. Cells were split into portions of 1-2 ml and incubated 30 min on ice with the antibodies examined. The antibody concentration were 10 µg/ml. Cells were washed three times in DMEM (250 g, 4 min, 4° C.) and re-suspended in 1.8 ml DMEM. Each portion were split into six FACS tubes containing each 300 µl cell suspension. Three tubes of each portion are placed in 37° C. water bath in exactly 40 min and the other three are put on ice immediately. After incubation, cells are washed twice at (250 g, 4 min, 4° C.) and pellets re-dissolved in 100 µl Rabbit anti human IgG Fcγ F(ab')$_2$—FITC in DMEM. Cells are incubated for 30 min at 4° C. before washed three times in 4° C. DMEM and analysed on FACSCalibur.

Figure 15:
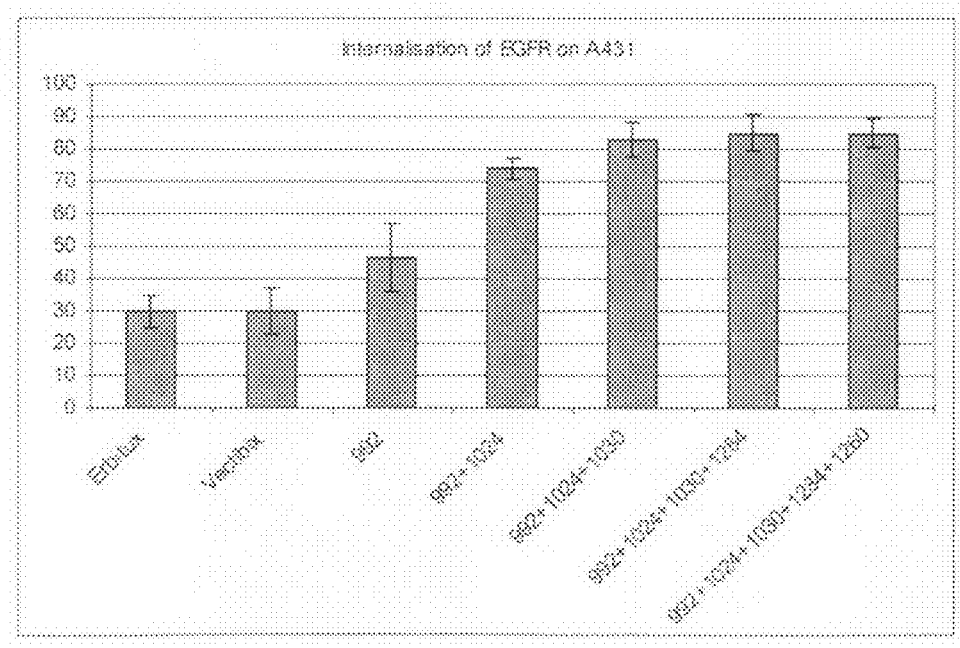
FIG. 15. The effect of incubation of antibodies on internalisation of EGFR. Data are shown as the percent of receptors removed from the cell surface relative to initial staining. Error bars corresponds to SEM.

Results are shown in FIG. 15. Incubation with Erbitux and Vectibix showed an equal level of internalisation of receptor of around 30% leaving 70% of initial surface staining. Incubation with 992 alone leads to around 45% receptor downregulation. Incubation with antibody mixtures containing two additional antibodies with non-overlapping epitopes leads to an increase in receptor downregulation: 992+1024, 74%; 992+1024+1030, 83%.

Addition of additional antibodies did not lead to further increase in receptor internalisation. Thus, at least three antibodies appear to be required to achieve the maximal level of internalisation in A431 cells.

Example 6

Proliferation Assays

Cellular damage will inevitably result in loss of the ability of the cell to maintain and provide energy for metabolic cell function and growth. Metabolic activity assays are based on this premise. Usually they measure mitochondrial activity. The Cell Proliferation Reagent WST-1 (Roche Cat. No. 11 644 807 001) is a ready-to-use substrate which measures the metabolic activity of viable cells. It is then assumed that the metabolic activity correlates with the number of viable cells. In this example the WST-1 assay was used to measure the number of metabolically active cells after treatment with different antibodies in different concentrations.

Prior to performing the WST-1 assay the appropriate antibodies and antibody mixes were diluted to a final total antibody concentration of 20 µg/ml in DMEM supplemented with 0.5% of FBS and 1% P/S yielding a final antibody concentration of 10 µg/ml in the well with the highest antibody concentration. 150 µl of these solutions were then added to wells in column 2 of a 96-well plate and a three-fold serial dilution were made down to column 9 so that each well contains 100 µl of antibody solution. 100 µl of media were added to column 11. 200 µl of media were added to Rows 1 and 8 as well as column 1 and 12 to the decrease effect of media evaporation in the experimental wells.

A431-NS cells are then washed with 1×PBS and detached by trypsination with 3 ml trypsin solution. 17 ml of complete media are then added and the cells spun down at 300×g (1200 rcf) for 5 min. The supernatant is removed and cells re-suspended in DMEM+0.5% FBS. Cells are the counted and their concentration adjusted to 15,000 cells/ml. 100 µl of the cell suspension (1500 cells/well) are then added to experimental wells in columns 2-11. The plates are incubated for 4 days in a humidified incubator at 37° C. Then 20 µl WST-1 reagent is added pr. well and the plates incubated for one hour at 37° C. Plates are then transferred to a orbital plate shaker and left another hour. The absorbance is measured at 450 and 620 nm (reference wavelength) on an ELISA reader. The amount of metabolically active cells (MAC) is calculated as percent of the untreated control as follows:

$$\% \ MAC = \left( \frac{(OD\,exp. - ODmedia)}{(ODuntreat. - ODmedia)} \right) \times 100$$

For the EGF titration studies, the ligand was diluted to concentration of 20 nM/ml in DMEM+0.5% FBS, yielding a final concentration of 10 nM/ml in the well with the highest EGF concentration. 150 µl of this solution was then added to wells in column 2 of a 96-well plate and a three-fold serial dilution were made down to column 9 so that each well contains 100 µl of EGF solution. 100 µl of media were added to column 11. 200 µl of media were added to Rows 1 and 8 as well as column 1 and 12 to the decrease effect of media evaporation in the experimental wells. The appropriate antibodies and antibody mixes were diluted to a final total antibody concentration of 40 µg/ml in DMEM supplemented with 0.5% of FBS and 1% P/S yielding a final antibody concentration of 10 µg/ml in the wells. 50 µl of these solutions were then added to wells in column 2-9 of the 96-well plate.

A431-NS cells are then washing with 1×PBS and detached by trypsination with 3 ml trypsin solution. 17 ml of complete media are then added and the cells spun down at 300×g (1200 rcf) for 5 min. The supernatant is removed and cells re-suspended in DMEM+0.5% FBS. Cells are the counted and their concentration adjusted to 40,000 cells/ml. 50 µl of the cell suspension (2000 cells/well) are then added to experimental wells in columns 2-11. The plates are incubated for 4 days in a humidified incubator at 37° C. Then 20 µl WST-1 reagent is added pr. well and the plates incubated for one hour at 37° C. Plates are then transferred to a orbital plate shaker and left another hour. The absorbance is measured at 450 and 620 nm (reference wavelength) on an ELISA reader. The amounts of metabolically active cells are indicated by the absorbance at 450 nm subtracted the absorbance at the reference wavelength of 620 nm.

The amount of metabolically active cells (MAC) is calculated as percent of the untreated control as follows:

$$\% \ MAC = \left( \frac{(OD\,exp. - ODmedia)}{(ODuntreat. - ODmedia)} \right) \times 100$$

Results

Figure 16A:
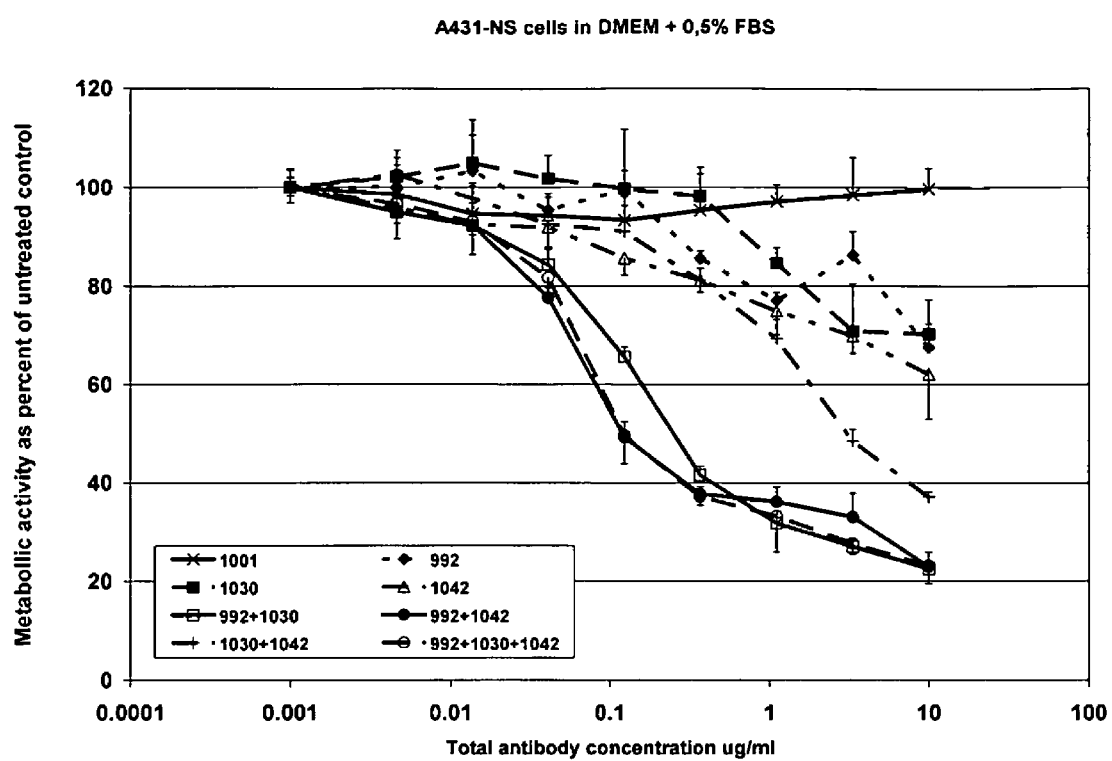
FIGS. 16A-16C: Growth curves of A431-NS cells in the presence of varying concentrations of the antibodies 992, 1030 and 1042 and mixes hereof as measured by the percent metabolically active cells as compared to untreated control. 1001 is a non-functional antibody with similar isotype used as negative control.

To show that a mixture of three anti-EGFR antibodies with non-overlapping epitopes within domain III is superior to the antibodies alone an experiment was performed which investigated the inhibition of A431-NS growth. As can be seen in FIG. 16A, the antibodies are poor inhibitors of A431-NS growth on their own, but when combined a synergistic inhibitory effect on 431-NS growth is obtained. Although mixes of 992 with either 1042 or 1030 is also very potent, the mix of all three is superior to these over all antibody concentration ranges.

The effects of individual antibodies and antibody mixes on the growth of A431-NS cells stimulated with varying concentrations of EGF were investigated and the results are shown in FIG. 17. As can be seen in FIG. 17 EGF concentrations above 0.1 nM in the absence of antibodies are toxic to the cells. However it is evident that a mix of three antibodies with non-overlapping epitopes within domain III of EGFR (992, 1030 and 1042) acts synergistically to inhibit growth of the A431-NS cells in the presence of EGF when tested up to at least 0.3 nM of EGF and the mix is superior to all monoclonal antibodies.

Figure 18:
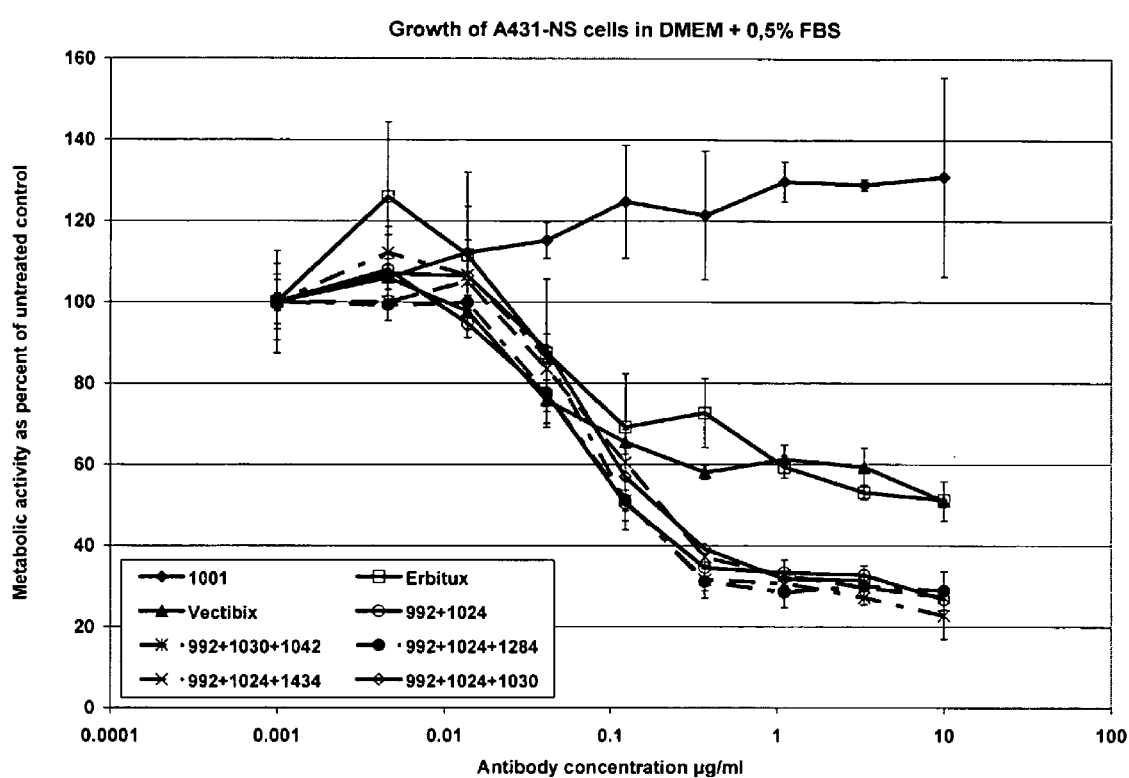
FIG. 18: Growth curves of A431-NS cells in the presence of varying concentrations of the antibody 992 and mixes of 992 and antibodies with non-overlapping epitopes present in domain I, II or III. 1001 is a non-functional antibody with similar isotype used as negative control.

Next we demonstrate that the synergistic inhibitory effect on A431-NS growth also can be obtained by combining two antibodies with non-overlapping epitopes in domain III of EGFR with antibodies with epitopes within either domain I or II of EGFR. As can be seen in FIG. 18 combinations of the antibody 992 and 1024 which are both domain III of EGFR, with either an antibody reactive with domain I (1284) or with domain I/II (1434) of EGFR are as potent as three antibodies reacting with non-overlapping epitopes within domain III of EGFR (992+1024+1030). In addition, these mixes of antibodies are more potent at inhibiting the growth of A431-NS than the therapeutic anti EGFR antibodies Erbitux and Vectibix.

Figure 16B:
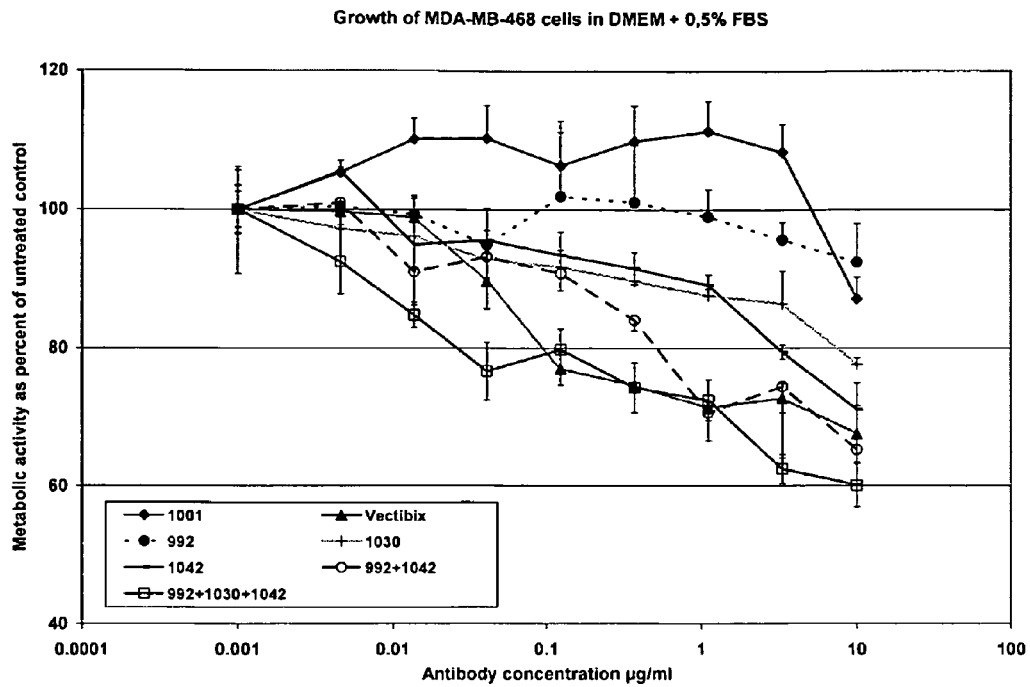
Figure 16C:
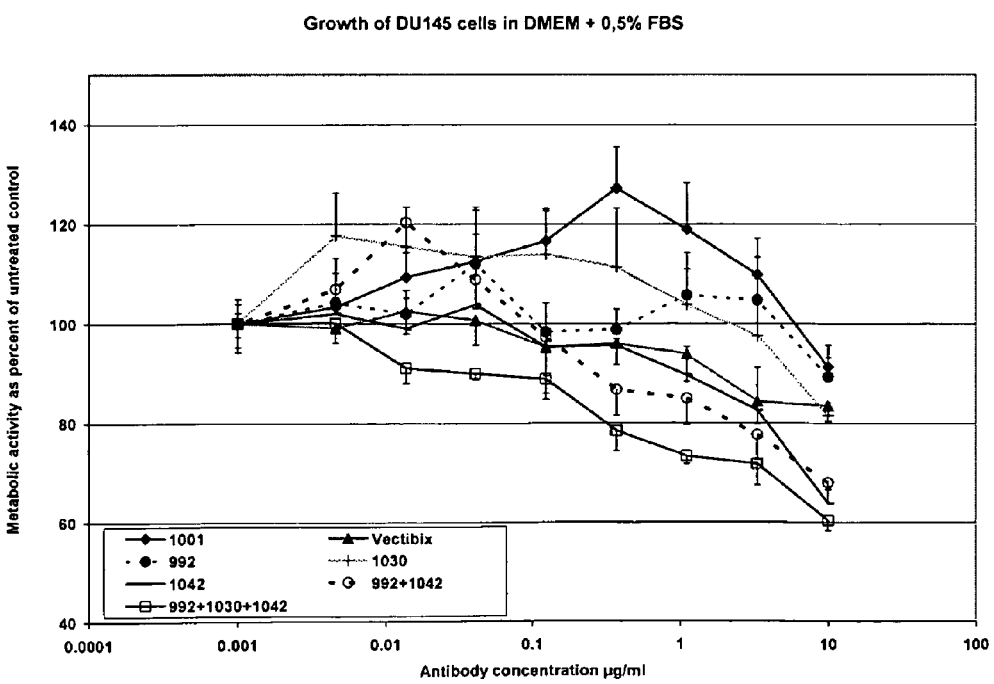

Similar assays were performed using two other cancer cell lines, DU145 (ATCC#HTB-81) and MDA-MB-468 (ATCC#HTB-132). Results from these proliferation assays are shown in FIGS. 16B and 16C. In both cases, a mix of three antibodies (992, 1030 and 1042) was superior to mixes of two antibodies and single antibodies. In DU145 cells the mix of three antibodies was superior to Vectibix at all concentrations, and in MDA-MB-468 at high concentrations.

Using a method similar to the one described above we tested different combinations of three anti-EGFR antibodies.

Results

The effects of different combinations of three antibodies were investigated in the A431NS cell line. The growth inhibitory activity of the twenty most potent of these is shown in FIG. 37. All the combinations inhibited the proliferation of the A431NS cell line more than 60% compared to a non-treated control. Another interesting observation is than with the exception of the combinations (992+1024+1254 and 992+1024+1320 and 992+1277+1320) the combinations contain antibodies with non-overlapping epitopes. This shows that it is possible to design several combinations of three antibodies binding distinct epitopes.

Example 7

Apoptosis

Apoptosis is a biological mechanism that leads to death of the cell. This mechanism has been reported previously by use of anti-EGFR antibodies, such as Erbitux (Baselga J. The EGFR as a target for anticancer therapy—focus on cetuximab. Eur J. Cancer. 2001 September: 37, Suppl 4:S16-22). It was therefore investigated to which extent the individual anti-EGFR antibodies 992, 1042, and 1030 as well as the mix (992+1042+1030) were able to induce apoptosis.

$1 \times 10^4$ A431NS cells were incubated in DMEM supplemented with 0.5% of FBS and antibiotics in triple determinations in 96 wells culture plates in the presence of the EGFR mix (equal parts of 992, 1030, 1042), 992, 1030, 1042, Erbitux or Vectibix, in concentrations ranging from 0.01 μg/ml to 10 μg/ml. Cells and antibodies were incubated for 22 h. Then supernatants were harvested and measured in an ELISA-kit from Roche, Cat No: 11774425001 (Basel, Switzerland), for the presence of histone-DNA complexes.

Figure 19:
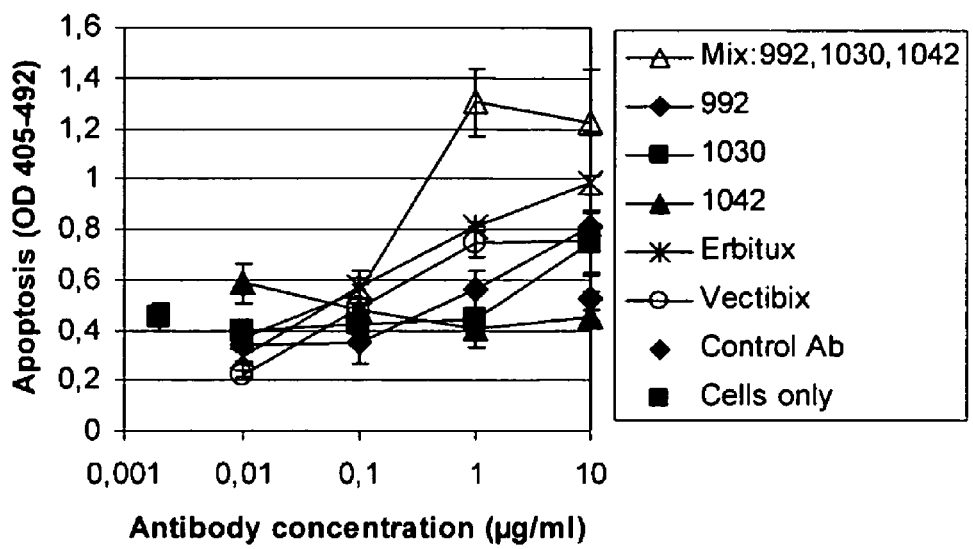
FIG. 19. Apoptosis in A431NS cells. The EGFR-mix, individual monoclonal antibodies, Erbitux and Vectibix were tested in 10-fold dilutions. Histone-DNA complex from apoptotic cells were measured using an ELISA-kit from Roche.

The effect of the mix was compared with each of the monoclonal antibodies alone as well as with the reference antibodies Vectibix and Erbitux using A431NS cells (results in FIG. 19). The antibodies were tested in 10-fold dilution. The mix is significantly ($P<0.05$) more efficient compared to the individual monoclonal antibodies as well as Vectibix when tested at concentrations of 1 μg/ml and 10 μg/ml. The mix increased apoptosis statistically significant ($p<0.05$) compared to Erbitux at 1 μg/ml.

Example 7b

Figure 35:
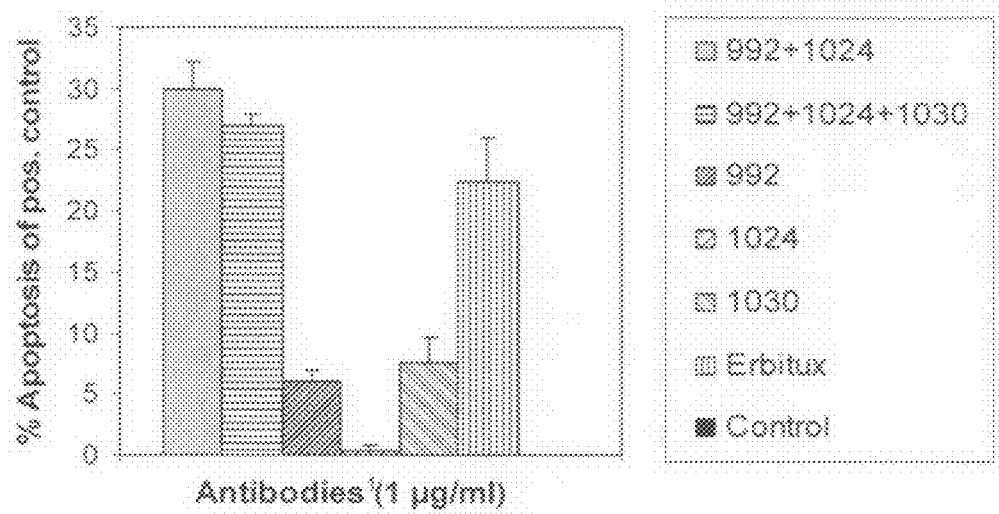
FIG. 35: Apoptosis obtained in A431NS with 1 μg/ml of the indicated antibodies/combinations. Histone-DNA complexes were detected in an ELISA kit from Roche. Levels of apoptosis were related to a positive control (maximal apoptosis).

In addition to example 7, the mixture of 992+1024 as well as the mixture of 992+1024+1030 were investigated for apoptotic activity according to the same method as described in example 7 (FIG. 35). The factual level of apoptosis was related to a maximum positive control. Both of the two mixtures were compared with Erbitux and the individual monoclonal antibodies 992, 1024 and 1030 as well as a control antibody in 1 μg/ml using A431NS cells. The mixture of 992+1024 was significantly better than Erbitux and the individual monoclonal antibodies (all $P<0.05$).

Example 8

In Vivo Efficacy

The anti-EGFR-mix consisting of the antibodies 992, 1030 and 1042 was investigated for in vivo efficacy in the nude mouse xenograft model using A431NS cells. This is a widely used model for investigating the potency of monoclonal anticancer antibodies, including anti-EGFR antibodies. Nude mice are immunocompromised and lack T-cells. This allows growth of human cells in the mice.

Two groups of nude mice 6-8 weeks were injected subcutaneously with $1 \times 10^6$ A431NS cells. When the average tumor size reached 100 mm$^3$, treatment was initiated. Mice received five injections of 1 mg antibody, intraperitoneally, with 2-3 days interval. Tumour sizes were measured in two diameters using digital calipers and the volume was calculated using the formula: Tumour volume (mm$^3$)=L×W$^2$×0.5, where L is the longest diameter and W is the shortest diameter (Teicher B A, Tumor Models in Cancer Research. Humana Press, NJ, USA 2002, p 596). By the end of the experiment, tumours were excised and weighted.

Synagis was used as control antibody. The experiment also included treatment with Erbitux and Vectibix in the same amount an using the same schedule as for the anti-EGFR-mix (antibodies 992, 1030, and 1024).

Figure 20:
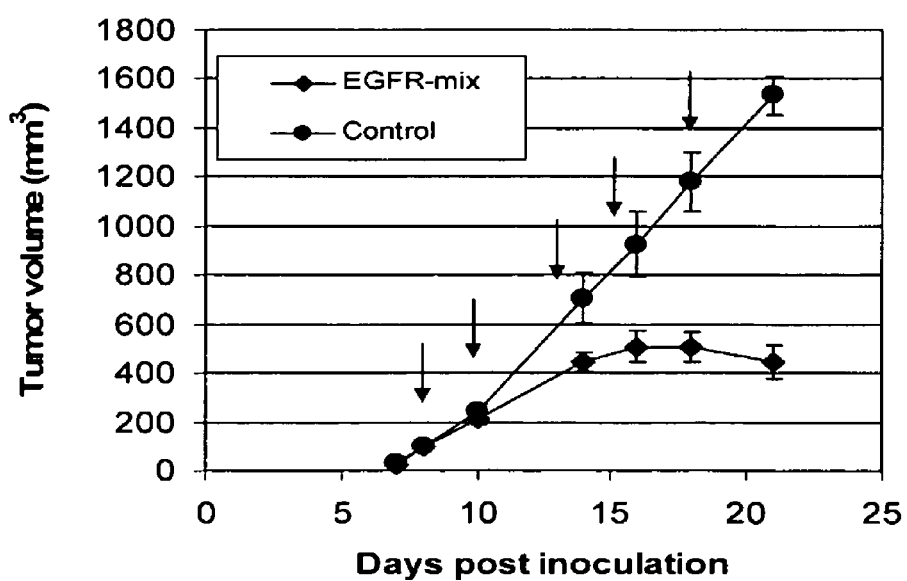
FIG. 20. Four groups of 10 nude Balb/C Nu/Nu mice were inoculated with $1\times10^6$ A431NS cells. When tumours were approximately 100 mm$^3$, treatment was initiated. Groups were injected with 1 mg/ml antibodies five times during the experiment as indicated with arrows. Tumour diameters were measured with digital calipers. Results are shown as the mean tumour volume (+/−SEM).
Figure 21:
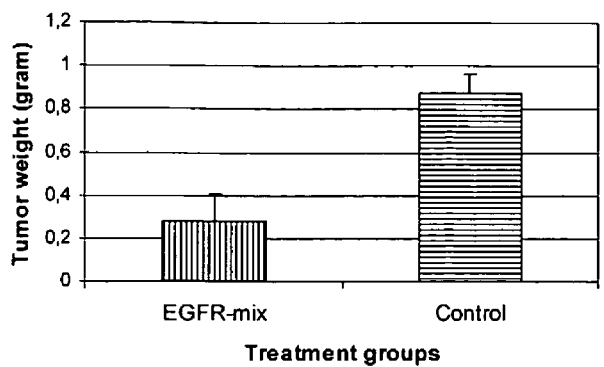
FIG. 21. When individual mice were killed in the experiment shown in FIG. 20, tumours were excised and weighted. Mean values+/−SEM are shown. Stars indicate significance at $P<0.05$.

As seen in FIG. 20, the mix of 992, 1030 and 1042 significantly inhibited tumour growth of A431NS ($P<0.05$). The average weights are shown in FIG. 21. The result correlated with the measured tumour sizes. There are significant difference between the treatment group and the control group.

Example 8b

In Vivo Efficacy

Figure 36:
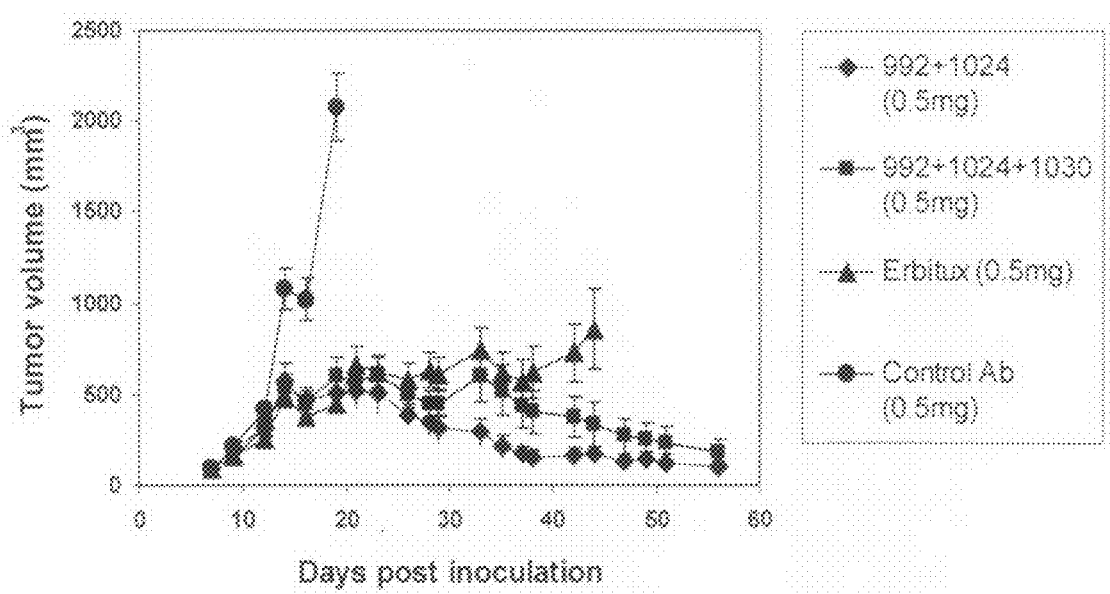
FIG. 36: Balb/C nu/nu mice were injected with $1 \times 10^6$ A431NS cells. When tumors were approximately 100 mm³ in average, treatments were initiated. Mice received 17 injections with antibody. The first treatment starting at day 8 and the last at day 34. Antibody/compositions were injected at 0.5 mg/dose or 0.17 mg/dose. Mean values of tumour volume+/−SEM are shown.

In addition to the described in vivo experiment in example 8, the mixtures of 992+1024 and 992+1024+1030 were investigated in the A431NS xenograft model described above (FIG. 36). Four groups each of 9 nude mice, 6-8 weeks, were injected subcutaneously with $1 \times 10^6$ A431NS cells. When the average tumour size reached 100 mm$^3$, mice received the first antibody injection. The three groups received either the mixture of 992+1024, 992+1024+1030, Erbitux or the control antibody, Synagis. In all, mice received 17 injections of 0.5 mg 4 times a week. The first injection was given on day 8 and the last injection was given on day 34. Tumour sizes were measured for 56 days. After termination of the antibody treatment, the tumours of the mice receiving Erbitux started expanding in size, whereas tumours continued to decreased in size for mice in the two groups receiving the mix of either 992+1024 or 992+1024+1030. No expansion in tumour size was observed for the 992+1024 group at day 91 (57 days following termination of treatment). The average tumour size for the combination of 992+1024 was significantly smaller ($P<0.01$) at day 56 than the average tumor size for mice receiving Erbitux.

The survival of mice in the experiment was also monitored. Mice were scored as dead when tumors reached the maximum allowed sizes. The table below shows the number of survived mice 56 days after inoculation of tumor cells. An improved survival is seen for both of the combinations compared to Erbitux.

| Group | 992 + 1024 | 992 + 1024 + 1030 | Erbitux | Control Ab |
| --- | --- | --- | --- | --- |
| Initial number of mice | 9 | 9 | 9 | 9 |
| Mice remaining at day 56 | 9 | 9 | 2 | 0 |

Additional Experiments

Preliminary data on tumour lysates from the xenograft experiment described in example 8 shows that the combination of 992+1042+1030 induces potent down regulation of VEGF production by A431NS, the former being an important mediator of angiogenesis. Increased formation of blood vessels is a phenomena seen in many solid tumours, a mechanism that participate in the sustained supply of nutrients etc., thereby affecting the survival conditions.

Furthermore, other preliminary data shows that an increased level of the antibody combination of 992+1042+

1030 can be observed in the tumour lysates from the xenograft experiment described in example 8, when compared to Erbitux and Vectibix.

Example 8c

Enhanced In Vivo Tumor Cell Differentiation

Terminal differentiation of cells is a complex process that includes activation of cell-type specific gene expression programs, leading in a multistep process to an irreversible loss of their proliferative capacity. In malignant disease, cancer cells are often in a dedifferentiated state characterized by an increased rate of proliferation, and it has been suggested that drugs capable of inducing terminal differentiation of cancer cells would be able to eliminate the malignant cells and reestablish normal cellular homeostasis (Pierce G B, Speers W C: Tumors as caricatures of the process of tissue renewal: prospects for therapy by directing differentiation. Cancer Res 48:1996-2004, 1988). Under certain experimental conditions, anti-EGFR monoclonal antibodies have previously been reported to be able to increase the rate of terminal differentiation of human squamous cancer cells grown as xenograft tumors in immunocompromised mice (Milas L, Mason K, Hunter N, Petersen S, Yamakawa M, Ang K, Mendelsohn J, Fan Z: In vivo enhancement of tumor radioresponse by C225 antiepidermal growth factor receptor antibody. Clin Cancer Res 6:701-8, 2000; Modjtahedi H, Eccles S, Sandle J, Box G, Titley J, Dean C: Differentiation or immune destruction: two pathways for therapy of squamous cell carcinomas with antibodies to the epidermal growth factor receptor. Cancer Res 54:1695-701, 1994).

We examined histologically the extent of terminal differentiation in anti-EGFR treated A431NS cells grown as xenografts in mice. The histological study included 3 randomly selected mouse xenograft tumors from each of the four experimental groups from the experiment described in example 8.

The tissues were dissected and snap frozen, then mounted with Tissue-Tek on a cryomicrotome (Leitz, model 1720), cut into 5 µm sections and sampled on superfrost plus slides, then processed for hematoxylin/eosin staining. Two independent observers then conducted a microscopic examination of all tissue sections in a blinded fashion, scoring keratinized areas ("keratin pearls") as a measure of the extent of terminal differention (Modjtahedi et al., 1994). Table 7 lists the result obtained. Mice treated with a mixture of three anti-EGFR antibodies (992+1024+1030, group 1) had markedly larger and more numerous foci of terminally differentiated cancer cells as compared to mice treated with reference antibodies Erbitux and Vectibix (Groups 2 and 3, respectively). No terminal differentiation was detected in the control group receiving PBS instead of antibody (group 4).

Figure 26:
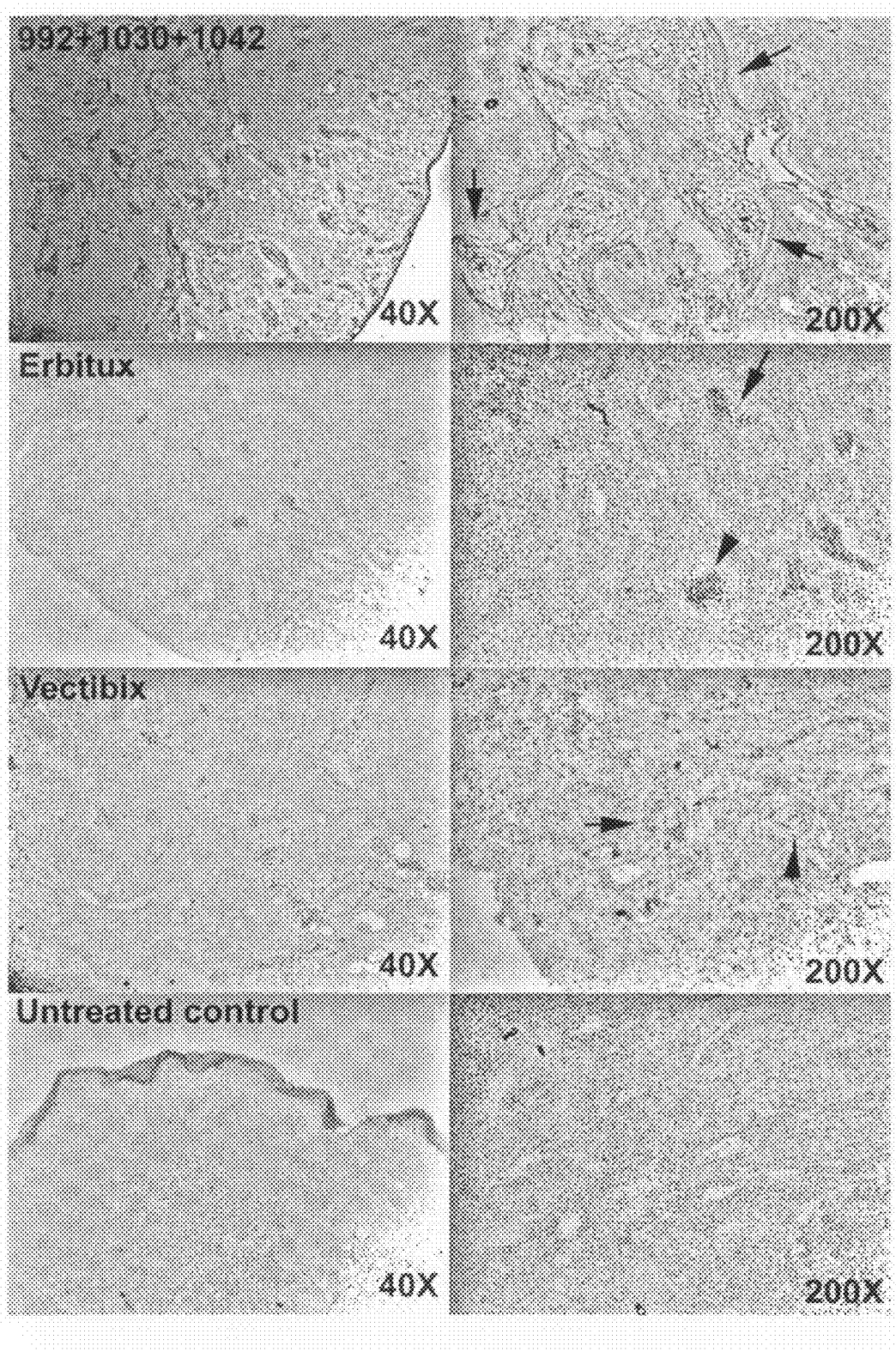
FIG. 26: Photomicrographs of representative tumor sections from each of the four experimental groups of xenografted mice. At a magnification of 200×, arrows point to foci of terminal differentiation of A431 cells in vivo. Note the markedly larger and more numerous foci of terminal differentiation in the tumour treated with a mixture of three anti-EGFR clones (992+1030+1042), upper two panels.
Figure 28:
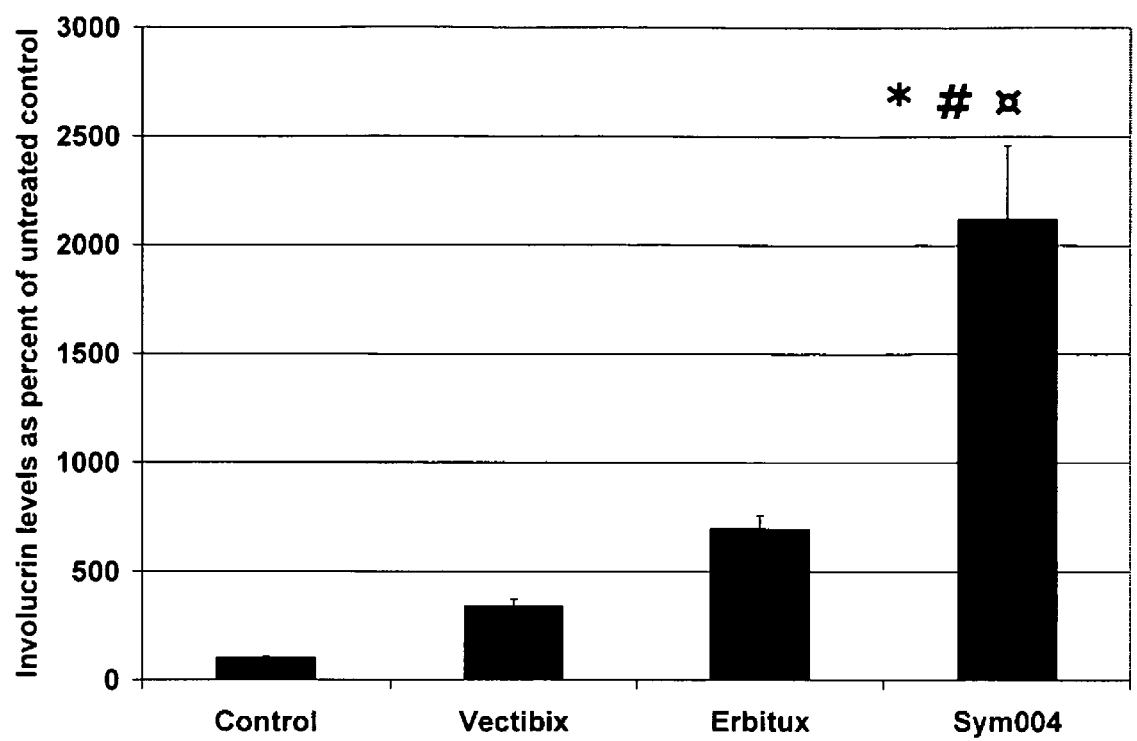
FIG. 28. Diagram showing the Involucrin levels in the four treatment groups as percent of the untreated control group (*#□$p<0.005$ as compared to Erbitux, Vectibix and the Negative control group respectively).

Representative microscope images were acquired using a microscope fitted with a digital camera, see FIG. 26.

In conclusion, a combination of three anti-EGFR antibodies with non-overlapping epitopes within domain III (clones 992, 1030 and 1042) showed an unexpected enhanced differentiation-inducing effect on tumour cells in vivo as compared to Erbitux and Vectibix monoclonal antibodies. The observed effects on terminal differentiation leads to the conclusion that the antibody compositions of the invention can be used in combination therapy with other differentiation inducing agents, such as retinoic acid, 4-phenyl butyrate.

TABLE 7

| Group | Tumour No. | Scoring of No. of keratin pearls | Comments |
|---|---|---|---|
| 1 | 16 | ++++ | Large keratin pearls |
| 1 | 17 | +++ | Large keratin pearls |
| 1 | 54 | ++++ | Large keratin pearls |
| 2 | 14 | ++ | Small keratin pearls |
| 2 | 45 | ++ | Small keratin pearls |
| 2 | 49 | ++ | Small keratin pearls |
| 3 | 11 | ++ | Small keratin pearls |
| 3 | 34 | ++ | Small keratin pearls |
| 3 | 56 | ++ | Small keratin pearls |
| 4 | 43 | − |  |
| 4 | 60 | − |  |
| 4 | 31 | − |  |

Example 8d

Sustained Growth Inhibitory Effect of an Antibody Composition of the Invention A repeat of the tumor xenograft experiment presented in examples 8 and 8b was performed to investigate the in vivo efficacy of the 992+1024 antibody mix. In brief, BALB/c nu/nu mice were injected subcutaneously with $10^6$ A431NS cells into the flank. Tumor xenografts were allowed to grow to an average tumor size of 100 mm$^3$ (day 7) at which point mice were randomized into five groups of nine animals and antibody treatments were initiated. The five groups received either high (2 mg/week) or low (1 mg/week) dose of the 992+1024 mixture or reference antibody Erbitux, or high dose (2 mg/week) control antibody Synagis. All mice received a total of 9 injections of 0.5 or 1 mg antibody twice weekly starting on day 7 and ending on day 33.

Figure 38:
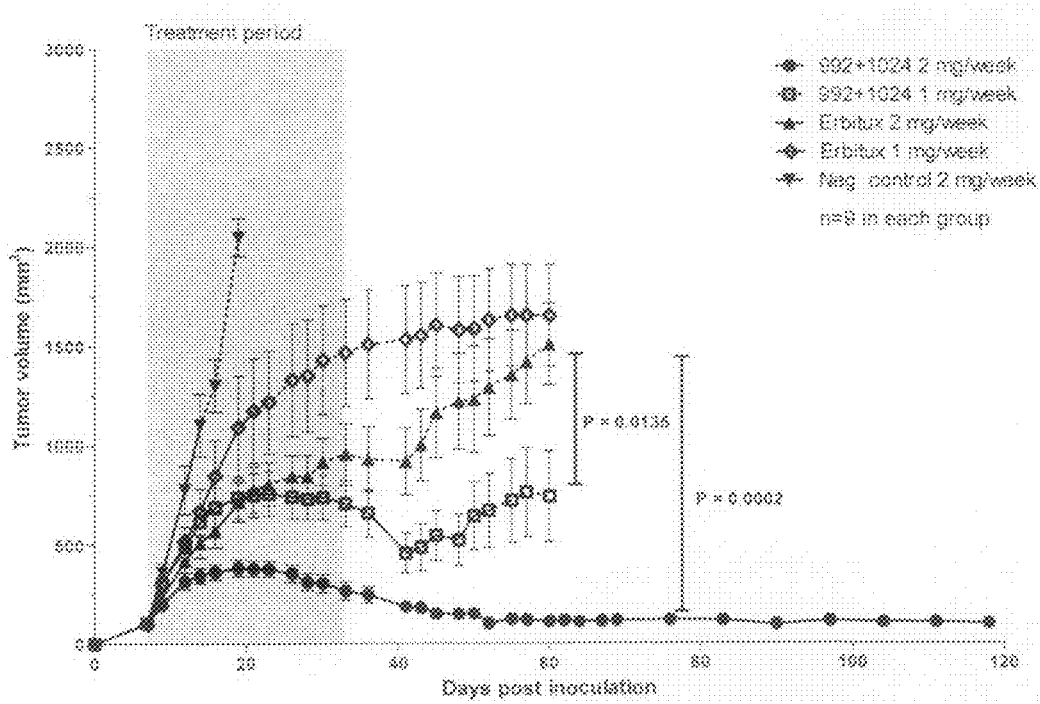
FIG. 38. Growth inhibitory effect of two different doses of 992+1024 mix compared to Erbitux in A431NS human tumor xenografts. BALB/c nu/nu mice were inoculated with $10^6$ A431NS cells. When tumors reached an average size of 100 mm³ (day 8) the mice were randomized into groups of 9 and treatment was started. Indicated antibodies were injected at 0.5 mg/dose or 1 mg/dose, twice weekly for a total of 9 injections. The light grey area on the graph indicates the treatment period. The start of a dotted line designate the time point at which the first mouse in a given group was euthanized due to excessive tumor size. The statistically significant differences between 2 mg/week 992+1024 vs. 2 mg/week Erbitux and 1 mg/week 992+1024 vs. 2 mg/week Erbitux has been calculated on day 60 where all except the 992+1024 2 mg/week group were terminated. The tumor size of animals excluded prior to day 60 was carried through, thus; the graph shows the accumulated tumor volume of all mice in a given group. Mean values+/−SEM are shown.
Figure 39:
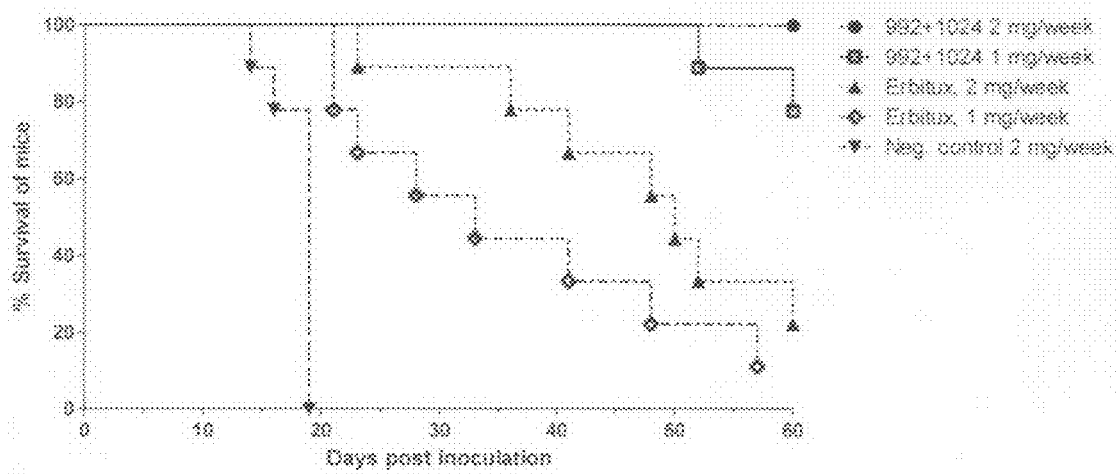
FIG. 39. Kaplan-Meyer plot of survival of mice treated with the 992+1024 antibody mix, Erbitux or control antibody (same experiment as shown in FIG. 38). Results presented as percent survival of treated mice. A significant difference between the percent survival of mice in the high dose (2 mg/week, P=0.0008)) and low dose (1 mg/week, P=0.0004) groups was observed when comparing 992+1024 and Erbitux. Also, low dose 992+1024 was significantly better when compared to high dose Erbitux (P=0.0087). The statistical difference was calculated using a Log-rank (Mantel-Cox) test.

High dose (2 mg/week) 992+1024 mix was very efficient at controlling initial tumor growth and at inducing long-term tumor regression when compared to Erbitux (P=0.0002, FIG. 38). None of the animals receiving 2 mg/week 992+1024 mix were terminated in the study period (118 days after the start of the experiment, FIGS. 38 and 39) a significantly better outcome than in the high dose Erbitux 2 mg/week group where only one of nine animal was left at day 60 (P=0.0008, FIG. 39). This shows the sustained effect of 992+1024 treatment on long-term survival. Although less efficient than the high dose, low dose 992+1024 mix (1 mg/week) was also able to control tumor growth and was significantly better compared to high dose 2 mg/week Erbitux when looking at both tumor suppression (P=0.0135, FIG. 38) and survival (P=0.0087, FIG. 39). These results demonstrate the superior potency of the 992+1024 combination when compared to Erbitux even at the low dosage. The results also demonstrate the sustained growth inhibition caused by the 992+1024 combination compared to an approved monoclonal antibody.

Example 9

Spheroid Growth

For the spheroid study, a round-bottomed 96-well plate is added 35 µl of 120 mg/ml Poly-HEMA solution and left to evaporate overnight in a flow-hood. Poly-HEMA prevents cell attachment. A431-NS cells are treated as above, counted and their concentration adjusted to 100,000 cells/ml. 50 µl of the cell suspension (5,000 cells/well) are then added to experimental wells in columns 2-11 together with 50 µl of a 5% matrigel solution. 200 µl of media were added to Rows 1 and 8 as well as column 1 and 12 to the decrease effect of media evaporation in the experimental wells. The plates are centrifuged at 300×g for 5 minutes and left to form overnight in a humidified incubator at 37° C. The following day the appropriate antibodies and antibody mixes were diluted to a final total antibody concentration of 20 µg/ml in an empty 96-well plate. This is done in DMEM supplemented with 0.5% of FBS and 1% P/S yielding a final antibody concentration of 10 µg/ml in the well with the highest antibody concentration. 150 µl of these solutions were then added to wells in column 2 of a 96-well plate and a three-fold serial dilution were made down to column 9 so that each well contains 100 µl of antibody solution. 100 µl of media were added to column 11. 100 µl of these solutions are then transferred to the plate containing the spheroids and left to incubate for 7 days. Then 20 µl WST-1 reagent is added pr. well and the plates incubated for one hour at 37° C. Plates are then transferred to a orbital plate shaker and left another hour. The absorbance is measured at 450 and 620 nm (reference wavelength) on an ELISA reader. The amount of metabolically active cells (MAC) is calculated as percent of the untreated control as follows:

$$\% \, MAC = \left( \frac{(OD\,exp. - ODmedia)}{(ODuntreat. - ODmedia)} \right) \times 100$$

Figure 22:
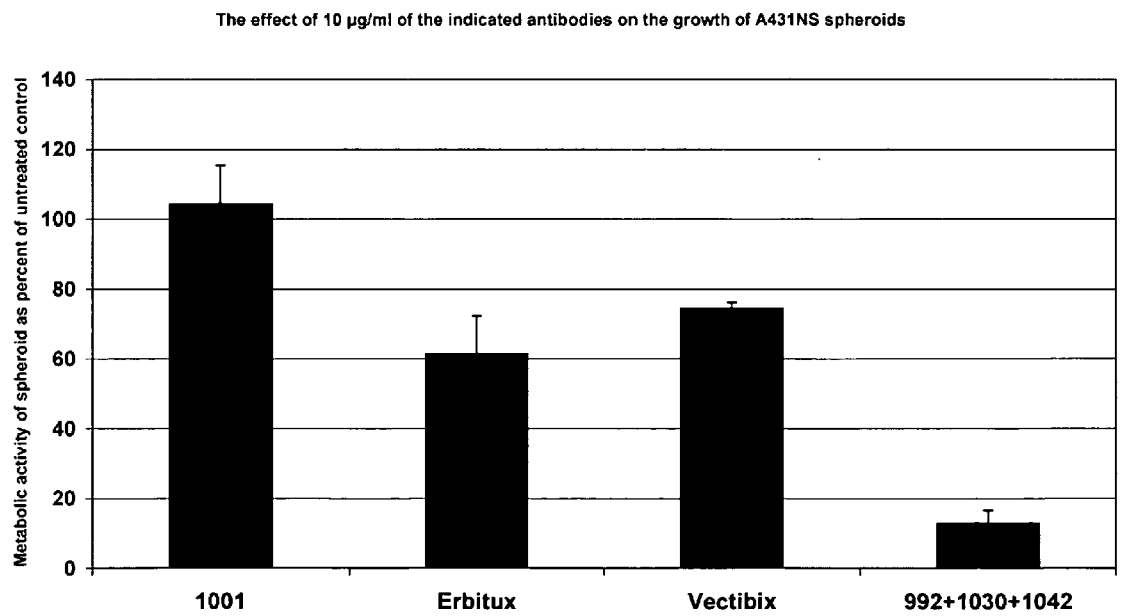
FIG. 22. Growth of A431-NS spheroids in the presence of 10 μg/ml of the antibodies 1001, Erbitux, Vectibix and a mix of three antibodies with non-overlapping epitopes 992+1030+1042. 1001 is a non-functional antibody with similar isotype used as negative control.

A mix of three antibodies with non-overlapping epitopes within domain III (992+1030+1042) effectively inhibits the growth of A431-NS spheroids and are more potent that the monoclonal therapeutic anti EGFR antibodies Erbitux and Vectibix (FIG. 22).

Example 10

Binding to Cynomolgus EGFR ECD

Cloning of Cynomolgus EGFR Extra Cellular Domain.

The extra cellular domain of Cynomolgus EGFR excluding signal peptide was cloned from Cynomolgus cDNA isolated from epidermis by using nested PCR and sequence specific primers derived from the published sequence of full length human EGFR (GENBANK X00588, Ullrich, A. et. al. Nature 309(5967), 418-425 (1984)).

PCR reagents:

Cynomolgus Monkey cDNA isolated from normal skin epidermis:

CytoMol Unimed, Cat. No: ccy34218, Lot No: A711054.

Phusion reaction buffer (5×): Finnzymes, Cat. no: F-518, Lot. No: 11.

Phusion enzyme: Finnzymes, F-530S (2 U/µL).

dNTP 25 mM: Bioline, Cat. No: BIO-39029, Lot. No: DM-103F.

Primers for amplification of Cynomolgus EGFR ECD including partial signal sequence and transmembrane domain:

```
                            (SEQ ID NO 135)
5' ATG primer:    5'-TCTTCGGGAAGCAGCTATGC-3'

(SEQ ID NO 136)
3' Tm 2 primer:   5'-TTCTCCACTGGGCGTAAGAG-3'
```

Primers for nested PCR amplifying Cynomolgus EGFR ECD Bp 1-1863 and incorporating XbaI, MluI restriction sites and stop codon before transmembrane domain:

```
5' EGFR XbaI:
                                   (SEQ ID NO 137)
5'-ATCTGCATTCTAGACTGGAGGAAAAGAAAGTTTGCCAAGGC-3'

3' EGFR MluI:
                                   (SEQ ID NO 138)
5'-TACTCGATGACGCGTTTAGGATGGGATCTTAGGCCCGTTCC-3'
```

PCR Conditions:

30 cycles: 98° C./30 sec melting, 55° C./30 sec annealing, 72° C./60 sec elongation. After 30 cycles PCR products were allowed to elongate for additional 5 min.

PCR reactions were performed with 1 µl template and 2 units Phusion Enzyme in a total volume of 50 µL reaction buffer containing 0.2 mM dNTP, 0.5 µM primer.

A final PCR band with an apparent length of approximately 1800-1900 Bp was obtained and cloned into expression vector. The DNA and protein sequence of the cloned extracellular domain of Cynomolgus EGFR is shown in FIGS. 23A and 23B and the protein sequence of Cynomolgus EGFR ECD aligned to human EGFR ECD is shown in FIG. 24. The alignment of the human EGFR ECD and Cynomolgus EGFR ECD DNA sequences showed 97.6% sequence identity, while the alignment of the corresponding protein sequences showed 98.6% sequence identity.

Demonstration of Antibody Cross Reactivity Between Extra Cellular Domain of Human and Cynomolgus EGFR in ELISA.

To verify that tested Anti-EGFR antibodies bound equally well to both Human and Cynomolgus EGFR ECD and accordingly warranting toxicology studies in Cynomolgus monkies, serial four fold dilutions of antibodies beginning from 1 µg/ml were tested by ELISA for binding to recombinant Human and Cynomolgus EGFR ECD proteins. Antibodies showing identical binding profiles in this assay were taken as indication for good species EGFR cross reactivity. ELISA wells were coated with 50 µl/well of full length EGFR at a concentration of 1 µg/ml in PBS overnight at 4° C. The next morning wells were washed twice with PBS-T and blocked for one hour with 100 µl PBS-T-1% BSA at room temperature, followed by wash twice in PBS-T. Next 50 µl of serially diluted Anti-EGFR antibodies and control antibodies were added to wells and incubated for one hour at room temperature. After antibody incubation wells were washed five times with PBS-T, followed by incubation with 50 µl/well Streptavidin-HRP secondary reagent diluted 1:3000 in blocking buffer and incubation at room temperature for 30 min. Finally wells were washed five times with PBS-T and plates were developed by adding 50 µL/well TMB substrate and incubated at room temperature. After incubation the reaction was stopped by addition of 1 M $H_2SO_4$; 100 µl/well and plates were read at OD 450 nm.

ELISA Reagents:

1. ELISA plate; NUNC Maxisorp; cat: 442404
2. Antigen: Human rEGFR ECD; Cynomolgus rEGFR ECD
3. Coating buffer: 1×PBS; Gibco cat:20012-019
4. Washing buffer: 1×PBS/0.05% Tween 20 (PBS-T)
5. Blocking/Dilution buffer: 1% BSA in PBS-T
6. Goat-anti-Human IgG HRP conjugate: Serotec, Star 106P 7. TMB Plus (KemEnTec cat #4390L)
8. (1 M $H_2SO_4$)

Figure 25A:
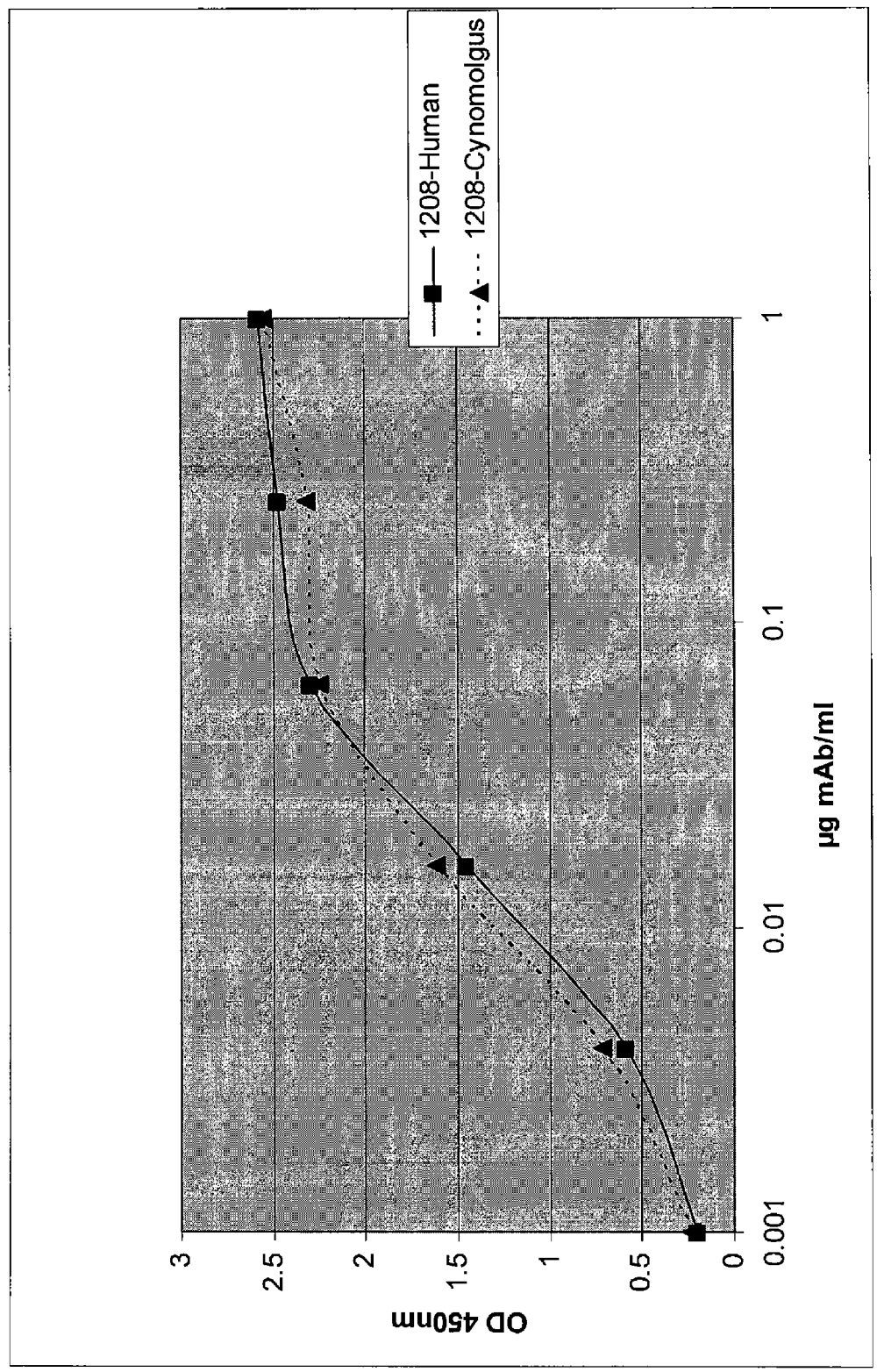
FIGS. 25A and 25B: Example of ELISA assay discrimination between cross reactive and species specific antibodies binding either Human or Cynomolgus EGFR ECD or both.
Figure 25B:
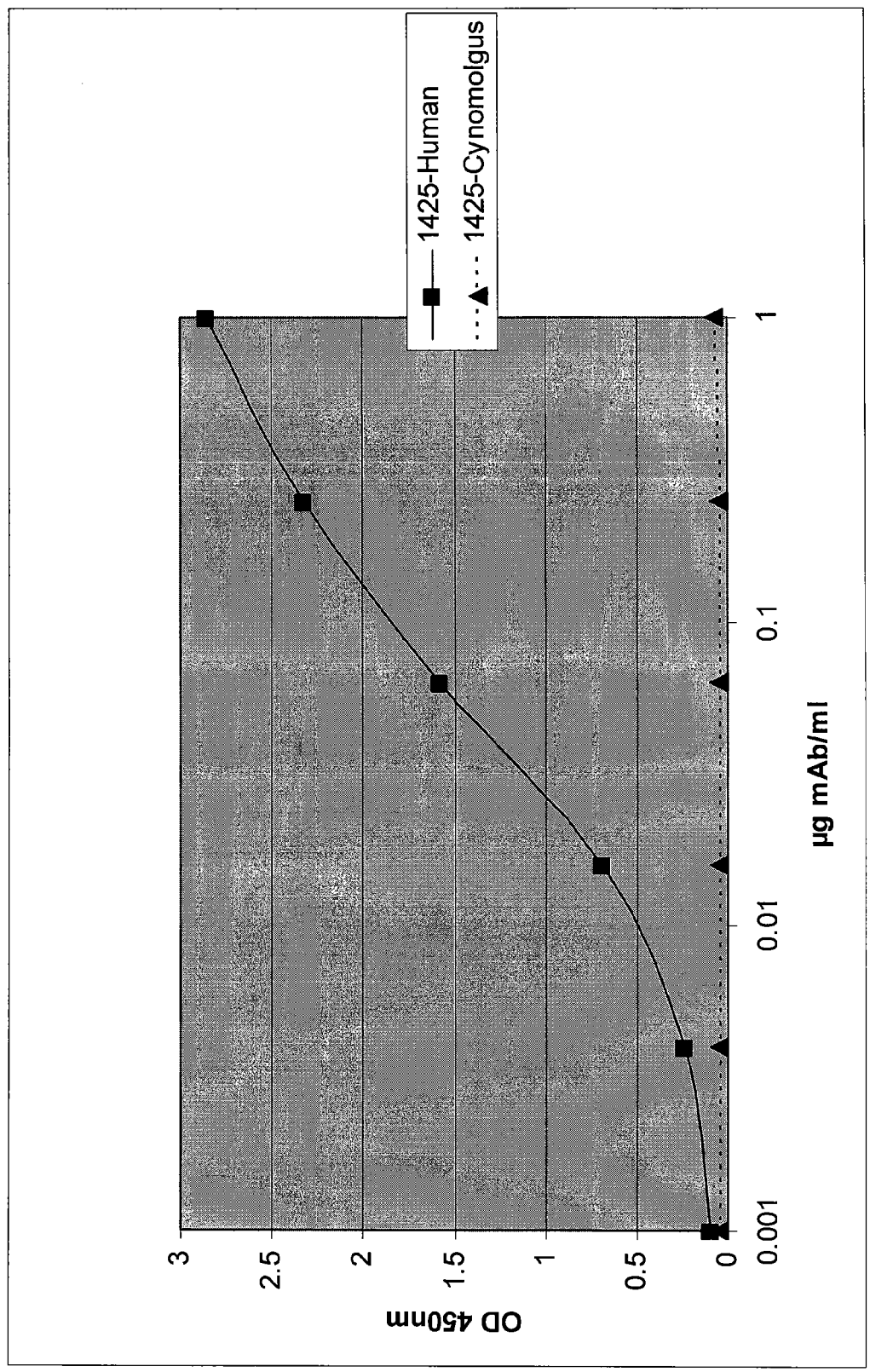

As shown in FIGS. 25A and 25B, the described ELISA assay could discriminate between cross reactive Human and Cynomolgus anti-EGFR ECD antibodies (FIG. 25 A) and species specific antibodies only recognizing the Human EGFR ECD used for mice immunizations (FIG. 25B).

Example 11

Inhibition of Motility

Most cancer deaths derive from the dissemination of tumor cells and subsequent growth in distant locations. Local invasion of adjacent normal tissue compromise homeostatic functions and prevent surgical or radiological excision of the tumor. Recent investigations have highlighted the central role that induced motility plays in promoting this spread. The EGFR is known to facility cell motility and spreading and therefore inhibition of EGFR mediated motility an important mechanism of EGFR targeted drugs.

The effect of a mixture of the two antibodies 992 and 1024 on the motility of the head and neck carcinoma cell line were investigated. Spheroids consisting of 10,000 cells were prepared overnight as described in example 9. The spheroids were then transferred to NUNC T25 cell culture flasks and adhering allowed overnight. 10 μg/ml of the antibody mix 992+1024 or a negative control antibody were then added and the spheroids were incubated for another 24 hours. Images were then taken at 40× magnification and the area covered by cells measured using the software Image J.

Results: As can be seen in FIG. 27A addition of the EGFR specific antibodies 992 and 1024 leads to a significant decrease in the area covered by tumor cells. The motility is quantified in FIG. 27B, which show that the motility is decreased approximately 60% as compared to the negative control antibody. This decrease in motility is highly significant $p<0.01$.

Thus a combination of the antibodies 992 and 1024 potently inhibits EGFR mediated tumor cell motility, which indicates that combinations of anti EGFR antibodies could be used for the treatment of disseminated disease.

Example 12

Upregulation of Involucrin by Sym004 Antibody Composition

Involucrin is a marker of early squamous cell differentiation and a protein that is involved in formation of the cornified envelope. Involucrin levels can therefore be used as measure of the number of tumor cells that have differentiated. The levels of Involucrin was estimated in protein lysates from A431NS xenograft tumors either untreated or treated with Erbitux, Vectibix or a mix of the antibodies 992+1030+1042 using a commercially available Involucrin ELISA kit (Biomedical Technologies). Tumor lysates were prepared by homogenizing 30-40 mg of tumor tissues in 1 ml of RIPA buffer using the TissueLyzer from Qiagen. The protein concentration in each cleared lysate was determined using the BCA protein assay kit from Pierce and the involucrin level estimated using the ELISA assay in 0.4 μg of protein from each sample.

Results: As can be seen in FIGS. 27A and 27B Involucrin is found in significantly higher levels in the 992+1030+1042 treatment group as compared to the negative control and Erbitux or Vectibix treatment groups. Thus a combination of the antibodies 992, 1030 and 1042 increases the levels of involucrin in the A431NS xenograft tumors and therefore presumably induces a higher degree of A431NS differentiation. A result that correlates well with the high number of keratin pearls found in this particular treatment group (See example 8).

Example 13

Internalisation of EGFR by Sym004 Antibody Composition

Some antibodies function by inducing internalization of their surface target. The EGFR is known to undergo internalization when activated by ligand such as EGF.

The ability of a mixture of the two antibodies 992 and 1024 to induce EGFR internalization was investigated using confocal microscopy. A431NS and HN5 cells were seeded in 8-well chamber slides from LabTek and incubated overnight in DMEM containing 0.5% FBS. Cells were then added 10 μg/ml of Alexa-488 labeled antibody mix of 992+1024 or the control antibody Erbitux and then incubated for different periods of time. Images were then taken at 60× magnification using a Biorad confocal microscope with either a large pin-hole or a small pin-hole.

Results: As shown in FIG. 29A addition of the Alexa-488 labeled EGFR specific antibodies 992 and 1024 for 2 hours leads to accumulation of the antibodies in intracellular vesicles in both the A431NS and HN5 cell lines. Erbitux in contrast is mainly found at the cell surface. FIG. 29B shows images of A431NS cells using a smaller pin-hole, which results in images of thinner sections of the cells. It is clear from these images that the antibodies 992+1024 are located inside the cells whereas Erbitux is mainly found at the cell surface. FIG. 30 shows a timeframe of the 992+1024 mediated internalization and as earlier as 30 minutes after addition of antibodies they can be found in intracellular vesicles. After 4 hours almost all of the antibodies 992+1024 are found inside the cells with low or very weak surface staining. Erbitux in contrast remains at the cell surface. Evidence has also been obtained showing that the internalization induced by 992+1024 leads to a sustained degradation and removal of EGFR in the cells.

Thus a combination of the antibodies 992 and 1024 rapidly and potently induce EGFR internalization whereas Erbitux does not.

Example 14

Measurement of Antibody Affinities with Surface Plasmon Resonance

Measurement of monovalent affinities of Sym004 IgG antibodies against recombinant soluble EGFR ECD.

Kinetic analysis of the full length IgG antibodies of the invention was performed on a BIAcore 2000, employing an assay as described in (Canziani, Klakamp, et al. 2004, Anal. Biochem, 325:301-307) allowing measurement of monovalent affinities of whole IgG molecules against soluble antigen. Briefly approximately 10,000 Ru of a polyclonal anti-human IgG Fc antibody was conjugated to a CM5 chip surface according to the manufacturers instructions, followed by capture of 25 μg of individual anti-EGFR antibodies of the invention or Synagis negative control on the anti-Fc Chip surface. The density of captured IgG was optimized for each clone, so that the binding of the highest antigen concentration employed in the assay did not exceed 25 Ru. Next 250 μL soluble human EGFR ECD, previously shown to contain only monovalent protein by gel exclusion chromatography, was injected at a flow rate of 25 µL/min in serial two fold dilutions in HBS-EP buffer to generate response curves. The chip surface was regenerated in between cycles by stripping the captured antibody/antigen complexes with a 10 second injection of 100 mM $H_3PO_4$. Kinetic analysis was performed by first subtracting the response of the flow cell containing the negative control antibody Synagis followed by subtraction of the response generated by injection of HBS-EP buffer only ("double referencing"). The association rate constant (ka) and dissociation constant (kd) were evaluated globally from the generated sensograms with the BIA evaluation software 4.1 provided by the manufacturer.

Reagents:
CM5 chip: Biacore, Cat. No. BR-1000-14
NHS: Biacore BR-1000-50
EDC: Biacore BR-1000-50
10 mM Acetate buffer pH 4.5: Biacore, Cat. No. BR-1003-50
Goat anti-Human IgG Fc: Caltag, Cat. No. H10500
Ethanolamine, 1.0 M pH 8.5: Biacore BR-1000-50
10×HBS-EP running buffer: 0.01 M HEPES pH 7.4, 0.15 M NaCl, 3 mM EDTA, 0.005% v/v Surfactant P20
Antigen: Human EGFR extracellular domain with 6×His.
100 mM $H_3PO_4$ The calculated monovalent affinities of the full length IgG's of the invention against soluble Human EGFR ECD are shown in Table 8 below.

TABLE 8

Measured affinities of anti-EGFR IgG antibodies against soluble receptor. Antibody measurements were performed by Surface Plasmon Resonance on a BIAcore 2000 employing evaluation software provided by the manufacturer.

| IgG | $k_{ON}$ ($M^{-1} s^{-1}$) | koff (1/s) | $t_{1/2}$ (min) | $K_D$ (nM) |
|---|---|---|---|---|
| 992* | NA | NA | 0.2 | 170.0 |
| 1024 | 1.8E+05 | 4.9E−03 | 2.4 | 26.7 |
| 1030 | 1.3E+04 | 3.7E−04 | 31.1 | 29.2 |
| 1254 | 8.1E+04 | 1.0E−03 | 11.3 | 12.7 |
| 1260 | 3.7E+04 | 1.6E−04 | 74.1 | 4.2 |
| 1261 | 1.7E+05 | 3.2E−03 | 3.6 | 18.6 |
| 1277 | 1.3E+05 | 5.3E−05 | 217.6 | 0.4 |
| 1284 | 3.2E+04 | 1.5E−04 | 78.1 | 4.6 |
| 1320 | 1.2E+05 | 2.8E−03 | 4.1 | 24.2 |
| 1347 | 2.4E+04 | 5.0E−04 | 22.9 | 21.4 |

*The affinity of 992 was determined by Scatchard Analysis.
NA. Not applicable.

Most tested Sym004 antibodies recognized soluble human EGFR ECD with affinities in the 10-20 nM range, except 1260, 1277, and 1284 which had higher affinities of 4.2 nM, 0.4 nM, and 4.6 nM respectively. Finally 992 was found to bind soluble EGFR ECD with a much lower affinity than the other tested antibodies. Consequently the kinetic analysis of this antibody had to be determined by Scatchard analysis which revealed an affinity of 170 nM against soluble human EGFR ECD.

Measurement of affinities of Sym004 Fab antibodies against immobilized recombinant EGFR ECD.

To investigate possible differences in antigen presentation between EGFR ECD presented in soluble and immobilized form, a new affinity measurement on an immobilized chimeric EGFR receptor antigen termed EGFR-Fc (R&D Systems, 344-ER), consisting of Human EGFR ECD fused to Human IgG Fc was performed. For this purpose Fab fragments of the IgG antibodies 992, 1024 & 1030 were generated to allow measurement of monovalent affinities.

Fab Production:

Fab fragments of 992, 1024 and 1030 were produced by Papain digestion using a Fab preparation Kit from Pierce and following the manufactures instructions. Briefly 2 mg of each IgG antibody was buffer exchanged on NAP-5 columns (Amersham Biosciences) with freshly prepared digestion buffer containing 20 mM Cystein-HCl, pH 7.0 following the instructions of the manufacturer. Then a 350 µl slurry of Papain beads was washed twice in the same digestion buffer before the beads were spun down and the supernatant discarded. Antibodies were digested by adding 1 ml buffer exchanged IgG antibody to the beads and incubating overnight at 37° C. with shaking at 1000 rpm. The next morning, undigested IgG was separated from crude Fab by depletion of full length IgG on HiTrap Protein A columns (Ge Healthcare). The produced Fab was finally dialyzed against PBS overnight and analyzed with SDS-PAGE under reducing and nonreducing conditions. A protein band of approximately 50 kDa under nonreducing conditions was taken as an indication of successful Fab production.

Reagents:
1. ImmunoPure Fab preparation Kit; Pierce; cat. No. 44885
2. NAPS desalting column; Amersham, Cat. No. 17-0853-02
3. PBS pH 7.2; Gibco; #20012-019
4. HiTrap Protein A HP, 1 ml column; GE Healthcare; #17-0402-01
5. NuPAGE 4-12% Novex Bis-Tris Gel; Invitrogen; #NPO322BOX
6. Molecular marker; Seeblue Plus 2,; Invitrogen; # LC5925
7. Anti-EGFR antibodies—2.0 mg of each Kinetic analysis of the Fab antibodies of the invention was performed on a Biacore 2000, using recombinant antigen immobilized onto the sensor surface at a very low density to avoid limitations in mass transport. Briefly a total of 285 Ru recombinant EGFR ECD-Fc chimera (R&D Systems, Cat. No. 344-ER) was conjugated to a CM5 chip surface according to the manufacturer's instructions. Then Fab fragments derived from the antibodies of the invention were tested in serial two fold dilutions, starting at an optimized concentration that did not result in Ru max values above 25 when tested on the chip with immobilized EGFR. Kinetic analysis was performed by first subtracting the response generated by injection of HBS-EP buffer only. The association rate constant (ka) and dissociation constant (kd) were evaluated globally from the generated sensograms with the BIA evaluation software 4.1 provided by the manufacturer.

The calculated affinities of the tested Fab fragments of the invention against immobilized Human EGFR ECD are shown in Table 9 below.

TABLE 9

Measured affinities of anti-EGFR Fab antibodies against immobilized receptor. Antibody measurements were performed by Surface Plasmon Resonance on a BIAcore 2000 employing evaluation software provided by the manufacturer.

| Fab | $k_{ON}$ ($M^{-1} s^{-1}$) | koff (1/s) | $t_{1/2}$ (min) | $K_D$ (nM) |
|---|---|---|---|---|
| Fab 992* | N.A. | N.A. | 0.2 | 150.0 |
| Fab 1024 | 1.9E+05 | 4.9E−03 | 2.3 | 25.6 |
| Fab 1030 | 8.7E+04 | 2.0E−04 | 57.5 | 2.3 |

*The affinity of 992 was determined by Scatchard Analysis.
NA. Not applicable.

As presented in Table 9 above the Fab fragments of 992 and 1024 were found to have affinities of 150 nM and 26 nM respectively in agreement with the affinities presented in the previous example, illustrating minor differences in the antibody recognition against soluble and immobilized EGFR for these two antibodies. However, antibody 1030 exhibited a ten fold higher affinity of 2.3 nM against immobilized antigen as compared to soluble receptor and consequently preferentially recognized an epitope exposed on immobilized antigen.

Example 15

Investigation of EGFR Antigen Presentation and Ranking of Functional Affinities on A431-NS Cells Comparison between antigen presentation on A431-NS cells and purified full length EGFR receptor.

Since the kinetic analysis revealed that antibody 992 recognized recombinant EGFR ECD with an affinity between 150-170 nM, it was investigated if this weak affinity was due to the fact that mAb 992 preferentially bound native conformations of EGFR as expressed on A431-NS cells as opposed to conformations presented on recombinant EGFR ECD or full length EGFR purified from A431 cells. To investigate differences in the EGF receptor antigen presentations, concurrent ELISA binding studies of a subpopulation of the antibodies of the invention was performed with Fab fragments to avoid avidity effects on tested A431-NS cells and purified full length EGFR from the same cells.

Fab Production: Production of Fab Fragments was Performed as Described in Example 14.

Indirect ELISA: For the indirect ELISA, full length EGFR (Sigma E2645) was coated at 1 µg/ml in Carbonate buffer (50 µl/well) overnight at 4° C. The next morning, wells were washed twice with PBS-T and blocked for one hour with PBS-T containing 1% BSA at room temperature followed by wash twice in PBS-T. Next 50 µl serial dilutions of Fab antibodies in DMEM containing 1% BSA were added to independent ELISA wells and incubated for 1 hour at room temperature, after which wells were washed four times with PBS-T. Next 50 µl of a secondary Goat-anti-Human (Fab specific) HRP conjugate diluted 1:5000 in DMEM containing 1% BSA was added and incubated on ice for 30 min. Finally, wells were washed four times with PBS-T and plates developed by adding 50 µl/well TMB substrate and read at 620 nm every 5-15-30 min. After incubation with substrate, the reaction was stopped by addition of 1 M $H_2SO_4$ and absorbance read at 450 nm.

Reagents, indirect ELISA:
Coating buffer: 50 mM Carbonate buffer, pH 9.8
Antigens: Wild type full length EGFR purified from A431 cells; Sigma E2645
ELISA plate: NUNC Maxisorp; Cat. No: 442404
Washing buffer: 1×PBS/0.05% Tween 20 (PBS-T)
Blocking/Dilution buffer: 1% BSA in PBS-T (PBS-T-1% BSA)
Antibody dilution buffer: DMEM containing 1% BSA
Goat-anti-Human (Fab specific) HRP conjugate: Jackson, Cat. No. 109-035-097
TMB Plus substrate: KemEnTec, Cat. No. 4390L
1M $H_2SO_4$ Cell ELISA: The relative binding affinities defined as the molar concentration giving the half maximal OD (ED50) were determined by antibody titrations on A431-NS cells. Briefly, 10,000 A431-NS cells were grown in 96 well ELISA plates containing DMEM with added 0.5% FCS and 1% P/S at 37° C., 5% $CO_2$ overnight. The next morning confluent cells (approximately 20,000/Well) were washed twice with PBS and fixed by incubation with a 1% paraformaldehyde solution for 15 min at room temperature followed by wash four times with PBS. Next, tested EGFR antibodies and the negative control antibody Synagis were serially diluted in DMEM containing 1% BSA and 50 µl of each dilution added to the wells and incubated for 1 hour at room temperature, after which wells were washed four times with PBS. Then 50 µl of a secondary Goat-anti-Human (Fab specific) HRP conjugate diluted 1:5000 in DMEM containing 1% BSA was added and incubated on ice for 30 min. Finally wells were washed four times with PBS and plates developed by adding 50 µl/well TMB Plus substrate and read at 620 nm every 5-15-30 min. After incubation with substrate the reaction was stopped by addition of 1 M $H_2SO_4$ and absorbance read at 450 nm. The functional affinity expressed as ED50 values were calculated by subtraction of the average background binding with secondary reagent only, followed by normalization of the binding curves by plotting % maximal binding relative to each antibody tested.

Figure 31A:
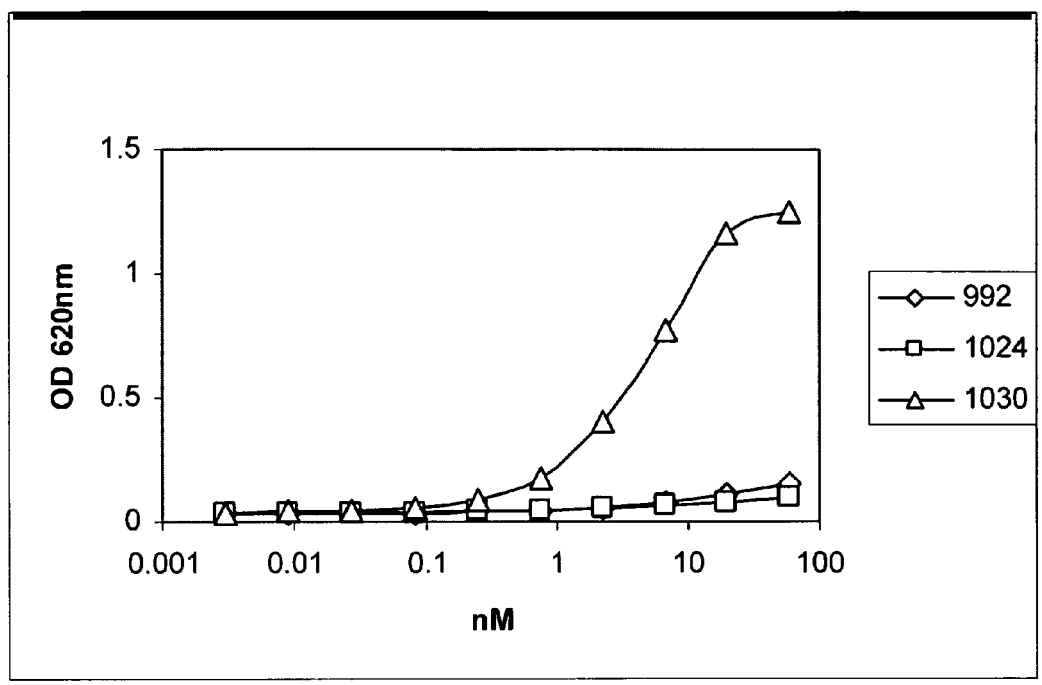
FIGS. 31A and 31B: Determination of antigen presentation specificity of Fabs 992, 1024 & 1030 by serial antibody titrations on A431-NS cells and purified full length EGFR in ELISA. Bound Fab antibodies were visualized by a secondary Goat anti-Human Fab specific HRP conjugate.
Figure 31B:
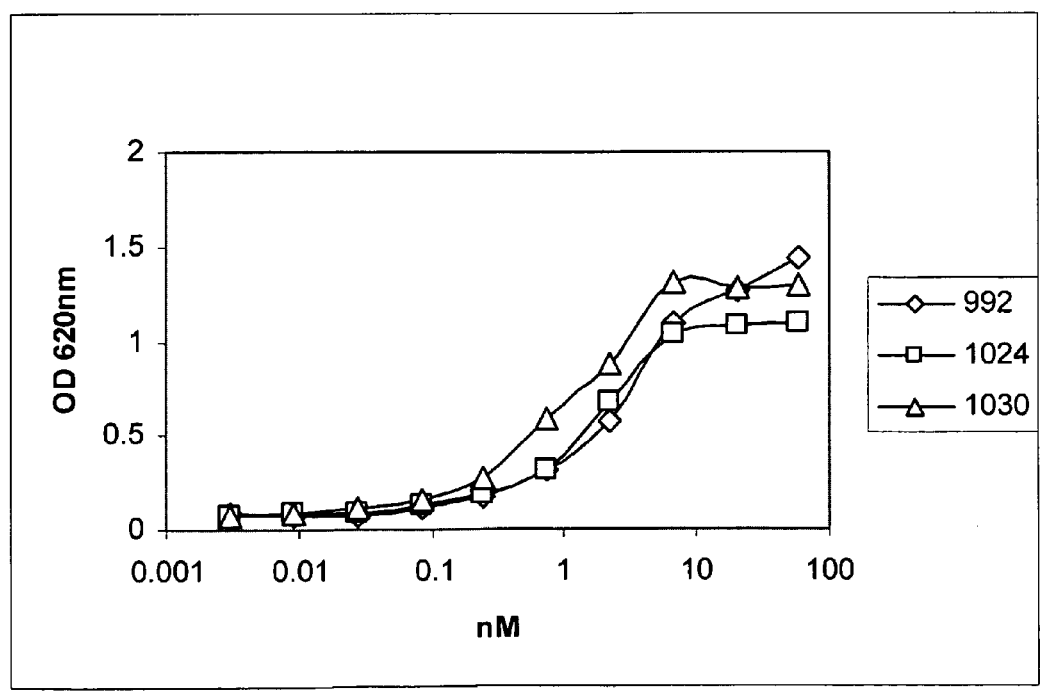

Reagents, cell ELISA:
DMEM media: Gibco, Cat. No 41966-029
FCS: Gibco, Cat. No. 10099-141
Pen strep (P/S): Gibco, Cat. No. 15140-122
ELISA plate: Costar, Cat. No. 3595
Wash buffer (PBS): Gibco cat. 20012-019
Antibody dilution buffer: DMEM containing 1% BSA
Cell fixation solution: BD Biosciences, Cat. No. 340181
Goat-anti-Human (Fab specific) HRP conjugate: Jackson, Cat. No. 109-035-097
TMB Plus substrate: KemEnTec, Cat. No. 4390L
1M $H_2SO_4$ Differences in the antigen presentation on EGF receptor expressed on A431-NS cells and on purified receptor from the same cells were determined with concurrent ELISA binding studies, employing same secondary antibody reagent and incubation times. The results are shown in FIGS. 31A and 31B. The experiment clearly showed that Fab antibodies 992 and 1024 bound weakly to purified full length EGFR coated to ELISA wells when compared to the binding of same concentrations of Fab 1030. However, this weak binding activity of 992 and 1024 was restored when the antibodies were tested on A431-NS cells against which all three Fabs showed strong binding activity. The comparison of the two different ELISAs clearly illustrated a preference of Fabs 992 and 1024 for binding native EGFR conformations as expressed on cell surfaces as opposed to conformations presented on purified antigen in ELISA wells. The result also suggested that the apparent weak affinity of 992 measured with surface plasmon resonance on recombinant soluble and immobilized EGFR ECD was due to unfavorable presentation of the 992 antibody epitope in the tested systems.

Ranking of Functional Affinities on A431-NS Cells.

Figure 32A:
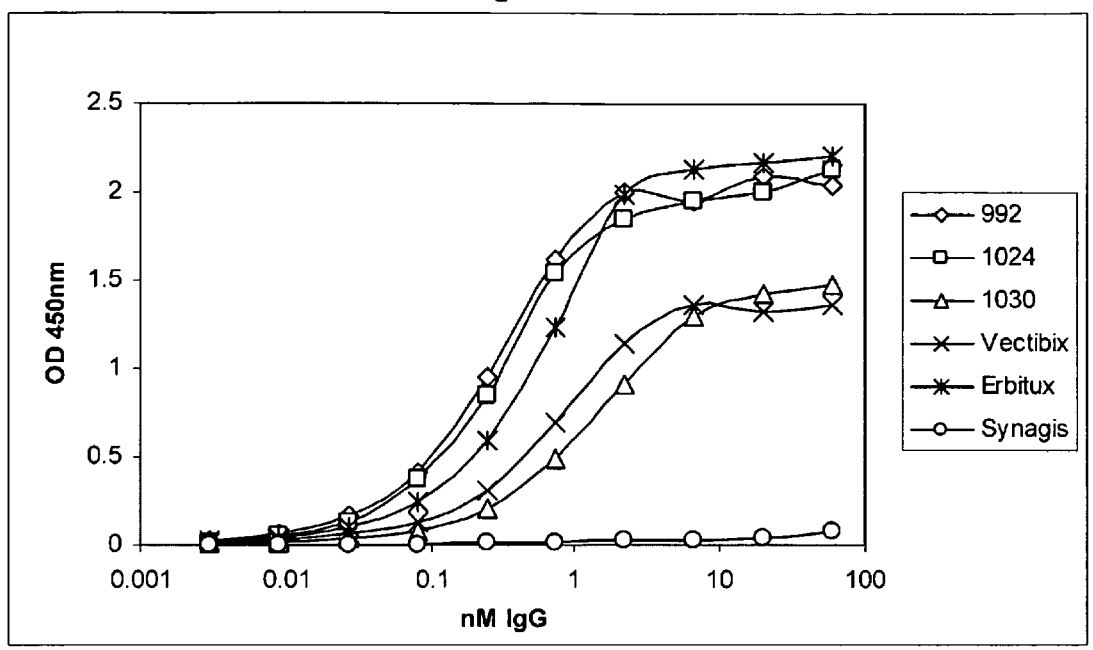
FIGS. 32A and 32B: Determination of the functional affinity of IgG and Fab fragments of antibodies 992, 1024, 1030, Erbitux & Vectibix by serial titration on paraformaldehyde fixed A431-NS cells in ELISA. Bound Fab and IgG antibodies were visualized by a secondary Goat anti-Human Fab specific HRP conjugate. The anti-RSV protein F antibody Synagis was employed as a negative control antibody, and did not show any binding in the employed ELISA assay.
Figure 32B:
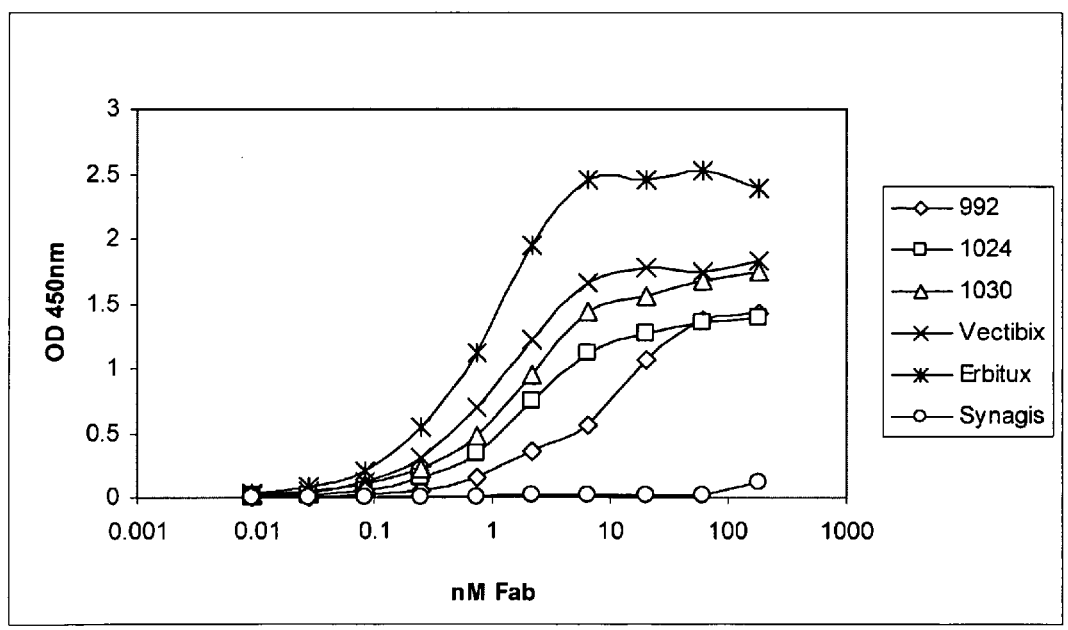

Cell ELISAs performed as described above were used to rank the functional affinities of IgG and Fab fragments of 992, 1024, 1030, Vectibix and Erbitux by calculation of the half maximal OD values expressed as ED50 values. The result of this analysis is shown in FIGS. 32A and 32B and calculated ED50 values are presented in Table 10 below.

TABLE 10

Ranking of functional affinities expressed as ED50 values based on avidity effects of IgG or monovalent affinity of Fab. ED50 values were determined by serial antibody titrations on A431-NS cells.

| IgG Avidity | | | | Fab Affinity | | | |
|---|---|---|---|---|---|---|---|
| IgG | Log ED50 | ED50 nM | SD | Fab | Log ED50 | ED50 nM | SD |
| 992 | −0.56 | 0.3 | 0.04 | 992 | 1.00 | 9.9 | 0.11 |
| 1024 | −0.49 | 0.3 | 0.05 | 1024 | 0.30 | 2.0 | 0.02 |
| 1030 | 0.17 | 1.5 | 0.02 | 1030 | 0.27 | 1.8 | 0.05 |
| Vectibix | −0.15 | 0.7 | 0.04 | Vectibix | 0.08 | 1.2 | 0.04 |
| Erbitux | −0.23 | 0.6 | 0.04 | Erbitux | −0.07 | 0.8 | 0.06 |

SD: Standard deviation of curve fitting.

The experiment clearly showed that when avidity effects were taken into account IgG 992 and 1024 appeared to be binding A431-NS cells with higher avidity than both Erbitux and Vectibix, while IgG 1030 had the lowest affinity of the tested IgG antibodies. However, when the monovalent affinity on cells was determined using Fab fragments, 992 had the lowest affinity of approximately 10 nM. Nonetheless, this monovalent functional affinity was still at least 15 fold lower than tested with BIAcore.

Example 16

Investigation of Antibody Induced Binding Enhancement

The BIAcore competition experiment performed on antibody pairs of the invention revealed that the binding of 992 and 1024 were enhanced approximately 55% and 58% respectively (FIG. 9A), when these antibodies were tested against each other in both directions. To investigate this phenomenon further, a cell ELISA using unfixed cells was designed to investigate the effect of IgG binding of one antibody clone upon prior receptor saturation with the Fab fragment of an antibody binding a non overlapping epitope.

Cell ELISA: The ELISA was performed essentially as described in example 15 with modifications. Cells were left unfixed to allow conformational EGFR flexibility after antibody additions. Briefly, 10,000 A431-NS cells were grown in 96 well ELISA plates containing DMEM with added 0.5% FCS and 1% P/S at 37° C., 5% $CO_2$ overnight. The next morning confluent cells (approximately 20,000/Well) were washed twice with PBS, and wells for investigation of antibody induced binding enhancements were preincubated with 25 µl of 40 nM single Fab fragments of either 992, 1024 or 1030, or 12.5 µl of 80 nM of each single Fab in double combinations previously shown to give saturated binding. 25 µl DMEM containing 1% BSA was added to wells used for testing of IgG antibodies without added Fab fragments. Following Fab and media addition, ELISA wells were incubated for 30 min at room temperature, after which 25 µl of serial three fold dilutions of IgGs of the invention or Synagis negative control, beginning at a concentration of 360 nM were added to wells and incubated on ice for one hour. Next, wells were washed four times with PBS and 50 µl of a secondary monoclonal Mouse-anti-Human (Fc specific) HRP conjugate diluted 1:5000 in DMEM containing 1% BSA was added and incubated on ice for 30 min. Finally wells were washed four times with PBS and plates developed by adding 50 µl/well TMB substrate and read at 620 nm every 5-15-30 min. After incubation with substrate the reaction was stopped by addition of 1 M $H_2SO_4$ and absorbance read at 450 nm. The functional affinity expressed as ED50 values were calculated by subtraction of the average background binding with secondary reagent only, followed by normalization of the binding curves by plotting % maximal binding relative to each antibody tested.

Figure 33A:
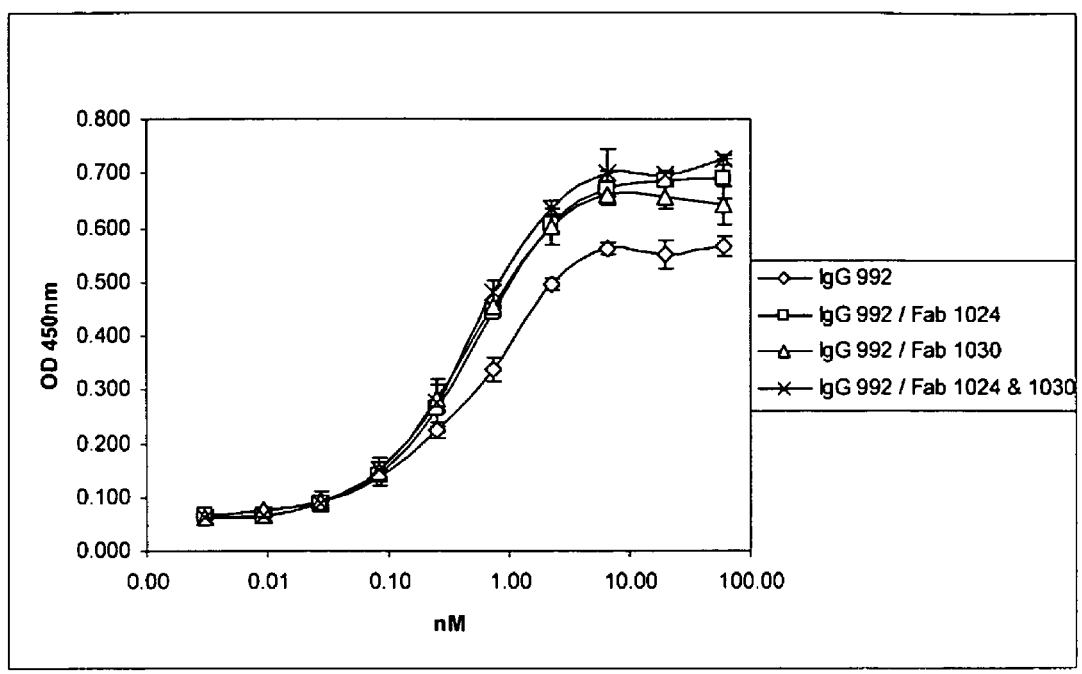
FIGS. 33A-33C: Determination of enhancement of IgG binding to EGFR on A431-NS cells upon prior receptor saturation with Fab fragments binding non overlapping epitopes. Indicated Fab fragments were allowed to saturate recognized EGFR epitope on A431-NS cells for 30 min after which specified IgG antibodies were serially titrated and bound IgG with or with out Fab addition visualized by a secondary Mouse anti-Human Fc HRP conjugate.
Figure 33B:
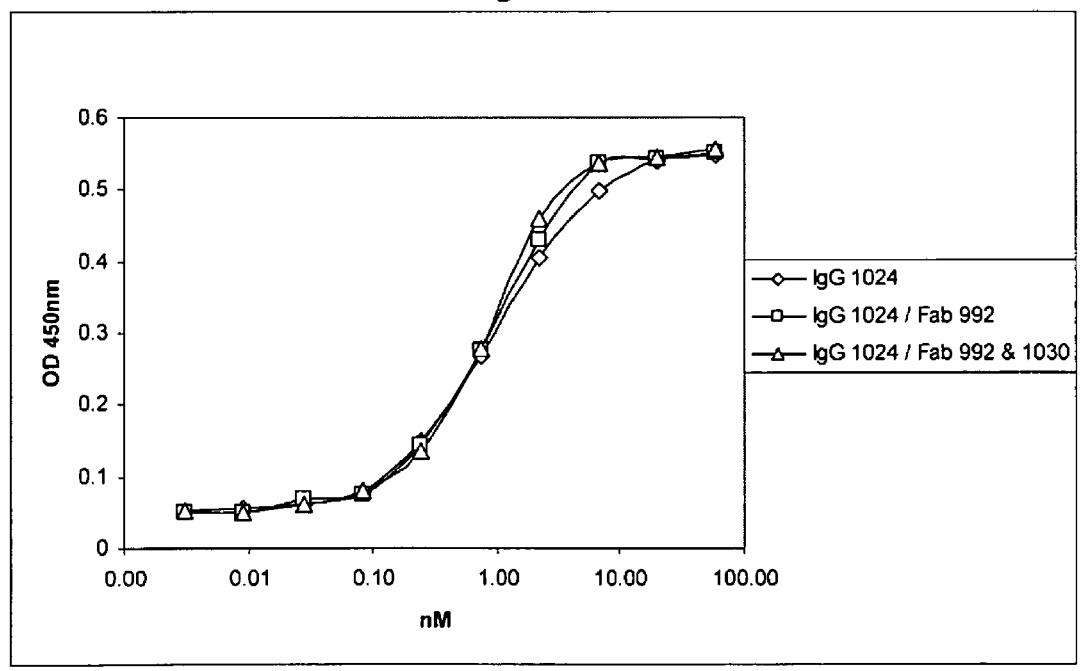
Figure 33C:
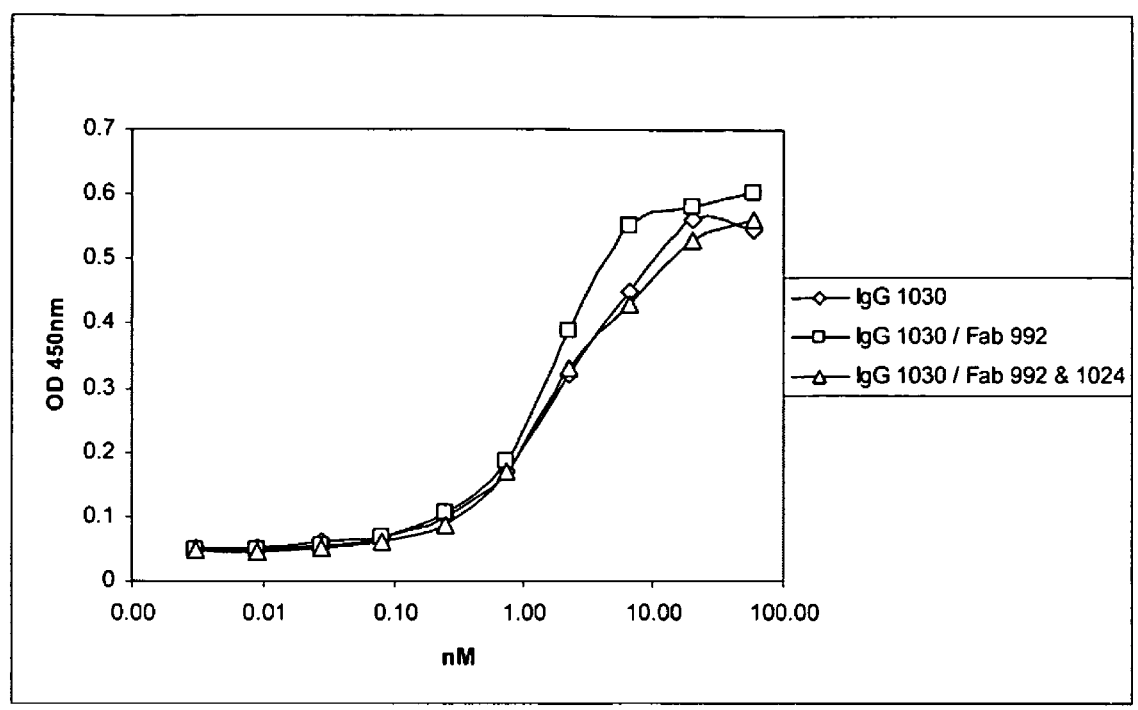

Reagents, cell ELISA:
1) DMEM media: Gibco, Cat. No 41966-029
2) FCS: Gibco, Cat. No. 10099-141
3) Pen strep (P/S): Gibco, Cat. No. 15140-122
4) ELISA plate: Costar, Cat. No. 3595
5) Wash buffer (PBS): Gibco cat. 20012-019
6) Antibody dilution buffer: DMEM containing 1% BSA
7) Mouse-anti-Human (Fc specific) HRP conjugate: Abdirect, Cat. No. MCA647P
8) TMB Plus substrate: KemEnTec, Cat. No. 4390L
9) 1M $H_2SO_4$ Investigations of antibody induced binding enhancements were determined by concurrent ELISA binding studies, employing same secondary antibody reagent and incubation times. The result of the study is shown in FIGS. 33A-33C and calculated ED50 values in Table 11 below.

TABLE 11

Ranking of functional affinities expressed as ED50 values based on avidity effects of IgG with or without prior receptor saturation with listed Fab fragments. ED50 values were determined by serial antibody IgG titrations on A431-NS cells.

| IgG | Log ED50 | ED50 nM | SD |
|---|---|---|---|
| IgG 992 | −0.24 | 0.6 | 0.07 |
| IgG 992/Fab 1024 | −0.31 | 0.5 | 0.02 |
| IgG 992/Fab 1030 | −0.38 | 0.4 | 0.05 |
| IgG 992/Fab 1024 & 1030 | −0.34 | 0.5 | 0.04 |
| IgG 1024 | −0.01 | 1.0 | 0.01 |
| IgG 1024/Fab 992 | −0.05 | 0.9 | 0.04 |
| IgG 1024/Fab 992 & 1030 | −0.08 | 0.8 | 0.02 |
| IgG 1030 | 0.33 | 2.2 | 0.06 |
| IgG 1030/Fab 992 | 0.20 | 1.6 | 0.03 |
| IgG 1030/Fab 992 & 1024 | 0.34 | 2.2 | 0.06 |

SD: Standard deviation of curve fitting.

As presented in FIGS. 33A-33C and Table 11 above, IgG 992 showed a clear enhancement of binding upon prior receptor saturation with Fab fragments of either 1024 or 1030 or 1024 together with 1030. The incubation with Fab fragments resulted in decreased ED50 values of 0.5; 0.4 & 0.5 nM respectively compared to 0.6 nM when IgG 992 was tested alone Likewise IgG 1024 and 1030 also showed increased binding when cells were first saturated with Fab 992 and only 1024 when both Fab 992 and 1030 were added to cells prior to IgG. This result clearly illustrated the benefit of having more than one antibody against nonoverlapping epitopes on the same target receptor.

Slightly lower functional affinities were determined in this experiment as compared to example 2. This outcome is probably due to the fact that a different secondary reagent was used in the present example and due to the fact that tested IgGs were incubated with unfixed cells on ice to avoid internalization.

Example 16b

Cloning of Full Length Cynomolgus EGFR

The full length Cynomolgus EGFR including signal peptide was cloned from Cynomolgus cDNA isolated from epidermis by using nested PCR and sequence specific primers derived from the published sequence of full length human EGFR (GENBANK X00588, Ullrich, A. et. al. Nature 309 (5967), 418-425 (1984)).

PCR Reagents:
Cynomolgus Monkey cDNA Isolated from Normal Skin Epidermis:
CytoMol Unimed, Cat. No: ccy34218, Lot No: A711054.
FastStart reaction buffer (10×): Roche, Cat. no: 03 553 361 001
FastStart enzyme: Roche, Roche, Cat. no: 03 553 361 001
Phusion enzyme: Finnzymes, F-530S (2 U/µL).
dNTP 25 mM: Bioline, Cat. No: BIO-39029
Primers for amplification of full length Cynomolgus EGFR including signal sequence:

```
                                    (SEQ ID NO 135)
5' ATG primer:   5'-TCTTCGGGAAGCAGCTATGC-3'

(SEQ ID NO 139)
3' STOP primer:  5'-TCATGCTCCAATAAATTCACTG-3'
```

PCR Conditions:
95° C./2 min, 40 cycles: 95° C./30 sec, 55° C./30 sec, 72° C./3 min 30 sec with a final incubation at 72° C. for 5 min.

Primers for nested PCR amplifying full length Cynomolgus EGFR and incorporating Not and Xho restriction sites:

```
E579 Cyn Not5'
                                    (SEQ ID NO 140)
5'-GGAGTCGGCGGCCGCACCATGCGACCCTCCGGGACGG-3

E580 Cyn Xho5'
                                    (SEQ ID NO 141)
5'-GCATGTGACTCGAGTCATGCTCCAATAAATTCACTGC-3
```

PCR Conditions:
95° C./2 min, then 30 cycles: 95° C./30 sec melting, 55° C./30 sec annealing, 72° C./3 min elongation. After 30 cycles PCR products were allowed to elongate for additional 10 min.

PCR reactions were performed with 0.5 µl template and 0.1 µl Phusion Enzyme, 0.4 µl FastStart enzyme in a total volume of 50 µL reaction buffer with a final concentration of 1× FastStart buffer, 0.2 mM dNTP and 0.2 µM of each primer.

A PCR fragment with an apparent length of approximately 4000 by was obtained and cloned using the TOPO TA cloning kit (Invitrogen, Part No. 4506-41) and sequenced. The DNA and protein sequence of the cloned Cynomolgus EGFR is shown in FIG. 34A and 34B. An alignment of the human EGFR and Cynomolgus EGFR protein sequences showed 99.2% sequence identity.

Demonstration of Antibody Cross Reactivity Between Full Length Human and Cynomolgus EGFR by FACS Analysis.

Full length Human and Cynomolgus EGFR were expressed on the surface of CHO cells by stable transfection, and cells tested for binding to a panel of serially diluted EGFR antibodies by FACS analysis. Determinations were done under $K_D$ dependent conditions, by keeping a molar excess of antibody that was at least 5 times higher than the number of EGFR antigen molecules expressed on the cell surface of a fixed number of cells in all antibody dilution series. This setup permitted FACS analysis of antibody binding at full receptor saturation for all tested antibody concentrations.

Briefly quantitative FACS analysis was performed on a BD FACS array Bioanalyzer System to determine the number of EGFR molecules expressed on the surface of CHO cells transfected with either Human or Cynomolgus full length EGFR. The analysis was performed by titrating PE labeled Erbitux IgG on cells, and determine the number of molecules of equivalent PE by comparison to a standard curve made from Rainbow calibration particles with known PE density. The quantitative analysis revealed that the EGFR transfected CHO cells displayed approximately 350,000 molecules on the surface of each cell. Next, serial 5 fold dilutions of antibodies of the invention starting at 5 nM were compared by incubating with 10,000 EGFR transfected CHO cells in increasing volumes, permitting at least 5 fold molar excess of antibody over surface displayed EGFR antigen in each determination. Antibodies were incubated with cells for 14 hours on a shaker, to promote full antigen saturation at all antibody concentrations tested, while FACS buffer was added 0.02% $NaN_3$ and temperature kept at 4° C. to prevent receptor internalization. After incubation, cells were pelleted at 1200 RPM for 5 min at 4° C. and resuspended in 200 ul FACS buffer. Next cells were stained with a secondary Goat F(ab')$_2$ anti-Human IgG FcGamma PE diluted 1:500 and incubated for 30 min at 4° C. on a shaker. Finally cells were washed twice in FACS buffer and analyzed on a BD FACS array Bioanalyzer System with gating on EGFR expressing CHO cells displaying uniform forward/side scatter properties.

FACS Reagents:

Rainbow calibration particles: BD, cat. no: 559123

FACS buffer: 1×PBS+2% FCS+0.02% $NaN_3$

Goat F(ab')$_2$ anti-Human IgG FcGamma PE: Jackson ImmunoResearch, cat. no. 109-116-170

Figure 40A:
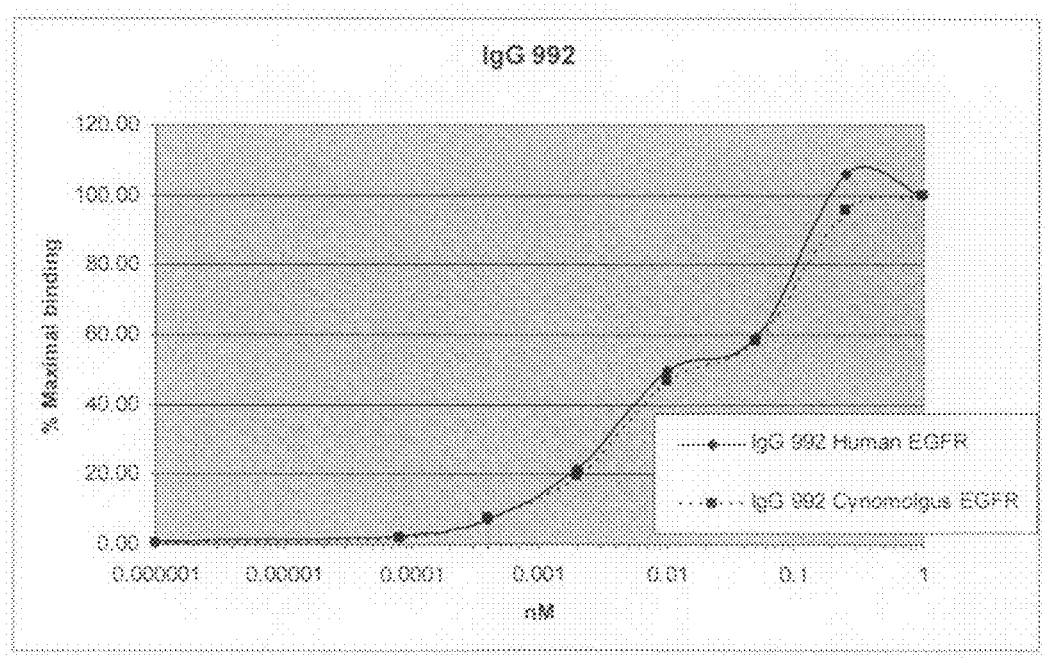
FIGS. 40A-40C: Analysis of cross reactivity of IgGs 992, 1024 & 1320 against full length Human and Cynomolgus EGFR transfected CHO cells by FACS analysis. Bound antibody was detected with a PE labelled goat $F(ab')_2$ anti-human IgG FC. Gating was performed on uniform cells (SCC/FCS properties) expressing EGFR. Binding is expressed as % maximal antibody binding at 1 nM concentration.
Figure 40B:
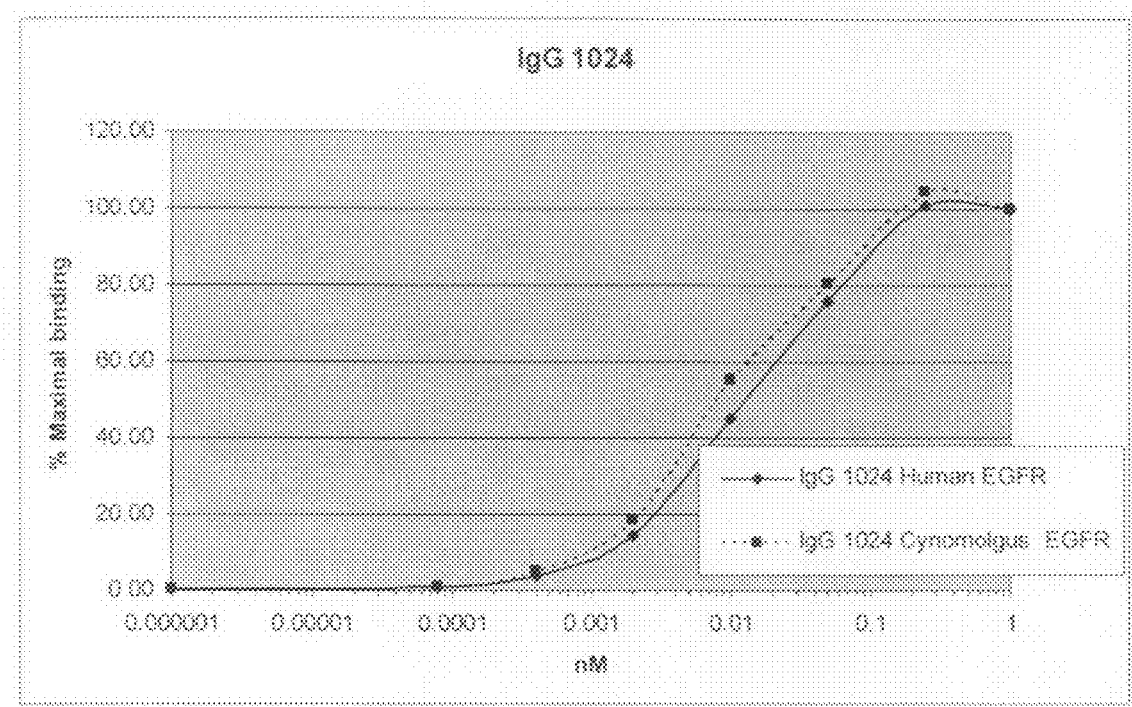
Figure 40C:
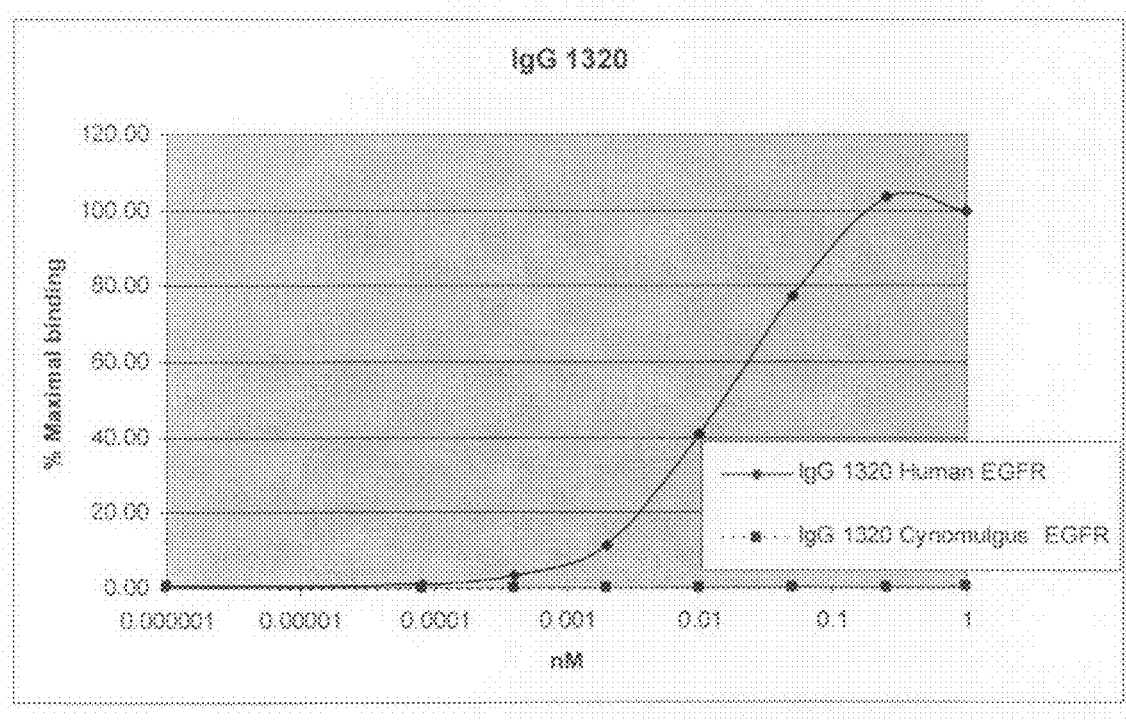
Figure 42A:
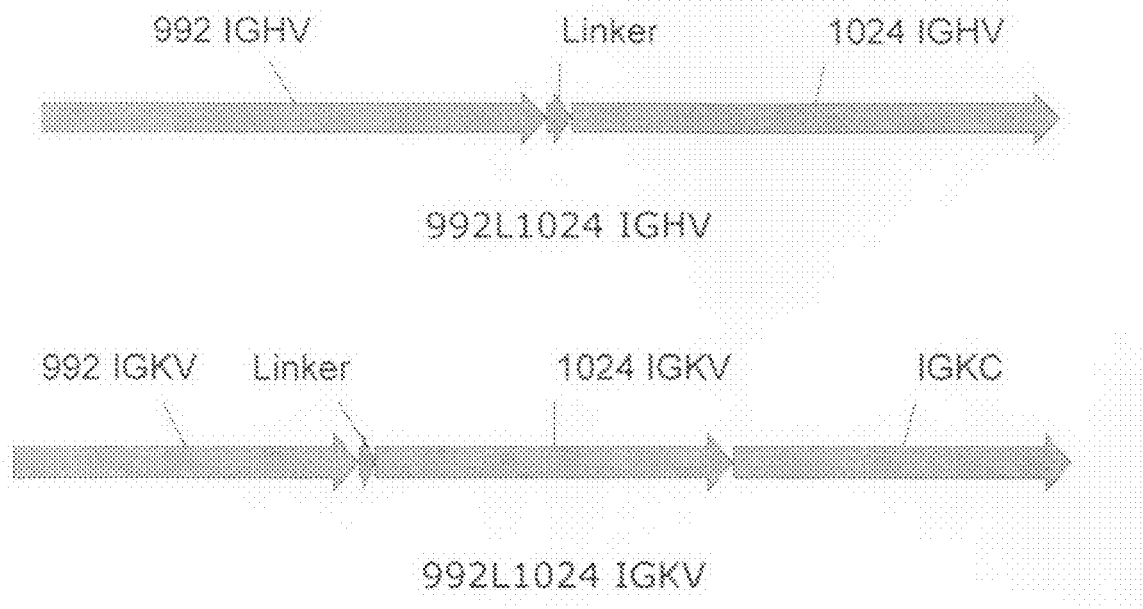
FIG. 42A: Schematic representation of the dual variable domain encoding genes for 992L1024; 992L1024 IGHV (751 bp) is represented from the 5' AscI restriction site followed by 992 IGHV, the ASTKGP linker, 1024 IGHV and ending at the 3' XhoI restriction site, 992L1024 IGKV (1071 bp) is represented from the 5' NheI restriction site followed by 992 IGKV, the TVAAP linker, 1024 IGKV, IGKC and ending at the 3' NotI restriction site.
Figure 42B:
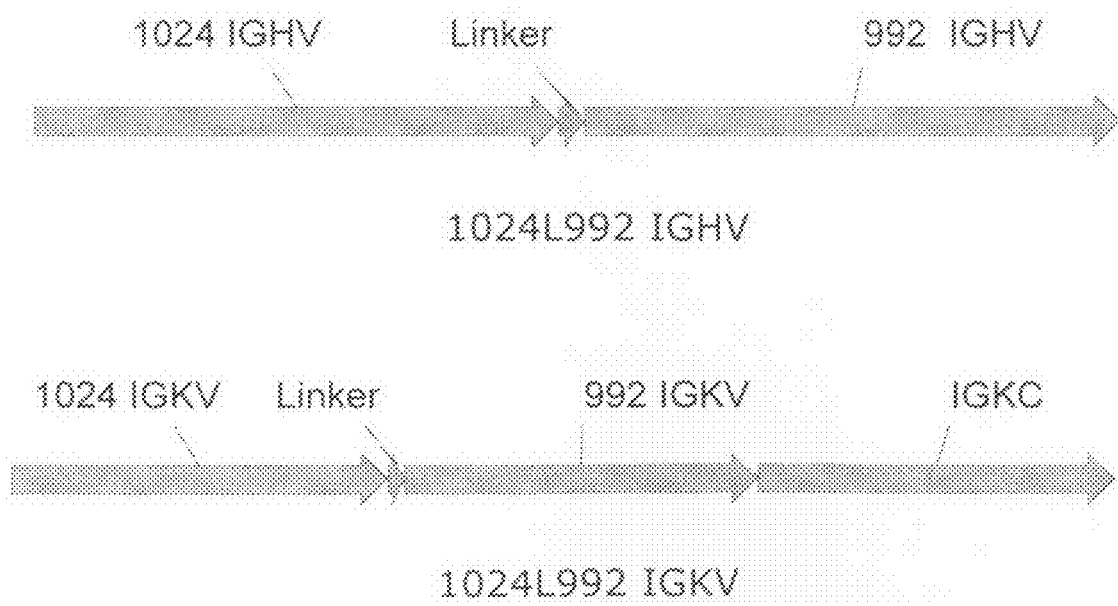
FIG. 42B: Schematic representation of the dual variable domain encoding genes for 1024L992; 1024L992 IGHV (751 bp) is represented from the 5' AscI restriction site followed by 1024 IGHV, the ASTKGP linker, 992 IGHV and ending at the 3' XhoI restriction site, 1024L992 IGKV (1071 bp) is represented from the 5' NheI restriction site followed by 1024 IGKV, the TVAAP linker, 992 IGKV, IGKC and ending at the 3' NotI restriction site.

The described FACS binding assay was used for determination of the cross reactivity of the EGFR antibodies IgG 992 and 1024 and compared to a control antibody IgG 1320, which did not cross react with Cynomolgus EGFR. As shown in FIG. 40A-40C below, the described FACS assay was very good at discriminating antibodies exhibiting good cross reactivity between Human and Cynomolgus full length EGFR (FIG. 40A, IgG 992 and FIG. 40B, IgG 1024) and species specific antibodies only recognizing the full length Human EGFR (FIG. 40C, IgG 1320). From this analysis it was concluded that both IgG 992 and 1024 exhibited excellent cross-reactivity against both Human and Cynomolgus full length EGFR expressed on the surface of stable transfected CHO cells. The difference in binding between cynomolgus and human EGFR is surprising in view of the high degree of sequence similarity and underscores the importance of testing antibodies for binding to the exact target sequence in the animals used for pre-clinical toxicology studies.

Example 17

Clones Homologous to 992, 1024 and 1030

The screening for EGFR-binding Antibody-clones, based on immunosorbent assays (ELISA and cell based assays), led to the identification of clones 992, 1024, 1030 as described in the previous examples. EGFR specific clones, homologous to 992, 1024, 1030, were also identified (Table 12).

Clones belonging to the same cluster are expected to have the same binding specificity but may bind with different affinities. Therefore, clones within a cluster can replace one another in the antibody compositions of the present invention, provided that the binding affinities of the clones do not differ too much.

TABLE 12

| | | IGHV | | | | | |
|---|---|---|---|---|---|---|---|
| Cluster | Clone name | IGHV gene | IGHJ gene | CDR3 | SEQ ID NO | Number of somatic mutations | Somatic mutations |
| 992 | 1209 | IGHV1S22*01 | IGHJ4*01 | CTRNGDYYISSGDAMDYW | 110 | 4 | H46P, G61R, G76A, H90Q |
| | 1204 | IGHV1S22*01 | IGHJ4*01 | CTRNGDYYVSSGDAMDYW | 111 | 5 | H46P, G59D, G61R, G76A, H90Q |
| | 992 | IGHV1S22*01 | IGHJ4*01 | CTRNGDYYVSSGDAMDYW | 111 | 4 | H46P, G61R, G76A, H90Q |
| | 996 | IGHV1S22*01 | IGHJ4*01 | CTRNGDYYVSSGDAMDYW | 111 | 4 | H46P, G61R, G76A, H90Q |
| | 1033 | IGHV1S22*01 | IGHJ4*01 | CTRNGDYYVSSGDAMDYW | 111 | 4 | H46P, G61R, G76A, H90Q |
| | 1220 | IGHV1S22*01 | IGHJ4*01 | CTRNGDYYVSSGDAMDYW | 111 | 4 | H46P, G61R, G76A, H90Q |
| 1030 | 1195 | IGHV5S9*01 | IGHJ4*01 | CARGSDGYFYAMDYW | 112 | 12 | K14R, M39L, T55S, S58G, G59V, Y62T, T63Y, Y66-, Y67F, I78M, K84R, T86I |
| | 1030 | IGHV5S9*01 | IGHJ4*01 | CARGSDGYFYAMDYW | 112 | 12 | M39L, K48R, T55S, S58G, G59V, Y62T, T63Y, Y66-, Y67F, I78M, K84R. T86I |
| | 1034 | IGHV5S12*01 | IGHJ4*01 | CARGSDGYFYAMDYW | 112 | 12 | M39L, T55S, I56T, S58G, G59V, Y62T, T63Y, Y66-, Y67F, I78M, K84R, T86I |
| | 1194 | IGHV5S9*01 | IGHJ4*01 | CARGSDGYFYAMDYW | 112 | 12 | M39L, T55S, S58G, G59V, Y62T, T63Y, Y66-, Y67F, D69G, I78M, K84R, T86I |
| | 980 | IGHV5S12*01 | IGHJ4*01 | CARGSDGYFYAMDYW | 112 | 11 | M39L, T55S, S58G, G59V, Y62T, T63Y, Y66-, Y67F, I78M, K84R T86I |
| | 981 | IGHV5S9*01 | IGHJ4*01 | CARGSDGYFYAMDYW | 112 | 11 | M39L, T55S, S58G, G59V, Y62T, T63Y, Y66-, Y67F, I78M, K84R, T86I |
| | 1246 | IGHV5S9*01 | IGHJ4*01 | CARGSDGYFYAMDYW | 112 | 11 | M39L, T55S, S58G, G59V, Y62T, T63Y, Y66-, Y67F, I78M, K64R, T86I |
| | 1223 | IGHV5S9*01 | IGHJ4*01 | CARGSDGYFYAMDYW | 112 | 12 | S32N, M39L, T55S, S58G, G59V, Y62T, T63Y, Y66-, Y67F, I78M, K84R, T86I |
| 1024 | 1031 | IGHV1S128*01 | IGHJ4*01 | CARYYGYDDAMDYW | 113 | 6 | Y33H, K43Q, N57H, S74N, S84P, P94L |
| | 1036 | IGHV1S128*01 | IGHJ4*01 | CARYYGYDDAMDYW | 113 | 6 | Y33H, K43Q, N57H, S74N, S84P, P94L |
| | 1042 | IGHV1S128*01 | IGHJ4*01 | CARYYGYDDAMDYW | 113 | 6 | Y33H, K43Q, N57H, S74N, S84P, P94L |
| | 984 | IGHV1S128*01 | IGHJ4*01 | CARYYGYDDAMDYW | 113 | 7 | Y33H, K43Q, N57H, S74N, T79A, S84P, P94L |
| | 1024 | IGHV1S128*01 | IGHJ4*01 | CVRYYGYDEAMDYW | 114 | 7 | K14E. A17G, Y33H, N60S, T63N, L91F, P94L |
| | 1210 | IGHV1S128*01 | IGHJ4*01 | CVRYYGYDEVMDYW | 115 | 7 | K14E, A17G, Y33H, N60S, T63N, L91F, P94L |
| | 1217 | IGHV1S128*01 | IGHJ4*01 | CVRYYGYDEVMDYW | 115 | 7 | K14E, A17G, Y33H, N60S, T63N, T63N, L91F, P94L |
| | 1221 | IGHV1S128*01 | IGHJ4*01 | CVRYYGYDEVMDYW | 115 | 7 | K14E, A17G, Y33H, N60S, T63N, T63N, L91F, P94L |

TABLE 12-continued

IGKV

| Cluster | Clone name | IGKV gene | IGKJ gene | CDR3 | SEQ ID NO | Number of somatic mutations | Somatic mutations |
|---|---|---|---|---|---|---|---|
| 992 | 1209 | IGKV10-96*01 | IGKJ1*02 | CQHYNTVPPTF | 116 | 6 | A25T, S30G, Y87F, S92N, L94V, I99V |
|  | 1204 | IGKV10-96*01 | IGKJ1*02 | CQHYNTVPPTF | 116 | 6 | A25T, S30G, Y87F, S92N, L94V, I99V |
|  | 992 | IGKV10-96*01 | IGKJ1*02 | CQHYNTVPPTF | 116 | 6 | A25T, S30G, Y87F, S92N, L94V, I99V |
|  | 996 | IGKV10-96*01 | IGKJ1*02 | CQHYNTVPPTF | 116 | 7 | T8A, A25T, S30G, Y87F, S92N, L94V, I99V |
|  | 1033 | IGKV10-94*03 | IGKJ2*01 | CQQFTTSPFTF | 117 | 8 | A25T, I29V, S30G, Y87F, N93S, L94M, P96G, I99V |
|  | 1220 | IGKV10-96*01 | IGKJ1*02 | CQHYNTVPPTF | 118 | 6 | A25T. S30G, Y87F, S92N, L94V, I99V |
| 1030 | 1195 | IGKV3-12*01 | IGKJ2*01 | CQHSREFPLTF | 119 | 3 | K27Q, Y36F, Q44L |
|  | 1030 | IGKV3-12*01 | IGKJ2*01 | CQHSREFPLTF | 119 | 2 | Y36F, Q44L |
|  | 1034 | IGKV3-12*01 | IGKJ2*01 | CQHSREFPLTF | 119 | 2 | Y36F, Q44L |
|  | 1194 | IGKV3-12*01 | IGKJ2*01 | CQHSREFPLTF | 119 | 2 | Y36F, Q44L |
|  | 980 | IGKV3-12*01 | IGKJ2*01 | CQHSREFPLTF | 119 | 3 | Y36F, Q44L, Q48R |
|  | 981 | IGKV3-12*01 | IGKJ2*01 | CQHSREFPLTF | 119 | 3 | Y36F, Q44L, H92Y |
|  | 1246 | IGKV3-12*01 | IGKJ2*01 | CQHSREFPLTF | 119 | 2 | Y36F, Q44L |
|  | 1223 | IGKV3-12*01 | IGKJ2*01 | CQHSREFPLTF | 119 | 2 | Y36F, Q44L |
| 1024 | 1031 | IGKV2-109*01 | IGKJ2*01 | CAQNLELPYTF | 120 | 0 |  |
|  | 1036 | IGKV2-109*01 | IGKJ2*01 | CAQNLELPYTF | 120 | 1 | T85A |
|  | 1042 | IGKV2-109*01 | IGKJ2*01 | CAQNLELPYTF | 120 | 1 | G84R |
|  | 984 | IGKV2-109*01 | IGKJ2*01 | CAQNLELPYTF | 120 | 0 |  |
|  | 1024 | IGKV2-109*01 | IGKJ2*01 | CAQNLELPYTF | 120 | 0 |  |
|  | 1210 | IGKV2-109*01 | IGKJ2*01 | CAQNLELPYTF | 120 | 1 | T17A |
|  | 1217 | IGKV2-109*01 | IGKJ2*01 | CAQNLELPYTF | 120 | 0 |  |
|  | 1221 | IGKV2-109*01 | IGKJ2*01 | CAQNLELPYTF | 120 | 1 | S32N |
|  | 1218 | IGKV2-109*01 | IGKJ2*01 | CAQNLELPYTF | 120 | 0 |  |

Example 18

Humanization of Antibodies 922 and 1024

All antibodies contain the potential for eliciting a human anti-antibody response. The response correlates to some extent with the degree of "humanness" of the applied therapeutic antibody. It is not possible to predict the immunogenicity and thereby the human anti-antibody but there is a tendency towards preferring antibodies with a high degree of humanness for clinic use. The humanness of the antibodies described in the present invention can be increased by a humanization process [Reichert J M. Monoclonal antibodies in the clinic. Nature Biotechnol, 2001; 19:819-822; Reichert J M, Rosensweig C J, Faden L B and Dewitz M C. Monoclonal antibody successes in the clinic. Nature Biotechnol, 2005; 23:1073-1078].

Humanization of a murine mAb is in principle achieved by grafting the complementarity determining regions (CDRs) onto human framework regions (FRs) of the IGHV and IGKV domains with closely related sequence by a procedure commonly referred to as CDR grafting (Jones P T, Dear P H, Foote J, Neuberger M S and Winter G. Replacing the complementarity-determining regions in a human antibody with those from a mouse. Nature, 1986; 321:522-525). However, simple CDR grafting of only the hyper variable regions can results in decreased affinity because some framework amino acids or regions make crucial contacts to the antigen or support the conformation of the antigen binding CDR loops [Queen C, Schneider W P, Selick H E, Payne P W, Landolfi N F, Duncan J F, Avdalovic N M, Levitt M, Junghans R P and Waldmann T A. A humanized antibody that binds to the interleukin 2 receptor. Proc Natl Acad Sci USA, 1989; 86:10029-10033; Al-Lazikani B, Lesk A M and Chothia C. Standard conformations for the canonical structures of immunoglobulins. J Mol Biol, 1997; 273:927-948]. Consequently antibody humanization should involve both grafting of CDR loops from the murine derived variable regions onto a closely homologous human framework while retaining key murine frame work residues with documented influence on antigen binding activity (Winter, G. and W. J. Harris. "Humanized antibodies." Immunol. Today 14.6 (1993): 243-46). Several methods have been developed and successfully applied to achieved humanization while retaining the antibody affinity and function (reviewed in Almagro, J. C. and J. Fransson. "Humanization of antibodies." Front Biosci. 13 (2008): 1619-33.). Humanization can be achieved by rational methods e.g. CDR grafting, resurfacing, superhumanization, human string content optimization which all rely on construction of a few humanized antibody candidates. The amino acids sequence of the candidates is based on insight and prediction in antibody structure and the contribution of the individual amino acids to antigen binding both directly and indirectly through stabilizing the overall structure of the antigen interacting regions. Usually the candidates have to be refined and some amino acids back-mutated to the original murine residue because each antibody has some unforeseen individual constraints. Common for the methods is that several successive rounds of design, testing and redesign may be required to retain the affinity and functions. Alternatives are the more empirical methods where large combinatorial libraries are generated and the antibodies with the desired features are enriched from the pool of variants by a selection by methods such as yeast or phage display or alternative screening methods.

Anti-EGFR antibodies described in the present invention may be humanised by CDR grafting into the human V regions. In the preferred scenario the human V region is selected based on the homology to the original murine V region. Human V gene regions with other desires features such as low immunogenicity may also be used. The present example describes a method to be used for humanization of 992 and 1024 anti-EGFR chimeric antibodies. The humanized sequences given in FIG. 41A have been generated by grafting the IMGT defined CDR regions from 992 IGHV into IGHV1-46/IGHJ4 and 992 IGKV into IGKV1-27/IGKJ1-01. The amino acid sequences given in FIG. 41B have been generated in silico by grafting the IMGT defined CDR regions from 1024 IGHV into IGHV1-2*02/IGHJ6*02 and 1024 IGKV into IGKV2-28*01/IGKJ2*01. Artificial genes encoding the specified humanized antibodies are synthesized and inserted into the mammalian expression vector. Antibodies are expressed, purified and tested for activity as described in Example 3. After initial testing, the binding kinetics of humanized antibodies may be determined by surface plasmon resonance as described in Example 14. Similarly binding to hEGFR expressed on the surface of cells can be determined as described in Example 15.

If the binding activity of the humanized amino acids is significantly lower than observed for the original antibodies a sequential back-mutation scheme will be employed for regeneration of the affinity, starting with the humanized framework residues located in the Vernier zone or residues proposed to support the structure if the CDR regions (Foote, J. and G. Winter. "Antibody framework residues affecting the conformation of the hypervariable loops." J. Mol. Biol. 224.2 (1992): 487-99; Padlan, E. A. "Anatomy of the antibody molecule." Mol. Immunol 31.3 (1994): 169-217.). These residues are in IMGT numbering for 992 IGHV amino acid number 13, 45, and 80; 992 IGKV amino acids 25; 1024 IGHV amino acids 13, 45, 80 and 82; 1024 IGKL amino acid 78. These mutants may be constructed by using PCR mediated site-directed mutagenesis using standard molecular biology methods. The constructed mutants will be tested as described above. It is expected that these sets of candidates will result in humanized antibodies with retained antigen binding properties. However additional back mutations or affinity maturation by introducing amino acid substitutions in the CDR regions by site directed mutagenesis cannot be excluded.

Example 19

Dual Variable Domain Antibody

A dual variable domain (DVD) antibody protein is engineered by fusing the IGHV domains of 992 and 1024 in tandem by a 6 amino acid linker (ASTKGP) and the IGKV domains of 992 and 1024 by a 5 amino acid linker (TVAAP) [Wu C, Ying H, Grinnell C, Bryant S, Miller R, Clabbers A, Bose S, McCarthy D, Zhu R R, Santora L, vis-Taber R, Kunes Y, Fung E, Schwartz A, Sakorafas P, Gu J, Tarcsa E, Murtaza A and Ghayur T. Simultaneous targeting of multiple disease mediators by a dual-variable-domain immunoglobulin. Nature Biotechnol, 2007; 25:1290-1297]. The dual IGHV and IGKV domain fusions are followed by the IGHC and IGKC domains, respectively. In one full length DVD antibody (992L1024), the 992 IGHV and IGKV is N-terminal, followed by the linker and the 1024 IGHV and IGKV, respectively. In a second full length DVD antibody (1024L992), the 1024 IGHV and IGKV is N-terminal, followed by the linker and the 992 IGHV and IGKV, respectively. Plasmid DNA encoding the 992 and the 1024 antibody is used as template for a two step PCR mediated construction of the DVD encoding genes. The two variable domain encoding regions of IGHV and IGKV are first amplified separately so that they contain overlap extension regions at the position of the linker encoding region (for template and primer combinations see Table 13 and Table 14). The IGKV gene encoding the C-terminus proximal variable domain is amplified so that the human light chain constant domain encoding gene (IGKC) is included in the coding sequence. Coding sequences and amino acids sequences of the subunits of the dual variable domain antibodies are shown in Appendix 3.

The first PCR is prepared with the following mixture in each tube (50-µl reactions) to obtain the given final concentration: 1× FastStart buffer (Roche), dNTP mix (200 µM each), primers (10 pmol each) (see Table 14), FastStart High Fidelity Enzyme Blend (2.2 U; Roche) and 100 ng plasmid template (see Table 14). The PCR were subjected to the following thermo cycle: 2 min. at 95° C., 20×(30 sec. at 95° C., 30 sec. at 55° C., 1 min. at 72° C.), 10 min. at 72° C. The resulting PCR products with the correct size from the first PCR reaction (see Table 14) are purified by preparative agarose gel electrophoresis and used in a second step where the two variable domains are spliced by overlap extension PCR. The second PCR, splicing of DNA fragments by overlap extension PCR, is prepared with the following mixture in each tube (50-µl reactions) to obtain the given final concentration: 1× FastStart buffer (Roche), dNTP mix (200 µM each), primers (10 µmol each, see Table 15), FastStart High Fidelity Enzyme Blend (2.2 U; Roche) and template (100 ng PCR fragment, see Table 15). The PCR were subjected to the thermo cycle as defined above. The resulting products from the second PCR step are purified by preparative agarose gel electrophoresis and treated with restriction enzymes, AscI and XhoI for the dual IGHV and NheI and NotI for the dual IGKV (IGKC included). The fragments are ligated consecutively into a mammalian IgG expression vector, 00-VP-002 (FIG. 4), by standard restriction enzyme digestion and ligation procedures. The resulting expression plasmid vector is amplified in *E. coli* and the plasmid preparation is purified by standard methods. The DVD antibodies are expressed and purified as in Example 2 and characterized for activity as in Example 3-13.

Other linkers can be tested if the resulting antibodies show reduced or no binding to target hEGFr.

TABLE 13

Primers for constructing DVD antibodies from 992 and 1024

| SEQ ID NO | Primer name | Sequence |
|---|---|---|
| 121 | 3'JH | GGAGGCGCTCGAGACGGTGACTGAGGTTCCTTGAC |
| 122 | 992_5'VH | CCAGCCGGGGCGCGCCGAGGTCCAACTGCAGCAACCTGGGTCTGAGCTGGTG |
| 123 | 1024_5'VH | CCAGCCGGGGCGCGCCCAGGTCCAACTGCAGCAGCCTGGGGCTGAACTG |
| 124 | 992_5'VK | catgggaatagctagccGACATTCAGATGACTCAGACTACATCCTCCCTG |
| 125 | 1024_5'VK | catgggaatagctagccGACATCGTGATGACACAAGCTGCATTCTCCAATC |

TABLE 13-continued

Primers for constructing DVD antibodies from 992 and 1024

| SEQ ID NO | Primer name | Sequence |
|---|---|---|
| 126 | Kappa3' | ACCGCCTCCACCGGCGGCCGCTTATTAACACTCTCCCCTGTTG |
| 127 | 992H_O3' | CTGGGGGCCCTTGGTGCTGGCTGACGAGACGGTGACTGAGGTTC |
| 128 | 1024H_O5' | GCCAGCACCAAGGGCCCCCAGGTCCAACTGCAGCAGC |
| 129 | 1024H_O3' | CGGGGCCCTTGGTGCTGGCTGACGAGACGGTGACTGAG |
| 130 | 992H_O5' | GCCAGCACCAAGGGCCCCGAGGTCCAACTGCAGCAAC |
| 131 | 992K_O3' | GTCTGGTGCAGCCACAGTTCGTTTGATTTCCAGCTTGGTG |
| 132 | 1024K_O5' | CGAACTGTGGCTGCACCAGACATCGTGATGACACAAGC |
| 133 | 1024K_O3' | GTCTGGTGCAGCCACAGTTCGTTTTATTTCCAGCTTGGTCC |
| 134 | 992K_O5' | CGAACTGTGGCTGCACCAGACATTCAGATGACTCAGACTAC |

TABLE 14

Primer and template combinations for 1$^{st}$ PCR step for constructing DVD encoding genes from 992 and 1024

| | | Primers for IGHV gene amplification | | Primers for IGKV gene amplification | |
|---|---|---|---|---|---|
| DVD | Template for PCR | 1$^{st}$ PCR step | 1$^{st}$ PCR product (size bp) | 1$^{st}$ PCR step | 1$^{st}$ PCR product (size bp) |
| 992L1024 | 992 | 992_5'VH 992H_O3' | 992HO (406 bp) | 992_5'VK 992K_O3' | 992KO (359 bp) |
| | 1024 | 1024H_O5' 3'JH | HO1024 (381 bp) | 1024K_O5' Kappa3' | KO1024* (702 bp) |
| 1024L992 | 992 | 992H_O5' 3'JH | HO992 (393 bp) | 992K_O5' Kappa3' | KO992 (687 bp) |
| | 1024 | 1024_5'VH 1024H_O3' | 1024HO (392 bp) | 1024_5'VK 1024K_O3' | 1024KO* (374 bp) |

*The amplified coding sequence includes the IGKC-gene

TABLE 15

Primer and template combinations for 2$^{nd}$ PCR step, splicing by overlap extension, for constructing DVD encoding genes from 992 and 1024

| | IGHV | | | IGKV | | |
|---|---|---|---|---|---|---|
| DVD | Template | Primers | Product (bp) | Template | Primers | Product (bp) |
| 992L1024 | 992HO HO1024 | 992_5'VH 3'JH | 766 | 992KO KO1024 | 992_5'VK Kappa3' | 1040 |
| 1024L992 | HO992 1024HO | 1024_5'VH 3'JH | 766 | KO992 1024KO | 1024_5'VK Kappa3' | 1040 |

Example 20

6 Week Intravenous Administration Toxicity Study in Combination with Erbitux in the Cynomolgus Monkey"

Objective of study: The objective of the study was to determine the toxicity of the test article, 992+1024, following once weekly intravenous administration to the cynomolgus monkey for 6 weeks.

Since toxicity is a dose limiting factor in clinical practice with EGFR inhibitors like Erbitux and Vectibix it was deemed important at an early stage to assess tolerability of 992+1024 at clinically relevant dose. This emphasized by the fact that 992+1024 seems to be acting by a different mechanism than the other EGFR targeting products. This could potentially lead to new adverse effects or a worsening of the effects seen with other EGFR inhibitors.

Groups of three female cynomolgus monkeys were treated with weekly IV doses of 992+1024 at 4/2.7 and 12/8 mg/kg and 12/8 mg/kg of Erbitux for 6 weeks. The first doses of 4 and 12 mg/kg being loading doses and the 2.7 and 8 mg/kg being maintenance doses administered 5 times. The 12/8 mg/kg dose is equivalent to the human clinical dose of Erbitux administered in clinical practice.

Study Design

| Group number | Group description | Dose level (mg/kg/day) | Dose volume (mL/kg) | Animal numbers Females |
|---|---|---|---|---|
| 1 | Control | 0 | 19/12# | 1-3 |
| 2 | 992 + 1024 Low | 4.2/2.7# | 19/12# | 4-6 |
| 3 | 992 + 1024 High | 12.6/8# | 19/12# | 7-9 |
| 4 | Erbitux | 12.6/8# | 19/12# | 10-12 |

First dose level is for loading dose, second dose level is for administration from Day 8 onwards The following parameters were followed during the study: Mortality, Clinical signs, Body weights, Food consumption, Haematology, Clinical chemistry, Organ weights, Macroscopic findings.

Results

Mortality: There were no unscheduled deaths during the course of the study.

Clinical signs: No treatment related adverse clinical observations

Body weights: There was no effect of treatment with either 992+1024 or Erbitux on body weight.

Food consumption: There were no obvious effects on food consumption.

Haematology: There were no effects on haematological parameters to suggest an effect of treatment with either 992+1024 or Erbitux.

Clinical chemistry: There were no changes in clinical chemistry parameters to suggest an effect of treatment with either test article.

In Week 4, one animal dosed at 4.2/2.7 mg/kg 992+1024/day had increased aspartate aminotransferase and alanine aminotransferase levels, in comparison to pretreatment values. These levels had returned to normal ranges by Week 6. In the absence of a similar effect in other treated animals, the toxicological significance of this increase in liver enzymes is unknown.

Organ weights: There were no differences of toxicological significance in organ weights between treated and control animals.

Macroscopic findings: There were no consistent observations noted at necropsy to suggest an effect of 992+1024 or Erbitux.

Preliminary conclusion: The preliminary data show that 992+1024 was well tolerated at the doses tested and no adverse effects related to treatment were observed.

Example 21

Growth Inhibition of Lung Cell Cancer Lines

Lung cancer cell lines are known to express EGFR with mutations in the tyrosine kinase domain (Steiner et al. Clin Cancer Res 13.5 (2007): 1540-51). By a method similar to the one used in example 6 the ability of a combination of the two antibodies 992 and 1024 to inhibit the growth of the lung cancer cell lines HCC827 and H1975 having different EGFR mutations were investigated.

Results

As can be seen in Table 16 and Table 17 the combination of 992 and 1024 is able to inhibit the growth of both cell lines. The combination is superior to the monoclonal antibodies 992 and 1024 and to Vectibix.

TABLE 16

IC50 values and maximum growth inhibition of the indicated antibodies against the HCC827 cell line

| HCC827 | IC50 (µg/ml) | Max inhibition |
|---|---|---|
| Erbitux | 0.013 | 80% |
| Vectibix | 0.100 | 60% |
| 992 | 0.050 | 80% |
| 1024 | 0.034 | 40% |
| 992 + 1024 | 0.031 | 80% |

TABLE 17

IC50 values and maximum growth inhibition of the indicated antibodies against the H1975 cell line

| H1975 | IC50 (µg/ml) | Max inhibition |
|---|---|---|
| Erbitux | 0.010 | 30% |
| Vectibix | 0.141 | 30% |
| 992 | 0.056 | 30% |
| 1024 | — | 0% |
| 992 + 1024 | 0.024 | 30% |

APPENDIX 1

Antibody variable region sequences

>992VH (Seq. no. 24)
cgcgccgaggtccaactgcagcaacctgggtctgagctggtgaggcctgg
agcttcagtgaagctgtcctgcaaggcttctggctacacattcaccagct
actggatgcactgggtgaagcagaggcctggacaaggccttgagtggatt
gggaatatttatcctggtagtcgtagtactaactacgatgagaagttcaa
gagcaaggccacactgactgtagacacatcctccagcacagcctacatgc
agctcagcagcctgacatctgaggactctgcggtctattactgtacaaga
aatggggattactacgttagtagcggggatgctatggactactggggtca
aggaacctcagtcaccgtctcg >1024VH (Seq. no. 25)
cgcgcccaggtccaactgcagcagcctggggctgaactggtggagcctgg
gggttcagtgaagctgtcctgcaaggcttctggctacaccttcaccagtc APPENDIX 1-continued Antibody variable region sequences

```
actggatgcactgggtgaagcagaggcctggacaaggccttgagtggata
ggtgagattaatcctagcagcggtcgtaataactacaatgagaagttcaa
gagtaaggccacactgactgtagacaaatcctccagcacagcctacatgc
aattcagcagcctgacatctgaggactctgcggtctattattgtgtaaga
tactatggttacgacgaagctatggactactgggtcaaggaacctcagt
caccgtctcg >1030VH (Seq. no. 26)
cgcgccgaagtgcagctggtggagtctgggggaggcttagtgaagcctgg
agggtccctgaaactctcctgtgcagcctctggattcactttcagtagtt
atgccctgtcttgggttcgccagactccagagaggaggctggagtgggtc
gcatccattagtggtgttggtagcacctacttccagacagtgtgaaggg
ccgtttcaccatgtccagagataatgccaggaacatcctgtacctccaaa
tgagcagtctgaggtctgaggacacggccatgtattactgtgcaagaggt
tctgatggttacttctatgctatggactactgggtcaaggaacctcagt
caccgtctcg >1042VH (Seq. no. 27)
cgcgcccaggtgcagcttcagcagcctggggctgaactggtgaagcctgg
ggcttcagtgaagctgtcctgtaaggcttctggctacaccttcaccagcc
actggatgcactgggtgcagcagaggcctggacaaggccttgagtggatt
ggagagattcatcctagcaacggtcgtactaactacaatgagaagttcaa
gaacaaggccacactgactgtagacaaatcccagcagctacatgc
aactcagcagtttgacatctgaggactctgcggtctattactgtgcaaga
tactatggttacgacgatgctatggactactgggtcaaggaacctcagt
caccgtctcg >1208VH (Seq. no. 28)
cgcgccgaagtgcagctggtggagtctgggggaggcttagtgaagcctgg
agggtccctgaaactctcctgtgcagcctctggattcgctttcagtagct
atgacatgtcttgggttcgccagactccggagaggaggctggagtgggtc
gcatacattggtagtggtgatgataataccccactatccagactctgtgaa
gggccgattcaccatctccagacacaatgccaaaacaccctataccctgc
aaatgagcagtctgaagtctgaggacacagccatgtattactgtgcaaga
cagaagtatggtaactacggggacactatggactactgggtcaaggaac
ctcagtcaccgtctcg >1229\VH (Seq. no. 29)
cgcgcccaggttcagctgaaggagtcaggacctggcctggtggcgccctc
acagagcctgtccatcacttgctctgtctctggttttttcattaaccatct
atggtgtacactgggttcgccagcctccaggaaagggtctggagtggctg
ggagttatgtgggctggtgaaatacagattataattcggctctcatgtc
cagactgaacatcagcaaggacaattccaagagccaagttttcttaaaag
tgaacagtctacaaactgatgacacagccatgtactattgtaccagagat
cccgatggttactacgtggggtggttcttcgatgtctgggcgcgggac
cacggtcaccgtctcg >1254VH (Seq. no. 30)
cgcgccgaagtgcagctggtggagtctgggggaggcttagtgaagcctgg
agggtccctgaaactctcctgtgcagcctctggattcgcttacagtacct
atgacatgtcttgggttcgccagactccggagaggaggctggagtgggtc
gcatacattagtagtggtggtgatgccgcctactactgcacgtgaa
gggccgattcaccatctccagacacaatgccaaaacaccctataccctgc
aaatgagcagtctgaagtctgaggacacagccatgtattactgtgcgagg
tctgctatggaaactacggggacgctatggactactgggtcaaggaac
ctcagtcaccgtctcg >1257VH (Seq. no. 31)
cgcgccgaggtccagctgcaacagtctggacctgagctggtgaaacctgg
ggcttcagtgaagatacccctgcaagcttctggatacaccttctcactgact
acaacatggcctgggtgaagcagagccatggaaagacccttgagtggatt
ggagatattattcctaacaatggtggtgctatctacaaccagaaattcaa
gggcaaggccacttttgactgtagacaaatcctccagtacagcctccatgg
agctccgcagcctgacatctgaggacactgcagtctatttctgtgcaaga
aagaatatctactataggtacgacggggcaggtgctctggactactgggg
tcaaggaacctcagtcaccgtctcg >1260VH (Seq. no. 32)
cgcgcccaggtgcagctgaaggagtcaggacctggcctggtggcgccctc
acagagcctgtccatcacttgcactgtctctgggttttcattaaccactt
atggggtacactgggttcgccagcctccaggaaagggtctggagtggctg
ggagtaatatgggctggtggaaagcacaaattataattcggctctcatgtc
cagactgagcatcaagaaagacaactccaagagccaagttttcttaaaaa
tgaacagtctgcaaactgatgacacagccatgtactactgtgccagagcc
tatggttacaactttgactattggggccaaggcaccactctcacagtctc
g
```

APPENDIX 1-continued

Antibody variable region sequences

```
>12G1VH (Seq. no. 33)
cgcgccgaagtgcagctggtggagtctgggggaggcttagtgaagcctgg
agggtccctgaaactctcctgtgcagtctctggattcactttcagtagct
atgtcatgtcttgggttcgccagactccggagaagaggctggagtgggtc
gcaaccattactagtggtggtaggaacatctactatctagacagtgtgaa
ggggcgattcactatctcccagagacaatgccaagaacaccctgtacctgc
aaatgagcagtctgaggtctgaggacacggccatgtattactgtgcaaga
catgaggactataggtacgacggttactatgctatggactactgggtca
aggaacctcagtcaccgtctcg >1277VH (Seq. no. 34)
cgcgccgaagtgcagctggtggagtctgggggaggcttagtgaagcctgg
agagtccttgaaactctcctgtgcagcctctggattcgctttcagttact
ctgacatgtcttgggttcgccagactccggagaagaggctggagtgggtc
gcatacatgagtagtgctggtgatgtcaccttctattcagacactgtgaa
gggccgattcaccattctccagagacaatgccaagaacaccctgtatctg
caagtgagcagtctgaagtctgaggacacagccatatattactgtgtaag
acaccgggacgtggctatggactactgggtcaaggaacctcagtcaccg
tctcg >1284VH (Seq. no. 35)
cgcgcccaggtccaactgcagcagcctggggctgaactggtgaagcctgg
ggcttcagtgaagctgtcctgcaaggcttctggctacaccttcaccagcc
actggatgcactgggatgaaacagaggcctggacaaggccttgagtggatt
ggagagattaatcctagtaacggtcgctctagctacaatgagaagttcaa
gagcaaggccacactgactgtagacaaatcctccagcacagcctacatgc
aactcagcagcctgacatctgaggactctgcggtctattactgtgcaaga
ataggtgtatctacgtggagacttactggggccaagggactctggtcac
tgtctcg >1308VH (Seq. no. 36)
cgcgccgaggtccagcttcagcagtctggagctgagctggtgaggcctgg
gtcctcagtgaagatttcctgcaaggcttctggctatgcattcagtagct
actggatgaactgggtgaggcagaggcctggacagggtcttgagtggatt
ggacagatttatcctggagatggtgatactaactacaatggaaagttcaa
gggtagagccacactgactgcaaacaatcctccagcacagcctacatgc
agctcagcagcctaacatctgaggactctgcggtctatttctgtgcaaga
agggcatcttccctctatgatgtttaccctactactttgactactgggg
ccaaggcaccactctcacagtctcg >1320VH (Seq. no. 37)
cgcgcccaggtccaactgcagcagcctggggctgaactggtgaagcctgg
ggcttcaatgaagctgtcctgcaaggcttctgctacaccttcaccact
actggatgcactgggtgaagcagaggcctggacaaggccttgaatggatt
ggagaaattaatcctagcaacggtcgtactaattacaatgagaagttcaa
gagcaaggccacactgactgtagacaaatcgtccagcacagcctacatgc
aactcagcagcctgacatctgaggactctggggtctattactgtgcaaaa
gggggaactactatgattacgactgggactactggggccaaggcaccac
tctcacagtctcg >1344VH (Seq. no. 38)
cgcgcccaggtgcagctgaaggagtcaggacctggcctggtggcgccctc
acagagcctgtccatcacttgcactgtctctggttttcattaaccatct
atggtgtacactgggttcgccagcctccaggaaagggtctggagtggctg
ggagtaatatgggctggtggaaacacaaattataattcggctctcatgtc
cagactgagcatcagcaagacaactccaagagtcaagttttcttaaaaa
tgaacagtctgcaaactgatgacacagccatgtacttctgtgccagaggc
tatggctacaatttagactattggggccaaggcaccactctcacagtctc
g >1347VH (Seq. no. 39)
cgcgcccaggtgcagctgaaggagtcaggacctggcctggtggcgccctc
acagagcctgtccatcacatgcaccgtctcaggattctcattaaccggcc
atggtaaactgggttcgccagcctccaggaaagggtctggagtggctg
ggaatgatatggggtgatggaagcacggactataattcaactctcaaatc
cagactgagtatcagcaaggacaactccaagagccaagttttcttaaaaa
tgaacagtctgcagactgatgacaccgccaggtactactgtgccagaggc
tacggctacctttactactttgactactgggccaagcaccactctcac
agtctcg >992VH (Seq. no. 40)
RAEVQLQQPGSELVRPGASVKLSCKASGYTFTSYWMHWVKQRPGQGLEWI
GNIYPGSRSTNYDEKFKSKATLTVDTSSSTAYMQLSSLTSEDSAVYYCTR
NGDYYVSSGDAMDYWGQGTSVTVS
```

APPENDIX 1-continued

Antibody variable region sequences

>1024VH (Seq. no. 41)
RAQVQLQQPGAELVEPGGSVKLSCKASGYTFTSHWMHWVKQRPGQGLEWI
GEINPSSGRNNYNEKFKSKATLTVDKSSSTAYMQFSSLTSEDSAVYYCVR
YYGYDEAMDYWGQGTSVTVS

>1030VH (Seq. no. 42)
RAEVQLVESGGGLVKPGGSLKLSCAASGFTFSSYALSWVRQTPERRLEWV
ASISGVGSTYFPDSVKGRFTMSRDNARNILYLQMSSLRSEDTAMYYCARG
SDGYFYAMDYWGQGTSVTVS

>1042VH (Seq. no. 43)
RAQVQLQQPGAELVKPGASVKLSCKASGYTFTSHWMHWVQQRPGQGLEWI
GEIHPSNGRTNYNEKFKNKATLTVDKSPSTAYMQLSSLTSEDSAVYYCAR
YYGYDDAMDYWGQGTSVTVS

>1208VH (Seq. no. 44)
RAEVQLVESGGGLVKPGGSLKLSCAASGFAFSSYDMSWVRQTPEKRLEWV
AYIGSGDDNTHYPDSVKGRFTISRHNAKNTLYLQMSSLKSEDTAMYYCAR
QKYGNYGDTMDYWGQGTSVTVS

>1229VH (Seq. no. 45)
RAQVQLKESGPGLVAPSQSLSITCSVSGFSLTIYGVHWVRQPPGKGLEWL
GVMWAGGNTDYNSALMSRLNISKDMSKSQVFLKVNSLQTDDTAMYYCTRD
PDGYYVGWFFDVWGAGTTVTVS

>1254VH (Seq. no. 46)
PAEVQLVESGGGLVKPGGSLKLSCAASGFAYSTYDMSWVRQTPEKRLEWV
AYISSGGDAAYYPDTVKGRFTILSRDNAKISITLYLQMSSLKSEDTANYY
CARSRYGNYGDANDYWGQGTSVTVS

>1257VH (Seq. no. 47)
RAEVQLQQSGPELVKPGASVKIPCKTSGYTFTDYNMAWVKQSHGKSLEWI
GDIIPNNGGAIYNQKFKGKATLTVDKSSSTASMELRSLTSEDTAVYFCAR
KNIYYRYDGAGALDYWGQGTSVTVS

>1260VH (Seq. no. 48)
RAQVQLKESGPGLVAPSQSLSITCTVSGFSLTTYGVHWVRQPPGKGLEWL
GVIWAGGSTNYNSALMSRLSIKKDNSKSQVFLKMNSLQTDDTAMYYCARA
YGYNFDYWGQGTTLTVS

>12G1VH (Seq. no. 49)
RAEVQLVESGGGLVKPGGSLKLSCAVSGFTFSSYVMSWVRQTPEKRLEWV
ATITSGGRNIYYLDSVKGRFTISRDMAKNTLYLQMSSLRSEDTAMYYCAR
HEDYRYDGYYAMDYWGQGTSVTVS

>1277VH (Seq. no. 50)
RAEVQLVESGGGLVKPGESLKLSCAASGFAFSYSDMSWVRQTPEKRLEWV
AYMSSAGDVTFYSDTVKGRFTISRDNAKNTLYLQVSSLKSEDTAIYYCVR
HPDVAMDYWGQGTSVTVS

>1284VH (Seq. no. 51)
RAQVQLQQPGAELVKPGASVKLSCKASGYTFTSDWMHWMKQRPGQGLEWI
GEINPSNGRSSYNEKFKSKATLTVDKSSSTAYMQLSSLTSEDSAVYYCAR
IGGIYVETYWGQGTLVTVS

>1308VH (Seq. no. 52)
RAEVQLQQSGAELVRPGSSVKISCKASGYAFSSYWMNWVRQRPGQGLEWI
GQIYPGDGDTNYNGKFKGRATLTANKSSSTAYMQLSSLTSEDSAVYFCAR
RASSLYDVYPYYFDYWGQGTTLTVS

>1320VH (Seq. no. 53)
RAQVQLQQPGAELVKPGASMKLSCKASGYTFTNYWMHWVKQRPGQGLEWI
GEINPSNGRTNYNEKEKSKATLTVDKSSSTAYMQLSSLTSEDSGVYYCAK
GGNYYDYDWDYWGQGTTLTVS

>1344VH (Seq. no. 54)
PAQVQLKESGPGLVAPSQSLSITCTVSGFSLTIYGVHWVRQPPGKGLEWL
GVIWAGGNTNYNSALMSRLSISKDNSKSQVFLKMINSLQTDDTAMYYCAR
GYGYNLDYWGQGTTLTVS

>1347VH (Seq. no. 55)
RAQVQLKESGPGLVAPSQSLSITCTVSGFSLTGHGVNWVRQPPGKGLEWL
GMIWGDSTDYNSTLKSRLSISKDNSKSQVFLKMNSLQTDDTARYYCARG
YGYLYYFDYWGQGTTLTVS

>992VL (Seq. no. 56)
ctagccgacattcagatgactcagactacatcctccctgtctgcctctct
gggagacagagtcaccatcagttgcaggacaagtcaggacattggcaatt
atttaaactggtatcagcagaaaccagatggaactgttaaactcctgatc
tactacacatcaagattacactcaggagtcccatcaaggttcagtggcag
tgggtctggaacagatttttctctcaccattaacaacgtggagcaagagg
atgttgccacttacttttgccaacactataatacggttcctccgacgttc
ggtggaggcaccaagctggaaatcaaacgaactgtggctgcaccatctgt
cttcatcttcccgccatctgatgagcagttgaaatctggaactgcctctg
ttgtgtgcctGctgaataacttctatcccagagaggccaaagtacagtgg
aaggtggataacgccctccaatcgggtaactcccaggagagtgtcacaga
gcaggacagcaaggacagcacctacagcctcagcagcaccctgacgctga
gcaaagcagactacgagaaacacaaagtctacgcctgcgaagtcacccat
cagggcctgagctcgcccgtcacaaagagcttcaacaggggagagtgt >1024VL (Seq. no. 57)
ctagccgacatcgtgatgacacaagctgcattctccaatccagtcactct
tggaacatcagcttccatctcctgcaggtctagtaagagtctcctacata
gtaatggcatcacttatttgtattggtatctgcagaagccaggccagtct
cctcagctcctgatttatcagatgttccaaccttgcctcaggagtcccag
acaggttcagtagcagtgggtcaggaacttgatttcacactgagaatcagc
agagtggaggctgaggatgtgggtgtttattactgtgctcaaaatctaga
acttccgtacacgttcggaggggggaccaagctggaaataaaacgaactg
tggctgcaccatctgtcttcatcttcccgccatctgatgagcagttgaaa
tctggaactgcctctgttgtgtgcctgctgaataacttctatcccagaga
ggccaaagtacagtggaaggtggataacgccctccaatcgggtaactccc
aggagagtgtcacagagcaggacagcaaggacagcacctacagcctcagc
agcaccctgacgctgagcaaagcagactacgagaaacacaaagtctacgc
ctgcgaagtcacccatcagggcctgagctcgcccgtcacaaagagcttca
acaggggagagtgt >1030VL (Seq. no. 58)
ctagccgacattgtgctgactcagtctcctgcttccttagctgtatctct
ggggcagagggccaccatttcatgcagggccagcaaaagtgtcagtacat
ctggctatagttttatgcactggtaccaactgaaaccaggacagccaccc
aaactcctcatctatcttgcatccaacctagaatctggggtccctgccag
gttcagtggcagtgggtctgggacagacttcaccctcaacatccatcctg
tggaagaggaggatgctgcaacctattactgtcagcacagtagggagttt
ccgttaacgttcggaggggggaccaagctggaaataaaacgaactgtggc
tgcaccatctgtcttcatcttcccgccatctgatgagcagttgaaatctg
gaactgcctctgttgtgtgcctgctgaataacttctatcccagagaggcc
aaagtacagtggaaggtggataacgccctccaatcgggtaactcccagga
gagtgtcacagagcaggacagcaaggacagcacctacagcctcagcagca
ccctgacgctgagcaaagcagactacgagaaacacaaagtctacgcctgc
gaagtcacccatcagggcctgagctcgcccgtcacaaagagcttcaacag
gggagagtgt >1042VL (Seq. no. 59)
gatattgtgatgactcaggctgcattctccaatccagtcactcttggaac
atcagcttccatctcctgcaggtctagtaagagtctcctacatagtaatg
gcatcacttatttgtattggtatctgcagaagccaggccagtctcctcag
ctcctgatttatcagatgttccaaccttgcctcaggagtcccagacaggtt
cagtagcagtgggtcaagaactgatttcacactgagaatcagcagagtgg
aggctgaggatgtgggtgtttattactgtgctcaaaatctagaacttccg
tacacgttcggaggggggaccaagctggaaataaaacgaactgtggctgc
accatctgtcttcatcttcccgccatctgatgagcagttgaaatctggaa
ctgcctctgttgtgtgcctgctgaataacttctatcccagagaggccaaa
gtacagtggaaggtggataacgccctccaatcgggtaactcccaggagag
tgtcacagagcaggacagcaaggacagcacctacagcctcagcagcaccc
tgacgctgagcaaagcagactacgagaaacacaaagtctacgcctgcgaa
gtcacccatcagggcctgagctcgcccgtcacaaagagcttcaacagggg
agagtgt >1208XTL (Seq. no. 60)
ctagccgatgttgtgatgactcagactccactctccctgcctgtcagtct
tggagatcaagcctccatctcttgcagatctagtcagagccttgtacaca
gtaatggaaacacctatttacattggtacctgcagaagccaggccagtct
ccaaaactcctgatctacaaagtttccaaccgattttctgggcccccaga
caggttcagtggcagtgggtcagggacagatttcacactcaagatcagca
gagtggaggctgaggatctgggagtttatttctgctctcaaagtacacat
gttcccacgttcggaggggggaccaagctggaaatcaaacgaactgtggc
tgcaccatctgtcttcatcttcccgccatctgatgagcagttgaaatctg
gaactgcctctgttgtgtgcctgctgaataacttctatcccagagaggcc
aaagtacagtggaaggtggataacgccctccaatcgggtaactcccagga
gagtgtcacagagcaggacagcaaggacagcacctacagcctcagcagca
ccctgacgctgagcaaagcagactacgagaaacacaaagtctacgcctgc

APPENDIX 1-continued

Antibody variable region sequences gaagtcacccatcagggcctgagctcgcccgtcacaaagagcttcaacag
gggagagtgt >1229VL (Seq. no. 61)
ctagccgacattgtgatgacccagtctcacaaattcatgtccacatcagt
gggagacagggtcagcatcacctgcaaggccagtcaggatgtgactaatg
ccgtagcctggtatcaacaaaaaccaggacaatctcctaaactactgatt
tactgggcatccatccgacacactggagtccctgatcgcttcacaggcag
tagatctgggacagattatactctcaccatcaacagtgtgcaggctgaag
acctggccctttattattgtcagcaacattataacactccgctcacgttc
ggtgctgggaccaagctggaaataaaacgaactgtggctgcaccatctgt
cttcatcttcccgccatctgatgagcagttgaaatctggaactgcctctg
ttgtgtgcctgctgaataacttctatcccagagaggccaaagtacagtgg
aaggtggataacgcccctccaatcgggtaactcccaggagagtgtcacaga
gcaggacagcaaggacagcacctacagcctcagcagcaccctgacgctga
gcaaagcagactacgagaaacacaaagtctacgcctgcgaagtcacccat
cagggcctgagctcgcccgtcacaaagagcttcaacaggggagagtgt >1254VL (Seq. no. 62)
ctagccgatgttgtgatgacacagactccactctccctgcctgtcagtct
tggagatcaagcctccatctcttgcagatctagtcagagcctttgtacaca
gtaatggtaacacctatttacattggtacctgcagaagccaggccagtct
ccaaagctcctgatctacaaagtttccaaccgattttctggggtcccaga
caggttcagtggcagtggatcagggacagatttcacactcaagatcagca
gagtggagtctgaggatctgggagtttattctgctctcaaaatacacat
gtgtacacgttcggaggggggacaaagttggaaataaaacgaactgtggc
tgcaccatctgtcttcatcttcccgccatctgatgagcagttgaaatctg
gaactgcctctgttgtgtgcctgctgaataacttctatcccagagaggcc
aaagtacagtggaaggtggataacgcccctccaatcgggtaactcccagga
gagtgtcacagagcaggacagcaaggacagcacctacagcctcagcagca
cccctgacgctgagcaaagcagactacgagaaacacaaagtctacgcctgc
gaagtcacccatcagggcctgagctcgcccgtcacaaagagcttcaacag
gggagagtgt >1257VL (Seq. no. 63)
ctagcccaaattgtgctcacacagtctccagcaatcatgtctgcatctcc
aggggagaaggtcaccatgacctgcagtgccagctcaagtgtaagttaca
tttactggtaccagcagaagccaggatcctcccccagactcctgatttat
gacgcatccaacctggcttctggagtccctgttcgcttcagtggcagtg
gtctgggacctcttactctctcacaatcagccgaatggaggctgaagatg
ctgccacttattactgccagcaatggagtagttacccatacacgttcggc
tcggggacaaagttggaaataaaacgaactgtggctgcaccatctgtctt
catcttcccgccatctgatgagcagttgaaatctggaactgcctctgttg
tgtgcctgctgaataacttctatcccagagaggccaaagtacagtggaag
gtggataacgcccctccaatcgggtaactcccaggagagtgtcacagagca
ggacagcaaggacagcacctacagcctcagcagcaccctgacgctgagca
aagcagactacgagaaacacaaagtctacgcctgcgaagtcacccatcag
ggcctgagctcgcccgtcacaaagagcttcaacaggggagagtgt >1260VL (Seq. no. 64)
ctagccgatatccagatgactcagactacatcctccctgtctgcctctct
gggagacagagtcaccatcacttgcagtgcaagtcaggtcaacattaagg
atttaaactggtatcagcagaaaccagatgaactgttaaaactcctgatc
tattactcatcaagtttacactcaggagtcccatcaaggttcagtggcag
tgggtctgggacagattattctctcaccatcagcaacctggaacctgaag
atattgccacttactattgtcagcagtatagtgagttccgtacacgttc
ggaggggggaccaagctggagtcgaaacgaactgtggctgcaccatctgt
cttcatcttcccgccatctgatgagcagttgaaatctggaactgcctctg
ttgtgtgcctgctgaataacttctatcccagagaggccaaagtacagtgg
aaggtggataacgcccctccaatcgggtaactcccaggagagtgtcacaga
gcaggacagcaaggacagcacctacagcctcagcagcaccctgacgctga
gcaaagcagactacgagaaacacaaagtctacgcctgcgaagtcacccat
cagggcctgagctcgcccgtcacaaagagcttcaacaggggagagtgt >1261VL (Seq. no. 65)
ctagcccaaattgtgctgacccagtctccagcaatcatgtctgcatctcc
aggggagaaggtcaccataacctgcagtgccagctcaagtgtaagttaca
tgcactggtttccagcagaagccaggcacttctcccaaactctggatttta
tagtacatccaacctggcttctggagtccctgctcgcttcagtggcagtg
gatctgggacctcttactctctcacaatcagcgaatggaggctgaagat
gctgccacttattactgccagcaaaggagtagttacccatacacgttcgg
aggggggaccaagctggagtcgaaacgaactgtggctgcaccatctgtct
tcatcttcccgccatctgatgagcagttgaaatctggaactgcctctgtt
gtgtgcctgctgaataacttctatcccagagaggccaaagtacagtggaa
ggtggataacgcccctccaatcgggtaactcccaggagagtgtcacagagc
aggacagcaaggacagcacctacagcctcagcagcaccctgacgctgagc aaagcagactacgagaaacacaaagtctacgcctgcgaagtcacccatca
gggcctgagctcgcccgtcacaaagagcttcaacaggggagagtgt >1277VL (Seq. no. 66)
ctagccgatgttgtgatgacccagactccactctccctgcctgtcagtct
tggagatcaagcctccatctcttgcagatctagtcagagccttgtacaca
gtaatggaaacacctatttacattggtacctgcagaagccaggccagtct
ccaaagctcctgatctacaaagtttccaaccgattttctggggtcccaga
caggttcagtggcagtggatcagggacagatttcacactcaagatcagca
gagtggaggctgaggatctgggagtttattctgctctcaaagtacacat
gttccgacgttcggtggaggcaccaagctggaaatcaaacgaactgtggc
tgcaccatctgtcttcatcttcccgccatctgatgagcagttgaaatctg
gaactgcctctgttgtgtgcctgctgaataacttctatcccagagaggcc
aaagtacagtggaaggtggataacgcccctccaatcgggtaactcccagga
gagtgtcacagagcaggacagcaaggacagcacctacagcctcagcagca
cccctgacgctgagcaaagcagactacgagaaacacaaagtctacgcctgc
gaagtcacccatcagggcctgagctcgcccgtcacaaagagcttcaacag
gggagagtgt >1284VL (Seq. no. 67)
ctagccgacattgtgctaacacagtctcctgcttccttagctgtatctct
ggggcagagggccaccatctcatgcagggccagccaaagtgtcagtacat
ctacctatagttatatgcactggtatcaacagaaatcaggacagccaccc
aaactcctcatcaagtatgcatccaacctagagtctggggtccctgccag
gttcagtggcagtgggtctgggacagacttcaccctcaacatccatcctg
tggaggaggaggatactgcaacatattactgtcagcacagtgggagatt
ccgtgagcttcggtggaggcaccaagctggaaatcaaacgaactgtggc
tgcaccatctgtcttcatcttcccgccatctgatgagcagttgaaatctg
gaactgcctctgttgtgtgcctgctgaataacttctatcccagagaggcc
aaagtacagtggaaggtggataacgcccctccaatcgggtaactcccagga
gagtgtcacagagcaggacagcaaggacagcacctacagcctcagcagca
cccctgacgctgagcaaagcagactacgagaaacacaaagtctacgcctgc
gaagtcacccatcagggcctgagctcgcccgtcacaaagagcttcaacag
gggagagtgt >1308VL (Seq. no. 68)
ctagccgacatccagatgacacaaactacatcctccctgtctgcctctct
gggagacagagtcaccatcagttgcagggcaagtcaggacattagcaatt
atttaaactggtatcagcagaaaccagatggaactgttaaagtcctgatc
tactacacatcaagattacactcaggagtcccatcaaggttcagtggcag
tgggtctgaacagattattctctcaccattagcaacctggagcaagaag
atattgccacttacttttgccaacagggtaatacgcttccgtacacgttc
ggagggggaccaagctggaaataaaacgaactgtggctgcaccatctgt
cttcatcttcccgccatctgatgagcagttgaaatctggaactgcctctg
ttgtgtgcctgctgaataacttctatcccagagaggccaaagtacagtgg
aaggtggataacgcccctccaatcgggtaactcccaggagagtgtcacaga
gcaggacagcaaggacagcacctacagcctcagcagcaccctgacgctga
gcaaagcagactacgagaaacacaaagtctacgcctgcgaagtcacccat
cagggcctgagctcgcccgtcacaaagagcttcaacaggggagagtgt >1320VL (Seq. no. 69)
ctagccgacattcagatgacccagactacatcctccctgtctgcctctct
gggagacagagtcaccatcagttgcagtgcaagtcaggacattagcaatt
atttaaactggtatcagcagaaaccagatggaactgttaaactcctgatc
tatcacacatcaactttacactcaggagtcccatcaaggttcagtggcag
tgggtctgggacagattattctctcaccatcagcaacctggaacctgaag
atattgccacttactattgtcagcaatatagtaagcttccgtgggacgttc
ggtggaggcaccaagctggaaatcaaacgaactgtggctgcaccatctgt
cttcatcttcccgccatctgatgagcagttgaaatctggaactgcctctg
ttgtgtgcctgctgaataacttctatcccagagaggccaaagtacagtgg
aaggtggataacgcccctccaatcgggtaactcccaggagagtgtcacaga
gcaggacagcaaggacagcacctacagcctcagcagcaccctgacgctga
gcaaagcagactacgagaaacacaaagtctacgcctgcgaagtcacccat
cagggcctgagctcgcccgtcacaaagagcttcaacaggggagagtgt >1344VL (Seq. no. 70)
ctagccgacattcagatgacacagactacttcctccctgtctgcctctct
gggagacagagtcaccattagttgcagtgcaagtcagggcattagtaatt
atttaaactggtatcagcagaaaccagatggaactgttaaactcctgatc
tattacacatcaagtttacactcaggagtcccatcaaggttcagtggcag
tgggtctgggacagattattctctcaccatcagcaacctggaacctgaag
atattgccacttactattgtcagcagtatagtaagcttccgtacacgttc
ggaggggggaccaagctggaaatcaaacgaactgtggctgcaccatctgtct
cttcatcttcccgccatctgatgagcagttgaaatctggaactgcctctg
ttgtgtgcctgctgaataacttctatcccagagaggccaaagtacagtgg
aaggtggataacgcccctccaatcgggtaactcccaggagagtgtcacaga
gcaggacagcaaggacagcacctacagcctcagcagcaccctgacgctga APPENDIX 1-continued Antibody variable region sequences gcaaagcagactacgagaaacacaaagtctacgcctgcgaagtcacccat
cagggcctgagctcgcccgtcacaaagagcttcaacaggggagagtgt >1347VL (Seq. no. 71)
ctagccgaaaatgtgctgactcagtctccagcaatcatgtctgcatctcc
aggggaaaaggtcaccatgacctgcagggccagctcaagtgtaagttcca
gttacttgcactggtaccagcaaaagtcaggtgcctcccccaaactctgg
atttatagcacatccaacttggcttctggagtccctgctcgcttcagtgg
cagtgggtctgggacctcttactctctcacagtcaacagtgtggagactg
aagatgctgccacttattactgccaccagtacagtggttcccattcacg
ttcggctcggggaccaagctggagctgaaacgaactgtggctgcaccatc
tgtcttcatcttcccgccatctgatgagcagttgaaatctggaactgcct
ctgttgtgtgcctgctgaataacttctatcccagagaggccaaagtacag
tggaaggtggataacgccctccaatcgggtaactcccaggagagtgtcac
agagcaggacagcaaggacagcacctacagcctcagcagcaccctgacgc
tgagcaaagcagactacgagaaacacaaagtctacgcctgcgaagtcacc
catcagggcctgagctcgcccgtcacaaagagcttcaacaggggagagtg
t >992VL (Seq. no. 72)
LADIQMTQTTSSLSASLGDRVTISCRTSQDIGNYLNWYQQKPDGTVKLLI
YYTSRLHSGVPSRFSGSGSGTDFSLTINNVEQEDVATYFCQHYNTVPPTF
GGGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFWRGEC >1024VL (Seq. no. 73)
LADIVMTQAAFSNPVTLGTSASISCRSSKSLLHSNGITYLYWYLQKPGQS
PQLLIYQMSNLASGVPDRFSSSGSGTDFTLRISRVEAEDVGVYYCAQNLE
LPYTFGGGTKLEIKRTVAAPSVFTFPPSDEQLKSGTASVVCLLNNFYPRE
AKVQWKVDNALQSGNSQESVTEQDSKDSTYSLSSTLTLSKADYEKHKVYA
CEVTHQGLSSPVTKSFNRGEC >1030VL (Seq. no. 74)
LADIVLTQSPASLAVSLGQRATISCRASKSVSTSGYSFMHWYQLKPGQPP
KLLIYLASNLESGVPARFSGSGSGTDFTLNIHPVEEEDAATYYCQHSREF
PLTFGGGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC >1042VL (Seq. no. 75)
DIVMTQAAFSNPVTLGTSASISCRSSKSLLHSNGITYLYWYLQKPGQSPQ
LLIYQMSNLASGVPDRFSSSGSRTDFTLRISRVEAEDVGVYYCAQNLELP
YTFGGGTKILEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC >1208VL (Seq. no. 76)
LADVVMTQTPLSLPVSLGDQASISCRSSQSLVHSNGNTYLHWYLQKPGQS
PKLLIYKVSNRFSGVPDRFSGSGSGTDFTLKISRVEAEDLGVYFCSQSTH
VPTFGGGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC >1229VL (Seq. no. 77)
LADIVMTQSHKFMSTSVGDRVSITCKASQDVTNAVAWYQQKPGQSPKLLI
YWASIRHTGVPDRFTGSRSGTDYTLTINSVQAEDLALYYCQQHYNTPLTF
GAGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC >1254VL (Seq. no. 78)
LADVVMTQTPLSLPVSLGDQASISCRSSQSLVHSNGNTYLHWYLQKPGQS
PKLLLYKVSNRFSGVPDRFSGSGSGTDFTLKISRVESEDLGVYFCSQNTH
VYTFGGGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC >1257VL (Seq. no. 79)
LAQIVLTQSPAIMSASPGEKVTMTCSASSSVSYIYWYQQKPGSSPRLLIY
DASNLASGVPVRFSGSGSGTSYSLTISRMEAEDAATYYCQQWSSYPITFG
SGTKLEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC >1260VL (Seq. no. 80)
LADIQMTQTTSSLSASLGDRVTISCSASQGITNYLNWYQQKPDGTVKLLI
YYSSSLHSGVPSRFSGSGSGTDYSLTISNLEPEDIATYYCQQYSEIPYTF
GGGTKLELKRTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC >1261VL (Seq. no. 81)
LAQIVLTQSPAIMSASPGEKVTITCSASSSVSYMHWFQQKPGTSPKLWIY
STSNLASGVPARFSGSGSGTSYSLTISRMEAEDAATYYCQQRSSYPYTFG
GGTKLELKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC >1277VL (Seq. no. 82)
LADVVMTQTPLSLPVSLGDQASISCRSSQSLVHSNGNTYLHWYLQKPGQS
PKLLIYKVSNRFSGVPDRFSGSGSGTDFTLKISRVEAEDLGVYFCSQSTH
VPTFGGGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC >1284VL (Seq. no. 83)
LADIVLTQSPASLAVSLGQRATISCRASQSVSTSTYSYMHWYQQKSGQPP
KLLIKYASNLESGVPARFSGSGSGTDFTLNIHPVEEEDTATYYCQHSWEI
PWTFGGGTKLEIKRTVAAPSVEIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC >1308VL (Seq. no. 84)
LADIQMTQTTSSLSASLGDRVTISCRASQDISNYLNWYQQKPDGTVKVLI
YYTSRLHSGVPSRFSGSGSGTDYSLTISNLEQEDIATYFCQQGNTLPYTF
GGGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC >1320VL (Seq. no. 85)
LADIQMTQTTSSLSASLGDRVTISCSASQDISNYLNWYQQKPDGTVKLLI
YHTSTLHSGVPSRFSGSGSGTDYSLTISNLEPEDIATYYCQQYSKLPWTF
GGGTKLEIKRTVAAPSVFTFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC >1344VL (Seq. no. 86)
LADIQMTQTTSSLSASLGDRVTISCSASQGISNYLNWYQQKPDGTVKLLI
YYTSSLHSGVPSRFSGSGSGTDYSLTISNLEPEDIATYYCQQYSKLPYTF
GGGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC >1347VL (Seq. no. 87)
LAENVLTQSPAIMSASPGEKVTMTCRASSSVSSSYLHWYQQKSGASPKLW
IYSTSNLASGVPARFSGSGSGTSYSLTVNSVETEDAATYYCHQYSGFPFT
FGSGTKLELKRTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGEC

APPENDIX 2

Antibody constant region sequences

>Human IGKC region (Seq. no. 88)
ttcatcttcccgccatctgatgagcagttgaaatctggaactgcctctgt
tgtgtgcctgctgaataacttctatcccagagaggccaaagtacagtgga
aggtggataacgccctccaatcgggtaactcccaggagagtgtcacagag
caggacagcaaggacagcacctacagcctcagcagcaccctgacgctgag
caaagcagactacgagaaacacaaagtctacgcctgcgaagtcacccatc
agggcctgagctcgcccgtcacaaagagcttcaacaggggagagtgttaa
taagcggccgccggtggaggcggt >Human IGKC region (Seq. no. 89)
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTTK
SFNRGEC

APPENDIX 2-continued

Antibody constant region sequences

```
Exon1     1 . . . 298
Intron  299 . . . 689
Exon2   690 . . . 734
Intron  735 . . . 852
Exon3   853 . . . 1182
Intron 1183 . . . 1279
Exon4  1280 . . . 1602
```

>human IGHG1 constant domain genomic sequence
(Seq. no. 90)
agtgcctccaccaagggcccatcggtcttccccctggcaccctcctccaa
gagcacctctgggggcacagcggccctgggctgcctggtcaaggactact
tccccgaaccggtgacggtgtcgtggaactcaggcgccctgaccagcggc
gtgcacaccttcccggctgtcctacagtcctcaggactctactccctcag
cagcgtggtgaccgtgccctccagcagcttgggcacccagacctacatct
gcaacgtgaatcacaagcccagcaacaccaaggtggacaagagagttggt
gagaggccagcacagggagggagggtgtctgctggaagccaggctcagcg
ctcctgcctggacgcatcccggctgcagtcccagtccaggcagcaag
gcaggccccgtctgcctcttcacccgtggaggcctctgcccgcccactcat
gctcaggagaggggtcttctggctttttcccaggctctgggcaggcaca
ggctaggtgcccctaacccaggccctgcacacaaaggggcaggtgctggg
ctcagacctgccaagagccatatccggggagaccctgcccctgacctaag
cccacccaaaggccaaactctccactcccctcagctcggacaccttctct
cctcccagattccagtaactcccaatcttctctctgcagagcccaaatct
tgtgacaaaactcacacatgcccaccgtgcccaggtaagccagcccaggc
ctcgccctccagctcaaggcgggacaggtgccctagatgcctgcatc
agggacaggccccagccgggtgctgacacgtccacctccatctcttcctc
agcacctgaactcctggggggaccgtcagtcttcctcttccccccaaaac
ccaaggacaccctcatgatctcccggacccctgaggtcacatgcgtggtg
gtggacgtgagccacgaagaccctgaggtcaagttcaactggtacgtgga
cggcgtggaggtgcataatgccaagacaaagccgcggaggagcagtaca
acagcacgtaccgtgtggtcagcgtcctcaccgtcctgcaccaggactgg
ctgaatggcaaggagtacaagtgcaaggtctccaacaaagccctcccagc
ccccatcgagaaaaccatctccaaagccaaagggcagccccgagaaccac
aggtgtacaccctgcccccatcccgggaggagatgaccaagaaccaggtc
agcctgacctgcctggtcaaaggcttctatcccagcgacatcgccgtggag
tgggagagcaatgggcagccggagaacaactacaagaccacgcctcccgtg
ctggactccgacggctccttcttcctctatagcaagctcaccgtggacaag
agcaggtggcagcaggggaacgtcttctcatgctccgtgatgcatgaggc
tctgcacaaccactacacgcagaagagcctctccctgtccccgggtaaat
ga >IGHG1 (Seq. no. 91)
SASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNNYTQKSLSLSPGK

APPENDIX 3

Dual variable domain antibody sequences

>992L1024\IGHV (Seq. no. 92)
ggcgcgccgaggtccaactgcagcaacctgggtctgagctggtgaggcct
ggagcttcagtgaagctgtcctgcaaggcttctggctacacattcaccag
ctactggatgcactgggtgaagcagaggcctggacaaggccttgagtgga
ttggaatatttatcctggtagtcgtagtactaactacgatgagaagttc
aagagcaaggccacactgactgtagacacatcctccagcacagcctacat
gcagctcagcagcctgacatctgaggactctgcggtctattactgtacaa
gaaatggggattactacgttagtagcggggatgctatggactactgggt
caaggaacctcagtcaccgtctccgtcagccagcaccaaggcccccaggt
ccaactgcagcagcctggggctgaactggtgagcctggggggttcagtga
agctgtcctgcaaggcttctggctacaccttccagtcactggatgcac
tggtgaagcagaggcctggacaaggccttgagtggataggtgagattaa
tcctagcagcggtcgtaataactacaatgagaagttcaagagtaaggcca
cactgactgtagacaaatcctccagcacagcctacatgcaattcagcagc
ctgacatctgaggactctgcggtctattattgtgtaagatactatggtta
cgacgaagctatggactactggggtcaaggaacctcagtcaccgtctcga
g >992L1024\IGKV (Seq. no. 93)
gctagccgacattcagatgactcagactacatcctccctgtctgcctctc
tgggagacagagtcaccatcagttgcaggacaagtcaggacattggcaat
tatttaaactggtatcagcagaaaccagatggaactgttaaactcctgat
ctactacacatcaagattacactcaggagtcccatcaaggttcagtggca
gtgggtctggaacagattttctctcaccattaacaacgtggagcaagag
gatgttgccacttacttttgccaacactataatacggttcctccgacgtt
cggtggaggcaccaagctggaaatcaaacgaactgtggctgcaccagaca
tcgtgatgacacaagctgcattctccaatccagtcactcttggaacatca
gcttccatctcctgcaggtctagtaagagtctcctacatagtaatggcaa
cacttatttgtattggtatctgcagaagccaggccagtctcctcagctcc
tgatttatcagatgtccaaccttgcctcaggagtcccagacaggttcagt
agcagtgggtcaggaactgatttcacactgagaatcagcagagtggaggc
tgaggatgtgggtgtttattactgtgctcaaaatctagaacttccgtaca
cgttcggaggggggaccaagctggaaataaaacgaactgtggctgcacca
tctgtcttcatcttcccgccatctgatgagcagttgaaatctggaactgc
ctctgttgtgtgcctgctgaataacttctatcccagagaggccaaagtac
agtggaaggtggataacgccctccaatcgggtaactcccaggagagtgtc
acagagcaggacagcaaggacagcacctacagcctcagcagcaccctgac
gctgagcaaagcagactacgagaaacacaaagtctacgcctgcgaagtca
cccatcagggcctgagctcgcccgtcacaaagagcttcaacaggggagag
tgttaataagcggccgc >1024L992\IGI-IV (Seq. no. 94)
ggcgcgccaggtccaactgcagcagcctggggctgaactggtggagcct
gggggttcagtgaagctgtcctgcaaggcttctggctacaccttcaccag
tcactggatgcactgggtgaagcagaggcctggacaaggccttgagtgga
taggtgagattaatcctagcagcggtcgtaataactacaatgagaagttc
aagagtaaggccacactgactgtagacaaatcctccagcacagcctacat
gcaattcagcagcctgacatctgaggactctgcggtctattattgtgtaa
gatactatggttacgacgaagctatggactactggggtcaaggaacctca
gtcaccgtctcgtcagccagcaccaaggcccccaggtccaactgcagca
acctgggtctgagctggtgaggcctggagcttcagtgaagctgtcctgca
aggcttctggctacacattcaccagctactggatgcactgggtgaagcag
aggcctggacaaggccttgagtggattggaatatttatcctggtagtcg
tagtactaactacgatgagaagttcaagagcaaggccacactgactgtag
acacatcctccagcacagcctacatgcagctcagcagcctgacatctgag
gactctgcggtctattactgtacaagaaatggggattactacgttagtag
cggggatgctatggactactggggtcaaggaacctcagtcaccgtctcga
g >1024L992\IGKV (Seq. no. 95)
gctagccgacatcgtgatgacacaagctgcattctccaatccagtcactc
ttggaacatcagcttccatctcctgcaggtctagtaagagtctcctacat
agtaatggcaacacttatttgtattggtatctgcagaagccaggccagtc
tcctcagctcctgatttatcagatgtccaaccttgcctcaggagtcccag
acaggttcagtagcagtgggtcaggaactgatttcacactgagaatcagc
agagtggaggctgaggatgtgggtgtttattactgtgctcaaaatctaga
acttccgtacacgttcggaggggggaccaagctggaaataaaacgaactg
tggctgcaccagacattcagatgactcagactacatcctccctgtctgcc
tctctgggagacagagtcaccatcagttgcaggacaagtcaggacattgg
caattatttaaactggtatcagcagaaaccagatggaactgttaaactcc
tgatctactacacatcaagattacactcaggagtcccatcaaggttcagt
ggcagtgggtctggaacagattttctctcaccattaacaacgtggagca
agaggatgttgccacttacttttgccaacactataatacggttcctccga
cgttcggtggaggcaccaagctggaaatcaaacgaactgtggctgcacca
tctgtcttcatcttcccgccatctgatgagcagttgaaatctggaactgc
ctctgttgtgtgcctgctgaataacttctatcccagagaggccaaagtac
agtggaaggtggataacgccctccaatcgggtaactcccaggagagtgtc
acagagcaggacagcaaggacagcacctacagcctcagcagcaccctgac
gctgagcaaagcagactacgagaaacacaaagtctacgcctgcgaagtca
cccatcagggcctgagctcgcccgtcacaaagagcttcaacaggggagag
tgttaataagcggccgc >992L1024\IGHV (Seq. no. 96)
RAEVQLQQPGSELVRPGASVKLSCKASGYTFTSYWMHWVKQRPGQGLEWI
GNIYPGSRSTNYDEKFKSKATLTVDTSSSTAYMQLSSLTSEDSAVYYCTR
NGDYYVSSGDAMDYWGQGTSVTVSSASTKGPQVQLQQPGAELVEPGGSVK
LSCKASGYTFTSHWMLHWVKQRPGQGLEWIGEENPSSGRNNYNEKFKSKA
TLTVDKSSSTAYMQFSSLTSEDSAVYYCVRYYGYDEAMDYWGQGTSVTVS >992L1024\IGKV (Seq. no. 97)
LADIQMTQTTSSLSASLGDRVTISCRTSQDIGNYLNWYQQKPDGTVKLLI
YYTSRLHSGVPSRFSGSGSGTDFSLTINNVEQEDVATYFCQHYNTVPPTF
GGGTKLEIKRTVAAPDIVMTQAAFSNPVTLGTSASTSCRSSKSLLHSNGI
TYLYWYLQKPGQSPQLLIYQMSNLASGVPDRFSSSGSGTDFTLRILSRVE
AEDVGVYYCAQNLELPYTFGGGTKLEIKRTVAAPSVFIFPPSDEQLKSGT
ASVVCLLNNFYPREAKVQWKVDNALQSGNSQESVTEQDSKDSTYSLSSTL
TLSKADYEKHKVTYACEVTHQGLSSPVTKSFNRGEC >1024L992\IGHV (Seq. no. 98)
RAQVQLQQPGAELVEPGGSVKLSCKASGYTFTSHWMHWVKQRPGQGLEWI
GEINPSSGRNNYNEKFKSKATLTVDKSSSTAYMQFSSLTSEDSAVYYCVR
YYGYDEAMDYWGQGTSVTVSSASTKGPEVQLQQPGSELVRPGASVKLSCK
ASGYTFTSYWMHWVKQRPGQGLEWIGNIYPGSRSTNYDEKFKSKATLTVD
TSSSTAYMQLSSLTSEDSAVYYCTRNGDYYVSSGDAMDYWGQGTSVTVS >1024L992\IGKV (Seq. no. 99)
LADIVMTQAAFSNPVTLGTSASISCRSSKSLLHSNGITYLYWYLQKPGQS
PQLLIYQMSHLASGVPDRFSSSGSGTDFTLRISRVEAEDVGVYYCAQNLE
LPYTFGGGTKLEIKRTVAAPDIQMTQTTSSLSASLGDRVTISCRTSQDIG
NYLNWYQQKPDGTVKLLIYYTSRLHSGVPSRFSGSGSGTDFSLTINNVEQ
EDVATYFCQHYNTVPPTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC

What is claimed is:

1. An antibody composition comprising at least two distinct anti-EGFR antibodies, wherein at least one of said anti-EGFR antibodies is selected from:
   (a) an antibody comprising CDR1, CDR2, and CDR3 of the heavy chain (SEQ ID NO: 40) and CDR1, CDR2, and CDR3 of the light chain (SEQ ID NO: 72) of 992,
   (b) an antibody comprising CDR1, CDR2, and CDR3 of the heavy chain (SEQ ID NO: 41) and CDR1, CDR2, and CDR3 of the light chain (SEQ ID NO: 73) of 1024,
   (c) an antibody comprising CDR1, CDR2, and CDR3 of the heavy chain (SEQ ID NO: 42) and CDR1, CDR2, and CDR3 of the light chain (SEQ ID NO: 74) of 1030,
   (d) an antibody comprising CDR1, CDR2, and CDR3 of the heavy chain (SEQ ID NO: 43) and CDR1, CDR2, and CDR3 of the light chain (SEQ ID NO: 75) of 1042,
   (e) an antibody comprising CDR1, CDR2, and CDR3 of the heavy chain (SEQ ID NO: 44) and CDR1, CDR2, and CDR3 of the light chain (SEQ ID NO: 76) of 1208,
   (f) an antibody comprising CDR1, CDR2, and CDR3 of the heavy chain (SEQ ID NO: 45) and CDR1, CDR2, and CDR3 of the light chain (SEQ ID NO: 77) of 1229,
   (g) an antibody comprising CDR1, CDR2, and CDR3 of the heavy chain (SEQ ID NO: 46) and CDR1, CDR2, and CDR3 of the light chain (SEQ ID NO: 78) of 1254,
   (h) an antibody comprising CDR1, CDR2, and CDR3 of the heavy chain (SEQ ID NO: 47) and CDR1, CDR2, and CDR3 of the light chain (SEQ ID NO: 79) of 1257,
   (i) an antibody comprising CDR1, CDR2, and CDR3 of the heavy chain (SEQ ID NO: 48) and CDR1, CDR2, and CDR3 of the light chain (SEQ ID NO: 80) of 1260,
   (j) an antibody comprising CDR1, CDR2, and CDR3 of the heavy chain (SEQ ID NO: 49) and CDR1, CDR2, and CDR3 of the light chain (SEQ ID NO: 81) of 1261,
   (k) an antibody comprising CDR1, CDR2, and CDR3 of the heavy chain (SEQ ID NO: 50) and CDR1, CDR2, and CDR3 of the light chain (SEQ ID NO: 82) of 1277,
   (l) an antibody comprising CDR1, CDR2, and CDR3 of the heavy chain (SEQ ID NO: 51) and CDR1, CDR2, and CDR3 of the light chain (SEQ ID NO: 83) of 1284,
   (m) an antibody comprising CDR1, CDR2, and CDR3 of the heavy chain (SEQ ID NO: 52) and CDR1, CDR2, and CDR3 of the light chain (SEQ ID NO: 84) of 1308,
   (n) an antibody comprising CDR1, CDR2, and CDR3 of the heavy chain (SEQ ID NO: 53) and CDR1, CDR2, and CDR3 of the light chain (SEQ ID NO: 85) of 1320,
   (o) an antibody comprising CDR1, CDR2, and CDR3 of the heavy chain (SEQ ID NO: 54) and CDR1, CDR2, and CDR3 of the light chain (SEQ ID NO: 86) of 1344,
   (p) an antibody comprising CDR1, CDR2, and CDR3 of the heavy chain (SEQ ID NO: 55) and CDR1, CDR2, and CDR3 of the light chain (SEQ ID NO: 87) of 1347, and
   (q) mixtures of two or more of said antibodies in (a)-(p).

2. The antibody composition of claim 1, wherein at least one of said anti-EGFR antibodies is selected from
   (a) an antibody comprising CDR1, CDR2, and CDR3 of the heavy chain (SEQ ID NO: 40) and CDR1, CDR2, and CDR3 of the light chain (SEQ ID NO: 72) of 992,
   (b) an antibody comprising CDR1, CDR2, and CDR3 of the heavy chain (SEQ ID NO: 42) and CDR1, CDR2, and CDR3 of the light chain (SEQ ID NO: 74) of 1030,
   (c) an antibody comprising CDR1, CDR2, and CDR3 of the heavy chain (SEQ ID NO: 41) and CDR1, CDR2, and CDR3 of the light chain (SEQ ID NO: 73) of 1024,
   (d) an antibody comprising CDR1, CDR2, and CDR3 of the heavy chain (SEQ ID NO: 55) and CDR1, CDR2, and CDR3 of the light chain (SEQ ID NO: 87) of 1347,
   (e) an antibody comprising CDR1, CDR2, and CDR3 of the heavy chain (SEQ ID NO: 50) and CDR1, CDR2, and CDR3 of the light chain (SEQ ID NO: 82) of 1277,
   (f) an antibody comprising CDR1, CDR2, and CDR3 of the heavy chain (SEQ ID NO: 46) and CDR1, CDR2, and CDR3 of the light chain (SEQ ID NO: 78) of 1254,
   (g) an antibody comprising CDR1, CDR2, and CDR3 of the heavy chain (SEQ ID NO: 53) and CDR1, CDR2, and CDR3 of the light chain (SEQ ID NO: 85) of 1320,
   (h) an antibody comprising CDR1, CDR2, and CDR3 of the heavy chain (SEQ ID NO: 48) and CDR1, CDR2, and CDR3 of the light chain (SEQ ID NO: 80) of 1260,
   (i) an antibody comprising CDR1CDR2 and CDR3 of the heavy chain (SEQ ID NO: 49) and CDR1, CDR2, and CDR3 of the light chain (SEQ ID NO: 81) of 1261,
   (j) an antibody comprising CDR1, CDR2, and CDR3 of the heavy chain (SEQ ID NO: 51) and CDR1, CDR2, and CDR3 of the light chain (SEQ ID NO: 83) of 1284, and
   (k) mixtures of two or more of said antibodies in (a)-(j).

3. The antibody composition of claim 1, wherein said composition is selected from:
   (a) a composition comprising an antibody comprising CDR1, CDR2, and CDR3 of the heavy chain (SEQ ID NO: 40) and CDR1, CDR2, and CDR3 of the light chain (SEQ ID NO: 72) of 992 and an antibody comprising CDR1, CDR2, and CDR3 of the heavy chain (SEQ ID NO: 42) and CDR1, CDR2, and CDR3 of the light chain (SEQ ID NO: 74) of 1030,
   (b) a composition comprising an antibody comprising CDR1, CDR2, and CDR3 of the heavy chain (SEQ ID NO: 40) and CDR1, CDR2, and CDR3 of the light chain (SEQ ID NO: 72) of 992 and an antibody comprising CDR1, CDR2, and CDR3 of the heavy chain (SEQ ID NO: 41) and CDR1, CDR2, and CDR3 of the light chain (SEQ ID NO: 73) of 1024,
   (c) a composition comprising an antibody comprising CDR1, CDR2, and CDR3 of the heavy chain (SEQ ID NO: 40) and CDR1, CDR2, and CDR3 of the light chain (SEQ ID NO: 72) of 992 and an antibody comprising CDR1, CDR2, and CDR3 of the heavy chain (SEQ ID NO: 43) and CDR1, CDR2, and CDR3 of the light chain (SEQ ID NO: 75) of 1042,
   (d) a composition comprising an antibody comprising CDR1, CDR2, and CDR3 of the heavy chain (SEQ ID NO: 40) and CDR1, CDR2, and CDR3 of the light chain (SEQ ID NO: 72) of 992 and an antibody comprising CDR1, CDR2, and CDR3 of the heavy chain (SEQ ID NO: 53) and CDR1, CDR2, and CDR3 of the light chain (SEQ ID NO: 85) of 1320, and (e) a composition comprising an antibody comprising CDR1, CDR2, and CDR3 of the heavy chain (SEQ ID NO: 50) and CDR1, CDR2, and CDR3 of the light chain (SEQ ID NO: 82) of 1277 and an antibody comprising CDR1, CDR2, and CDR3 of the heavy chain (SEQ ID NO: 41) and CDR1, CDR2, and CDR3 of the light chain (SEQ ID NO: 73) of 1024.

4. An antibody composition comprising at least 2 distinct anti-human EGFR antibodies:
(a) wherein a first distinct anti-EGFR antibody is an antibody capable of inhibiting the binding of and which binds the same epitope as an antibody comprising the CDR1, CDR2, and CDR3 of the heavy chain (SEQ ID NO: 40) and CDR1, CDR2, and CDR3 of the light chain (SEQ ID NO: 72) of antibody 992 to human EGFR; and
(b) wherein a second distinct anti-EGFR antibody is an antibody capable of inhibiting the binding of and which binds the same epitope as an antibody comprising the CDR1, CDR2, and CDR3 of the heavy chain (SEQ ID NO: 41) and CDR1, CDR2, and CDR3 of the light chain (SEQ ID NO: 73) of antibody 1024 to human EGFR.

5. The composition of claim 4, wherein:
(a) said first distinct anti-EGFR antibody is an antibody comprising the CDR1, CDR2, and CDR3 of the heavy chain (SEQ ID NO: 40) and CDR1, CDR2, and CDR3 of the light chain (SEQ ID NO: 72) of antibody 99; and
(b) said second distinct anti-EGFR antibody is an antibody comprising the CDR1, CDR2, and CDR3 of the heavy chain (SEQ ID NO: 41) and CDR1, CDR2, and CDR3 of the light chain (SEQ ID NO: 73) of antibody 1024.

6. The composition of claim 4, wherein
(a) said first distinct anti-EGFR antibody is an antibody comprising the $V_L$ (amino acids 3-109 of SEQ ID NO: 72) and $V_H$ (amino acids 3-124 of SEQ ID NO: 40) of antibody 992; and
(b) said second distinct anti-EGFR antibody is an antibody comprising the $V_L$ (amino acids 3-114 of SEQ ID NO: 73) and $V_H$ (amino acids 3-120 of SEQ ID NO: 41) of antibody 1024.

7. The composition of claim 4, wherein the first and second anti-EGFR antibodies do not inhibit the binding of each other to human EGFR.

8. The composition of claim 4, wherein at least one of the distinct anti-EGFR antibodies is capable of increasing the maximum binding capacity of the other distinct anti-EGFR antibody with respect to human EGFR.

9. The composition of claim 4, wherein the proportion of the first antibody relative to the second antibody in the composition is between 5% and 95% (mole/mole).

10. The composition of claim 4, wherein the first and second antibodies are of isotype IgG1 or IgG2.

11. The composition of claim 4, wherein the antibody capable of inhibiting the binding of and which binds to the same epitope as an antibody comprising the CDR1, CDR2, and CDR3 of the heavy chain (SEQ ID NO: 40) and CDR1, CDR2, and CDR3 of the light chain (SE0 ID NO: 72) of antibody 992 is selected from antibody cluster 992 consisting of antibodies 1209, 1204, 992, 996, 1033, and 1220 in Table 12.

12. The composition of claim 4, wherein the antibody capable of inhibiting the binding of and which binds to the same epitope as an antibody comprising the CDR1, CDR2, and CDR3 of the heavy chain (SEQ ID NO: 41) and CDR1, CDR2, and CDR3 of the light chain (SEQ ID NO: 73) of antibody 1024 is selected from antibody cluster 1024 consisting of antibodies 1031, 1036, 1042, 984, 1024, 1210, 1217, 1221, and 1218 in Table 12.

13. The composition of claim 4, wherein the antibody capable of inhibiting the binding of and which binds the same epitope as an antibody comprising the CDR1, CDR2, and CDR3 of the heavy chain (SEQ ID NO: 40) and CDR1, CDR2, and CDR3 of the light chain (SEQ ID NO: 72) of antibody 992 to human EGFR is selected from:
(a) an antibody comprising CDR1, CDR2, and CDR3 of the heavy chain (SEQ ID NO: 44) and CDR1, CDR2, and CDR3 of the light chain (SEQ ID NO: 76) of 1208,
(b) an antibody comprising CDR1, CDR2, and CDR3 of the heavy chain (SEQ ID NO: 46) and CDR1, CDR2, and CDR3 of the light chain (SEQ ID NO: 78) of 1254, and
(c) an antibody comprising CDR1, CDR2, and CDR3 of the heavy chain (SEQ ID NO: 50) and CDR1, CDR2, and CDR3 of the light chain (SEQ ID NO: 82) of 1277.

14. The composition of claim 4, wherein the antibody capable of inhibiting the binding of and which binds the same epitope as an antibody comprising the CDR1, CDR2, and CDR3 of the heavy chain (SEQ ID NO: 41) and CDR1, CDR2, and CDR3 of the light chain (SEQ ID NO: 73) of antibody 1024 is selected from:
(a) an antibody comprising CDR1, CDR2, and CDR3 of the heavy chain (SEQ ID NO: 43) and CDR1, CDR2, and CDR3 of the light chain (SEQ ID NO: 75) of 1042 and
(b) an antibody comprising CDR1, CDR2, and CDR3 of the heavy chain (SEQ ID NO: 53) and CDR1, CDR2, and CDR3 of the light chain (SEQ ID NO: 85) of 1320.

15. The composition of claim 4, wherein the composition does not contain further anti-EGFR antibodies in addition to said first and second antibodies.

16. The composition of claim 4, wherein the distinct antibodies are prepared for simultaneous, successive or separate administration.

17. The composition of claim 4, wherein the composition is capable of enhancing internalisation of EGFR.

18. The composition of claim 4, wherein the composition is capable of enhancing regression of A431NS tumours in vivo.

19. The composition of claim 4, wherein the composition is capable of inducing terminal differentiation in A431NS cells in vivo.

20. The composition of claim 4, wherein the composition is capable of up-regulating tumour involucrin expression in vivo.

21. A bi-specific binding molecule having the binding specificities of the antibody composition of claim 4.

22. The bi-specific binding molecule of claim 21, comprising the CDR1, CDR2, and CDR3 of the heavy chain (SEQ ID NO: 40) and CDR1, CDR2, and CDR3 of the light chain (SEQ ID NO: 72) of 992 and the CDR1, CDR2, and CDR3 of the heavy chain (SEQ ID NO: 41) and CDR1, CDR2, and CDR3 of the light chain (SEQ ID NO: 73) of 1024.

23. The bi-specific binding molecule of claim 21, comprising a dual-variable-domain antibody.

24. The bi-specific binding molecule of claim 21, comprising a bi-specific Fab-fragment or a bi-specific scFV.

25. A method of reducing EGFR signalling comprising administering to a composition of cells expressing EGFR an antibody composition of claim 1, or the bi-specific binding molecule of claim 21, thereby reducing the EGFR signalling.

26. A method of killing cells expressing EGFR comprising administering to a composition of cells expressing EGFR an antibody composition of claim 1 or 4, or the bi-specific binding molecule of claim 21, thereby killing the cells expressing EGFR.

27. A method of inducing apoptosis in cells expressing EGFR, comprising administering to a composition of cells expressing EGFR an antibody composition of claim 1 or 4, or the bi-specific binding molecule of claim 21, thereby inducing apoptosis.

28. A method of inhibiting proliferation of cells expressing EGFR comprising administering to a composition of cells expressing EGFR an antibody composition of claim 1 or 4, or the bi-specific binding molecule of claim 21, thereby inhibiting proliferation.

29. A method of inducing differentiation of tumour cells in vivo, comprising administering to an individual inflicted with cancer an antibody composition of claim 1 or 4, or the bi-specific binding molecule of claim 21, thereby inducing differentiation of the tumour cells.

30. The method of claim 29, wherein said differentiation is terminal.

31. The method of claim 29, wherein said differentiation is accompanied by an increase in involucrin expression.

32. A method for inducing internalisation of EGFR, comprising administering to cells expressing EGFR an effective amount of an antibody composition of claim 1 or 4, or the bi-specific binding molecule of claim 21, thereby inducing internalisation of EGFR.

33. A pharmaceutical composition comprising a combination of two or more antibodies of the composition of claim 1 for simultaneous, separate or successive administration in cancer therapy.

34. The pharmaceutical composition of claim 33, further comprising at least one compound capable of inducing differentiation of cancer cells.

35. The pharmaceutical composition of claim 34, wherein the compound is selected from the group consisting of retinoic acid, phenylbutyrate, all-trans-retinoic acid, and active form vitamin D.

36. The pharmaceutical composition of claim 33, further comprising at least one chemotherapeutic or at least one additional antineoplastic compound.

37. The pharmaceutical composition of claim 36, wherein the chemotherapeutic compound is selected from the group consisting of adriamycin, cisplatin, taxol, doxorubicin, topotecan, fluoropyrimidine, oxaliplatin, and irinotecan.

38. A pharmaceutical composition comprising a combination of two or more antibodies of the composition of claim 4 for simultaneous, separate or successive administration in cancer therapy.

39. The pharmaceutical composition of claim 38, further comprising at least one compound capable of inducing differentiation of cancer cells.

40. The pharmaceutical composition of claim 39, wherein the compound is selected from the group consisting of retinoic acid, phenylbutyrate, all-trans-retinoic acid, and active form vitamin D.

41. The pharmaceutical composition of claim 38, further comprising at least one chemotherapeutic or at least one additional antineoplastic compound.

42. The pharmaceutical composition of claim 41, wherein the chemotherapeutic compound is selected from the group consisting of adriamycin, cisplatin, taxol, doxorubicin, topotecan, fluoropyrimidine, oxaliplatin, and irinotecan.

43. A pharmaceutical composition comprising the bi-specific binding molecule of claim 21 for simultaneous, separate or successive administration in cancer therapy.

44. The pharmaceutical composition of claim 43, further comprising at least one compound capable of inducing differentiation of cancer cells.

45. The pharmaceutical composition of claim 44, wherein the compound is selected from the group consisting of retinoic acid, phenylbutyrate, all-trans-retinoic acid, and active form vitamin D.

46. The pharmaceutical composition of claim 43, further comprising at least one chemotherapeutic or at least one additional antineoplastic compound.

47. The pharmaceutical composition of claim 46, wherein the chemotherapeutic compound is selected from the group consisting of adriamycin, cisplatin, taxol, doxorubicin, topotecan, fluoropyrimidine, oxaliplatin, and irinotecan.

48. The composition of claim 4, further comprising a third distinct anti-EGFR antibody, wherein said third distinct anti-EGFR antibody is an antibody capable of inhibiting the binding of and which binds the same epitope as an antibody comprising the CDR1, CDR2, and CDR3 of the heavy chain (SEQ ID NO: 42) and CDR1, CDR2, and CDR3 of the light chain (SEQ ID NO: 74) of antibody 1030 to human EGFR.

49. The composition of claim 4, further comprising a third distinct anti-EGFR antibody, wherein said third distinct anti-EGFR antibody is an antibody comprising the $V_L$ (amino acids 3 to 114 of SEQ ID NO: 74) and $V_H$ (amino acids 3-120 of SEQ ID NO: 42) sequences of antibody 1030.

50. The composition of claim 4, further comprising a third distinct anti-EGFR antibody, wherein said third distinct anti-EGFR antibody is an antibody comprising the CDR1, CDR2, and CDR3 of the heavy chain (SEQ ID NO: 42) and CDR1, CDR2, and CDR3 of the light chain (SEQ ID NO: 74) of antibody 1030.

51. The composition of claim 48, wherein said third distinct anti-EGFR antibody results in an enhanced binding to human EGFR of said first and/or second antibody.

52. The composition of claim 48, wherein said antibody capable of binding to the same epitope as an antibody comprising the CDR1, CDR2, and CDR3 of the heavy chain (SEQ ID NO: 42) and CDR1, CDR2, and CDR3 of the light chain (SEQ ID NO: 74) of antibody 1030 is selected from antibody cluster 1030 comprising antibodies 1195, 1030, 1034, 1194, 980, 981, 1246, or 1223 in Table 12.

53. The composition of claim 48, wherein the composition does not contain further anti-EGFR antibodies in addition to said first, second, and third antibodies.

\* \* \* \* \*

SEQUENCE LISTING

<160> NUMBER OF SEQ ID NOS: 141

<210> SEQ ID NO 1
<211> LENGTH: 20
<212> TYPE: DNA
<213> ORGANISM: artificial
<220> FEATURE:
<223> OTHER INFORMATION: PCR primer

<400> SEQUENCE: 1
gacsgatggg cccttggtgg                                              20

<210> SEQ ID NO 2
<211> LENGTH: 20
<212> TYPE: DNA
<213> ORGANISM: artificial
<220> FEATURE:
<223> OTHER INFORMATION: PCR primer

<400> SEQUENCE: 2
gctgtaggtg ctgtctttgc                                              20

<210> SEQ ID NO 3
<211> LENGTH: 39
<212> TYPE: DNA
<213> ORGANISM: artificial
<220> FEATURE:
<223> OTHER INFORMATION: PCR primer

<400> SEQUENCE: 3
tattcccatg gcgcgccsag gtccarctgc arcagyctg                         39

<210> SEQ ID NO 4
<211> LENGTH: 37
<212> TYPE: DNA
<213> ORGANISM: artificial
<220> FEATURE:
<223> OTHER INFORMATION: PCR primer

<400> SEQUENCE: 4
tattcccatg gcgcgccgar gtgmagctkg tkgagtc                           37

<210> SEQ ID NO 5
<211> LENGTH: 37
<212> TYPE: DNA
<213> ORGANISM: artificial
<220> FEATURE:
<223> OTHER INFORMATION: PCR primer

<400> SEQUENCE: 5
tattcccatg gcgcgccsag gtgcagctkm aggagtc                           37

<210> SEQ ID NO 6

-continued

```
<211> LENGTH: 37
<212> TYPE: DNA
<213> ORGANISM: artificial
<220> FEATURE:
<223> OTHER INFORMATION: PCR primer

<400> SEQUENCE: 6
tattcccatg gcgcgcccag gttactctga aagagtc                              37

<210> SEQ ID NO 7
<211> LENGTH: 39
<212> TYPE: DNA
<213> ORGANISM: artificial
<220> FEATURE:
<223> OTHER INFORMATION: PCR primer

<400> SEQUENCE: 7
tattcccatg gcgcgcccag atccagttgg tgcagtctg                            39

<210> SEQ ID NO 8
<211> LENGTH: 45
<212> TYPE: DNA
<213> ORGANISM: artificial
<220> FEATURE:
<223> OTHER INFORMATION: PCR primer

<400> SEQUENCE: 8
ggcgcgccat gggaatagct agccgayatc cagatgachc arwct                    45

<210> SEQ ID NO 9
<211> LENGTH: 44
<212> TYPE: DNA
<213> ORGANISM: artificial
<220> FEATURE:
<223> OTHER INFORMATION: PCR primer

<400> SEQUENCE: 9
ggcgcgccat gggaatagct agccracatt gtgmtgachc agtc                     44

<210> SEQ ID NO 10
<211> LENGTH: 46
<212> TYPE: DNA
<213> ORGANISM: artificial
<220> FEATURE:
<223> OTHER INFORMATION: PCR primer

<400> SEQUENCE: 10
ggcgcgccat gggaatagct agccsamatt gtkctsaccc artctc                   46

<210> SEQ ID NO 11
<211> LENGTH: 45
<212> TYPE: DNA
<213> ORGANISM: artificial
<220> FEATURE:
<223> OTHER INFORMATION: PCR primer

<400> SEQUENCE: 11
ggcgcgccat gggaatagct agccgatrtt gtgatgacbc arrct                    45

<210> SEQ ID NO 12
<211> LENGTH: 30
<212> TYPE: DNA
<213> ORGANISM: artificial
<220> FEATURE:
<223> OTHER INFORMATION: PCR primer

<400> SEQUENCE: 12
```
ggaggcgctc gagacggtga ccgtggtccc                                30

<210> SEQ ID NO 13
<211> LENGTH: 30
<212> TYPE: DNA
<213> ORGANISM: artificial
<220> FEATURE:
<223> OTHER INFORMATION: PCR primer

<400> SEQUENCE: 13
ggaggcgctc gagactgtga gagtggtgcc                                30

<210> SEQ ID NO 14
<211> LENGTH: 30
<212> TYPE: DNA
<213> ORGANISM: artificial
<220> FEATURE:
<223> OTHER INFORMATION: PCR primer

<400> SEQUENCE: 14
ggaggcgctc gagacagtga ccagagtccc                                30

<210> SEQ ID NO 15
<211> LENGTH: 30
<212> TYPE: DNA
<213> ORGANISM: artificial
<220> FEATURE:
<223> OTHER INFORMATION: PCR primer

<400> SEQUENCE: 15
ggaggcgctc gagacggtga ctgaggttcc                                30

<210> SEQ ID NO 16
<211> LENGTH: 24
<212> TYPE: DNA
<213> ORGANISM: artificial
<220> FEATURE:
<223> OTHER INFORMATION: PCR primer

<400> SEQUENCE: 16
ggacagggmt ccakagttcc adkt                                      24

<210> SEQ ID NO 17
<211> LENGTH: 43
<212> TYPE: DNA
<213> ORGANISM: artificial
<220> FEATURE:
<223> OTHER INFORMATION: PCR primer

<400> SEQUENCE: 17
gacagatggt gcagccacag ttcgtttgat ttccagcttg gtg                 43

<210> SEQ ID NO 18
<211> LENGTH: 43
<212> TYPE: DNA
<213> ORGANISM: artificial
<220> FEATURE:
<223> OTHER INFORMATION: PCR primer

<400> SEQUENCE: 18
gacagatggt gcagccacag ttcgttttat ttccagcttg gtc                 43

<210> SEQ ID NO 19
<211> LENGTH: 43
<212> TYPE: DNA

```
<213> ORGANISM: artificial
<220> FEATURE:
<223> OTHER INFORMATION: PCR primer

<400> SEQUENCE: 19
gacagatggt gcagccacag ttcgttttat ttccaacttt gtc            43

<210> SEQ ID NO 20
<211> LENGTH: 43
<212> TYPE: DNA
<213> ORGANISM: artificial
<220> FEATURE:
<223> OTHER INFORMATION: PCR primer

<400> SEQUENCE: 20
gacagatggt gcagccacag ttcgtttcag ctccagcttg gtc            43

<210> SEQ ID NO 21
<211> LENGTH: 23
<212> TYPE: DNA
<213> ORGANISM: artificial
<220> FEATURE:
<223> OTHER INFORMATION: PCR primer

<400> SEQUENCE: 21
gaactgtggc tgcaccatct gtc                                  23

<210> SEQ ID NO 22
<211> LENGTH: 43
<212> TYPE: DNA
<213> ORGANISM: artificial
<220> FEATURE:
<223> OTHER INFORMATION: PCR primer

<400> SEQUENCE: 22
accgcctcca ccggcggccg cttattaaca ctctcccctg ttg            43

<210> SEQ ID NO 23
<211> LENGTH: 51
<212> TYPE: DNA
<213> ORGANISM: artificial
<220> FEATURE:
<223> OTHER INFORMATION: PCR primer

<400> SEQUENCE: 23
accgcctcca ccggcggccg cttattaaca ctctcccctg ttgaagctct t   51

<210> SEQ ID NO 24
<211> LENGTH: 372
<212> TYPE: DNA
<213> ORGANISM: Homo sapiens

<400> SEQUENCE: 24
cgcgccgagg tccaactgca gcaacctggg tctgagctgg tgaggcctgg agcttcagtg    60
aagctgtcct gcaaggcttc tggctacaca ttcaccagct actggatgca ctgggtgaag   120
cagaggcctg gacaaggcct tgagtggatt gggaatattt atcctggtag tgtagtact    180 aactacgatg agaagttcaa gagcaaggcc acactgactg tagacacatc ctccagcaca   240
gcctacatgc agctcagcag cctgacatct gaggactctg cggtctatta ctgtacaaga   300
aatggggatt actacgttag tagcggggat gctatggact actgggtca aggaaccctca  360 gtcaccgtct cg                                                       372
```

<210> SEQ ID NO 25
<211> LENGTH: 360
<212> TYPE: DNA
<213> ORGANISM: Homo sapiens

<400> SEQUENCE: 25

```
cgcgcccagg tccaactgca gcagcctggg gctgaactgg tggagcctgg gggttcagtg      60
aagctgtcct gcaaggcttc tggctacacc ttcaccagtc actggatgca ctgggtgaag     120
cagaggcctg acaaggcct  tgagtggata  ggtgagatta atcctagcag cggtcgtaat    180
aactacaatg agaagttcaa gagtaaggcc acactgactg tagacaaatc ctccagcaca     240
gcctacatgc aattcagcag cctgacatct gaggactctg cggtctatta ttgtgtaaga     300
tactatggtt acgacgaagc tatggactac tggggtcaag gaacctcagt caccgtctcg     360
```

<210> SEQ ID NO 26
<211> LENGTH: 360
<212> TYPE: DNA
<213> ORGANISM: Homo sapiens

<400> SEQUENCE: 26

```
cgcgccgaag tgcagctggt ggagtctggg ggaggcttag tgaagcctgg agggtccctg      60
aaactctcct gtgcagcctc tggattcact ttcagtagtt atgccctgtc ttgggttcgc     120
cagactccag agaggaggct ggagtgggtc gcatccatta tggtgttgg  tagcacctac     180
tttccagaca gtgtgaaggg ccgtttcacc atgtccagag ataatgccag gaacatcctg     240
tacctccaaa tgagcagtct gaggtctgag gacacggcca tgtattactg tgcaagaggt     300
tctgatggtt acttctatgc tatggactac tggggtcaag gaacctcagt caccgtctcg     360
```

<210> SEQ ID NO 27
<211> LENGTH: 360
<212> TYPE: DNA
<213> ORGANISM: Homo sapiens

<400> SEQUENCE: 27

```
cgcgcccagg tgcagcttca gcagcctggg gctgaactgg tgaagcctgg ggcttcagtg      60
aagctgtcct gtaaggcttc tggctacacc ttcaccagcc actggatgca ctgggtgcag     120
cagaggcctg acaaggcct  tgagtggatt ggagagatta tcctagcaa  cggtcgtact     180
aactacaatg agaagttcaa gaacaaggcc acactgactg tagacaaatc tcccagcaca     240
gcctacatgc aactcagcag tttgacatct gaggactctg cggtctatta ctgtgcaaga     300
tactatggtt acgacgatgc tatggactac tggggtcaag gaacctcagt caccgtctcg     360
```

<210> SEQ ID NO 28
<211> LENGTH: 366
<212> TYPE: DNA
<213> ORGANISM: Homo sapiens

<400> SEQUENCE: 28

```
cgcgccgaag tgcagctggt ggagtctggg ggaggcttag tgaagcctgg agggtccctg      60
aaactctcct gtgcagcctc tggattcgct ttcagtagct atgacatgtc ttgggttcgc     120
cagactccgg agaagaggct ggagtgggtc gcatacattg gtagtggtga tgataatacc     180
cactatccag actctgtgaa gggccgattc accatctcca gacacaatgc caaaaacacc     240
ctataccctgc aaatgagcag tctgaagtct gaggacacag ccatgtatta ctgtgcaaga     300
cagaagtatg gtaactacgg ggacactatg gactactggg gtcaaggaac ctcagtcacc     360
```

```
                                                 -continued gtctcg                                                            366

<210> SEQ ID NO 29
<211> LENGTH: 366
<212> TYPE: DNA
<213> ORGANISM: Homo sapiens

<400> SEQUENCE: 29
cgcgcccagg ttcagctgaa ggagtcagga cctggcctgg tggcgccctc acagagcctg      60
tccatcactt gctctgtctc tggttttca ttaaccatct atggtgtaca ctgggttcgc     120
cagcctccag gaaagggtct ggagtggctg gagttatgt gggctggtgg aaatacagat     180
tataattcgg ctctcatgtc cagactgaac atcagcaagg acaattccaa gagccaagtt     240
ttcttaaaag tgaacagtct acaaactgat gacacagcca tgtactattg taccagagat     300
cccgatggtt actacgtggg gtggttcttc gatgtctggg gcgcggggac cacggtcacc     360
gtctcg                                                            366

<210> SEQ ID NO 30
<211> LENGTH: 366
<212> TYPE: DNA
<213> ORGANISM: Homo sapiens

<400> SEQUENCE: 30
cgcgccgaag tgcagctggt ggagtctggg ggaggcttag tgaagcctgg agggtccctg      60
aaactctcct gtgcagcctc tggattcgct tacagtacct atgacatgtc ttgggttcgc     120
cagactccgg agaagaggct ggagtgggtc gcatacatta gtagtggtgg tgatgccgcc     180
tactatcccg acactgtgaa gggccgattc accatctcca gagacaatgc caaaaacacc     240
ctatacctgc aaatgagcag tctgaagtct gaggacacag ccatgtatta ctgtgcgagg     300
tctcgctatg gaaactacgg ggacgctatg gactactggg gtcaaggaac ctcagtcacc     360
gtctcg                                                            366

<210> SEQ ID NO 31
<211> LENGTH: 375
<212> TYPE: DNA
<213> ORGANISM: Homo sapiens

<400> SEQUENCE: 31
cgcgccgagg tccagctgca acagtctgga cctgagctgg tgaaacctgg ggcttcagtg      60
aagataccct gcaagacttc tggatacact ttcactgact acaacatggc ctgggtgaag     120
cagagccatg gaaagagcct tgagtggatt ggagatatta ttcctaacaa tggtggtgct     180
atctacaacc agaaattcaa gggcaaggcc actttgactt agacaaatc ctccagtaca     240 gcctccatgg agctccgcag cctgacatct gaggacactg cagtctattt ctgtgcaaga     300
aagaatatct actataggta cgacggggca ggtgctctgg actactgggg tcaaggaacc     360
tcagtcaccg tctcg                                                  375

<210> SEQ ID NO 32
<211> LENGTH: 351
<212> TYPE: DNA
<213> ORGANISM: Homo sapiens

<400> SEQUENCE: 32
cgcgcccagg tgcagctgaa ggagtcagga cctggcctgg tggcgccctc acagagcctg      60
tccatcactt gcactgtctc tgggttttca ttaaccacct atgggtgtaca ctgggttcgc     120
```

| | |
|---|---|
| cagcctccag gaaagggtct ggagtggctg ggagtaatat gggctggtgg aagcacaaat | 180 |
| tataattcgg ctctcatgtc cagactgagc atcaagaaag acaactccaa gagccaagtt | 240 |
| ttcttaaaaa tgaacagtct gcaaactgat gacacagcca tgtactactg tgccagagcc | 300 |
| tatggttaca actttgacta ttggggccaa ggcaccactc tcacagtctc g | 351 |

```
<210> SEQ ID NO 33
<211> LENGTH: 372
<212> TYPE: DNA
<213> ORGANISM: Homo sapiens

<400> SEQUENCE: 33
```

| | |
|---|---|
| cgcgccgaag tgcagctggt ggagtctggg ggaggcttag tgaagcctgg agggtccctg | 60 |
| aaactctcct gtgcagtctc tggattcact ttcagtagct atgtcatgtc ttgggttcgc | 120 |
| cagactccgg agaagaggct ggagtgggtc gcaaccatta ctagtggtgg taggaacatc | 180 |
| tactatctag acagtgtgaa gggcgattc actatctcca gagacaatgc caagaacacc | 240 |
| ctgtacctgc aaatgagcag tctgaggtct gaggacacgg ccatgtatta ctgtgcaaga | 300 |
| catgaggact ataggtacga cggttactat gctatggact actggggtca aggaacctca | 360 |
| gtcaccgtct cg | 372 |

```
<210> SEQ ID NO 34
<211> LENGTH: 354
<212> TYPE: DNA
<213> ORGANISM: Homo sapiens

<400> SEQUENCE: 34
```

| | |
|---|---|
| cgcgccgaag tgcagctggt ggagtctggg ggaggcttag tgaagcctgg agagtccttg | 60 |
| aaactctcct gtgcagcctc tggattcgct ttcagttact ctgacatgtc ttgggttcgc | 120 |
| cagactccgg agaagaggct ggagtgggtc gcatacatga gtagtgctgg tgatgtcacc | 180 |
| ttctattcag acactgtgaa gggccgattc accatctcca gagacaatgc caagaacacc | 240 |
| ctgtatctgc aagtgagcag tctgaagtct gaggacacag ccatatatta ctgtgtaaga | 300 |
| caccgggacg tggctatgga ctactgggt caaggaacct cagtcaccgt ctcg | 354 |

```
<210> SEQ ID NO 35
<211> LENGTH: 357
<212> TYPE: DNA
<213> ORGANISM: Homo sapiens

<400> SEQUENCE: 35
```

| | |
|---|---|
| cgcgcccagg tccaactgca gcagcctggg gctgaactgg tgaagcctgg ggcttcagtg | 60 |
| aagctgtcct gcaaggcttc tggctacacc ttcaccagcg actggatgca ctggatgaaa | 120 |
| cagaggcctg acaaggcct tgagtggatt ggagagatta tcctagtaa cggtcgctct | 180 |
| agctacaatg agaagttcaa gagcaaggcc acactgactg tagacaaatc ctccagcaca | 240 |
| gcctacatgc aactcagcag cctgacatct gaggactctg cggtctatta ctgtgcaaga | 300 |
| ataggtggta tctacgtgga gacttactgg ggccaaggga ctctggtcac tgtctcg | 357 |

```
<210> SEQ ID NO 36
<211> LENGTH: 375
<212> TYPE: DNA
<213> ORGANISM: Homo sapiens

<400> SEQUENCE: 36
```

```
cgcgccgagg tccagcttca gcagtctgga gctgagctgg tgaggcctgg gtcctcagtg      60
aagatttcct gcaaggcttc tggctatgca ttcagtagct actggatgaa ctgggtgagg     120
cagaggcctg acagggtct tgagtggatt ggacagattt atcctggaga tggtgatact      180
aactacaatg gaaagttcaa gggtagagcc acactgactg caaacaaatc ctccagcaca     240
gcctacatgc agctcagcag cctaacatct gaggactctg cggtctattt ctgtgcaaga     300
agggcatctt ccctctatga tgtttacccc tactactttg actactgggg ccaaggcacc     360
actctcacag tctcg                                                      375
```

<210> SEQ ID NO 37
<211> LENGTH: 363
<212> TYPE: DNA
<213> ORGANISM: Homo sapiens

<400> SEQUENCE: 37

```
cgcgcccagg tccaactgca gcagcctggg gctgaactgg tgaagcctgg ggcttcaatg      60
aagctgtcct gcaaggcttc tggctacacc ttcaccaact actggatgca ctgggtgaag     120
cagaggcctg acaaggcct tgaatggatt ggagaaatta atcctagcaa cggtcgtact      180
aattacaatg agaagttcaa gagcaaggcc acactgactg tagacaaatc gtccagcaca     240
gcctacatgc aactcagcag cctgacatct gaggactctg gggtctatta ctgtgcaaaa     300 gggggggaact actatgatta cgactgggac tactgggggcc aaggcaccac tctcacagtc     360
tcg                                                                   363
```

<210> SEQ ID NO 38
<211> LENGTH: 351
<212> TYPE: DNA
<213> ORGANISM: Homo sapiens

<400> SEQUENCE: 38

```
cgcgcccagg tgcagctgaa ggagtcagga cctggcctgg tggcgccctc acagagcctg      60
tccatcactt gcactgtctc tgggttttca ttaaccatct atggtgtaca ctgggttcgc     120
cagcctccag gaaagggtct ggagtggctg ggagtaatat gggctggtgg aaacacaaat     180
tataattcgg ctctcatgtc cagactgagc atcagcaaag acaactccaa gagtcaagtt     240
ttcttaaaaa tgaacagtct gcaaactgat gacacagcca tgtacttctg tgccagaggc     300
tatggctaca atttagacta ttggggccaa ggcaccactc tcacagtctc g              351
```

<210> SEQ ID NO 39
<211> LENGTH: 357
<212> TYPE: DNA
<213> ORGANISM: Homo sapiens

<400> SEQUENCE: 39

```
cgcgcccagg tgcagctgaa ggagtcagga cctggcctgg tggcgccctc acagagcctg      60
tccatcacat gcaccgtctc aggattctca ttaaccggcc atggtgtaaa ctgggttcgc     120
cagcctccag gaaagggtct ggagtggctg ggaatgatat ggggtgatgg aagcacggac     180
tataattcaa ctctcaaatc cagactgagt atcagcaagg caactccaa gagccaagtt      240 ttcttaaaaa tgaacagtct gcagactgat gacaccgcca ggtactactg tgccagaggc     300
tacggctacc tttactactt tgactactgg ggccaaggca ccactctcac agtctcg        357
```

<210> SEQ ID NO 40
<211> LENGTH: 124

<212> TYPE: PRT
<213> ORGANISM: Homo sapiens

<400> SEQUENCE: 40

Arg Ala Glu Val Gln Leu Gln Gln Pro Gly Ser Glu Leu Val Arg Pro
1               5                   10                  15

Gly Ala Ser Val Lys Leu Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Asn Ile Tyr Pro Gly Ser Arg Ser Thr Asn Tyr Asp Glu
    50                  55                  60

Lys Phe Lys Ser Lys Ala Thr Leu Thr Val Asp Thr Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Thr Arg Asn Gly Asp Tyr Val Ser Gly Asp Ala Met
            100                 105                 110

Asp Tyr Trp Gly Gln Gly Thr Ser Val Thr Val Ser
        115                 120

<210> SEQ ID NO 41
<211> LENGTH: 120
<212> TYPE: PRT
<213> ORGANISM: Homo sapiens

<400> SEQUENCE: 41

Arg Ala Gln Val Gln Leu Gln Pro Gly Ala Glu Leu Val Glu Pro
1               5                   10                  15

Gly Gly Ser Val Lys Leu Ser Cys Lys Ala Ser Gly Tyr Thr Phe Thr
            20                  25                  30

Ser His Trp Met His Trp Val Lys Gln Arg Pro Gly Gln Gly Leu Glu
        35                  40                  45

Trp Ile Gly Glu Ile Asn Pro Ser Ser Gly Arg Asn Asn Tyr Asn Glu
    50                  55                  60

Lys Phe Lys Ser Lys Ala Thr Leu Thr Val Asp Lys Ser Ser Ser Thr
65                  70                  75                  80

Ala Tyr Met Gln Phe Ser Ser Leu Thr Ser Glu Asp Ser Ala Val Tyr
                85                  90                  95

Tyr Cys Val Arg Tyr Tyr Gly Tyr Asp Glu Ala Met Asp Tyr Trp Gly
            100                 105                 110

Gln Gly Thr Ser Val Thr Val Ser
        115                 120

<210> SEQ ID NO 42
<211> LENGTH: 120
<212> TYPE: PRT
<213> ORGANISM: Homo sapiens

<400> SEQUENCE: 42

Arg Ala Glu Val Gln Leu Val Glu Ser Gly Gly Gly Leu Val Lys Pro
1               5                   10                  15

Gly Gly Ser Leu Lys Leu Ser Cys Ala Ala Ser Gly Phe Thr Phe Ser
            20                  25                  30

Ser Tyr Ala Leu Ser Trp Val Arg Gln Thr Pro Glu Arg Arg Leu Glu
        35                  40                  45

Trp Val Ala Ser Ile Ser Gly Val Gly Ser Thr Tyr Phe Pro Asp Ser

```
                    50                  55                  60
Val Lys Gly Arg Phe Thr Met Ser Arg Asp Asn Ala Arg Asn Ile Leu
 65                  70                  75                  80

Tyr Leu Gln Met Ser Ser Leu Arg Ser Glu Asp Thr Ala Met Tyr Tyr
                     85                  90                  95

Cys Ala Arg Gly Ser Asp Gly Tyr Phe Tyr Ala Met Asp Tyr Trp Gly
                    100                 105                 110

Gln Gly Thr Ser Val Thr Val Ser
                    115                 120

<210> SEQ ID NO 43
<211> LENGTH: 120
<212> TYPE: PRT
<213> ORGANISM: Homo sapiens

<400> SEQUENCE: 43

Arg Ala Gln Val Gln Leu Gln Gln Pro Gly Ala Glu Leu Val Lys Pro
  1               5                  10                  15

Gly Ala Ser Val Lys Leu Ser Cys Lys Ala Ser Gly Tyr Thr Phe Thr
                 20                  25                  30

Ser His Trp Met His Trp Val Gln Gln Arg Pro Gly Gln Gly Leu Glu
                 35                  40                  45

Trp Ile Gly Glu Ile His Pro Ser Asn Gly Arg Thr Asn Tyr Asn Glu
 50                  55                  60

Lys Phe Lys Asn Lys Ala Thr Leu Thr Val Asp Lys Ser Pro Ser Thr
 65                  70                  75                  80

Ala Tyr Met Gln Leu Ser Ser Leu Thr Ser Glu Asp Ser Ala Val Tyr
                     85                  90                  95

Tyr Cys Ala Arg Tyr Tyr Gly Tyr Asp Asp Ala Met Asp Tyr Trp Gly
                    100                 105                 110

Gln Gly Thr Ser Val Thr Val Ser
                    115                 120

<210> SEQ ID NO 44
<211> LENGTH: 122
<212> TYPE: PRT
<213> ORGANISM: Homo sapiens

<400> SEQUENCE: 44

Arg Ala Glu Val Gln Leu Val Glu Ser Gly Gly Gly Leu Val Lys Pro
  1               5                  10                  15

Gly Gly Ser Leu Lys Leu Ser Cys Ala Ala Ser Gly Phe Ala Phe Ser
                 20                  25                  30

Ser Tyr Asp Met Ser Trp Val Arg Gln Thr Pro Glu Lys Arg Leu Glu
                 35                  40                  45

Trp Val Ala Tyr Ile Gly Ser Gly Asp Asp Asn Thr His Tyr Pro Asp
 50                  55                  60

Ser Val Lys Gly Arg Phe Thr Ile Ser Arg His Asn Ala Lys Asn Thr
 65                  70                  75                  80

Leu Tyr Leu Gln Met Ser Ser Leu Lys Ser Glu Asp Thr Ala Met Tyr
                     85                  90                  95

Tyr Cys Ala Arg Gln Lys Tyr Gly Asn Tyr Gly Asp Thr Met Asp Tyr
                    100                 105                 110

Trp Gly Gln Gly Thr Ser Val Thr Val Ser
                    115                 120
```

-continued

```
<210> SEQ ID NO 45
<211> LENGTH: 122
<212> TYPE: PRT
<213> ORGANISM: Homo sapiens

<400> SEQUENCE: 45

Arg Ala Gln Val Gln Leu Lys Glu Ser Gly Pro Gly Leu Val Ala Pro
1               5                   10                  15

Ser Gln Ser Leu Ser Ile Thr Cys Ser Val Ser Gly Phe Ser Leu Thr
            20                  25                  30

Ile Tyr Gly Val His Trp Val Arg Gln Pro Pro Gly Lys Gly Leu Glu
        35                  40                  45

Trp Leu Gly Val Met Trp Ala Gly Gly Asn Thr Asp Tyr Asn Ser Ala
    50                  55                  60

Leu Met Ser Arg Leu Asn Ile Ser Lys Asp Asn Ser Lys Ser Gln Val
65                  70                  75                  80

Phe Leu Lys Val Asn Ser Leu Gln Thr Asp Asp Thr Ala Met Tyr Tyr
                85                  90                  95

Cys Thr Arg Asp Pro Asp Gly Tyr Tyr Val Gly Trp Phe Phe Asp Val
            100                 105                 110

Trp Gly Ala Gly Thr Thr Val Thr Val Ser
        115                 120

<210> SEQ ID NO 46
<211> LENGTH: 122
<212> TYPE: PRT
<213> ORGANISM: Homo sapiens

<400> SEQUENCE: 46

Arg Ala Glu Val Gln Leu Val Glu Ser Gly Gly Gly Leu Val Lys Pro
1               5                   10                  15

Gly Gly Ser Leu Lys Leu Ser Cys Ala Ala Ser Gly Phe Ala Tyr Ser
            20                  25                  30

Thr Tyr Asp Met Ser Trp Val Arg Gln Thr Pro Glu Lys Arg Leu Glu
        35                  40                  45

Trp Val Ala Tyr Ile Ser Ser Gly Gly Asp Ala Ala Tyr Tyr Pro Asp
    50                  55                  60

Thr Val Lys Gly Arg Phe Thr Ile Ser Arg Asp Asn Ala Lys Asn Thr
65                  70                  75                  80

Leu Tyr Leu Gln Met Ser Ser Leu Lys Ser Glu Asp Thr Ala Met Tyr
                85                  90                  95

Tyr Cys Ala Arg Ser Arg Tyr Gly Asn Tyr Gly Asp Ala Met Asp Tyr
            100                 105                 110

Trp Gly Gln Gly Thr Ser Val Thr Val Ser
        115                 120

<210> SEQ ID NO 47
<211> LENGTH: 125
<212> TYPE: PRT
<213> ORGANISM: Homo sapiens

<400> SEQUENCE: 47

Arg Ala Glu Val Gln Leu Gln Gln Ser Gly Pro Glu Leu Val Lys Pro
1               5                   10                  15

Gly Ala Ser Val Lys Ile Pro Cys Lys Thr Ser Gly Tyr Thr Phe Thr
            20                  25                  30

Asp Tyr Asn Met Ala Trp Val Lys Gln Ser His Gly Lys Ser Leu Glu
        35                  40                  45
```

```
Trp Ile Gly Asp Ile Ile Pro Asn Asn Gly Gly Ala Ile Tyr Asn Gln
        50                  55                  60

Lys Phe Lys Gly Lys Ala Thr Leu Thr Val Asp Lys Ser Ser Ser Thr
 65                  70                  75                  80

Ala Ser Met Glu Leu Arg Ser Leu Thr Ser Glu Asp Thr Ala Val Tyr
                 85                  90                  95

Phe Cys Ala Arg Lys Asn Ile Tyr Tyr Arg Tyr Asp Gly Ala Gly Ala
                100                 105                 110

Leu Asp Tyr Trp Gly Gln Gly Thr Ser Val Thr Val Ser
            115                 120                 125

<210> SEQ ID NO 48
<211> LENGTH: 117
<212> TYPE: PRT
<213> ORGANISM: Homo sapiens

<400> SEQUENCE: 48

Arg Ala Gln Val Gln Leu Lys Glu Ser Gly Pro Gly Leu Val Ala Pro
  1               5                  10                  15

Ser Gln Ser Leu Ser Ile Thr Cys Thr Val Ser Gly Phe Ser Leu Thr
                 20                  25                  30

Thr Tyr Gly Val His Trp Val Arg Gln Pro Pro Gly Lys Gly Leu Glu
             35                  40                  45

Trp Leu Gly Val Ile Trp Ala Gly Gly Ser Thr Asn Tyr Asn Ser Ala
         50                  55                  60

Leu Met Ser Arg Leu Ser Ile Lys Lys Asp Asn Ser Lys Ser Gln Val
 65                  70                  75                  80

Phe Leu Lys Met Asn Ser Leu Gln Thr Asp Asp Thr Ala Met Tyr Tyr
                 85                  90                  95

Cys Ala Arg Ala Tyr Gly Tyr Asn Phe Asp Tyr Trp Gly Gln Gly Thr
                100                 105                 110

Thr Leu Thr Val Ser
            115

<210> SEQ ID NO 49
<211> LENGTH: 124
<212> TYPE: PRT
<213> ORGANISM: Homo sapiens

<400> SEQUENCE: 49

Arg Ala Glu Val Gln Leu Val Glu Ser Gly Gly Gly Leu Val Lys Pro
  1               5                  10                  15

Gly Gly Ser Leu Lys Leu Ser Cys Ala Val Ser Gly Phe Thr Phe Ser
                 20                  25                  30

Ser Tyr Val Met Ser Trp Val Arg Gln Thr Pro Glu Lys Arg Leu Glu
             35                  40                  45

Trp Val Ala Thr Ile Thr Ser Gly Gly Arg Asn Ile Tyr Tyr Leu Asp
         50                  55                  60

Ser Val Lys Gly Arg Phe Thr Ile Ser Arg Asp Asn Ala Lys Asn Thr
 65                  70                  75                  80

Leu Tyr Leu Gln Met Ser Ser Leu Arg Ser Glu Asp Thr Ala Met Tyr
                 85                  90                  95

Tyr Cys Ala Arg His Glu Asp Tyr Arg Tyr Asp Gly Tyr Tyr Ala Met
                100                 105                 110

Asp Tyr Trp Gly Gln Gly Thr Ser Val Thr Val Ser
            115                 120
```

<210> SEQ ID NO 50
<211> LENGTH: 118
<212> TYPE: PRT
<213> ORGANISM: Homo sapiens

<400> SEQUENCE: 50

Arg Ala Glu Val Gln Leu Val Glu Ser Gly Gly Gly Leu Val Lys Pro
1               5                   10                  15

Gly Glu Ser Leu Lys Leu Ser Cys Ala Ala Ser Gly Phe Ala Phe Ser
            20                  25                  30

Tyr Ser Asp Met Ser Trp Val Arg Gln Thr Pro Glu Lys Arg Leu Glu
        35                  40                  45

Trp Val Ala Tyr Met Ser Ser Ala Gly Asp Val Thr Phe Tyr Ser Asp
    50                  55                  60

Thr Val Lys Gly Arg Phe Thr Ile Ser Arg Asp Asn Ala Lys Asn Thr
65                  70                  75                  80

Leu Tyr Leu Gln Val Ser Ser Leu Lys Ser Glu Asp Thr Ala Ile Tyr
                85                  90                  95

Tyr Cys Val Arg His Arg Asp Val Ala Met Asp Tyr Trp Gly Gln Gly
            100                 105                 110

Thr Ser Val Thr Val Ser
        115

<210> SEQ ID NO 51
<211> LENGTH: 119
<212> TYPE: PRT
<213> ORGANISM: Homo sapiens

<400> SEQUENCE: 51

Arg Ala Gln Val Gln Leu Gln Gln Pro Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser Asp Trp Met His Trp Met Lys Gln Arg Pro Gly Gln Gly Leu Glu
        35                  40                  45

Trp Ile Gly Glu Ile Asn Pro Ser Asn Gly Arg Ser Ser Tyr Asn Glu
    50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Ile Gly Gly Ile Tyr Val Glu Thr Tyr Trp Gly Gln
            100                 105                 110

Gly Thr Leu Val Thr Val Ser
        115

<210> SEQ ID NO 52
<211> LENGTH: 125
<212> TYPE: PRT
<213> ORGANISM: Homo sapiens

<400> SEQUENCE: 52

Arg Ala Glu Val Gln Leu Gln Gln Ser Gly Ala Glu Leu Val Arg Pro
1               5                   10                  15

Gly Ser Ser Val Lys Ile Ser Cys Lys Ala Ser Gly Tyr Ala Phe Ser
            20                  25                  30

Ser Tyr Trp Met Asn Trp Val Arg Gln Arg Pro Gly Gln Gly Leu Glu
            35                  40                  45

Trp Ile Gly Gln Ile Tyr Pro Gly Asp Gly Asp Thr Asn Tyr Asn Gly
        50                  55                  60

Lys Phe Lys Gly Arg Ala Thr Leu Thr Ala Asn Lys Ser Ser Ser Thr
 65                  70                  75                  80

Ala Tyr Met Gln Leu Ser Ser Leu Thr Ser Glu Asp Ser Ala Val Tyr
                85                  90                  95

Phe Cys Ala Arg Arg Ala Ser Ser Leu Tyr Asp Val Tyr Pro Tyr Tyr
            100                 105                 110

Phe Asp Tyr Trp Gly Gln Gly Thr Thr Leu Thr Val Ser
            115                 120                 125

<210> SEQ ID NO 53
<211> LENGTH: 121
<212> TYPE: PRT
<213> ORGANISM: Homo sapiens

<400> SEQUENCE: 53

Arg Ala Gln Val Gln Leu Gln Gln Pro Gly Ala Glu Leu Val Lys Pro
 1               5                  10                  15

Gly Ala Ser Met Lys Leu Ser Cys Lys Ala Ser Gly Tyr Thr Phe Thr
                20                  25                  30

Asn Tyr Trp Met His Trp Val Lys Gln Arg Pro Gly Gln Gly Leu Glu
            35                  40                  45

Trp Ile Gly Glu Ile Asn Pro Ser Asn Gly Arg Thr Asn Tyr Asn Glu
        50                  55                  60

Lys Phe Lys Ser Lys Ala Thr Leu Thr Val Asp Lys Ser Ser Ser Thr
 65                  70                  75                  80

Ala Tyr Met Gln Leu Ser Ser Leu Thr Ser Glu Asp Ser Gly Val Tyr
                85                  90                  95

Tyr Cys Ala Lys Gly Gly Asn Tyr Tyr Asp Tyr Asp Trp Asp Tyr Trp
            100                 105                 110

Gly Gln Gly Thr Thr Leu Thr Val Ser
            115                 120

<210> SEQ ID NO 54
<211> LENGTH: 117
<212> TYPE: PRT
<213> ORGANISM: Homo sapiens

<400> SEQUENCE: 54

Arg Ala Gln Val Gln Leu Lys Glu Ser Gly Pro Gly Leu Val Ala Pro
 1               5                  10                  15

Ser Gln Ser Leu Ser Ile Thr Cys Thr Val Ser Gly Phe Ser Leu Thr
                20                  25                  30

Ile Tyr Gly Val His Trp Val Arg Gln Pro Pro Gly Lys Gly Leu Glu
            35                  40                  45

Trp Leu Gly Val Ile Trp Ala Gly Gly Asn Thr Asn Tyr Asn Ser Ala
        50                  55                  60

Leu Met Ser Arg Leu Ser Ile Ser Lys Asp Asn Ser Lys Ser Gln Val
 65                  70                  75                  80

Phe Leu Lys Met Asn Ser Leu Gln Thr Asp Asp Thr Ala Met Tyr Phe
                85                  90                  95

Cys Ala Arg Gly Tyr Gly Tyr Asn Leu Asp Tyr Trp Gly Gln Gly Thr
            100                 105                 110

```
Thr Leu Thr Val Ser
        115

<210> SEQ ID NO 55
<211> LENGTH: 119
<212> TYPE: PRT
<213> ORGANISM: Homo sapiens

<400> SEQUENCE: 55

Arg Ala Gln Val Gln Leu Lys Glu Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Gly His Gly Val Asn Trp Val Arg Gln Pro Pro Gly Lys Gly Leu Glu
        35                  40                  45

Trp Leu Gly Met Ile Trp Gly Asp Gly Ser Thr Asp Tyr Asn Ser Thr
    50                  55                  60

Leu Lys Ser Arg Leu Ser Ile Ser Lys Asp Asn Ser Lys Ser Gln Val
65                  70                  75                  80

Phe Leu Lys Met Asn Ser Leu Gln Thr Asp Asp Thr Ala Arg Tyr Tyr
                85                  90                  95

Cys Ala Arg Gly Tyr Gly Tyr Leu Tyr Tyr Phe Asp Tyr Trp Gly Gln
            100                 105                 110

Gly Thr Thr Leu Thr Val Ser
        115

<210> SEQ ID NO 56
<211> LENGTH: 648
<212> TYPE: DNA
<213> ORGANISM: Homo sapiens

<400> SEQUENCE: 56
ctagccgaca ttcagatgac tcagactaca tcctccctgt ctgcctctct gggagacaga      60
gtcaccatca gttgcaggac aagtcaggac attggcaatt atttaaactg gtatcagcag     120
aaaccagatg gaactgttaa actcctgatc tactacacat caagattaca ctcaggagtc     180
ccatcaaggt tcagtggcag tgggtctgga acagattttt ctctcaccat taacaacgtg     240
gagcaagagg atgttgccac ttactttgc caacactata atacggttcc tcgacgttc      300 ggtggaggca ccaagctgga aatcaaacga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                  648

<210> SEQ ID NO 57
<211> LENGTH: 663
<212> TYPE: DNA
<213> ORGANISM: Homo sapiens

<400> SEQUENCE: 57
ctagccgaca tcgtgatgac acaagctgca ttctccaatc cagtcactct tggaacatca      60
gcttccatct cctgcaggtc tagtaagagt ctcctacata gtaatggcat cacttatttg     120
tattggtatc tgcagaagcc aggccagtct cctcagctcc tgatttatca gatgtccaac     180
```

```
cttgcctcag gagtcccaga caggttcagt agcagtgggt caggaactga tttcacactg      240
agaatcagca gagtggaggc tgaggatgtg ggtgtttatt actgtgctca aaatctagaa      300
cttccgtaca cgttcggagg ggggaccaag ctggaaataa aacgaactgt ggctgcacca      360
tctgtcttca tcttcccgcc atctgatgag cagttgaaat ctggaactgc ctctgttgtg      420
tgcctgctga ataacttcta tcccagagag gccaaagtac agtggaaggt ggataacgcc      480
ctccaatcgg gtaactccca ggagagtgtc acagagcagg acagcaagga cagcacctac      540
agcctcagca gcaccctgac gctgagcaaa gcagactacg agaaacacaa agtctacgcc      600
tgcgaagtca cccatcaggg cctgagctcg cccgtcacaa agagcttcaa caggggagag      660
tgt                                                                   663
```

<210> SEQ ID NO 58
<211> LENGTH: 660
<212> TYPE: DNA
<213> ORGANISM: Homo sapiens

<400> SEQUENCE: 58

```
ctagccgaca ttgtgctgac tcagtctcct gcttccttag ctgtatctct ggggcagagg       60
gccaccattt catgcagggc cagcaaaagt gtcagtacat ctggctatag ttttatgcac      120
tggtaccaac tgaaaccagg acagccaccc aaactcctca tctatcttgc atccaaccta      180
gaatctgggg tccctgccag gttcagtggc agtgggtctg ggacagactt caccctcaac      240
atccatcctg tggaagagga ggatgctgca acctattact gtcagcacag tagggagttt      300
ccgttaacgt tcggagggggg gaccaagctg gaaataaaac gaactgtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc      600 gaagtcaccc atcagggcct gagctcgccc gtcacaaaga gcttcaacag gggagagtgt      660
```

<210> SEQ ID NO 59
<211> LENGTH: 657
<212> TYPE: DNA
<213> ORGANISM: Homo sapiens

<400> SEQUENCE: 59

```
gatattgtga tgactcaggc tgcattctcc aatccagtca ctcttggaac atcagcttcc       60
atctcctgca ggtctagtaa gagtctccta catagtaatg gcatcactta tttgtattgg      120
tatctgcaga agccaggcca gtctcctcag ctcctgattt atcagatgtc caaccttgcc      180
tcaggagtcc cagacaggtt cagtagcagt gggtcaagaa ctgatttcac actgagaatc      240
agcagagtgg aggctgagga tgtgggtgtt tattactgtg ctcaaaatct agaacttccg      300
tacacgttcg gagggggggac caagctggaa ataaaacgaa ctgtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt        657
```

<210> SEQ ID NO 60
<211> LENGTH: 660
<212> TYPE: DNA
<213> ORGANISM: Homo sapiens

<400> SEQUENCE: 60

```
ctagccgatg ttgtgatgac tcagactcca ctctccctgc ctgtcagtct tggagatcaa      60
gcctccatct cttgcagatc tagtcagagc cttgtacaca gtaatggaaa cacctattta     120
cattggtacc tgcagaagcc aggccagtct ccaaaactcc tgatctacaa agtttccaac     180
cgattttctg gggtcccaga caggttcagt ggcagtggat cagggacaga tttcacactc     240
aagatcagca gagtggaggc tgaggatctg ggagtttatt tctgctctca agtacacat      300
gttcccacgt tcggagggggg gaccaagctg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600
gaagtcaccc atcagggcct gagctcgccc gtcacaaaga gcttcaacag gggagagtgt    660
```

<210> SEQ ID NO 61
<211> LENGTH: 648
<212> TYPE: DNA
<213> ORGANISM: Homo sapiens

<400> SEQUENCE: 61

```
ctagccgaca ttgtgatgac ccagtctcac aaattcatgt ccacatcagt gggagacagg      60
gtcagcatca cctgcaaggc cagtcaggat gtgactaatg ccgtagcctg gtatcaacaa     120
aaaccaggac aatctcctaa actactgatt tactgggcat ccatccgaca cactggagtc     180
cctgatcgct tcacaggcag tagatctggg acagattata ctctcaccat caacagtgtg     240
caggctgaag acctggccct ttattattgt cagcaacatt ataacactcc gctcacgttc     300
ggtgctggga ccaagctgga aataaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac     480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                  648
```

<210> SEQ ID NO 62
<211> LENGTH: 660
<212> TYPE: DNA
<213> ORGANISM: Homo sapiens

<400> SEQUENCE: 62

```
ctagccgatg ttgtgatgac acagactcca ctctccctgc ctgtcagtct tggagatcaa      60
gcctccatct cttgcagatc tagtcagagc cttgtacaca gtaatggtaa cacctattta     120
cattggtacc tgcagaagcc aggccagtct ccaaagctcc tgctctacaa agtttccaac     180
cgattttctg gggtcccaga caggttcagt ggcagtggat cagggacaga tttcacactc     240
aagatcagca gagtggagtc tgaggatctg ggagtttatt tctgctctca aaatacacat     300
gtgtacacgt tcggaggggg gacaaagttg gaaataaaac gaactgtggc tgcaccatct    360
```

```
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
```

<210> SEQ ID NO 63
<211> LENGTH: 645
<212> TYPE: DNA
<213> ORGANISM: Homo sapiens

<400> SEQUENCE: 63

```
ctagcccaaa ttgtgctcac acagtctcca gcaatcatgt ctgcatctcc aggggagaag     60
gtcaccatga cctgcagtgc cagctcaagt gtaagttaca tttactggta ccagcagaag    120
ccaggatcct cccccagact cctgatttat gacgcatcca acctggcttc tggagtccct    180
gttcgcttca gtggcagtgg gtctgggacc tcttactctc tcacaatcag ccgaatggag    240
gctgaagatg ctgccactta ttactgccag cagtggagca gttacccaat cacgttcggc    300
tcggggacaa agttggaaat aaaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 64
<211> LENGTH: 648
<212> TYPE: DNA
<213> ORGANISM: Homo sapiens

<400> SEQUENCE: 64

```
ctagccgata tccagatgac tcagactaca tcctccctgt ctgcctctct gggagacaga     60
gtcaccatca gttgcagtgc aagtcagggc attaccaatt atttaaactg gtatcagcag    120
aaaccagatg gaactgttaa actcctgatc tattactcat caagtttaca ctcaggagtc    180
ccatcaaggt tcagtggcag tgggtctggg acagattatt ctctcaccat cagcaacctg    240
gaacctgaag atattgccac ttactattgt cagcagtata gtgagattcc gtacacgttc    300 ggaggggggga ccaagctgga gctgaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac    480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648
```

<210> SEQ ID NO 65
<211> LENGTH: 645
<212> TYPE: DNA
<213> ORGANISM: Homo sapiens

<400> SEQUENCE: 65

```
ctagcccaaa ttgtgctgac ccagtctcca gcaatcatgt ctgcatctcc aggggagaag     60
```

```
gtcaccataa cctgcagtgc cagctcaagt gtaagttaca tgcactggtt ccagcagaag    120
ccaggcactt ctcccaaact ctggatttat agtacatcca acctggcttc tggagtccct    180
gctcgcttca gtggcagtgg atctgggacc tcttactctc tcacaatcag ccgaatggag    240
gctgaagatg ctgccactta ttactgccag caaaggagta gttacccata cacgttcgga    300
ggggggacca agctggagct gaaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacaca aaagtctacg cctgcgaagt cacccatcag    600
ggcctgagct cgcccgtcac aaagagcttc aacaggggag agtgt                    645
```

<210> SEQ ID NO 66
<211> LENGTH: 660
<212> TYPE: DNA
<213> ORGANISM: Homo sapiens

<400> SEQUENCE: 66

```
ctagccgatg ttgtgatgac ccagactcca ctctccctgc ctgtcagtct tggagatcaa     60
gcctccatct cttgcagatc tagtcagagc cttgtacaca gtaatggaaa cacctatttg    120
cattggtacc tgcagaagcc aggccagtct ccaaagctcc tgatctacaa agtttccaac    180
cgattttctg ggtcccccaga caggttcagt ggcagtggat cagggacaga tttcacactc    240
aagatcagca gagtggaggc tgaggatctg ggagtttatt tctgctctca agtacacat    300 gttccgacgt tcggtggagg caccaagctg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaagt ctacgcctgc    600
gaagtcaccc catcagggcct gagctcgccc gtcacaaaga gcttcaacag gggagagtgt    660
```

<210> SEQ ID NO 67
<211> LENGTH: 660
<212> TYPE: DNA
<213> ORGANISM: Homo sapiens

<400> SEQUENCE: 67

```
ctagccgaca ttgtgctaac acagtctcct gcttccttag ctgtatctct ggggcagagg     60
gccaccatct catgcagggc cagccaaagt gtcagtacat ctaccctatag ttatatgcac    120 tggtatcaac agaaatcagg acagccaccc aaactcctca tcaagtatgc atccaaccta    180
gagtctgggg tccctgccag gttcagtggc agtgggtctg ggacagactt caccctcaac    240
atccatcctg tggaggagga ggatactgca acatattact gtcagcacag ttgggagatt    300
ccgtggacgt tcggtggagg caccaagctg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaagt ctacgcctgc    600
```

```
gaagtcaccc atcagggcct gagctcgccc gtcacaaaga gcttcaacag gggagagtgt      660

<210> SEQ ID NO 68
<211> LENGTH: 648
<212> TYPE: DNA
<213> ORGANISM: Homo sapiens

<400> SEQUENCE: 68
ctagccgaca tccagatgac acaaactaca tcctcccctgt ctgcctctct gggagacaga     60
gtcaccatca gttgcagggc aagtcaggac attagcaatt atttaaactg gtatcagcag    120
aaaccagatg gaactgttaa agtcctgatc tactacacat caagattaca ctcaggagtc    180
ccatcaaggt tcagtggcag tgggtctgga acagattatt ctctcaccat tagcaacctg    240
gagcaagaag atattgccac ttacttttgc aacagggta atacgcttcc gtacacgttc    300 ggaggggga ccaagctgga ataaaacga actgtggctg caccatctgt cttcatcttc     360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt              648

<210> SEQ ID NO 69
<211> LENGTH: 648
<212> TYPE: DNA
<213> ORGANISM: Homo sapiens

<400> SEQUENCE: 69
ctagccgaca ttcagatgac ccagactaca tcctccctgt ctgcctctct gggagacaga     60
gtcaccatca gttgcagtgc aagtcaggac attagcaatt atttaaactg gtatcagcag    120
aaaccagatg gaactgttaa actcctgatc tatcacacat caactttaca ctcaggagtc    180
ccatcaaggt tcagtggcag tgggtctggg acagattatt ctctcaccat cagcaacctg    240
gaacctgaag atattgccac ttactattgt cagcaatata gtaagcttcc gtggacgttc    300
ggtggaggca ccaagctgga aatcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt              648

<210> SEQ ID NO 70
<211> LENGTH: 648
<212> TYPE: DNA
<213> ORGANISM: Homo sapiens

<400> SEQUENCE: 70
ctagccgaca ttcagatgac acagactact tcctccctgt ctgcctctct gggagacaga     60
gtcaccatta gttgcagtgc aagtcagggc attagtaatt atttaaactg gtatcagcag    120
aaaccagatg gaactgttaa actcctgatc tattacacat caagtttaca ctcaggagtc    180
ccatcaaggt tcagtggcag tgggtctggg acagattatt ctctcaccat cagcaacctg    240
gaacctgaag atattgccac ttactattgt cagcagtata gtaagcttcc gtacacgttc    300
```

```
ggaggggga   ccaagctgga   aatcaaacga   actgtggctg   caccatctgt   cttcatcttc      360
ccgccatctg   atgagcagtt   gaaatctgga   actgcctctg   ttgtgtgcct   gctgaataac      420
ttctatccca   gagaggccaa   agtacagtgg   aaggtggata   acgccctcca   atcgggtaac      480
tcccaggaga   gtgtcacaga   gcaggacagc   aaggacagca   cctacagcct   cagcagcacc      540
ctgacgctga   gcaaagcaga   ctacgagaaa   cacaaagtct   acgcctgcga   agtcacccat      600
cagggcctga   gctcgcccgt   cacaaagagc   ttcaacaggg   gagagtgt                     648
```

```
<210> SEQ ID NO 71
<211> LENGTH: 651
<212> TYPE: DNA
<213> ORGANISM: Homo sapiens

<400> SEQUENCE: 71
```

```
ctagccgaaa   atgtgctgac   tcagtctcca   gcaatcatgt   ctgcatctcc   aggggaaaag       60
gtcaccatga   cctgcagggc   cagctcaagt   gtaagttcca   gttacttgca   ctggtaccag      120
caaaagtcag   gtgcctcccc   caaactctgg   atttatagca   catccaactt   ggcttctgga      180
gtccctgctc   gcttcagtgg   cagtgggtct   gggacctctt   actctctcac   agtcaacagt      240
gtggagactg   aagatgctgc   cacttattac   tgccaccagt   acagtggttt   cccattcacg      300
ttcggctcgg   ggaccaagct   ggagctgaaa   cgaactgtgg   ctgcaccatc   tgtcttcatc      360
ttcccgccat   ctgatgagca   gttgaaatct   ggaactgcct   ctgttgtgtg   cctgctgaat      420
aacttctatc   ccagagaggc   caagtacag   tggaaggtg   ataacgccct   ccaatcgggt      480
aactcccagg   agagtgtcac   agagcaggac   agcaaggaca   gcacctacag   cctcagcagc      540
accctgacgc   tgagcaaagc   agactacgag   aaacacaaag   tctacgcctg   cgaagtcacc      600
catcagggcc   tgagctcgcc   cgtcacaaag   agcttcaaca   ggggagagtg   t                651
```

```
<210> SEQ ID NO 72
<211> LENGTH: 216
<212> TYPE: PRT
<213> ORGANISM: Homo sapiens

<400> SEQUENCE: 72
```

Leu Ala Asp Ile Gln Met Thr Gln Thr Thr Ser Ser Leu Ser Ala Ser
1               5                   10                  15

Leu Gly Asp Arg Val Thr Ile Ser Cys Arg Thr Ser Gln Asp Ile Gly
            20                  25                  30

Asn Tyr Leu Asn Trp Tyr Gln Gln Lys Pro Asp Gly Thr Val Lys Leu
        35                  40                  45

Leu Ile Tyr Tyr Thr Ser Arg Leu His Ser Gly Val Pro Ser Arg Phe
    50                  55                  60

Ser Gly Ser Gly Ser Gly Thr Asp Phe Ser Leu Thr Ile Asn Asn Val
65                  70                  75                  80

Glu Gln Glu Asp Val Ala Thr Tyr Phe Cys Gln His Tyr Asn Thr Val
                85                  90                  95

Pro Pro Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn

```
                145                 150                 155                 160
Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 73
<211> LENGTH: 221
<212> TYPE: PRT
<213> ORGANISM: Homo sapiens

<400> SEQUENCE: 73

Leu Ala Asp Ile Val Met Thr Gln Ala Ala Phe Ser Asn Pro Val Thr
1               5                   10                  15

Leu Gly Thr Ser Ala Ser Ile Ser Cys Arg Ser Ser Lys Ser Leu Leu
            20                  25                  30

His Ser Asn Gly Ile Thr Tyr Leu Tyr Trp Tyr Leu Gln Lys Pro Gly
        35                  40                  45

Gln Ser Pro Gln Leu Leu Ile Tyr Gln Met Ser Asn Leu Ala Ser Gly
    50                  55                  60

Val Pro Asp Arg Phe Ser Ser Gly Ser Gly Thr Asp Phe Thr Leu
65                  70                  75                  80

Arg Ile Ser Arg Val Glu Ala Glu Asp Val Gly Val Tyr Tyr Cys Ala
                85                  90                  95

Gln Asn Leu Glu Leu Pro Tyr Thr Phe Gly Gly Gly Thr Lys Leu Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 74
<211> LENGTH: 220
<212> TYPE: PRT
<213> ORGANISM: Homo sapiens

<400> SEQUENCE: 74

Leu Ala Asp Ile Val Leu Thr Gln Ser Pro Ala Ser Leu Ala Val Ser
1               5                   10                  15

Leu Gly Gln Arg Ala Thr Ile Ser Cys Arg Ala Ser Lys Ser Val Ser
            20                  25                  30

Thr Ser Gly Tyr Ser Phe Met His Trp Tyr Gln Leu Lys Pro Gly Gln
```

-continued

```
                35                  40                  45
Pro Pro Lys Leu Leu Ile Tyr Leu Ala Ser Asn Leu Glu Ser Gly Val
 50                  55                  60

Pro Ala Arg Phe Ser Gly Ser Gly Ser Gly Thr Asp Phe Thr Leu Asn
 65                  70                  75                  80

Ile His Pro Val Glu Glu Asp Ala Ala Thr Tyr Tyr Cys Gln His
                 85                  90                  95

Ser Arg Glu Phe Pro Leu Thr Phe Gly Gly Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 75
<211> LENGTH: 219
<212> TYPE: PRT
<213> ORGANISM: Homo sapiens

<400> SEQUENCE: 75

Asp Ile Val Met Thr Gln Ala Ala Phe Ser Asn Pro Val Thr Leu Gly
  1               5                  10                  15

Thr Ser Ala Ser Ile Ser Cys Arg Ser Ser Lys Ser Leu Leu His Ser
                 20                  25                  30

Asn Gly Ile Thr Tyr Leu Tyr Trp Tyr Leu Gln Lys Pro Gly Gln Ser
                 35                  40                  45

Pro Gln Leu Leu Ile Tyr Gln Met Ser Asn Leu Ala Ser Gly Val Pro
 50                  55                  60

Asp Arg Phe Ser Ser Gly Ser Arg Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

<210> SEQ ID NO 76
<211> LENGTH: 220
<212> TYPE: PRT
<213> ORGANISM: Homo sapiens

<400> SEQUENCE: 76

```
Leu Ala Asp Val Val Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
            20                  25                  30

His Ser Asn Gly Asn Thr Tyr Leu His Trp Tyr Leu Gln Lys Pro Gly
        35                  40                  45

Gln Ser Pro Lys Leu Leu Ile Tyr Lys Val Ser Asn Arg Phe Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Leu Gly Val Tyr Phe Cys Ser
                85                  90                  95

Gln Ser Thr His Val Pro Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 77
<211> LENGTH: 216
<212> TYPE: PRT
<213> ORGANISM: Homo sapiens

<400> SEQUENCE: 77

```
Leu Ala Asp Ile Val Met Thr Gln Ser His Lys Phe Met Ser Thr Ser
1               5                   10                  15

Val Gly Asp Arg Val Ser Ile Thr Cys Lys Ala Ser Gln Asp Val Thr
            20                  25                  30

Asn Ala Val Ala Trp Tyr Gln Gln Lys Pro Gly Gln Ser Pro Lys Leu
        35                  40                  45

Leu Ile Tyr Trp Ala Ser Ile Arg His Thr Gly Val Pro Asp Arg Phe
    50                  55                  60

Thr Gly Ser Arg Ser Gly Thr Asp Tyr Thr Leu Thr Ile Asn Ser Val
65                  70                  75                  80
```

```
Gln Ala Glu Asp Leu Ala Leu Tyr Tyr Cys Gln Gln His Tyr Asn Thr
                85                  90                  95

Pro Leu Thr Phe Gly Ala Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 78
<211> LENGTH: 220
<212> TYPE: PRT
<213> ORGANISM: Homo sapiens

<400> SEQUENCE: 78

Leu Ala Asp Val Val Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
            20                  25                  30

His Ser Asn Gly Asn Thr Tyr Leu His Trp Tyr Leu Gln Lys Pro Gly
        35                  40                  45

Gln Ser Pro Lys Leu Leu Leu Tyr Lys Val Ser Asn Arg Phe Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ser Glu Asp Leu Gly Val Tyr Phe Cys Ser
                85                  90                  95

Gln Asn Thr His Val Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 79
```

```
<211> LENGTH: 215
<212> TYPE: PRT
<213> ORGANISM: Homo sapiens

<400> SEQUENCE: 79

Leu Ala Gln Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
            20                  25                  30

Tyr Ile Tyr Trp Tyr Gln Gln Lys Pro Gly Ser Ser Pro Arg Leu Leu
        35                  40                  45

Ile Tyr Asp Ala Ser Asn Leu Ala Ser Gly Val Pro Val Arg Phe Ser
    50                  55                  60

Gly Ser Gly Ser Gly Thr Ser Tyr Ser Leu Thr Ile Ser Arg Met Glu
65                  70                  75                  80

Ala Glu Asp Ala Ala Thr Tyr Tyr Cys Gln Gln Trp Ser Ser Tyr Pro
                85                  90                  95

Ile Thr Phe Gly Ser Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 80
<211> LENGTH: 216
<212> TYPE: PRT
<213> ORGANISM: Homo sapiens

<400> SEQUENCE: 80

Leu Ala Asp Ile Gln Met Thr Gln Thr Thr Ser Ser Leu Ser Ala Ser
1               5                   10                  15

Leu Gly Asp Arg Val Thr Ile Ser Cys Ser Ala Ser Gln Gly Ile Thr
            20                  25                  30

Asn Tyr Leu Asn Trp Tyr Gln Gln Lys Pro Asp Gly Thr Val Lys Leu
        35                  40                  45

Leu Ile Tyr Tyr Ser Ser Ser Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Pro Glu Asp Ile Ala Thr Tyr Tyr Cys Gln Gln Tyr Ser Glu Ile
                85                  90                  95

Pro Tyr Thr Phe Gly Gly Gly Thr Lys Leu Glu Leu Lys Arg Thr Val
            100                 105                 110

Ala Ala Pro Ser Val Phe Ile Phe Pro Pro Ser Asp Glu Gln Leu Lys
        115                 120                 125
```

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 81
<211> LENGTH: 215
<212> TYPE: PRT
<213> ORGANISM: Homo sapiens

<400> SEQUENCE: 81

Leu Ala Gln Ile Val Leu Thr Gln Ser Pro Ala Ile Met Ser Ala Ser
1               5                   10                  15

Pro Gly Glu Lys Val Thr Ile Thr Cys Ser Ala Ser Ser Ser Val Ser
            20                  25                  30

Tyr Met His Trp Phe Gln Gln Lys Pro Gly Thr Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Arg Met Glu
65                  70                  75                  80

Ala Glu Asp Ala Ala Thr Tyr Tyr Cys Gln Gln Arg Ser Ser Tyr Pro
                85                  90                  95

Tyr Thr Phe Gly Gly Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 82
<211> LENGTH: 220
<212> TYPE: PRT
<213> ORGANISM: Homo sapiens

<400> SEQUENCE: 82

Leu Ala Asp Val Val Met Thr Gln Thr Pro Leu Ser Leu Pro Val Ser
1               5                   10                  15

```
Leu Gly Asp Gln Ala Ser Ile Ser Cys Arg Ser Ser Gln Ser Leu Val
         20                  25                  30

His Ser Asn Gly Asn Thr Tyr Leu His Trp Tyr Leu Gln Lys Pro Gly
         35                  40                  45

Gln Ser Pro Lys Leu Leu Ile Tyr Lys Val Ser Asn Arg Phe Ser Gly
         50                  55                  60

Val Pro Asp Arg Phe Ser Gly Ser Gly Thr Asp Phe Thr Leu
 65              70                  75                  80

Lys Ile Ser Arg Val Glu Ala Glu Asp Leu Gly Val Tyr Phe Cys Ser
                 85                  90                  95

Gln Ser Thr His Val Pro Thr Phe Gly Gly Gly Thr Lys Leu Glu Ile
             100                 105                 110

Lys Arg Thr Val Ala Ala Pro Ser Val Phe Ile Phe Pro Pro Ser Asp
             115                 120                 125

Glu Gln Leu Lys Ser Gly Thr Ala Ser Val Val Cys Leu Leu Asn Asn
             130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 83
<211> LENGTH: 220
<212> TYPE: PRT
<213> ORGANISM: Homo sapiens

<400> SEQUENCE: 83

Leu Ala Asp Ile Val Leu Thr Gln Ser Pro Ala Ser Leu Ala Val Ser
 1               5                  10                  15

Leu Gly Gln Arg Ala Thr Ile Ser Cys Arg Ala Ser Gln Ser Val Ser
             20                  25                  30

Thr Ser Thr Tyr Ser Tyr Met His Trp Tyr Gln Gln Lys Ser Gly Gln
             35                  40                  45

Pro Pro Lys Leu Leu Ile Lys Tyr Ala Ser Asn Leu Glu Ser Gly Val
 50                  55                  60

Pro Ala Arg Phe Ser Gly Ser Gly Ser Gly Thr Asp Phe Thr Leu Asn
 65              70                  75                  80

Ile His Pro Val Glu Glu Glu Asp Thr Ala Thr Tyr Tyr Cys Gln His
                 85                  90                  95

Ser Trp Glu Ile Pro Trp Thr Phe Gly Gly Gly Thr Lys Leu Glu Ile
             100                 105                 110

Lys Arg Thr Val Ala Ala Pro Ser Val Phe Ile Phe Pro Pro Ser Asp
             115                 120                 125

Glu Gln Leu Lys Ser Gly Thr Ala Ser Val Val Cys Leu Leu Asn Asn
             130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
                165                 170                 175
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 84
<211> LENGTH: 216
<212> TYPE: PRT
<213> ORGANISM: Homo sapiens

<400> SEQUENCE: 84

Leu Ala Asp Ile Gln Met Thr Gln Thr Thr Ser Ser Leu Ser Ala Ser
1               5                   10                  15

Leu Gly Asp Arg Val Thr Ile Ser Cys Arg Ala Ser Gln Asp Ile Ser
            20                  25                  30

Asn Tyr Leu Asn Trp Tyr Gln Gln Lys Pro Asp Gly Thr Val Lys Val
        35                  40                  45

Leu Ile Tyr Tyr Thr Ser Arg Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95

Pro Tyr Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 85
<211> LENGTH: 216
<212> TYPE: PRT
<213> ORGANISM: Homo sapiens

<400> SEQUENCE: 85

Leu Ala Asp Ile Gln Met Thr Gln Thr Thr Ser Ser Leu Ser Ala Ser
1               5                   10                  15

Leu Gly Asp Arg Val Thr Ile Ser Cys Ser Ala Ser Gln Asp Ile Ser
            20                  25                  30

Asn Tyr Leu Asn Trp Tyr Gln Gln Lys Pro Asp Gly Thr Val Lys Leu
        35                  40                  45

Leu Ile Tyr His Thr Ser Thr Leu His Ser Gly Val Pro Ser Arg Phe
```

```
                50                  55                  60
Ser Gly Ser Gly Ser Gly Thr Asp Tyr Ser Leu Thr Ile Ser Asn Leu
 65                  70                  75                  80

Glu Pro Glu Asp Ile Ala Thr Tyr Tyr Cys Gln Gln Tyr Ser Lys Leu
                 85                  90                  95

Pro Trp Thr Phe Gly Gly Gly Thr Lys Leu Glu Ile Lys Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
                130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
                210                 215

<210> SEQ ID NO 86
<211> LENGTH: 216
<212> TYPE: PRT
<213> ORGANISM: Homo sapiens

<400> SEQUENCE: 86

Leu Ala Asp Ile Gln Met Thr Gln Thr Thr Ser Ser Leu Ser Ala Ser
 1               5                  10                  15

Leu Gly Asp Arg Val Thr Ile Ser Cys Ser Ala Ser Gln Gly Ile Ser
                 20                  25                  30

Asn Tyr Leu Asn Trp Tyr Gln Gln Lys Pro Asp Gly Thr Val Lys Leu
                 35                  40                  45

Leu Ile Tyr Tyr Thr Ser Ser Leu His Ser Gly Val Pro Ser Arg Phe
 50                  55                  60

Ser Gly Ser Gly Ser Gly Thr Asp Tyr Ser Leu Thr Ile Ser Asn Leu
 65                  70                  75                  80

Glu Pro Glu Asp Ile Ala Thr Tyr Tyr Cys Gln Gln Tyr Ser Lys Leu
                 85                  90                  95

Pro Tyr Thr Phe Gly Gly Gly Thr Lys Leu Glu Ile Lys Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
                130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205
```

Lys Ser Phe Asn Arg Gly Glu Cys
    210                 215

<210> SEQ ID NO 87
<211> LENGTH: 217
<212> TYPE: PRT
<213> ORGANISM: Homo sapiens

<400> SEQUENCE: 87

Leu Ala Glu Asn Val Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Ser Ser Tyr Leu His Trp Tyr Gln Gln Lys Ser Gly Ala Ser Pro Lys
        35                  40                  45

Leu Trp Ile Tyr Ser Thr Ser Asn Leu Ala Ser Gly Val Pro Ala Arg
    50                  55                  60

Phe Ser Gly Ser Gly Ser Gly Thr Ser Tyr Ser Leu Thr Val Asn Ser
65                  70                  75                  80

Val Glu Thr Glu Asp Ala Ala Thr Tyr Tyr Cys His Gln Tyr Ser Gly
                85                  90                  95

Phe Pro Phe Thr Phe Gly Ser Gly Thr Lys Leu Glu Leu Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 88
<211> LENGTH: 324
<212> TYPE: DNA
<213> ORGANISM: Homo sapiens

<400> SEQUENCE: 88
ttcatcttcc cgccatctga tgagcagttg aaatctggaa ctgcctctgt tgtgtgcctg     60
ctgaataact tctatcccag agaggccaaa gtacagtgga aggtggataa cgccctccaa    120
tcgggtaact cccaggagag tgtcacagag caggacagca aggacagcac ctacagcctc    180
agcagcaccc tgacgctgag caaagcagac tacgagaaac acaaagtcta cgcctgcgaa    240
gtcacccatc agggcctgag ctcgcccgtc acaaagagct tcaacagggg agagtgttaa    300
taagcggccg ccggtggagg cggt                                          324

<210> SEQ ID NO 89
<211> LENGTH: 106
<212> TYPE: PRT
<213> ORGANISM: Homo sapiens

<400> SEQUENCE: 89

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 90
<211> LENGTH: 1602
<212> TYPE: DNA
<213> ORGANISM: Homo sapiens
<220> FEATURE:
<221> NAME/KEY: exon
<222> LOCATION: (1)..(298)
<220> FEATURE:
<221> NAME/KEY: Intron
<222> LOCATION: (299)..(689)
<220> FEATURE:
<221> NAME/KEY: exon
<222> LOCATION: (690)..(734)
<220> FEATURE:
<221> NAME/KEY: Intron
<222> LOCATION: (735)..(852)
<220> FEATURE:
<221> NAME/KEY: exon
<222> LOCATION: (853)..(1182)
<220> FEATURE:
<221> NAME/KEY: Intron
<222> LOCATION: (1183)..(1279)
<220> FEATURE:
<221> NAME/KEY: exon
<222> LOCATION: (1280)..(1602)

<400> SEQUENCE: 90

```
agt gcc tcc acc aag ggc cca tcg gtc ttc ccc ctg gca ccc tcc tcc      48
Ser Ala Ser Thr Lys Gly Pro Ser Val Phe Pro Leu Ala Pro Ser Ser
1               5                   10                  15 aag agc acc tct ggg ggc aca gcg gcc ctg ggc tgc ctg gtc aag gac      96
Lys Ser Thr Ser Gly Gly Thr Ala Ala Leu Gly Cys Leu Val Lys Asp
            20                  25                  30 tac ttc ccc gaa ccg gtg acg gtg tcg tgg aac tca ggc gcc ctg acc     144
Tyr Phe Pro Glu Pro Val Thr Val Ser Trp Asn Ser Gly Ala Leu Thr
        35                  40                  45 agc ggc gtg cac acc ttc ccg gct gtc cta cag tcc tca gga ctc tac     192
Ser Gly Val His Thr Phe Pro Ala Val Leu Gln Ser Ser Gly Leu Tyr
    50                  55                  60 tcc ctc agc agc gtg gtg acc gtg ccc tcc agc agc ttg ggc acc cag     240
Ser Leu Ser Ser Val Val Thr Val Pro Ser Ser Ser Leu Gly Thr Gln
65                  70                  75                  80 acc tac atc tgc aac gtg aat cac aag ccc agc aac acc aag gtg gac     288
Thr Tyr Ile Cys Asn Val Asn His Lys Pro Ser Asn Thr Lys Val Asp
                85                  90                  95 aag aga gtt ggtgagaggcc agcacaggga gggagggtgt ctgctggaag            338
Lys Arg Val
```

-continued

```
ccaggctcag cgctcctgcc tggacgcatc ccggctatgc agtcccagtc cagggcagca      398
aggcaggccc cgtctgcctc ttcacccgga ggcctctgcc cgccccactc atgctcaggg      458
agagggtctt ctggcttttt ccccaggctc tgggcaggca caggctaggt gcccctaacc      518
caggccctgc acacaaaggg gcaggtgctg ggctcagacc tgccaagagc catatccggg      578
aggaccctgc ccctgaccta agccaccccc aaaggccaaa ctctccactc cctcagctcg      638
gacaccttct ctcctcccag attccagtaa ctcccaatct tctctctgca  gag ccc        694
                                                        Glu Pro aaa tct tgt gac aaa act cac aca tgc cca ccg tgc cca ggtaagccagc        744
Lys Ser Cys Asp Lys Thr His Thr Cys Pro Pro Cys Pro
        105                 110 ccaggcctcg ccctccagct caaggcggga caggtgccct agagtagcct gcatccaggg      804
acaggcccca gccgggtgct gacacgtcca cctccatctc ttcctca  gca cct gaa       860
                                                    Ala Pro Glu ctc ctg ggg gga ccg tca gtc ttc ctc ttc ccc cca aaa ccc aag gac        908
Leu Leu Gly Gly Pro Ser Val Phe Leu Phe Pro Pro Lys Pro Lys Asp
        120                 125                 130 acc ctc atg atc tcc cgg acc cct gag gtc aca tgc gtg gtg gtg gac        956
Thr Leu Met Ile Ser Arg Thr Pro Glu Val Thr Cys Val Val Val Asp
    135                 140                 145 gtg agc cac gaa gac cct gag gtc aag ttc aac tgg tac gtg gac ggc       1004
Val Ser His Glu Asp Pro Glu Val Lys Phe Asn Trp Tyr Val Asp Gly
150                 155                 160                 165 gtg gag gtg cat aat gcc aag aca aag ccg cgg gag gag cag tac aac       1052
Val Glu Val His Asn Ala Lys Thr Lys Pro Arg Glu Glu Gln Tyr Asn
            170                 175                 180 agc acg tac cgt gtg gtc agc gtc ctc acc gtc ctg cac cag gac tgg       1100
Ser Thr Tyr Arg Val Val Ser Val Leu Thr Val Leu His Gln Asp Trp
        185                 190                 195 ctg aat ggc aag gag tac aag tgc aag gtc tcc aac aaa gcc ctc cca       1148
Leu Asn Gly Lys Glu Tyr Lys Cys Lys Val Ser Asn Lys Ala Leu Pro
    200                 205                 210 gcc ccc atc gag aaa acc atc tcc aaa gcc aaa ggtgggacccg                1192
Ala Pro Ile Glu Lys Thr Ile Ser Lys Ala Lys
215                 220 tggggtgcga gggccacatg gacagaggcc ggctcggccc accctctgcc ctgagagtga     1252
ccgctgtacc aacctctgtc cctaca ggg cag ccc cga gaa cca cag gtg tac      1305
                              Gly Gln Pro Arg Glu Pro Gln Val Tyr
                                      225                 230 acc ctg ccc cca tcc cgg gag gag atg acc aag aac cag gtc agc ctg       1353
Thr Leu Pro Pro Ser Arg Glu Glu Met Thr Lys Asn Gln Val Ser Leu
    235                 240                 245 acc tgc ctg gtc aaa ggc ttc tat ccc agc gac atc gcc gtg gag tgg       1401
Thr Cys Leu Val Lys Gly Phe Tyr Pro Ser Asp Ile Ala Val Glu Trp
250                 255                 260                 265 gag agc aat ggg cag ccg gag aac aac tac aag acc acg cct ccc gtg       1449
Glu Ser Asn Gly Gln Pro Glu Asn Asn Tyr Lys Thr Thr Pro Pro Val
            270                 275                 280 ctg gac tcc gac ggc tcc ttc ttc ctc tat agc aag ctc acc gtg gac       1497
Leu Asp Ser Asp Gly Ser Phe Phe Leu Tyr Ser Lys Leu Thr Val Asp
        285                 290                 295 aag agc agg tgg cag cag ggg aac gtc ttc tca tgc tcc gtg atg cat       1545
Lys Ser Arg Trp Gln Gln Gly Asn Val Phe Ser Cys Ser Val Met His
    300                 305                 310 gag gct ctg cac aac cac tac acg cag aag agc ctc tcc ctg tcc ccg       1593
Glu Ala Leu His Asn His Tyr Thr Gln Lys Ser Leu Ser Leu Ser Pro
315                 320                 325
```

```
ggt aaa tga                                                        1602
Gly Lys
330

<210> SEQ ID NO 91
<211> LENGTH: 331
<212> TYPE: PRT
<213> ORGANISM: Homo sapiens

<400> SEQUENCE: 91

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Arg Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 92
<211> LENGTH: 751
```

```
<212> TYPE: DNA
<213> ORGANISM: artificial
<220> FEATURE:
<223> OTHER INFORMATION: Synthetic construct

<400> SEQUENCE: 92
ggcgcgccga ggtccaactg cagcaacctg gtctgagct  ggtgaggcct ggagcttcag      60
tgaagctgtc ctgcaaggct tctggctaca cattcaccag ctactggatg cactgggtga     120
agcagaggcc tggacaaggc cttgagtgga ttgggaatat ttatcctggt agtcgtagta     180
ctaactacga tgagaagttc aagagcaagg ccacactgac tgtagacaca tcctccagca     240
cagcctacat gcagctcagc agcctgacat ctgaggactc tgcggtctat tactgtacaa     300
gaaatgggga ttactacgtt agtagcgggg atgctatgga ctactgggt  caaggaacct     360
cagtcaccgt ctcgtcagcc agcaccaagg cccccaggt  ccaactgcag cagcctgggg     420
ctgaactggt ggagcctggg ggttcagtga agctgtcctg caaggcttct ggctacacct     480
tcaccagtca ctggatgcac tgggtgaagc agaggcctgg acaaggcctt gagtggatag     540
gtgagattaa tcctagcagc ggtcgtaata actacaatga agttcaag   agtaaggcca     600
cactgactgt agacaaatcc tccagcacag cctacatgca attcagcagc ctgacatctg     660
aggactctgc ggtctattat tgtgtaagat actatggtta cgacgaagct atggactact     720
ggggtcaagg aacctcagtc accgtctcga g                                    751

<210> SEQ ID NO 93
<211> LENGTH: 1017
<212> TYPE: DNA
<213> ORGANISM: artificial
<220> FEATURE:
<223> OTHER INFORMATION: Synthetic construct

<400> SEQUENCE: 93
gctagccgac attcagatga ctcagactac atcctccctg tctgcctctc tgggagacag      60
agtcaccatc agttgcagga caagtcagga cattggcaat tatttaaact ggtatcagca     120
gaaaccagat ggaactgtta aactcctgat ctactacaca tcaagattac actcaggagt     180
cccatcaagg ttcagtggca gtgggtctgg aacagatttt tctctcacca ttaacaacgt     240
ggagcaagag gatgttgcca cttactttg  ccaacactat aatacggttc ctccgacgtt     300
cggtggaggc accaagctgg aaatcaaacg aactgtggct gcaccagaca tcgtgatgac     360
acaagctgca ttctccaatc cagtcactct tggaacatca gcttccatct cctgcaggtc     420
tagtaagagt ctcctacata gtaatggcat cacttatttg tattggtatc tgcagaagcc     480
aggccagtct cctcagctcc tgatttatca gatgtccaac cttgcctcag agtcccaga     540
caggttcagt agcagtgggt caggaactga tttcacactg agaatcagca gagtggaggc     600
tgaggatgtg ggtgtttatt actgtgctca aaatctagaa cttccgtaca cgttcggagg     660
ggggaccaag ctggaaataa aacgaactgt ggctgcacca tctgtcttca tcttcccgcc     720
atctgatgag cagttgaaat ctggaactgc ctctgttgtg tgcctgctga ataacttcta     780
tcccagagag gccaaagtac agtggaaggt ggataacgcc ctccaatcgg gtaactccca     840
ggagagtgtc acagagcagg acagcaagga cagcacctac agcctcagca gcaccctgac     900
gctgagcaaa gcagactacg agaaacacaa agtctacgcc tgcgaagtca cccatcaggg     960
cctgagctcg cccgtcacaa agagcttcaa caggggagag tgttaataag cggccgc      1017

<210> SEQ ID NO 94
```

```
<211> LENGTH: 751
<212> TYPE: DNA
<213> ORGANISM: artificial
<220> FEATURE:
<223> OTHER INFORMATION: Synthetic construct

<400> SEQUENCE: 94
ggcgcgccca ggtccaactg cagcagcctg gggctgaact ggtggagcct gggggttcag      60
tgaagctgtc ctgcaaggct tctggctaca ccttcaccag tcactggatg cactgggtga     120
agcagaggcc tggacaaggc cttgagtgga taggtgagat taatcctagc agcggtcgta     180
ataactacaa tgagaagttc aagagtaagg ccacactgac tgtagacaaa tcctccagca     240
cagcctacat gcaattcagc agcctgacat ctgaggactc tgcggtctat tattgtgtaa     300
gatactatgg ttacgacgaa gctatggact actggggtca aggaacctca gtcaccgtct     360
cgtcagccag caccaagggc cccgaggtcc aactgcagca acctgggtct gagctggtga     420
ggcctggagc ttcagtgaag ctgtcctgca aggcttctgg ctacacattc accagctact     480
ggatgcactg ggtgaagcag aggcctggac aaggccttga gtggattggg aatatttatc     540
ctggtagtcg tagtactaac tacgatgaga agttcaagag caaggccaca ctgactgtag     600
acacatcctc cagcacagcc tacatgcagc tcagcagcct gacatctgag gactctgcgg     660
tctattactg tacaagaaat ggggattact acgttagtag cggggatgct atggactact     720
ggggtcaagg aacctcagtc accgtctcga g                                    751

<210> SEQ ID NO 95
<211> LENGTH: 1017
<212> TYPE: DNA
<213> ORGANISM: artificial
<220> FEATURE:
<223> OTHER INFORMATION: Synthetic construct

<400> SEQUENCE: 95
gctagccgac atcgtgatga cacaagctgc attctccaat ccagtcactc ttggaacatc      60
agcttccatc tcctgcaggt ctagtaagag tctcctacat agtaatggca tcacttattt     120
gtattggtat ctgcagaagc caggccagtc tcctcagctc ctgatttatc agatgtccaa     180
ccttgcctca ggagtcccag acaggttcag tagcagtggg tcaggaactg atttcacact     240
gagaatcagc agagtggagg ctgaggatgt gggtgtttat tactgtgctc aaaatctaga     300
acttccgtac acgttcggag gggggaccaa gctggaaata aaacgaactg tggctgcacc     360
agacattcag atgactcaga ctacatcctc cctgtctgcc tctctgggag acagagtcac     420
catcagttgc aggacaagtc aggacattgg caattattta aactggtatc agcagaaacc     480
agatggaact gttaaactcc tgatctacta cacatcaaga ttacactcag gagtcccatc     540
aaggttcagt ggcagtgggt ctggaacaga ttttctctc accattaaca cgtggagca     600
agaggatgtt gccacttact tttgccaaca ctataatacg gttcctccga cgttcggtgg     660
aggcaccaag ctggaaatca aacgaactgt ggctgcacca tctgtcttca tcttcccgcc     720
atctgatgag cagttgaaat ctggaactgc ctctgttgtg tgcctgctga ataacttcta     780
tcccagagag gccaaagtac agtggaaggt ggataacgcc ctccaatcgg gtaactccca     840
ggagagtgtc acagagcagg acagcaagga cagcacctac agcctcagca gcaccctgac     900
gctgagcaaa gcagactacg agaaacacaa agtctacgcc tgcgaagtca cccatcaggg     960
cctgagctcg cccgtcacaa agagcttcaa caggggagag tgttaataag cggccgc      1017
```

<210> SEQ ID NO 96
<211> LENGTH: 249
<212> TYPE: PRT
<213> ORGANISM: artificial
<220> FEATURE:
<223> OTHER INFORMATION: Synthetic construct

<400> SEQUENCE: 96

```
Arg Ala Glu Val Gln Leu Gln Gln Pro Gly Ser Glu Leu Val Arg Pro
 1               5                  10                  15

Gly Ala Ser Val Lys Leu Ser Cys Lys Ala Ser Gly Tyr Thr Phe Thr
                20                  25                  30

Ser Tyr Trp Met His Trp Val Lys Gln Arg Pro Gly Gln Gly Leu Glu
            35                  40                  45

Trp Ile Gly Asn Ile Tyr Pro Gly Ser Arg Ser Thr Asn Tyr Asp Glu
 50                  55                  60

Lys Phe Lys Ser Lys Ala Thr Leu Thr Val Asp Thr Ser Ser Ser Thr
 65                  70                  75                  80

Ala Tyr Met Gln Leu Ser Ser Leu Thr Ser Glu Asp Ser Ala Val Tyr
                85                  90                  95

Tyr Cys Thr Arg Asn Gly Asp Tyr Tyr Val Ser Gly Asp Ala Met
            100                 105                 110

Asp Tyr Trp Gly Gln Gly Thr Ser Val Thr Val Ser Ser Ala Ser Thr
        115                 120                 125

Lys Gly Pro Gln Val Gln Leu Gln Gln Pro Gly Ala Glu Leu Val Glu
130                 135                 140

Pro Gly Gly Ser Val Lys Leu Ser Cys Lys Ala Ser Gly Tyr Thr Phe
145                 150                 155                 160

Thr Ser His Trp Met His Trp Val Lys Gln Arg Pro Gly Gln Gly Leu
                165                 170                 175

Glu Trp Ile Gly Glu Ile Asn Pro Ser Ser Gly Arg Asn Asn Tyr Asn
            180                 185                 190

Glu Lys Phe Lys Ser Lys Ala Thr Leu Thr Val Asp Lys Ser Ser Ser
        195                 200                 205

Thr Ala Tyr Met Gln Phe Ser Leu Thr Ser Glu Asp Ser Ala Val
    210                 215                 220

Tyr Tyr Cys Val Arg Tyr Tyr Gly Tyr Asp Glu Ala Met Asp Tyr Trp
225                 230                 235                 240

Gly Gln Gly Thr Ser Val Thr Val Ser
                245
```

<210> SEQ ID NO 97
<211> LENGTH: 334
<212> TYPE: PRT
<213> ORGANISM: artificial
<220> FEATURE:
<223> OTHER INFORMATION: Synthetic construct

<400> SEQUENCE: 97

```
Leu Ala Asp Ile Gln Met Thr Gln Thr Thr Ser Ser Leu Ser Ala Ser
 1               5                  10                  15

Leu Gly Asp Arg Val Thr Ile Ser Cys Arg Thr Ser Gln Asp Ile Gly
                20                  25                  30

Asn Tyr Leu Asn Trp Tyr Gln Gln Lys Pro Asp Gly Thr Val Lys Leu
            35                  40                  45

Leu Ile Tyr Tyr Thr Ser Arg Leu His Ser Gly Val Pro Ser Arg Phe
 50                  55                  60
```

```
Ser Gly Ser Gly Ser Gly Thr Asp Phe Ser Leu Thr Ile Asn Asn Val
 65                  70                  75                  80

Glu Gln Glu Asp Val Ala Thr Tyr Phe Cys Gln His Tyr Asn Thr Val
             85                  90                  95

Pro Pro Thr Phe Gly Gly Gly Thr Lys Leu Glu Ile Lys Arg Thr Val
            100                 105                 110

Ala Ala Pro Asp Ile Val Met Thr Gln Ala Ala Phe Ser Asn Pro Val
            115                 120                 125

Thr Leu Gly Thr Ser Ala Ser Ile Ser Cys Arg Ser Ser Lys Ser Leu
        130                 135                 140

Leu His Ser Asn Gly Ile Thr Tyr Leu Tyr Trp Tyr Leu Gln Lys Pro
145                 150                 155                 160

Gly Gln Ser Pro Gln Leu Leu Ile Tyr Gln Met Ser Asn Leu Ala Ser
                165                 170                 175

Gly Val Pro Asp Arg Phe Ser Ser Gly Ser Gly Thr Asp Phe Thr
            180                 185                 190

Leu Arg Ile Ser Arg Val Glu Ala Glu Asp Val Gly Val Tyr Tyr Cys
            195                 200                 205

Ala Gln Asn Leu Glu Leu Pro Tyr Thr Phe Gly Gly Gly Thr Lys Leu
        210                 215                 220

Glu Ile Lys Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
    290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330

<210> SEQ ID NO 98
<211> LENGTH: 249
<212> TYPE: PRT
<213> ORGANISM: artificial
<220> FEATURE:
<223> OTHER INFORMATION: Synthetic construct

<400> SEQUENCE: 98

Arg Ala Gln Val Gln Leu Gln Gln Pro Gly Ala Glu Leu Val Glu Pro
1               5                   10                  15

Gly Gly Ser Val Lys Leu Ser Cys Lys Ala Ser Gly Tyr Thr Phe Thr
            20                  25                  30

Ser His Trp Met His Trp Val Lys Gln Arg Pro Gly Gln Gly Leu Glu
        35                  40                  45

Trp Ile Gly Glu Ile Asn Pro Ser Gly Arg Asn Asn Tyr Asn Glu
    50                  55                  60

Lys Phe Lys Ser Lys Ala Thr Leu Thr Val Asp Lys Ser Ser Ser Thr
65                  70                  75                  80

Ala Tyr Met Gln Phe Ser Ser Leu Thr Ser Glu Asp Ser Ala Val Tyr
            85                  90                  95
```

```
Tyr Cys Val Arg Tyr Tyr Gly Tyr Asp Glu Ala Met Asp Tyr Trp Gly
                100                 105                 110

Gln Gly Thr Ser Val Thr Val Ser Ser Ala Ser Thr Lys Gly Pro Glu
            115                 120                 125

Val Gln Leu Gln Gln Pro Gly Ser Glu Leu Val Arg Pro Gly Ala Ser
    130                 135                 140

Val Lys Leu Ser Cys Lys Ala Ser Gly Tyr Thr Phe Thr Ser Tyr Trp
145                 150                 155                 160

Met His Trp Val Lys Gln Arg Pro Gly Gln Gly Leu Glu Trp Ile Gly
                165                 170                 175

Asn Ile Tyr Pro Gly Ser Arg Ser Thr Asn Tyr Asp Glu Lys Phe Lys
            180                 185                 190

Ser Lys Ala Thr Leu Thr Val Asp Thr Ser Ser Ser Thr Ala Tyr Met
        195                 200                 205

Gln Leu Ser Ser Leu Thr Ser Glu Asp Ser Ala Val Tyr Tyr Cys Thr
    210                 215                 220

Arg Asn Gly Asp Tyr Tyr Val Ser Ser Gly Asp Ala Met Asp Tyr Trp
225                 230                 235                 240

Gly Gln Gly Thr Ser Val Thr Val Ser
                245

<210> SEQ ID NO 99
<211> LENGTH: 334
<212> TYPE: PRT
<213> ORGANISM: artificial
<220> FEATURE:
<223> OTHER INFORMATION: Synthetic construct

<400> SEQUENCE: 99

Leu Ala Asp Ile Val Met Thr Gln Ala Ala Phe Ser Asn Pro Val Thr
1               5                   10                  15

Leu Gly Thr Ser Ala Ser Ile Ser Cys Arg Ser Ser Lys Ser Leu Leu
            20                  25                  30

His Ser Asn Gly Ile Thr Tyr Leu Tyr Trp Tyr Leu Gln Lys Pro Gly
        35                  40                  45

Gln Ser Pro Gln Leu Leu Ile Tyr Gln Met Ser Asn Leu Ala Ser Gly
    50                  55                  60

Val Pro Asp Arg Phe Ser Ser Gly Ser Gly Thr Asp Phe Thr Leu
65                  70                  75                  80

Arg Ile Ser Arg Val Glu Ala Glu Asp Val Gly Val Tyr Tyr Cys Ala
                85                  90                  95

Gln Asn Leu Glu Leu Pro Tyr Thr Phe Gly Gly Gly Thr Lys Leu Glu
            100                 105                 110

Ile Lys Arg Thr Val Ala Ala Pro Asp Ile Gln Met Thr Gln Thr Thr
        115                 120                 125

Ser Ser Leu Ser Ala Ser Leu Gly Asp Arg Val Thr Ile Ser Cys Arg
    130                 135                 140

Thr Ser Gln Asp Ile Gly Asn Tyr Leu Asn Trp Tyr Gln Gln Lys Pro
145                 150                 155                 160

Asp Gly Thr Val Lys Leu Leu Ile Tyr Tyr Thr Ser Arg Leu His Ser
                165                 170                 175

Gly Val Pro Ser Arg Phe Ser Gly Ser Gly Ser Gly Thr Asp Phe Ser
            180                 185                 190

Leu Thr Ile Asn Asn Val Glu Gln Glu Asp Val Ala Thr Tyr Phe Cys
        195                 200                 205
```

```
Gln His Tyr Asn Thr Val Pro Pro Thr Phe Gly Gly Thr Lys Leu
    210                 215                 220
Glu Ile Lys Arg Thr Val Ala Ala Pro Ser Val Phe Ile Phe Pro Pro
225                 230                 235                 240
Ser Asp Glu Gln Leu Lys Ser Gly Thr Ala Ser Val Val Cys Leu Leu
                245                 250                 255
Asn Asn Phe Tyr Pro Arg Glu Ala Lys Val Gln Trp Lys Val Asp Asn
                260                 265                 270
Ala Leu Gln Ser Gly Asn Ser Gln Glu Ser Val Thr Glu Gln Asp Ser
            275                 280                 285
Lys Asp Ser Thr Tyr Ser Leu Ser Ser Thr Leu Thr Leu Ser Lys Ala
    290                 295                 300
Asp Tyr Glu Lys His Lys Val Tyr Ala Cys Glu Val Thr His Gln Gly
305                 310                 315                 320
Leu Ser Ser Pro Val Thr Lys Ser Phe Asn Arg Gly Glu Cys
                325                 330

<210> SEQ ID NO 100
<211> LENGTH: 1863
<212> TYPE: DNA
<213> ORGANISM: Macaca fascicularis

<400> SEQUENCE: 100
ctggaggaaa agaaagtttg ccaaggcacg agtaacaaac tcacgcagtt gggcactttt      60
gaagatcatt ttctcagcct ccagaggatg ttcaataact gtgaggtggt ccttgggaat    120
ttggaaatta cctacgtgca gaggaattat gatctttcct tcttaaagac catccaggag    180
gtggctggtt atgtcctcat cgccctcaac acagtggagc ggattccttt ggaaaacctg    240
cagatcatca gaggaaacat gtactatgaa aattcctatg ccttagcagt cttatctaac    300
tatgatgcaa ataaaaccgg actgaaggag ctgcccatga aaacttaca ggaaatcctg    360
catggcgccg tgcggttcag caacaaccct gccctgtgca acgtggagag catccagtgg    420
cgggacatag tcagcagcga gtttctcagc aacatgtcga tggacttcca gaaccacctg    480
ggcagctgcc aaaagtgtga tccaagctgt cccaatggga gctgctgggg tgcaggagag    540
gagaactgcc agaaactgac caaaatcatc tgtgcccagc agtgctccgg cgcgctgccg    600
ggcaagtccc ccagtgactg ctgccacaac cagtgtgccg cgggctgcac gggcccccgg    660
gagagcgact gcctggtctg ccgcaaattc cgagacgaag ccacgtgcaa ggacacctgc    720
cccccactca tgctctacaa ccccaccaca taccagatgg atgtgaaccc cgagggcaaa    780
tacagctttg gtgccacctg cgtgaagaag tgtccccgta attatgtggt gacagatcac    840
ggctcgtgcg tccgagcctg cggggccgac agctatgaga tggaggaaga cggcgtccgc    900
aagtgtaaga gtgcgaaggg ccttgccgc aaagtgtgta atggaatagg tattggtgaa    960
tttaaagaca cactctccat aaatgctaca aatattaaac acttcaaaaa ctgcacctcc   1020
atcagtggcg atctccacat cctgccggtg gcatttaggg gtgactcctt cacacacact   1080
ccgcctctgg atccacagga actggatatt ctgaaaaccg taaggaaat cacagggttt   1140
ttgctgattc aggcttggcc tgaaaacagg acggacctcc atgcttttga aacctagaa   1200
atcatacgtg gcaggaccaa gcaacacggt cagttttctc ttgcggtcgt cagcctgaac   1260
ataacatcct tgggattacg ctccctcaag gagataagcg atggagatgt gataatttca   1320
ggaaacaaaa atttgtgcta tgcaaataca ataaactgga aaaaactgtt tgggacctcc   1380
agtcagaaaa ccaaaattat aagcaacaga ggtgaaaaca gctgcaaggc cacgggccag   1440
```

-continued

```
gtctgccatg ccttgtgctc ccccgagggc tgctggggcc cggagcccag ggactgcgtc    1500
tcctgccaga atgtcagccg aggcagagaa tgcgtggaca agtgcaacat cctggagggc    1560
gagccaaggg agtttgtgga aactctgag tgcatacagt gccacccaga atgcctgccc     1620
caggtcatga acatcacctg cacaggacgg ggaccagaca actgtatcca gtgtgcccac    1680
tacattgacg ccccccactg cgtcaagacc tgcccagcag gagtcatggg agaaaacaac    1740
accctggtct ggaagtacgc agacgccggc cacgtgtgcc acctgtgcca tccaaactgc    1800
acctacggat gcactgggcc aggtcttgaa ggctgtgcaa ggaacgggcc taagatccca    1860
tcc                                                                  1863
```

<210> SEQ ID NO 101
<211> LENGTH: 621
<212> TYPE: PRT
<213> ORGANISM: Macaca fascicularis

<400> SEQUENCE: 101

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Glu Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285
```

| | | | | | | | | | | | | |
|---|---|---|---|---|---|---|---|---|---|---|---|---|
|Ala|Asp|Ser|Tyr|Glu|Met|Glu|Glu|Asp|Gly|Val|Arg|Lys|Cys|Lys|Lys|
| |290| | | |295| | | |300| | | |
|Cys|Glu|Gly|Pro|Cys|Arg|Lys|Val|Cys|Asn|Gly|Ile|Gly|Ile|Gly|Glu|
|305| | | | |310| | | | |315| | | | |320|
|Phe|Lys|Asp|Thr|Leu|Ser|Ile|Asn|Ala|Thr|Asn|Ile|Lys|His|Phe|Lys|
| | | | |325| | | | |330| | | | |335| |
|Asn|Cys|Thr|Ser|Ile|Ser|Gly|Asp|Leu|His|Ile|Leu|Pro|Val|Ala|Phe|
| | | |340| | | | |345| | | | |350| | |
|Arg|Gly|Asp|Ser|Phe|Thr|His|Thr|Pro|Pro|Leu|Asp|Pro|Gln|Glu|Leu|
| | |355| | | | |360| | | | |365| | | |
|Asp|Ile|Leu|Lys|Thr|Val|Lys|Glu|Ile|Thr|Gly|Phe|Leu|Leu|Ile|Gln|
| |370| | | | |375| | | | |380| | | | |
|Ala|Trp|Pro|Glu|Asn|Arg|Thr|Asp|Leu|His|Ala|Phe|Glu|Asn|Leu|Glu|
|385| | | | |390| | | | |395| | | | |400|
|Ile|Ile|Arg|Gly|Arg|Thr|Lys|Gln|His|Gly|Gln|Phe|Ser|Leu|Ala|Val|
| | | | |405| | | | |410| | | | |415| |
|Val|Ser|Leu|Asn|Ile|Thr|Ser|Leu|Gly|Leu|Arg|Ser|Leu|Lys|Glu|Ile|
| | | |420| | | | |425| | | | |430| | |
|Ser|Asp|Gly|Asp|Val|Ile|Ile|Ser|Gly|Asn|Lys|Asn|Leu|Cys|Tyr|Ala|
| | |435| | | | |440| | | | |445| | | |
|Asn|Thr|Ile|Asn|Trp|Lys|Lys|Leu|Phe|Gly|Thr|Ser|Ser|Gln|Lys|Thr|
| |450| | | | |455| | | | |460| | | | |
|Lys|Ile|Ile|Ser|Asn|Arg|Gly|Glu|Asn|Ser|Cys|Lys|Ala|Thr|Gly|Gln|
|465| | | | |470| | | | |475| | | | |480|
|Val|Cys|His|Ala|Leu|Cys|Ser|Pro|Glu|Gly|Cys|Trp|Gly|Pro|Glu|Pro|
| | | | |485| | | | |490| | | | |495| |
|Arg|Asp|Cys|Val|Ser|Cys|Gln|Asn|Val|Ser|Arg|Gly|Arg|Glu|Cys|Val|
| | | |500| | | | |505| | | | |510| | |
|Asp|Lys|Cys|Asn|Ile|Leu|Glu|Gly|Glu|Pro|Arg|Glu|Phe|Val|Glu|Asn|
| | |515| | | | |520| | | | |525| | | |
|Ser|Glu|Cys|Ile|Gln|Cys|His|Pro|Glu|Cys|Leu|Pro|Gln|Val|Met|Asn|
| |530| | | | |535| | | | |540| | | | |
|Ile|Thr|Cys|Thr|Gly|Arg|Gly|Pro|Asp|Asn|Cys|Ile|Gln|Cys|Ala|His|
|545| | | | |550| | | | |555| | | | |560|
|Tyr|Ile|Asp|Gly|Pro|His|Cys|Val|Lys|Thr|Cys|Pro|Ala|Gly|Val|Met|
| | | | |565| | | | |570| | | | |575| |
|Gly|Glu|Asn|Asn|Thr|Leu|Val|Trp|Lys|Tyr|Ala|Asp|Ala|Gly|His|Val|
| | | |580| | | | |585| | | | |590| | |
|Cys|His|Leu|Cys|His|Pro|Asn|Cys|Thr|Tyr|Gly|Cys|Thr|Gly|Pro|Gly|
| | |595| | | | |600| | | | |605| | | |
|Leu|Glu|Gly|Cys|Ala|Arg|Asn|Gly|Pro|Lys|Ile|Pro|Ser| | | |
| |610| | | | |615| | | | |620| | | | |

<210> SEQ ID NO 102
<211> LENGTH: 3633
<212> TYPE: DNA
<213> ORGANISM: Macaca fascicularis

<400> SEQUENCE: 102

| | | | | |
|---|---|---|---|---|
|atgcgaccct|ccgggacggc|cggggccgcg|ctcctggcgc|tgctggctgc|gctttgcccc|60|
|gcgagtcggg|ctctggagga|aaagaaagtt|tgccaaggca|cgagtaacaa|actcacgcag|120|
|ttgggcactt|ttgaagatca|ttttctcagc|ctccagagga|tgttcaataa|ctgtgaggtg|180|
|gtccttggga|atttggaaat|tacctacgtg|cagaggaatt|atgatctttc|cttcttaaag|240|

```
accatccagg aggtggctgg ttatgtcctc atcgccctca acacagtgga gcggattcct      300
ttggaaaacc tgcagatcat cagaggaaac atgtactatg aaaattccta tgccttagca      360
gtcttatcta actatgatgc aaataaaacc ggactgaagg agctgcccat gagaaactta      420
caggaaatcc tgcatggcgc cgtgcggttc agcaacaacc ctgccctgtg caacgtggag      480
agcatccagt ggcgggacat agtcagcagc gagtttctca gcaacatgtc gatggacttc      540
cagaaccacc tgggcagctg ccaaaagtgt gatccaagct gtcccaatgg gagctgctgg      600
ggtgcaggag aggagaactg ccagaaactg accaaaatca tctgtgccca gcagtgctcc      660
gggcgctgcc gcggcaagtc ccccagtgac tgctgccaca accagtgtgc cgcgggctgc      720
acgggccccc gggagagcga ctgcctggtc tgccgcaaat ccgagacga agccacgtgc      780
aaggacacct gccccccact catgctctac aaccccacca cataccagat ggatgtgaac      840
cccgagggca atacagcctt tggtgccacc tgcgtgaaga gtgtccccg taattatgtg      900
gtgacagatc acggctcgtg cgtccgagcc tgcggggccg acagctatga gatggaggaa      960
gacggcgtcc gcaagtgtaa gaagtgcgaa gggccttgcc gcaaagtgtg taatggaata     1020
ggtattggtg aatttaaaga cacactctcc ataaatgcta caaatattaa acacttcaaa     1080
aactgcacct ccatcagtgg cgatctccac atcctgccgg tggcatttag gggtgactcc     1140
ttcacacaca ctccgcctct ggatccacag gaactggata ttctgaaaac cgtaaaggaa     1200
atcacagggt ttttgctgat tcaggcttgg cctgaaaaca ggacggacct ccatgctttt     1260
gagaacctag aaatcatacg tggcaggacc aagcaacacg tcagttttc tcttgcggtc     1320
gtcagcctga acataacatc cttgggatta cgctccctca aggagataag cgatggagat     1380
gtgataattt caggaaacaa aaatttgtgc tatgcaaata ataaactg gaaaaaactg     1440
tttgggacct ccagtcagaa aaccaaaatt ataagcaaca gaggtgaaaa cagctgcaag     1500
gccacgggcc aggtctgcca tgccttgtgc tcccccgagg gctgctgggg cccggagccc     1560
agggactgcg tctcctgtca gaatgtcagc cgaggcagag aatgcgtgga caagtgcaac     1620
atcctggagg gcgagccaag ggagtttgtg gagaactctg agtgcataca gtgtcaccca     1680
gaatgcctgc cccaggtcat gaacatcacc tgcacaggac ggggaccaga caactgtatc     1740
cagtgtgccc actacattga cggccccac tgcgtcaaga cctgcccagc aggagtcatg     1800
ggagaaaaca cacccctggt ctggaagtac gcagacgccg gccacgtgtg ccacctgtgc     1860
catccaaact gcacctacgg atgcactggg ccaggtcttg aaggctgtgc aaggaacggg     1920
cctaagatcc catccatcgc cactgggatg gtggggccc tcctcttgct gctggtggtg     1980
gccctgggga tcggcctctt catgcgaagg cgccacatcg ttcggaagcg cacactgcgg     2040
aggctgctga gagagggga gcttgtggag cctcttacgc ccagtggaga agctcccaac     2100
caagctctct tgaggatctt gaaggaaact gaattcaaga agatcaaagt gctgggctcc     2160
ggtgcgttcg gaactgtgta tagggactc tggatcccag aaggtgagaa agttaaaatt     2220
cccgtcgcta tcaaggaatt aagagaagca acatctccga agccaacaa ggaaatcctc     2280
gatgaagcct acgtgatggc cagcgtggac aacccccatg tgtgccgcct gctgggcatc     2340
tgcctcacct ccaccgtgca gctcattacg cagctcatgc ccttcggctg cctcctggac     2400
tacgtccggg aacacaagga caatatcggc tcccagtacc tgctcaactg gtgtgtgcag     2460
attgcaaagg gcatgaacta cttggaggac cggcgcttgg tgcaccgcga cctggcagcc     2520
aggaacgtac tggtgaaaac gccacagcat gtcaagatca cagattttgg gctggccaaa     2580
ctgctgggtg cagaagagaa agaataccat gcagaaggag gcaaagtgcc tatcaagtgg     2640
```

-continued

```
atggcgttgg aatcaatttt acaccgaatt tatacccacc agagtgatgt ctggagctac    2700
ggggtgaccg tttgggagtt gatgaccttt ggatccaagc catatgacgg aatccctgcc    2760
agcgagatct cctccatcct ggagaaagga gaacgcctcc cccagccacc catatgtacc    2820
atcgatgtct acatgatcat ggtcaagtgc tggatgatag acgcagatag tcgcccaaag    2880
ttccgtgagt tgatcattga attctccaaa atggcccgag accccagcg ctaccttgtt     2940 attcaggggg atgaaagaat gcatttgcca agccctacag actccaactt ctaccgtgcc    3000
ctgatggatg aagaagacat ggacgacgtg gtggatgccg acgagtacct catcccacag    3060
caaggcttct tcagcagccc ctccacgtca cggactcccc tcctgagctc tctgagtgca    3120
actagcaaca attccactgt ggcttgcatt gatagaaatg gctgcaaag ctgttccatc      3180 aaggaagaca gcttcttaca gcgatacagc tcagacccca caggcgcctt gactgaggac    3240
agcatagacg acaccttcct cccagtgcct gaatacataa accagtctgt tcccaaaagg    3300
cccgctggct ctgtgcagaa tcctgtctat cacaatcagc ctctgaaccc tgcgcccagc    3360
agagacccac actaccagga ccccacagc accgcagtgg gcaaccccga gtatctcaac     3420
actgtccagc ccacctgtgt caacagcaca ttcgacagcc ctgctcattg ggcccagaaa    3480
ggcagccacc aaattagcct ggacaaccct gactaccagc aggacttctt tccaaggaa     3540 gccaagccaa atggcatctt taagggctcc acagctgaaa atgcagaata cctaagggtc    3600
gcaccacaaa gcagtgaatt tattggagca tga                                3633
```

<210> SEQ ID NO 103
<211> LENGTH: 1210
<212> TYPE: PRT
<213> ORGANISM: Macaca fascicularis

<400> SEQUENCE: 103

| Met | Arg | Pro | Ser | Gly | Thr | Ala | Gly | Ala | Ala | Leu | Leu | Ala | Leu | Leu | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Glu Phe Leu Ser Asn Met
                165                 170                 175

Ser Met Asp Phe Gln Asn His Leu Gly Ser Cys Gln Lys Cys Asp Pro
            180                 185                 190

-continued

```
Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Thr Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Ser Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Gln Asn
        515                 520                 525

Val Ser Arg Gly Arg Glu Cys Val Asp Lys Cys Asn Ile Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Val Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
```

-continued

```
            610                 615                 620
Thr Tyr Gly Cys Thr Gly Pro Gly Leu Glu Gly Cys Ala Arg Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg His
                660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
                850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala  Leu Met Asp Glu Glu  Asp Met Asp
                995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035
```

```
Ser Ala Thr Ser Asn Asn Ser Thr Val Ala Cys Ile Asp Arg Asn
    1040                1045                1050

Gly Leu Gln Ser Cys Ser Ile Lys Glu Asp Ser Phe Leu Gln Arg
    1055                1060                1065

Tyr Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 104
<211> LENGTH: 122
<212> TYPE: PRT
<213> ORGANISM: artificial
<220> FEATURE:
<223> OTHER INFORMATION: Synthetic construct

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Ile Ile Tyr Pro Gly Ser Arg Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Asn Gly Asp Tyr Tyr Val Ser Ser Gly Asp Ala Met Asp Tyr
                100                 105                 110

Trp Gly Gln Gly Thr Leu Val Thr Val Ser
        115                 120

<210> SEQ ID NO 105
<211> LENGTH: 107
<212> TYPE: PRT
<213> ORGANISM: artificial
<220> FEATURE:
<223> OTHER INFORMATION: Synthetic construct
```

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ala Trp Tyr Gln Gln Lys Pro Gly Lys Val Pro Lys Leu Leu Ile
        35                  40                  45

Tyr Tyr Thr Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Tyr Asn Thr Val Pro Pro
                85                  90                  95

Thr Phe Gly Gly Gly Thr Lys Val Glu Ile Lys
            100                 105
```

<210> SEQ ID NO 106
<211> LENGTH: 118
<212> TYPE: PRT
<213> ORGANISM: artificial
<220> FEATURE:
<223> OTHER INFORMATION: Synthetic construct

<400> SEQUENCE: 106

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Met
        35                  40                  45

Gly Trp Ile Asn Pro Ser Ser Gly Arg Asn Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Tyr Tyr Gly Tyr Asp Glu Ala Met Asp Tyr Trp Gly Gln Gly
            100                 105                 110

Thr Ser Val Thr Val Ser
        115
```

<210> SEQ ID NO 107
<211> LENGTH: 112
<212> TYPE: PRT
<213> ORGANISM: artificial
<220> FEATURE:
<223> OTHER INFORMATION: Synthetic construct

<400> SEQUENCE: 107

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Asp Trp Tyr Leu Gln Lys Pro Gly Gln Ser
        35                  40                  45

Pro Gln Leu Leu Ile Tyr Gln Met Ser Asn Leu Ala Ser Gly Val Pro
50                  55                  60
```

```
Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Leu Glu Ile Lys
            100                 105                 110

<210> SEQ ID NO 108
<211> LENGTH: 621
<212> TYPE: PRT
<213> ORGANISM: Homo sapiens

<400> SEQUENCE: 108

Leu Glu Glu Lys Lys Val Cys Gln Gly Thr Ser Asn Lys Leu Thr Gln
 1               5                  10                  15

Leu Gly Thr Phe Glu Asp His Phe Leu Ser Leu Gln Arg Met Phe Asn
             20                  25                  30

Asn Cys Glu Val Val Leu Gly Asn Leu Glu Ile Thr Tyr Val Gln Arg
         35                  40                  45

Asn Tyr Asp Leu Ser Phe Leu Lys Thr Ile Gln Glu Val Ala Gly Tyr
 50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335
```

```
Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
            370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
            450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Lys Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
            530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser
            610                 615                 620

<210> SEQ ID NO 109
<211> LENGTH: 616
<212> TYPE: PRT
<213> ORGANISM: artificial
<220> FEATURE:
<223> OTHER INFORMATION: Consensus sequence

<400> SEQUENCE: 109

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80
```

```
Gln Ile Ile Arg Gly Asn Met Tyr Tyr Glu Asn Ser Tyr Ala Leu Ala
                85                  90                  95
Val Leu Ser Asn Tyr Asp Ala Asn Lys Thr Gly Leu Lys Glu Leu Pro
            100                 105                 110
Met Arg Asn Leu Gln Glu Ile Leu His Gly Ala Val Arg Phe Ser Asn
        115                 120                 125
Asn Pro Ala Leu Cys Asn Val Glu Ser Ile Gln Trp Arg Asp Ile Val
    130                 135                 140
Ser Ser Asp Phe Leu Ser Asn Met Ser Met Asp Phe Gln Asn His Leu
145                 150                 155                 160
Gly Ser Cys Gln Lys Cys Asp Pro Ser Cys Pro Asn Gly Ser Cys Trp
                165                 170                 175
Gly Ala Gly Glu Glu Asn Cys Gln Lys Leu Thr Lys Ile Ile Cys Ala
            180                 185                 190
Gln Gln Cys Ser Gly Arg Cys Arg Gly Lys Ser Pro Ser Asp Cys Cys
        195                 200                 205
His Asn Gln Cys Ala Ala Gly Cys Thr Gly Pro Arg Glu Ser Asp Cys
    210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
                245                 250                 255
Pro Glu Gly Lys Tyr Ser Phe Gly Ala Thr Cys Val Lys Lys Cys Pro
            260                 265                 270
Arg Asn Tyr Val Val Thr Asp His Gly Ser Cys Val Arg Ala Cys Gly
        275                 280                 285
Ala Asp Ser Tyr Glu Met Glu Glu Asp Gly Val Arg Lys Cys Lys Lys
    290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
            340                 345                 350
Arg Gly Asp Ser Phe Thr His Thr Pro Pro Leu Asp Pro Gln Glu Leu
        355                 360                 365
Asp Ile Leu Lys Thr Val Lys Glu Ile Thr Gly Phe Leu Leu Ile Gln
    370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
            420                 425                 430
Ser Asp Gly Asp Val Ile Ile Ser Gly Asn Lys Asn Leu Cys Tyr Ala
        435                 440                 445
Asn Thr Ile Asn Trp Lys Lys Leu Phe Gly Thr Ser Gln Lys Thr Lys
    450                 455                 460
Ile Ile Ser Asn Arg Gly Glu Asn Ser Cys Lys Ala Thr Gly Gln Val
465                 470                 475                 480
Cys His Ala Leu Cys Ser Pro Glu Gly Cys Trp Gly Pro Glu Pro Lys
                485                 490                 495
```

```
Asp Cys Val Ser Cys Asn Val Ser Arg Gly Arg Glu Cys Val Asp Lys
            500                 505                 510

Cys Asn Ile Leu Glu Gly Glu Pro Arg Glu Phe Val Glu Asn Ser Glu
        515                 520                 525

Cys Ile Gln Cys His Pro Glu Cys Leu Pro Gln Met Asn Ile Thr Cys
    530                 535                 540

Thr Gly Arg Gly Pro Asp Asn Cys Ile Gln Cys Ala His Tyr Ile Asp
545                 550                 555                 560

Gly Pro His Cys Val Lys Thr Cys Pro Ala Gly Val Met Gly Glu Asn
                565                 570                 575

Asn Thr Leu Val Trp Lys Tyr Ala Asp Ala Gly His Val Cys His Leu
            580                 585                 590

Cys His Pro Asn Cys Thr Tyr Gly Cys Thr Gly Pro Gly Leu Glu Gly
        595                 600                 605

Cys Asn Gly Pro Lys Ile Pro Ser
    610                 615

<210> SEQ ID NO 110
<211> LENGTH: 18
<212> TYPE: PRT
<213> ORGANISM: Mus musculus

<400> SEQUENCE: 110

Cys Thr Arg Asn Gly Asp Tyr Tyr Ile Ser Ser Gly Asp Ala Met Asp
1               5                   10                  15

Tyr Trp

<210> SEQ ID NO 111
<211> LENGTH: 18
<212> TYPE: PRT
<213> ORGANISM: Mus musculus

<400> SEQUENCE: 111

Cys Thr Arg Asn Gly Asp Tyr Tyr Val Ser Ser Gly Asp Ala Met Asp
1               5                   10                  15

Tyr Trp

<210> SEQ ID NO 112
<211> LENGTH: 15
<212> TYPE: PRT
<213> ORGANISM: Mus musculus

<400> SEQUENCE: 112

Cys Ala Arg Gly Ser Asp Gly Tyr Phe Tyr Ala Met Asp Tyr Trp
1               5                   10                  15

<210> SEQ ID NO 113
<211> LENGTH: 14
<212> TYPE: PRT
<213> ORGANISM: Mus musculus

<400> SEQUENCE: 113

Cys Ala Arg Tyr Tyr Gly Tyr Asp Asp Ala Met Asp Tyr Trp
1               5                   10

<210> SEQ ID NO 114
<211> LENGTH: 14
<212> TYPE: PRT

<400> SEQUENCE: 114
```

Cys Val Arg Tyr Tyr Gly Tyr Asp Glu Ala Met Asp Tyr Trp
1               5                   10

<210> SEQ ID NO 115
<211> LENGTH: 14
<212> TYPE: PRT
<213> ORGANISM: Mus musculus

<400> SEQUENCE: 115

Cys Val Arg Tyr Tyr Gly Tyr Asp Glu Val Met Asp Tyr Trp
1               5                   10

<210> SEQ ID NO 116
<211> LENGTH: 11
<212> TYPE: PRT
<213> ORGANISM: Mus musculus

<400> SEQUENCE: 116

Cys Gln His Tyr Asn Thr Val Pro Pro Thr Phe
1               5                   10

<210> SEQ ID NO 117
<211> LENGTH: 11
<212> TYPE: PRT
<213> ORGANISM: Mus musculus

<400> SEQUENCE: 117

Cys Gln Gln Phe Thr Thr Ser Pro Phe Thr Phe
1               5                   10

<210> SEQ ID NO 118
<211> LENGTH: 11
<212> TYPE: PRT
<213> ORGANISM: Mus musculus

<400> SEQUENCE: 118

Cys Gln His Tyr Asn Thr Val Pro Pro Thr Phe
1               5                   10

<210> SEQ ID NO 119
<211> LENGTH: 11
<212> TYPE: PRT
<213> ORGANISM: Mus musculus

<400> SEQUENCE: 119

Cys Gln His Ser Arg Glu Phe Pro Leu Thr Phe
1               5                   10

<210> SEQ ID NO 120
<211> LENGTH: 11
<212> TYPE: PRT
<213> ORGANISM: Mus musculus

<400> SEQUENCE: 120

Cys Ala Gln Asn Leu Glu Leu Pro Tyr Thr Phe
1               5                   10

<210> SEQ ID NO 121
<211> LENGTH: 35
<212> TYPE: DNA
<213> ORGANISM: artificial
<220> FEATURE:
<223> OTHER INFORMATION: PCR primer

<400> SEQUENCE: 121
ggaggcgctc gagacggtga ctgaggttcc ttgac                                    35

<210> SEQ ID NO 122
<211> LENGTH: 52
<212> TYPE: DNA
<213> ORGANISM: artificial
<220> FEATURE:
<223> OTHER INFORMATION: PCR primer

<400> SEQUENCE: 122
ccagccgggg cgcgccgagg tccaactgca gcaacctggg tctgagctgg tg               52

<210> SEQ ID NO 123
<211> LENGTH: 49
<212> TYPE: DNA
<213> ORGANISM: artificial
<220> FEATURE:
<223> OTHER INFORMATION: PCR primer

<400> SEQUENCE: 123
ccagccgggg cgcgcccagg tccaactgca gcagcctggg gctgaactg                   49

<210> SEQ ID NO 124
<211> LENGTH: 50
<212> TYPE: DNA
<213> ORGANISM: artificial
<220> FEATURE:
<223> OTHER INFORMATION: PCR primer

<400> SEQUENCE: 124
catgggaata gctagccgac attcagatga ctcagactac atcctccctg                  50

<210> SEQ ID NO 125
<211> LENGTH: 51
<212> TYPE: DNA
<213> ORGANISM: artificial
<220> FEATURE:
<223> OTHER INFORMATION: PCR primer

<400> SEQUENCE: 125
catgggaata gctagccgac atcgtgatga cacaagctgc attctccaat c                51

<210> SEQ ID NO 126
<211> LENGTH: 43
<212> TYPE: DNA
<213> ORGANISM: artificial
<220> FEATURE:
<223> OTHER INFORMATION: PCR primer

<400> SEQUENCE: 126
accgcctcca ccggcggccg cttattaaca ctctcccctg ttg                         43

<210> SEQ ID NO 127
<211> LENGTH: 44
<212> TYPE: DNA
<213> ORGANISM: artificial
<220> FEATURE:
<223> OTHER INFORMATION: PCR primer

<400> SEQUENCE: 127
ctgggggccc ttggtgctgg ctgacgagac ggtgactgag gttc                        44

<210> SEQ ID NO 128
<211> LENGTH: 37
<212> TYPE: DNA

```
<213> ORGANISM: artificial
<220> FEATURE:
<223> OTHER INFORMATION: PCR primer

<400> SEQUENCE: 128
gccagcacca agggccccca ggtccaactg cagcagc                              37

<210> SEQ ID NO 129
<211> LENGTH: 38
<212> TYPE: DNA
<213> ORGANISM: artificial
<220> FEATURE:
<223> OTHER INFORMATION: PCR primer

<400> SEQUENCE: 129
cggggccctt ggtgctggct gacgagacgg tgactgag                             38

<210> SEQ ID NO 130
<211> LENGTH: 37
<212> TYPE: DNA
<213> ORGANISM: artificial
<220> FEATURE:
<223> OTHER INFORMATION: PCR primer

<400> SEQUENCE: 130
gccagcacca agggccccga ggtccaactg cagcaac                              37

<210> SEQ ID NO 131
<211> LENGTH: 40
<212> TYPE: DNA
<213> ORGANISM: artificial
<220> FEATURE:
<223> OTHER INFORMATION: PCR primer

<400> SEQUENCE: 131
gtctggtgca gccacagttc gtttgatttc cagcttggtg                           40

<210> SEQ ID NO 132
<211> LENGTH: 38
<212> TYPE: DNA
<213> ORGANISM: artificial
<220> FEATURE:
<223> OTHER INFORMATION: PCR primer

<400> SEQUENCE: 132
cgaactgtgg ctgcaccaga catcgtgatg acacaagc                             38

<210> SEQ ID NO 133
<211> LENGTH: 41
<212> TYPE: DNA
<213> ORGANISM: artificial
<220> FEATURE:
<223> OTHER INFORMATION: PCR primer

<400> SEQUENCE: 133
gtctggtgca gccacagttc gttttatttc cagcttggtc c                         41

<210> SEQ ID NO 134
<211> LENGTH: 41
<212> TYPE: DNA
<213> ORGANISM: artificial
<220> FEATURE:
<223> OTHER INFORMATION: PCR primer

<400> SEQUENCE: 134
cgaactgtgg ctgcaccaga cattcagatg actcagacta c                         41
```

```
<210> SEQ ID NO 135
<211> LENGTH: 20
<212> TYPE: DNA
<213> ORGANISM: Artificial
<220> FEATURE:
<223> OTHER INFORMATION: PCR primer

<400> SEQUENCE: 135
tcttcgggaa gcagctatgc                                              20

<210> SEQ ID NO 136
<211> LENGTH: 20
<212> TYPE: DNA
<213> ORGANISM: artificial
<220> FEATURE:
<223> OTHER INFORMATION: PCR primer

<400> SEQUENCE: 136
ttctccactg ggcgtaagag                                              20

<210> SEQ ID NO 137
<211> LENGTH: 41
<212> TYPE: DNA
<213> ORGANISM: artificial
<220> FEATURE:
<223> OTHER INFORMATION: PCR primer

<400> SEQUENCE: 137
atctgcattc tagactggag gaaaagaaag tttgccaagg c                      41

<210> SEQ ID NO 138
<211> LENGTH: 41
<212> TYPE: DNA
<213> ORGANISM: artificial
<220> FEATURE:
<223> OTHER INFORMATION: PCR primer

<400> SEQUENCE: 138
tactcgatga cgcgtttagg atgggatctt aggcccgttc c                      41

<210> SEQ ID NO 139
<211> LENGTH: 22
<212> TYPE: DNA
<213> ORGANISM: artificial
<220> FEATURE:
<223> OTHER INFORMATION: PCR primer

<400> SEQUENCE: 139
tcatgctcca ataaattcac tg                                           22

<210> SEQ ID NO 140
<211> LENGTH: 37
<212> TYPE: DNA
<213> ORGANISM: artificial
<220> FEATURE:
<223> OTHER INFORMATION: PCR primer

<400> SEQUENCE: 140
ggagtcggcg gccgcaccat gcgaccctcc gggacgg                           37

<210> SEQ ID NO 141
<211> LENGTH: 37
<212> TYPE: DNA
<213> ORGANISM: artificial
<220> FEATURE:
```

```
<223> OTHER INFORMATION: PCR primer

<400> SEQUENCE: 141
gcatgtgact cgagtcatgc tccaataaat tcactgc                                    37
```